US010325687B2

(12) United States Patent
Jiang

(10) Patent No.: US 10,325,687 B2
(45) Date of Patent: Jun. 18, 2019

(54) POPULATION PHARMACOKINETICS TOOLS AND USES THEREOF

(71) Applicant: Bioverativ Therapeutics Inc., Waltham, MA (US)

(72) Inventor: Haiyan Jiang, Belmont, MA (US)

(73) Assignee: Bioverativ Therapeutics Inc., Waltham, MA (US)

(*) Notice: Subject to any disclaimer, the term of this patent is extended or adjusted under 35 U.S.C. 154(b) by 414 days.

(21) Appl. No.: 15/101,756

(22) PCT Filed: Dec. 6, 2014

(86) PCT No.: PCT/US2014/068956
§ 371 (c)(1),
(2) Date: Jun. 3, 2016

(87) PCT Pub. No.: WO2015/085276
PCT Pub. Date: Jun. 11, 2015

(65) Prior Publication Data

US 2016/0306945 A1 Oct. 20, 2016

Related U.S. Application Data

(60) Provisional application No. 61/944,467, filed on Feb. 25, 2014, provisional application No. 61/934,286, (Continued)

(51) Int. Cl.
*G16H 50/50* (2018.01)
*A61K 38/37* (2006.01)
(Continued)

(52) U.S. Cl.
CPC ............ *G16H 50/50* (2018.01); *A61K 38/37* (2013.01); *A61K 38/4846* (2013.01);
(Continued)

(58) Field of Classification Search
CPC .... A61K 38/4846; A61K 38/37; A61K 38/36; G06F 19/704; G06F 19/3456;
(Continued)

(56) References Cited

U.S. PATENT DOCUMENTS

| | | | |
|---|---|---|---|
| 4,757,006 A | 7/1988 | Toole, Jr. et al. | |
| 4,868,112 A | 9/1989 | Toole, Jr. | |

(Continued)

FOREIGN PATENT DOCUMENTS

| | | |
|---|---|---|
| EP | 0154316 A2 | 9/1985 |
| EP | 0295597 A2 | 12/1988 |

(Continued)

OTHER PUBLICATIONS

Collins, P. W. et al. Implications of coagulation factor VII and IX pharmacokinetics in the prophylactic treatment of haemophilia. Haemophilia (2010) 17, 2-10 (PTO-1449).*

(Continued)

*Primary Examiner* — Mary K Zeman
(74) *Attorney, Agent, or Firm* — Lathrop Gage LLP; James H. Velema, Esq.

(57) ABSTRACT

The present invention is directed to computer based pharmacokinetics systems, such as. web-based pharmacokinetics systems, and their use to predict a dose and a dosing interval for a patient in need of a clotting factor therapy.

23 Claims, 66 Drawing Sheets

Specification includes a Sequence Listing.

Related U.S. Application Data filed on Jan. 31, 2014, provisional application No. 61/913,149, filed on Dec. 6, 2013.

(51) Int. Cl.

| | |
|---|---|
| *A61K 38/48* | (2006.01) |
| *G06N 7/00* | (2006.01) |
| *G06F 19/00* | (2018.01) |
| *C07K 14/755* | (2006.01) |
| *C12N 9/64* | (2006.01) |

(52) U.S. Cl.

CPC ............ *C07K 14/755* (2013.01); *C12N 9/644* (2013.01); *C12Y 304/21022* (2013.01); *G06F 19/3456* (2013.01); *G06F 19/704* (2013.01); *G06N 7/005* (2013.01); *C07K 2319/30* (2013.01); *G06F 19/707* (2013.01); *G06F 19/709* (2013.01)

(58) Field of Classification Search

CPC ...... G06F 19/00; G06F 19/12; G06F 19/3437; G06F 19/70; G06F 19/707; G06F 19/709; A61P 7/04; G06N 7/005; G16H 10/60; G16H 20/10; G16H 50/50

See application file for complete search history.

(56) References Cited

U.S. PATENT DOCUMENTS

| | | | |
|---|---|---|---|
| 4,965,199 | A | 10/1990 | Capon et al. |
| 4,994,371 | A | 2/1991 | Davie et al. |
| 5,004,803 | A | 4/1991 | Kaufman et al. |
| 5,112,950 | A | 5/1992 | Meulien et al. |
| 5,171,844 | A | 12/1992 | Van Ooyen et al. |
| 5,364,771 | A | 11/1994 | Lollar et al. |
| 5,543,502 | A | 8/1996 | Nordfang et al. |
| 5,595,886 | A | 1/1997 | Chapman et al. |
| 5,610,278 | A | 3/1997 | Nordfang et al. |
| 5,712,122 | A | 1/1998 | Boime et al. |
| 5,789,203 | A | 8/1998 | Chapman et al. |
| 5,859,204 | A | 1/1999 | Lollar |
| 5,972,885 | A | 10/1999 | Spira et al. |
| 6,048,720 | A | 4/2000 | Dalborg et al. |
| 6,060,447 | A | 5/2000 | Chapman et al. |
| 6,228,620 | B1 | 5/2001 | Chapman et al. |
| 6,251,632 | B1 | 6/2001 | Lillicrap et al. |
| 6,316,226 | B1 | 11/2001 | Van Ooyen et al. |
| 6,346,513 | B1 | 2/2002 | Van Ooyen et al. |
| 6,376,463 | B1 | 4/2002 | Lollar |
| 6,458,563 | B1 | 10/2002 | Lollar |
| 6,686,179 | B2 | 2/2004 | Fleer et al. |
| 7,041,635 | B2 | 5/2006 | Kim et al. |
| 7,348,004 | B2 | 3/2008 | Peters et al. |
| 7,404,956 | B2 | 7/2008 | Peters et al. |
| 7,592,010 | B2 | 9/2009 | Rosen et al. |
| 7,632,921 | B2 | 12/2009 | Pan et al. |
| 10,083,400 | B2 * | 9/2018 | Mould ................ G06F 19/3456 |
| 2005/0100990 | A1 | 5/2005 | Saenko et al. |
| 2009/0087411 | A1 | 4/2009 | Fares et al. |
| 2009/0163699 | A1 | 6/2009 | Chamberlain et al. |
| 2009/0264627 | A1 | 10/2009 | Gillies et al. |
| 2010/0286067 | A1 | 11/2010 | Defrees |
| 2010/0292130 | A1 | 11/2010 | Skerra et al. |
| 2011/0152830 | A1 | 6/2011 | Ruchti et al. |
| 2012/0093840 | A1 | 4/2012 | Ostergaard et al. |
| 2013/0209565 | A1 | 8/2013 | Hedner et al. |
| 2014/0379629 | A1 * | 12/2014 | Loew-Baselli ..... G06F 19/3456 706/52 |

FOREIGN PATENT DOCUMENTS

| | | | |
|---|---|---|---|
| EP | 0401384 | A1 | 12/1990 |
| EP | 2173890 | B1 | 3/2011 |
| WO | WO-8704187 | A1 | 7/1987 |
| WO | WO-8800831 | A1 | 2/1988 |
| WO | WO-8803558 | A1 | 5/1988 |
| WO | WO-8808035 | A1 | 10/1988 |
| WO | WO-9109122 | A1 | 6/1991 |
| WO | WO-9216221 | A1 | 10/1992 |
| WO | WO-9320093 | A1 | 10/1993 |
| WO | WO-9411503 | A2 | 5/1994 |
| WO | WO-9534326 | A1 | 12/1995 |
| WO | WO-0240544 | A2 | 5/2002 |
| WO | WO-03020764 | A2 | 3/2003 |
| WO | WO-2004101740 | A2 | 11/2004 |
| WO | WO-2005001025 | A2 | 1/2005 |
| WO | WO-2006074199 | A1 | 7/2006 |
| WO | WO-2007149406 | A2 | 12/2007 |
| WO | WO-2008118507 | A2 | 10/2008 |
| WO | WO-2008155134 | A1 | 12/2008 |
| WO | WO-2009051717 | A2 | 4/2009 |
| WO | WO-2009130198 | A2 | 10/2009 |
| WO | WO-2009137254 | A2 | 11/2009 |
| WO | WO-2009140015 | A2 | 11/2009 |
| WO | WO-2012006624 | A2 | 1/2012 |

OTHER PUBLICATIONS

Carlsson, M. et al. Multidose pharmacokinetics of factor IX: implications for dosing in prophylaxis. Haemphilia (1998) 4: 83-88. PTO-1449.*

Fuchs, A. et al. Benchmarking Therapeutic Drug Monitoring Software: a Review of Available Computer Tools. Clinical Pharmacokinetics. (2013) 52: 9-22.*

Iorio, A. et al. Development of a Web-accessible population pharmacokinetic service—Haemophilia (WAPPS-Hemo): Study Protocol. (2016) JMIR (5) 4 e239.*

Ahn, J.E., et al., "Likelihood Based Approaches to Handling Data Below the Quantification Limit Using NONMEM VI," *Journal of Pharmacokinetics and Pharmacodynamics* 35(4):401-421, Springer Science+Business Media, LLC, United States (2008).

Armour, K.L., et al., "Recombinant Human IgG Molecules Lacking Fcγ Receptor I Binding and Monocyte Triggering Activities," *European Journal of Immunology* 29(8):2613-2624, Wiley-VCH Verlag GmbH, Germany (1999).

Bai, Y., et al., "Recombinant granulocyte colony-stimulating factor-transferrin fusion protein as an oral myelopoietic agent," *Proceedings of the National Academy of Sciences USA* 102(20):7292-7296, National Academy of Sciences, United States (2005).

Beal, S.L., "Ways to Fit a PK Model with Some Data Below the Quantification Limit," *Journal of Pharmacokinetics and Pharmacodynamics* 28(5):481-504, Plenum Publishing Corporation, United States (2001).

Björkman, S., and Ahlen, V., et al., "Population Pharmacokinetics of Plasma-Derived Factor IX in Adult Patients with Haemophilia B: Implications for Dosing in Prophylaxis," *European Journal of Clinical Pharmacology* 68(6):969-977, Springer-Verlag, Germany (2012).

Bjorkman, S., et al., "Comparative Pharmacokinetics of Plasma- and Albumin-free Recombinant Factor VIII in Children and Adults: The Influence of Blood Sampling Schedule on Observed Age-related Differences and Implications for Dose Tailoring," *Journal of Thrombosis and Haemostasis* 8(4):730-736, International Society on Thrombosis and Haemostasis, England (2010).

Bjorkman, S., et al., "Pharmacokinetics and Dose Requirements of Factor VIII Over the Age Range 3-74 years: A Population Analysis Based on 50 Patients with Long-term Prophylactic Treatment for Haemophilia A," *European Journal of Clinical Pharmacology* 65(10):989-998, Springer, Germany (2009).

Bjorkman, S., et al., "Pharmacokinetics of Factor IX in Patients With Haemophilia B. Methodological Aspects and Physiological Interpretation," *European Journal of Clinical Pharmacology* 46(4):325-332, Springer-Verlag, Germany (1994).

Bjorkman, S., et al., "Pharmacokinetics of Recombinant Factor IX in Relation to Age of the Patient: Implications for Dosing in Prophylaxis," *Haemophilia* 7(2):133-139, Blackwell Science Ltd., England (2001).

(56) References Cited

OTHER PUBLICATIONS

Bjorkman, S., et al., "Population Pharmacokinetics of Recombinant Factor VIII: The Relationships of Pharmacokinetics to Age and Body Weight," *Blood* 119(2):612-618, American Society of Hematology, United States (2012).
Bjorkman, S., "Population Pharmacokinetics of Recombinant Factor IX: Implications for Dose Tailoring," *Haemophilia* 19(5):753-757, John Wiley & Sons Ltd., England (Sep. 2013).
Blankenship, C.S., "To Manage Costs of Hemophilia, Patients Need More than Clotting Factor," *Biotechnology Healthcare* 5(4):37-40, MediMedia, United States (2008).
Brandsma, M.E., et al., "Recombinant human transferrin: Beyond iron binding and transport," *Biotechnology Advances* 29(2):230-238, Elsevier Inc., United States (2011).
Burmeister, W.P., et al., "Crystal Structure of the Complex of Rat Neonatal Fc Receptor with Fc," *Nature* 372(6504):379-383, Nature Publishing Group, England (1994).
Cameron, C., et al., "The Canine Factor VIII cDNA and 5' Flanking Sequence," *Thrombosis and Haemostasis* 79(2):317-322, Schattauer Verlag, Germany (1998).
Carlsson, M., et al., "Multidose Pharmacokinetics of Factor IX: Implications for Dosing in Prophylaxis," *Haemophilia* 4(2):83-88, Blackwell Science Ltd., England (1998).
Collins, P.W., et al., "Break-Through Bleeding in Relation to Predicted Factor VIII Levels in Patients Receiving Prophylactic Treatment for Severe Hemophilia A," *Journal of Thrombosis and Haemostasis* 7(3):413-420, International Society on Thrombosis and Haemostasis, England, (2009).
Collins, P.W., et al., "Implications of Coagulation Factor VIII and IX Pharmacokinetics in the Prophylactic Treatment of Haemophilia," *Haemophilia*, 17(1):2-10, Blackwell Publishing Limited., England (2011).
Cutler, J.A., et al., "The Identification and Classification of 41 novel Mutations in the Factor VIII Gene (F8C)," *Human Mutation* 19(3):274-278, Wiley-Liss, Inc., United States (2002).
Dennis, M.S., et al., "Albumin Binding as a General Strategy for Improving the Pharmacokinetics of Proteins," *The Journal of Biological Chemistry* 277(38):35035-35043, American Society for Biochemistry and Molecular Biology, United States (2002).
Eaton, D.L., et al., "Construction and Characterization of an Active Factor VIII Variant Lacking the Central One-Third of the Molecule," *Biochemistry* 25(26):8343-8347, American Chemical Society, United States (1986).
Ette, E.I. and Ludden, T.M., "Population Pharmacokinetic Modeling: the Importance of Informative Graphics," *Pharmaceutical Research* 12(12):1845-1855, Plenum Publishing Corporation, United States (1995).
Fatouros, A., et al., "Recombinant Factor VIII SQ—Influence of Oxygen, Metal Ions, pH and Ionic Strength on its Stability in Aqueous Solution," *International Journal of Pharmaceutics* 155(1):121-131, Elsevier Science B.V., Netherlands (1997).
Francis, G.E., "Protein Modification and Fusion Proteins," *Focus on Growth Factors* 3(2):4-10, Mediscript, England (1992).
Friend, P.J., et al., "Phase I Study of an Engineered Aglycosylated Humanized CD3 Antibody in Renal Transplant Rejection," *Transplantation* 68(11):1632-1637, Lippincott Williams & Wilkins, Inc., United States (1999).
GenBank, "*Homo sapiens* Transferrin (TF), mRNA," Accession No. NM001063.3, published on May 25, 2014, accessed at http://www.ncbi.nlm.nih.gov/nuccore/NM_001063, accessed on Sep. 24, 2014, 5 pages.
GenBank, "*Homo sapiens* Transferrin (TF), mRNA," Accession No. XM002793, published on May 13, 2002, accessed at https://www.ncbi.nlm.nih.gov/nuccore/XM_002793.7?report=genbank, accessed on Sep. 24, 2014, 2 pages.
GenBank, "*Homo sapiens* Transferrin (TF), mRNA," Accession No. XM039847, published on Jul. 16, 2001, accessed at http://www.ncbi.nlm.nih.gov/nuccore/XM_039847.1?report=genbank, accessed on Sep. 24, 2014, 2 pages.
GenBank, "*Homo sapiens* Transferrin (TF), mRNA," Accession No. XM039845, published Jul. 16, 2001, accessed at https://www.ncbi.nlm.nih.gov/nuccore/XM_039845.1?report=genbank, accessed on Sep. 24, 2014, 2 pages.
GenBank, "Human Transferrin mRNA, Complete cds," Accession No. M12530.1, published on Jan. 14, 1995, accessed at http://www.ncbi.nlm.nih.gov/nuccore/M1253014, accessed on Jan. 15, 2015, 2 pages.
GenBank, "Transferrin [human, liver, mRNA, 2347 nt]," Accession No. S95936.1, published on May 7, 1993, accessed at http://www.ncbi.nlm.nih.gov/nuccore/S95936, accessed on Sep. 24, 2014, 2 pages.
Gitschier, J., et al., "Characterization of the Human Factor VIII Gene," *Nature* 312(5992):326-330, Nature Publishing Group, England (1984).
Healey, J.F., et al., "The cDNA and Derived Amino Acid Sequence of Porcine Factor VIII," *Blood* 88(11):4209-4214, The American Society of Hematology, United States (1996).
Hoeben, R.C., et al., "Expression of Functional Factor VIII in Primary Human Skin Fibroblasts after Retrovirus-mediated Gene Transfer," *The Journal of Biological Chemistry* 265(13):7318-7323, The American Society for Biochemistry and Molecular Biology, United States (1990).
Holt, L.J., et al., "Anti-Serum Albumin Domain Antibodies for Extending the Half-Lives of Short Lived Drugs," *Protein Engineering, Design & Selection* 21(5):283-288, Oxford University Press, England (2008).
International Preliminary Report on Patentability and Written Opinion for Application No. PCT/US2014/068956, The International Bureau of WIPO, Switzerland, dated Jun. 7, 2016, 22 pages.
International Search Report for Application No. PCT/US2014/068956, ISA/US, Alexandria, Virginia, United States, dated May 5, 2015, 9 pages.
Jonsson, E.N. and Karlsson, M.O., "Xpose—an S-plus Based Population Pharmacokinetic/pharmacodynamic Model Building Aid for NONMEM," *Computer Methods and Programs in Biomedicine* 58(1):51-64, Elsevier Science Ireland Ltd., Ireland (1999).
Karafoulidou, A., et al., "Population Pharmacokinetics of Recombinant Factor VIII:C (ReFacto) in Adult HIV-negative and HIV-positive Haemophilia Patients," *European Journal of Clinical Pharmacology* 65(11):1121-1130, Springer, Germany (2009).
Karlsson, M.O. and Sheiner, L.B., "The Importance of Modeling Interoccasion Variability in Population Pharmacokinetic Analyses," *Journal of Pharmacokinetics and Biopharmaceutics* 21(6):735-750, Plenum Publishing Corporation, United States (1993).
Kiang, T.K.L., et al., "Fundamentals of Population Pharmacokinetic Modelling, Modelling and Software," *Clinical Pharmacokinetics* 51(8):515-525, Springer International Publishing AG, New Zealand (2012).
Kim, B-J., et al., "Transferrin Fusion Technology: A Novel Approach to Prolonging Biological Half-Life of Insulinotropic Peptides," *The Journal of Pharmacology and Experimental Therapeutics* 334(3):682-692, American Society for Pharmacology and Experimental Therapeutics, United States (2010).
Kraulis, P.J., et al., "The Serum Albumin-Binding Domain of Streptococcal Protein G is a Three-Helical Bundle: a Heteronuclear NMR study," *FEBS Letters* 378(2):190-194, Federation of European Biochemical Societies, Netherlands (1996).
Langner, K-D., et al., "Synthesis of Biologically Active Deletion Mutants of Human Factor VIII:C," *Behring Institute Mitteilungen* 82:16-25, Behringwerke AG, Germany (1988).
Li, H., et al., "The role of the transferrin-transferrin-receptor system in drug delivery and targeting," *Trends in Pharmacological Sciences* 23(5):206-209, Elsevier Science Ltd., England (2002).
Lillicrap, D., "Extending Half-life in Coagulation Factors: Where do We Stand?" *Thrombosis Research* 122(Suppl 4):S2-S8, Elsevier Ltd., England (2008).
Lindbom, L., et al., "Perl-speaks-NONMEM (PsN)—a Perl Module for NONMEM Related Programming," *Computer Methods and Programs in Biomedicine* 75(2):85-94, Elsevier Ireland Ltd., Ireland (2004).
Linhult, M., et al., "Mutational Analysis of the Interaction Between Albumin-Binding Domain from Streptococcal Protein G and Human

(56) References Cited

OTHER PUBLICATIONS

Serum Albumin," *Protein Science* 11(2):206-213, Cold Spring Harbor Laboratory Press, United States (2002).
Mahlangu, J., et al., "Phase 3 Study of Recombinant Factor VIII Fc Fusion Protein in Severe Hemophilia A," *Blood* 123(3):317-325, The American Society of Hematology, United States (Jan. 2014).
Malik, F., et al., "Polyethylene Glycol (PEG)-modified Granulocyte-Macrophage Colony-stimulating Factor (GM-CSF) with Conserved Biological Activity," *Experimental Hematology* 20(8):1028-1035, International Society for Experimental Hematology, United States (1992).
Mannucci, P.M. And Tuddenham, E.G.D., "The Hemophilias—from Royal Genes to Gene Therapy," *New England Journal of Medicine* 344(23):1773-1779, Massachusetts Medical Society, United States (2001).
MASAC, MASAC Recommendation #190: MASAC Recommendations Concerning Products Licensed for the Treatment of Hemophilia and other Bleeding Disorders (Revised Mar. 2009), accessed at https://web.archive.org/web/20100523064913/http://www.hemophilia.org/NHFWeb/MainPgs/MainNHF.aspx?menuid=57&contentid=693, accessed on Dec. 7, 2016, 7 pages.
Mei, B., et al., "Rational Design of a Fully active, Long-Acting PEGylated Factor VIII for Hemophilia A Treatment," *Blood* 116(2):270-279, The American Society of Hematology, United States (2010).
Meulien, P., et al., "A New Recombinant Procoagulant Protein Derived from the cDNA Encoding Human Factor VIII," *Protein Engineering* 2(4):301-306, IRL Press Ltd., England (1988).
Müller, D. and Kontermann, R.E., "Recombinant Bispecific Antibodies for Cellular Cancer Immunotherapy," *Current Opinion in Molecular Therapeutics* 9(4):319-326, The Thomson Corporation, United States (2007).
National Institute of Health, "Morbidity & Mortality: 2012 Chart Book on Cardiovascular, Lung and Blood Diseases," accessed at https://www.nhlbi.nih.gov/files/docs/research/2012_ChartBook.pdf, accessed on Dec. 7, 2016, 116 pages.
Oganesyan, V., et al., "Structural Characterization of a Human Fc Fragment Engineered for Extended Serum Half-Life," *Molecular Immunology* 46(8-9)1750-1755, Elsevier Ltd., England (2009).
Powell, J.S., et al., "Safety and Prolonged Activity of Recombinant Factor VIII Fc Fusion Protein in Hemophilia A Patients," *Blood* 119(13):3031-3037, The American Society of Hematology, United States (2012).
Roovers, R.C., et al., "Efficient Inhibition of EGFR Signaling and of Tumour Growth by Antagonistic Anti-EGFR Nanobodies," *Cancer Immunology, Immunotherapy* 56(3):303-317, Springer-Verlag, Germany (2007).
Routledge, E.G., et al., "The Effect of Aglycosylation on the Immunogenicity of a Humanized Therapeutic CD3 Monoclonal Antibody," *Transplantation* 60(8):847-853, Lippincott Williams & Wilkins, United States (1995).
Sarver, N., et al., "Stable Expression of Recombinant Factor VIII Molecules Using a Bovine Papillomavirus Vector," *DNA* 6(6):553-564, Mary Ann Liebert, Inc., United States (1987).
Savic, R.M. and Karlsson, M.O., "Importance of Shrinkage in Empirical Bayes Estimates for Diagnostics: Problems and Solutions," *The AAPS Journal* 11(3):558-569, American Association of Pharmaceutical Scientists, United States (2009).
Schulte, S., "Half-life Extension Through Albumin Fusion Technologies," *Thrombosis Research 124(Suppl. 2)*:S6-S8, Elsevier Ltd., England (2009).
Sherwin, C.M.T., et al., "Fundamentals of Population Pharmacokinetic Modelling, Validation Methods," *Clinical Pharmacokinetics* 51(9):573-590, Springer International Publishing AG, New Zealand (2012).
Shields, R.L., et al., "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry* 276(9):6591-6604, American Society for Biochemistry and Molecular Biology, United States (2001).
Sommermeyer, V.K., et al., "Klinisch Verwendete Hydroxyethylstarke: Physikalisch-Chemische Charakterisierung," *Krankenhauspharmazie* 8(8):271-278, Deutscher Apotheker Verlag, Birkenwaldstr, Germany (1987).
Story, C.M., et al., "A Major Histocompatibility Complex Class I-like Fc Receptor Cloned from Human Placenta: Possible Role in Transfer of Immunoglobulin G from Mother to Fetus," *The Journal of Experimental Medicine* 180(6):2377-2381, The Rockefeller University Press, United States (1994).
Toole, J.J., et al., "A Large Region (≈95 kDa) of Human Factor VIII is Dispensable for in vitro Procoagulant Activity," *Proceedings of the National Academy of Sciences USA* 83(16):5939-5942, National Academy of Sciences, United States (1986).
Toole, J.J., et al., "Molecular Cloning of a cDNA Encoding Human Antihaemophilic Factor," *Nature* 312(5992):342-347, Nature Publishing Group, England (1984).
Trüssel, S., et al., "New Strategy for the Extension of the Serum Half-Life of Antibody Fragments," *Bioconjugate Chemistry* 20(12):2286-2292, American Chemical Society, United States (2009).
Udata, C., et al., "Population Pharmacokinetic Modeling of BeneFIX in Pediatric and Adult Patients with Hemophilia B Demonstrates Weight as an Important Factor Contributing to Inter-patient PK Variability," *Blood* 112(11):443-444 (2008).
Vaccaro, C., et al., "Engineering the Fc region of Immunoglobulin G to Modulate in vivo Antibody Levels," *Nature Biotechnology* 23(10)1283-1288, Nature America Publishing, United States (2005).
Vehar, G.A., et al., "Structure of Human Factor VIII," *Nature* 312(5992):337-342, Nature Publishing Group, England (1984).
Wade, J.R., et al., "A Guide for Reporting the Results of Population Pharmacokinetic Analyses: a Swedish Perspective," *The AAPS Journal* 7(2):45:E456-E460, American Association of Pharmaceutical Scientists, United States (2005).
Wakabayashi, H., et al., "Residues 110-126 in the A1 Domain of Factor VIII Contain a $Ca^{2+}$ Binding Site Required for Cofactor Activity," *The Journal of Biological Chemistry* 279(13):12677-12684, The American Society for Biochemistry and Molecular Biology, Inc., United States (2004).
Wang, Y., et al., "Receptor-Mediated Activation of a Proinsulin-Transferrin Fusion Protein in Hepatoma Cells," *Journal of Controlled Release* 155(3):386-392, Elsevier B.V., Netherlands (2011).
Ward, E.S. and Ghetie, V., "The Effector Functions of Immunoglobulins: Implications for Therapy," *Therapeutic Immunology* 2(2):77-94, Blackwell Science Ltd., England (1995).
Weidler, B., et al., "Pharmakokinetische Merkmale als Kriterien für den klinischen Einsatz von Hydroxyethylstarke," *Arzneimittel-Forschung* 41(5):494-498, Editio Cantor, Germany (1991).
Wood, W.I., et al., "Expression of Active Human Factor VIII from Recombinant DNA Clones," *Nature* 312(5992):330-337, Nature Publishing Group, England (1984).
Xu, X.S., et al., "Shrinkage in Nonlinear Mixed-effects Population Models: Quantification, Influencing Factors, and Impact," *The AAPS Journal* 14(4):927-936, American Association of Pharmaceutical Scientists, United States (2012).
Donadel-Claeyssens, S., "Current co-ordinated activities of the PEDNET (European Paediatric Network for Haemophilia Management)," *Haemophilia* 12(2):124-127, Blackwell Publishing Ltd., England (2006).
Extended European Search Report for EP Application No. EP 1486715.8, Munich, Germany, dated Aug. 18, 2017, 11 pages.
Kessler, C.M., et al., "B-domain deleted recombinant factor VIII preparations are bioequivalent to a monoclonal antibody purified plasma-derived factor VIII concentrate: a randomized, three-way crossover study," *Haemophilia* 11:84-91, Blackwell Publishing Ltd., United States (2005).
Shapiro, A.D., et al., "Recombinant factor IX-Fc fusion protein (rFIXFc) demonstrates safety and prolonged activity in a phase 1/2a study in hemophilia B patients," *Blood* 119(3):666-672, American Society of Hematology, United States (2012).
"Factor IX Dosage Calculator", retrieved from, "http://www.oncologynurseadvisor.com/medical-calculators/factor-ixdosage-calculator/article/170949/", Jul. 26, 2017, XP055393959.

(56) References Cited

OTHER PUBLICATIONS

"Factor VIII Dosage Calculator", retrieved from, "http://www.oncologynurseadvisor.com/medical-calculators/factorviii-dosage-calculator/article/1709501", Jul. 26, 2017, XP055393962.

* cited by examiner

A. Phase 1/2a Study Design

| Screening (~ 14 days) | Washout (~ 7 days) | Safety & Pharmacokinetics (3-17 days) | Follow up (30 days post injection) |
|---|---|---|---|

Dose escalation: 1, 5, 12.5, 25, 50, and 100 IU/kg

B. Phase 3 Study Design

| | | | | | | |
|---|---|---|---|---|---|---|
| Arm 1 Fixed Interval (1x weekly) | Sequential Pharmacokinetics (BeneFIX vs rFIXFc) | BeneFIX® 50 IU/kg Day 1-4 | rFIXFc 50 IU/kg Day 1-10 | 1x weekly dosing 20-100 IU/kg Week ~2-25 | rFIXFc 50 IU/kg Day 1-10 | 1x weekly dosing 20-100 IU/kg Week 27-52 |
| | rFIXFc Pharmacokinetics Only | rFIXFc 50 IU/kg Day 1-10 | | 1x weekly dosing 20-100 IU/kg Week 2-52 | | |
| Arm 2 Individualized Interval | | rFIXFc 100 IU/kg Day 1-14 | | Individualized interval dosing Starting 10 days pharmacokinetic-driven adjustment 7-14 days 100 IU/kg At least 26 weeks, up to ~50 exposure days | | |
| Arm 3 On Demand | | rFIXFc 40 IU/kg Day 1-7 | | On Demand 20-100 IU/kg dose adjusted to the severity of the bleed At least 26 weeks, up to 52 weeks | | |
| Arm 4 Surgery | | rFIXFc 50 IU/kg Day 1-7 | | Surgery 40-100 IU/kg dose adjusted to the type of surgery Pre-op, surgery, Post-op, rehab | | |
| 8 Week Screening | | | | | | |

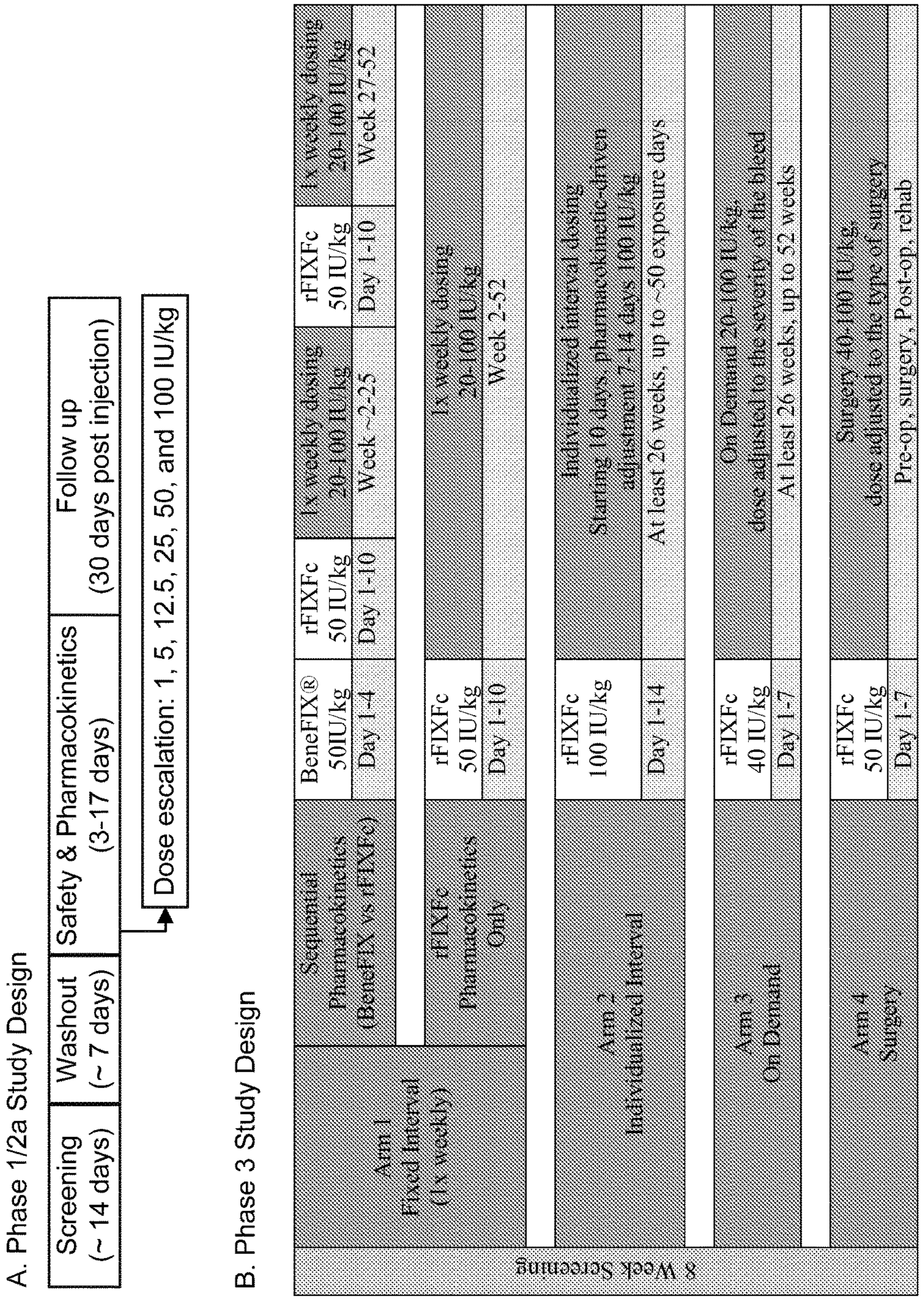

FIG. 2

C. rFIXFc Pharmacokinetic Sampling Schemes

| Study Arm/Subgroup | Sampling Timepoints |
|---|---|
| Phase 1/2a 12.5 to 100 IU/kg rFIXFc | Predose; end of infusion (10 min), 15 min after the end of infusion, 1, 3, 6, 24, 48, 72, 96, 120, 168, 240 h (288 h and 336 h if FIX activity was above baseline at day 13) |
| Phase 3 Arm 1/sequential pharmacokinetics[a] | Predose; 10 min, 1, 3, 6, 24, 48, 96, 144, 168 192 and 240 h[c] |
| Phase 3 Arm 1/non-sequential pharmacokinetics[a] | Predose; 10 min, 3, 24, 28, 96, 168 and 240 h |
| Phase 3 Arm 2[b] | Predose; 10 min, 3, 24, 48, 96, 168, 240, 28 and 336 h |
| Phase Arms 3 and 4[a] | Predose; 10 min, 3, 24, 48, 96 and 168h |

[a] Pharmacokinetic dose was 50 IU/kg.
[b] Pharmacokinetic dose was 100 IU/kg.
[c] Same sampling schedule was used for repeat pharmacokinetics at week 26.

FIG. 2

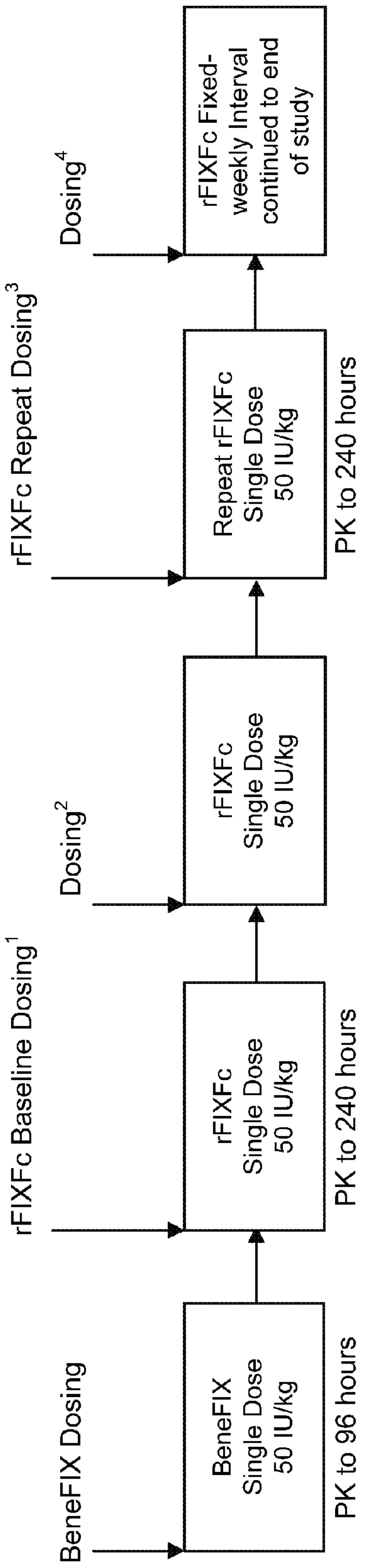

[1] A 120-hour interval is required prior to baseline dose of rFIXFc.
[2] Starting dose of 50 IU/kg adjusted to achieve a target trough level of approximately 1% to 3% above baseline. FIX level assessed periodically, at peak and trough.
[3] Repeat dose of 50 IU/kg rFIXFc for sequential PK profiling administered 26 (±1) weeks following baseline dosing.
[4] Continue fixed-weekly interval regimen until up to 52 (±1) weeks.

FIG. 3

For clinicians who are interested in determining the PK for their patients, the program will recommend 2-3 optimized PK sampling time points Clinician will input -
- body weight
- diagnostic (baseline) factor level
- dosing history if PK samples were taken from multiple doses
- actual dose
- actual time of PK sampling
- factor activity level Program will output -
- PK curve
- PK parameters
  - incremental recovery (Cmax/Dose)
  - mean residence time
  - terminal t½
  - clearance
  - Vss
  - AUC/Dose

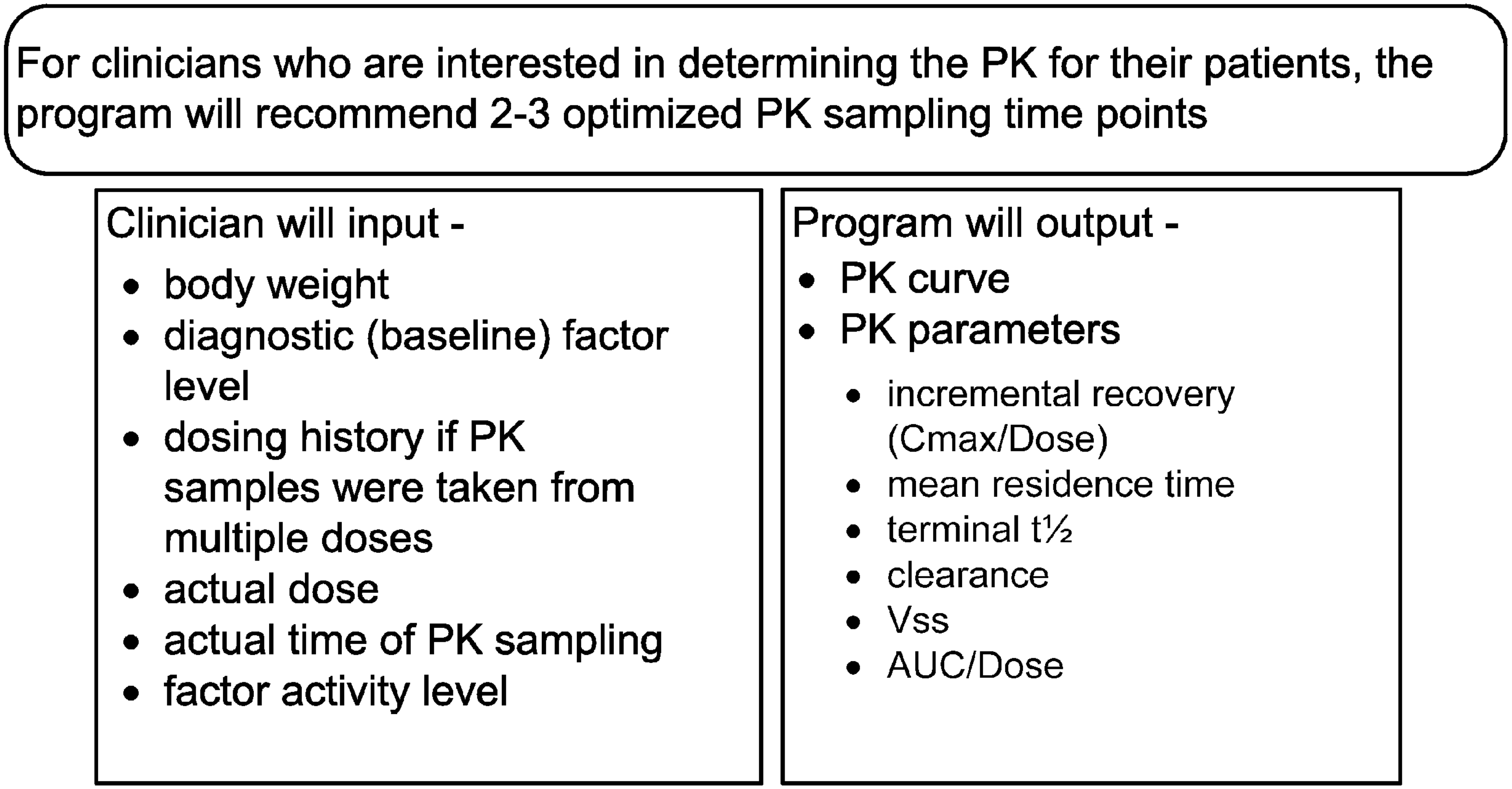

FIG. 13

Alternatively, for clinicians who skip individualized PK estimation, post product label (see below) without providing the option to estimate other potential doses, intervals, or troughs

| Dose, IU/kg | EOI median [$5^{th}$, 95th] | Day 1 median [$5^{th}$, 95th] | Day 3 median [$5^{th}$, 95th] | Day 5 median [$5^{th}$, 95th] | Day 7 median [$5^{th}$, 95th] | Day 10 median [$5^{th}$, 95th] | Day 14 median [$5^{th}$, 95th] |
|---|---|---|---|---|---|---|---|
| 50 | 52.6 [32.1, 89.3] | 16.9 [11.2, 26.1] | 7.17 [3.85, 12.3] | 4.16 [1.93, 7.83] | 2.67 [1.02, 5.49] | NA | NA |
| 100 | 102 [60.0, 166] | 30.0 [19.6, 46.7] | 12.0 [6.62, 19.9] | 6.78 [3.24, 12.2] | 4.28 [1.82, 8.06] | 2.29 [0.688, 5.33] | 1.07 [0.0758, 3.23] |

EOI, end of Infusion; NA, not applicable.

FIG. 16

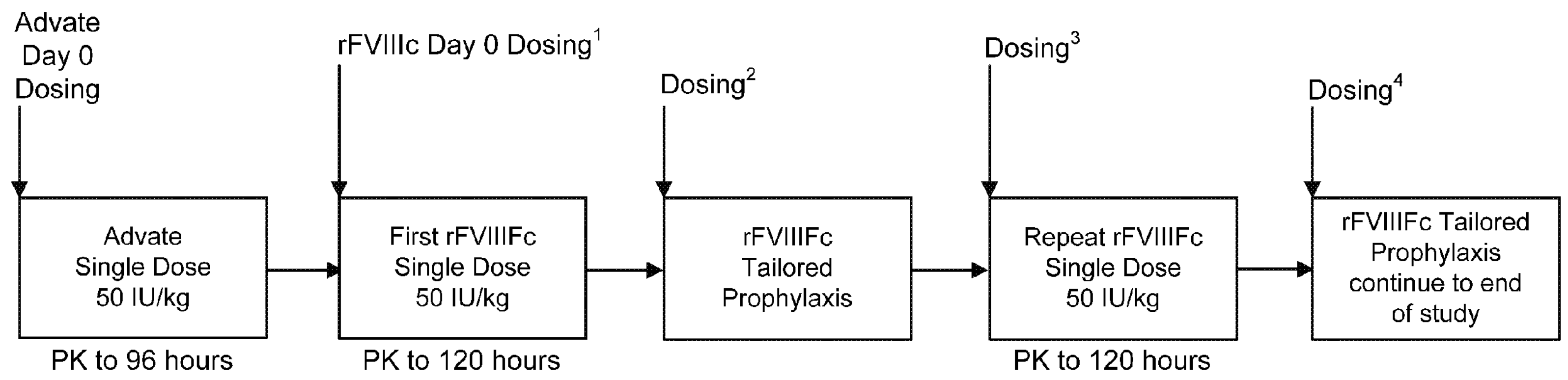

[1] Minimum interval of 96 hours, maximum interval of 8 weeks from rFVIII injection to first injection of 50 IU/kg rFVIIIFc for sequential PK profiling.

[2] Starting regimen for twice weekly individualized (tailored) prophylaxis of 25 IU/kg on first day of week followed by 50 IU/kg on fourth day, with dose and interval adjusted to achieve target trough level of approximately 1% to 3% (or higher, as clinically indicated). FVIII level asessed at peak trough.

[3] Repeat dose of 50 IU/kg rFVIIIFc for sequential PK profiling administered at Week 14, or at 12 to 24 weeks after first injection of rFVIIIFc.

[4] Continued individualized prophylaxis regimen until 28 (±2) weeks.

PK, pharmacokinetic

FIG. 21

Alternatively, for clinicians who skip individualized PK estimation, post product label (see below) without providing the option to estimate other potential doses, intervals, or troughs

| Dose, IU/kg | EOI median [$5^{th}$, 95th] | Day 1 median [$5^{th}$, 95th] | Day 3 median [$5^{th}$, 95th] | Day 5 median [$5^{th}$, 95th] | Day 7 median [$5^{th}$, 95th] | Day 10 median [$5^{th}$, 95th] | Day 14 median [$5^{th}$, 95th] |
|---|---|---|---|---|---|---|---|
| 50 | 52.6 [32.1, 89.3] | 16.9 [11.2, 26.1] | 7.17 [3.85, 12.3] | 4.16 [1.93, 7.83] | 2.67 [1.02, 5.49] | NA | NA |
| 100 | 102 [60.0, 166] | 30.0 [19.6, 46.7] | 12.0 [6.62, 19.9] | 6.78 [3.24, 12.2] | 4.28 [1.82, 8.06] | 2.29 [0.688, 5.33] | 1.07 [0.0758, 3.23] |

EOI, end of Infusion; NA, not applicable.

FVIII, factor VIII; rFVIIIFc, recombinant factor VIII Fc fusion protein.
[a]Patient-reported.

Simulated dosing regimens: predicted proportion of individuals with steady-state FVIII trough levels above 1 IU/dL (1%)

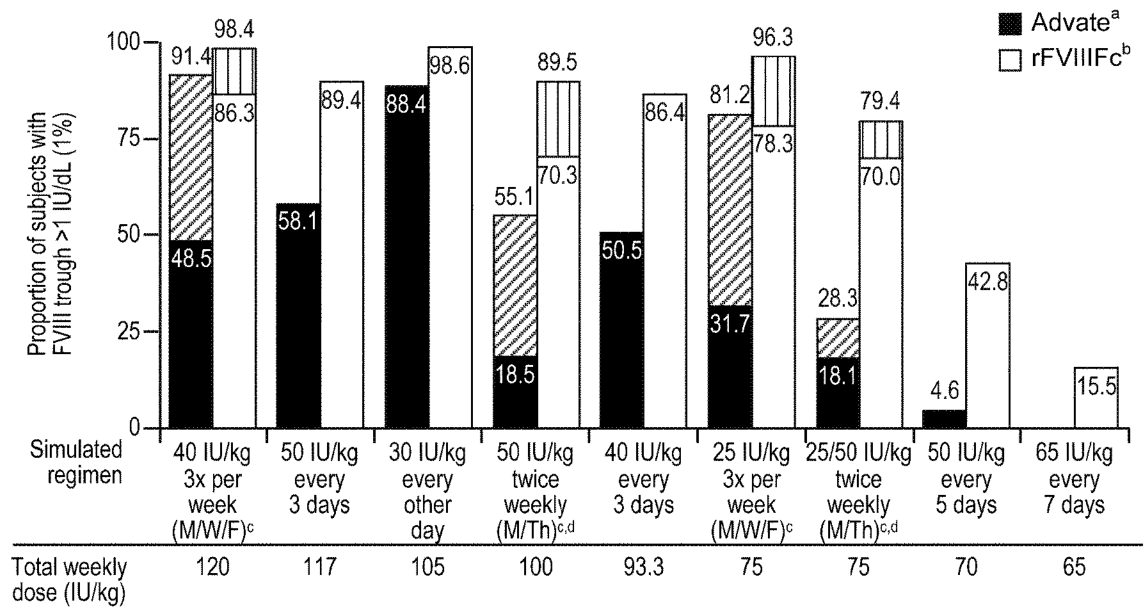

FVIII, factor VIII; rFVIIIFc, recombinant factor VIII Fc fusion protein; BLQ, below the limit of quantification; PK, pharmacokinetic; M, Monday; W, Wednesday; Th, Thursday; F, Friday

[a]Advate model parameters based on PK data from A-LONG phase 3 study.[5]

[b]rFVIIIFc base model with BLQ and parameters based on A-LONG phase 3 study.[5]

[c]Values inside dark and light colored bars report the predicted proportion of subjects who would remain protected (eg. FVIII trough level ≥1%) during the long and short portions of the dosing interval, respectively.

[d]Dosing interval of 3-4 days; equivalent to the starting study regiment of 25 IU/kg on Day 1 (M) and 50 IU/kg on Day 4 (Th).

FIG. 41

Figure 43. Predicted ABR versus time under target trough FVIII levels of 1 IU/dL, 3 IU/dL, and 5 IU/dL based on (A) the unadjusted NBR model, and (B) the adjusted NBR model. [a,b]

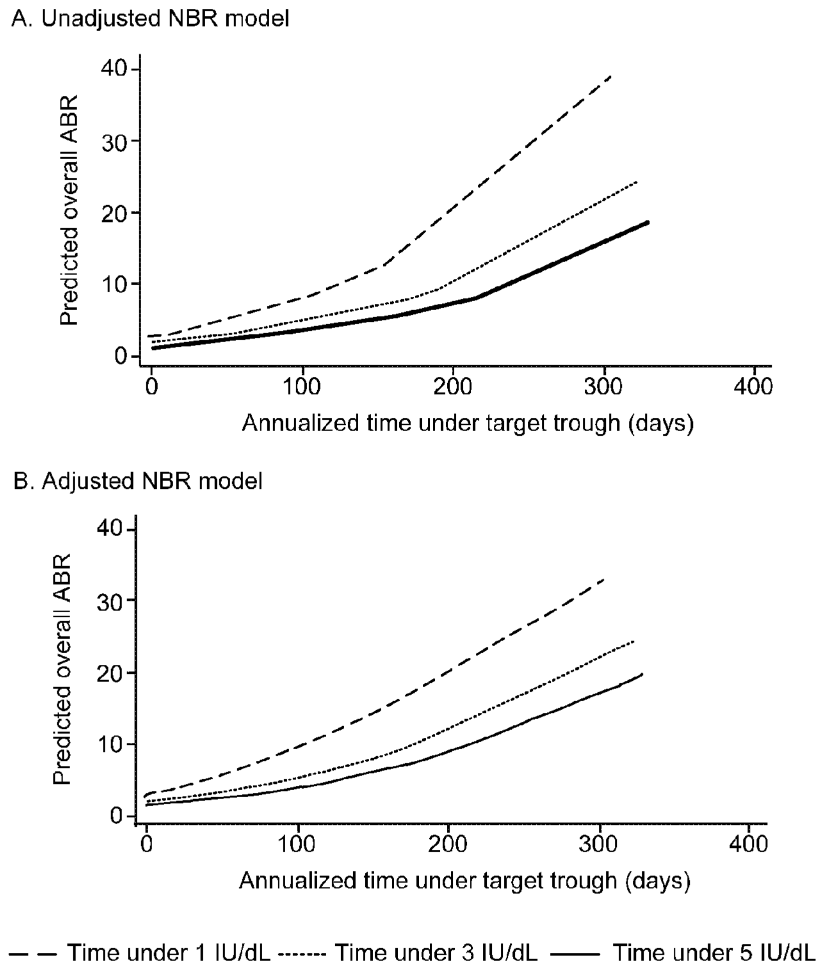

ABR, annualized bleeding rate; FVIII, factor VIII; NBR, negative binomial regression.
[a]For the adjusted NBR model, the model was adjusted for the number of pre-study bleeding episodes and pre-treatment switch (ie, switching from on-demand to prophylaxis).
[b]The curves shown are Lowess (locally weighted scatter plot smoothing) curves.

FIG. 43

Figure 44. Probability of bleeding versus the time under the target trough FVIII levels of 1 IU/dL, 3 IU/dL, and 5 IU/dL for (A) any bleed, (B) spontaneous bleeds, (c) traumatic bleeds, and (D) joint bleeds.[a]

FVIII, factor VIII
[a]The curves shown are Lowess (locally weighted scatter plot smoothing) curves.

DOSING TOOL

Empiric Dosing (F VIII) | Empiric Dosing (F IX) | PK-based Dosing (F VIII) | PK-based Dosing (F IX)

PATIENT INFORMATION

Weight [ ] kg ▽

Endogenous Level [ ] IU/dL

*Please enter valid weight value.*

PRE-PK DOSE TROUGH

Trough Level [ 0 ] IU/dL

ALPROLIX PK DOSE

Dose [ ] IU

Date [ ] 📅

Start Time [ ] : [ ] AM ▽

*Please enter valid Dose value*
*Please enter valid Date and Time*

POST ALPROLIX PK DOSE

| Activity Level | Date | Time | |
|---|---|---|---|
| Sample 1 [ ] IU/dL | [ ] 📅 | [ ] : [ ] | AM ▽ |
| Sample 2 [ ] IU/dL | [ ] 📅 | [ ] : [ ] | AM ▽ |

➕ Add Another Sample

*Please fill in required samples data*

[ CALCULATE ]

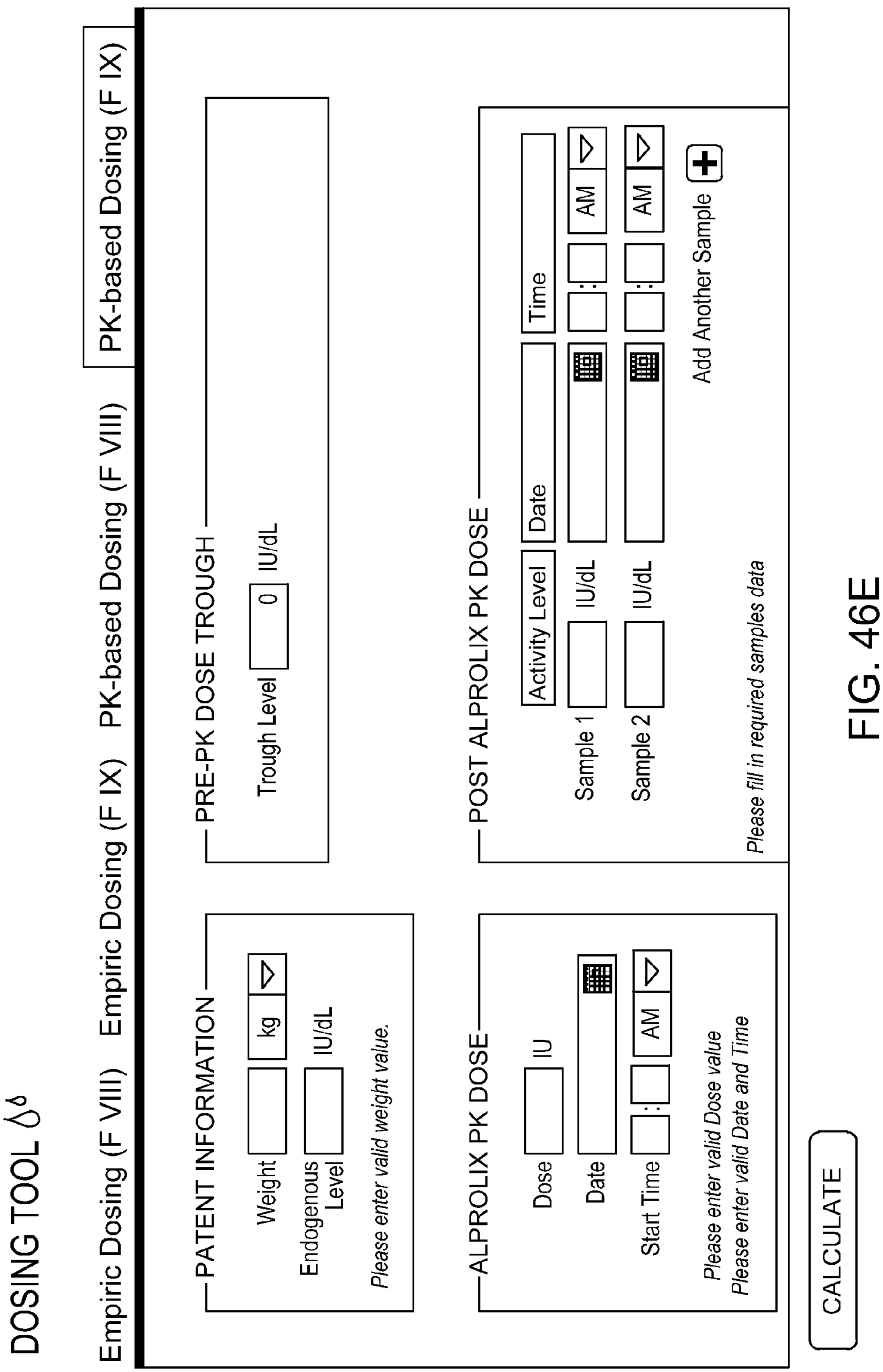

FIG. 46E

DOSING TOOL 𝛿𝛿

Empiric Dosing (F VIII) | Empiric Dosing (F IX) | PK-based Dosing (F VIII) | PK-based Dosing (F IX)

---- PATIENT INFORMATION ----

Weight [ 85 ] kg ▽

Endogenous Level [    ] IU/dL

---- PRE-PK DOSE TROUGH ----

Trough Level [ 0 ] IU/dL

---- ALPROLIX PK DOSE ----

Dose [ 4000 ] IU

Date [ 01 Feb 2014 ] 🗓

Start Time [ 10 ]:[ 00 ] AM ▽

---- POST ALPROLIX PK DOSE ----

| | Activity Level | Date | | Time | |
|---|---|---|---|---|---|
| Sample 1 | 65 IU/dL | 02 Feb 2014 🗓 | | 1:00 | PM ▽ |
| Sample 2 | 20 IU/dL | 03 Feb 2014 🗓 | | 5:00 | PM ▽ |

⊕ Add Another Sample

[ CALCULATE ]

DOSING TOOL

Home Page | Admin Page

Jane Likhtarnikova | Logout

User Administration | Prior Therapy

| User Name ➕ Add New User | User Last Name | User Role | User E-mail | User Country | User Login | User Password | Action |
|---|---|---|---|---|---|---|---|
| Mr. Black | Asshurbanipalovich | User | User | USA | borr123 | Snake | ✎ ✖ |
| Osvaldo | Tesser | User | User | USA | USA123 | Snakers_09 | ✎ ✖ |
| Alexander | Alexander | User ▽ | User.administrator@tochka.com | Russian Federation ▽ | Alexander1998 | Alexander12345 | ✓ ✖ |
| Osvaldo | Rudenko | Admin | Admin | UK | Vodovorot | Vodovorot1 | ✎ ✖ |
| Serjant | Stydenko | Admin | User | China | Will | Will14_#% | ✎ ✖ |
| Osip | Asshurbanipalovich | Admin | Admin | Indonesia | Indonesia | In234_esia | ✎ ✖ |
| Bill | Laswell | Admin | Admin | India | India | In()dia | ✎ ✖ |
| Corey | Talor | User | User | USA | Collab123 | ColUob_ab123 | ✎ ✖ |

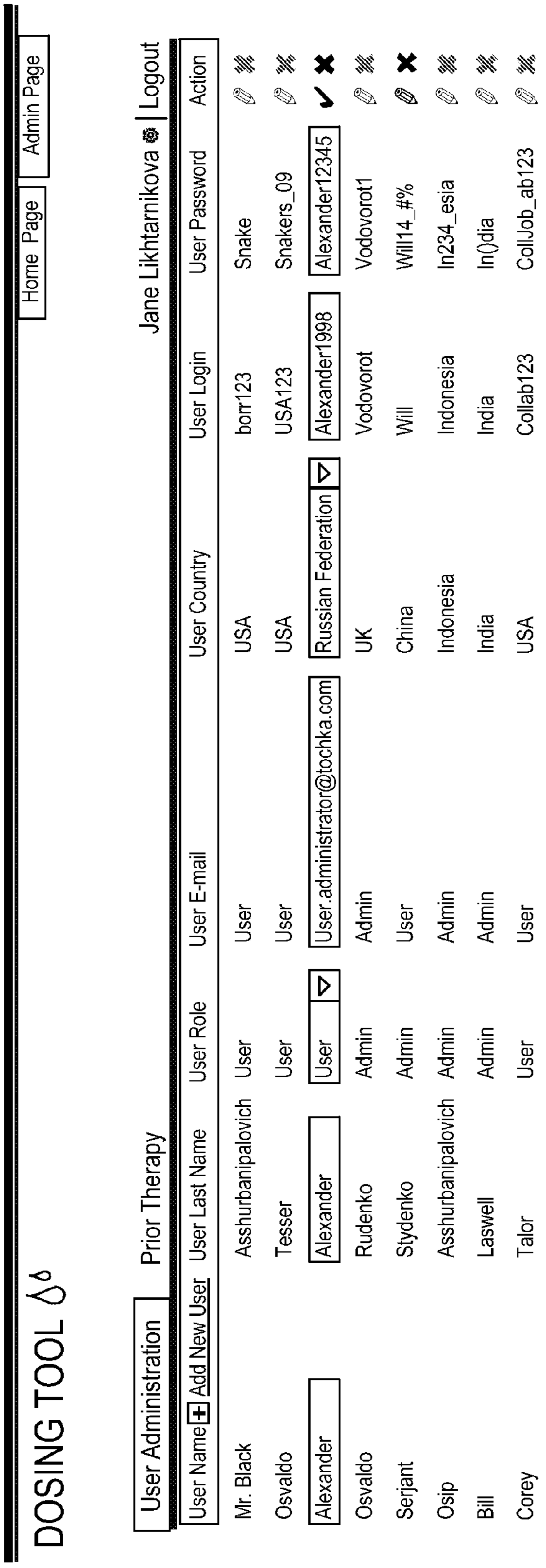

FIG. 47A

DOSING TOOL

User Administration | Prior Therapy | Home Page | Administration

Jane Likhtarnikova | Logout

F VIII

| Drug | Residial Decay | Action |
|---|---|---|
| Recombinant Factor 9 | 0.0016 | ✏ ✖ |
| Recombinant Factor 9 | 0.2014 | ✏ ✖ |
| Recombinant Factor 9 ▽ | | ✓ ✖ |
| | | |
| | | |

➕ Add New

F IX

| Drug | Residial Decay | Action |
|---|---|---|
| Recombinant Factor 9 | 0.0016 | ✏ ✖ |
| Recombinant Factor 9 | 0.2014 | ✏ ✖ |

➕ Add New

SEQUENCE LISTING

<160> NUMBER OF SEQ ID NOS: 21

<210> SEQ ID NO 1
<211> LENGTH: 7583
<212> TYPE: DNA
<213> ORGANISM: Artificial Sequence
<220> FEATURE:
<223> OTHER INFORMATION: pSYN-FIX-030

<400> SEQUENCE: 1
gcgcgcgttg acattgatta ttgactagtt attaatagta atcaattacg gggtcattag 60
ttcatagccc atatatggag ttccgcgtta cataacttac ggtaaatggc ccgcctggct 120
gaccgcccaa cgacccccgc ccattgacgt caataatgac gtatgttccc atagtaacgc 180
caatagggac tttccattga cgtcaatggg tggagtattt acggtaaact gcccacttgg 240
cagtacatca agtgtatcat atgccaagta cgccccctat tgacgtcaat gacggtaaat 300
ggcccgcctg gcattatgcc cagtacatga ccttatggga ctttcctact tggcagtaca 360
tctacgtatt agtcatcgct attaccatgg tgatgcggtt ttggcagtac atcaatgggc 420
gtggatagcg gtttgactca cggggatttc caagtctcca ccccattgac gtcaatggga 480
gtttgttttg gcaccaaaat caacgggact ttccaaaatg tcgtaacaac tccgccccat 540
tgacgcaaat gggcggtagg cgtgtacggt gggaggtcta tataagcaga gctctctggc 600
taactagaga acccactgct tactggctta tcgaaattaa tacgactcac tatagggaga 660
cccaagcttc gcgacgtacg gccgccacca tgcagcgcgt gaacatgatc atggcagaat 720
caccaggcct catcaccatc tgccttttag gatatctact cagtgctgaa tgtacaggtt 780
tgtttccttt tttaaaatac attgagtatg cttgcctttt agatatagaa atatctgatg 840

-continued

```
ctgtcttctt cactaaattt tgattacatg atttgacagc aatattgaag agtctaacag    900
ccagcacgca ggttggtaag tactgtggga acatcacaga ttttggctcc atgccctaaa    960
gagaaattgg ctttcagatt atttggatta aaaacaaaga ctttcttaag agatgtaaaa   1020
ttttcatgat gttttctttt ttgctaaaac taaagaatta ttcttttaca tttcagtttt   1080
tcttgatcat gaaaacgcca acaaaattct gaatcggcca aagaggtata attcaggtaa   1140
attggaagag tttgttcaag ggaatctaga gagagaatgt atggaagaaa agtgtagttt   1200
tgaagaagca cgagaagttt ttgaaaacac tgaaagaaca actgaatttt ggaagcagta   1260
tgttgatgga gatcagtgtg agtccaatcc atgtttaaat ggcggcagtt gcaaggatga   1320
cattaattcc tatgaatgtt ggtgtccctt tggatttgaa ggaaagaact gtgaattaga   1380
tgtaacatgt aacattaaga atggcagatg cgagcagttt tgtaaaaata gtgctgataa   1440
caaggtggtt tgctcctgta ctgagggata tcgacttgca gaaaaccaga agtcctgtga   1500
accagcagtg ccatttccat gtggaagagt ttctgtttca caaacttcta agctcacccg   1560
tgctgagact gtttttcctg atgtggacta tgtaaattct actgaagctg aaaccatttt   1620
ggataacatc actcaaagca cccaatcatt taatgacttc actcgggttg ttggtggaga   1680
agatgccaaa ccaggtcaat tcccttggca ggttgttttg aatggtaaag ttgatgcatt   1740
ctgtggaggc tctatcgtta atgaaaaatg gattgtaact gctgcccact gtgttgaaac   1800
tggtgttaaa attacagttg tcgcaggtga acataatatt gaggagacag aacatacaga   1860
gcaaaagcga aatgtgattc gaattattcc tcaccacaac tacaatgcag ctattaataa   1920
gtacaaccat gacattgccc ttctggaact ggacgaaccc ttagtgctaa acagctacgt   1980
tacacctatt tgcattgctg acaaggaata cacgaacatc ttcctcaaat ttggatctgg   2040
ctatgtaagt ggctggggaa gagtcttcca caaagggaga tcagctttag ttcttcagta   2100
ccttagagtt ccacttgttg accgagccac atgtcttcga tctacaaagt tcaccatcta   2160
taacaacatg ttctgtgctg gcttccatga aggaggtaga gattcatgtc aaggagatag   2220
tgggggaccc catgttactg aagtggaagg gaccagtttc ttaactggaa ttattagctg   2280
gggtgaagag tgtgcaatga aaggcaaata tggaatatat accaaggtgt cccggtatgt   2340
caactggatt aaggaaaaaa caaagctcac tgacaaaact cacacatgcc caccgtgccc   2400
agctccggaa ctcctgggcg gaccgtcagt cttcctcttc cccccaaaac ccaaggacac   2460
cctcatgatc tcccggaccc ctgaggtcac atgcgtggtg gtggacgtga gccacgaaga   2520
ccctgaggtc aagttcaact ggtacgtgga cggcgtggag gtgcataatg ccaagacaaa   2580
gccgcgggag gagcagtaca acagcacgta ccgtgtggtc agcgtcctca ccgtcctgca   2640
ccaggactgg ctgaatggca aggagtacaa gtgcaaggtc tccaacaaag ccctcccagc   2700
ccccatcgag aaaaccatct ccaaagccaa agggcagccc cgagaaccac aggtgtacac   2760
cctgccccca tcccgggatg agctgaccaa gaaccaggtc agcctgacct gcctggtcaa   2820
aggcttctat cccagcgaca tcgccgtgga gtgggagagc aatgggcagc cggagaacaa   2880
ctacaagacc acgcctcccg tgttggactc cgacggctcc ttcttcctct acagcaagct   2940
caccgtggac aagagcaggt ggcagcaggg gaacgtcttc tcatgctccg tgatgcatga   3000
ggctctgcac aaccactaca cgcagaagag cctctccctg tctccgggta aatgagaatt   3060
cagacatgat aagatacatt gatgagtttg gacaaaccac aactagaatg cagtgaaaaa   3120
aatgctttat ttgtgaaatt tgtgatgcta ttgctttatt tgtaaccatt ataagctgca   3180
ataaacaagt tggggtgggc gaagaactcc agcatgagat ccccgcgctg gaggatcatc   3240
```

-continued cagccggcgt cccggaaaac gattccgaag cccaaccttt catagaaggc ggcggtggaa 3300
tcgaaatctc gtagcacgtg tcagtcctgc tcctcggcca cgaagtgcac gcagttgccg 3360
gccgggtcgc gcagggcgaa ctcccgcccc cacggctgct cgccgatctc ggtcatggcc 3420
ggcccggagg cgtcccggaa gttcgtggac acgacctccg accactcggc gtacagctcg 3480
tccaggccgc gcacccacac ccaggccagg gtgttgtccg gcaccacctg gtcctggacc 3540
gcgctgatga acagggtcac gtcgtcccgg accacaccgg cgaagtcgtc ctccacgaag 3600
tcccgggaga acccgagccg gtcggtccag aactcgaccg ctccggcgac gtcgcgcgcg 3660
gtgagcaccg gaacggcact ggtcaacttg gccatggttt agttcctcac cttgtcgtat 3720
tatactatgc cgatatacta tgccgatgat taattgtcaa cacgtgctga tcagatccga 3780
aaatggatat acaagctccc gggagctttt tgcaaaagcc taggcctcca aaaaagcctc 3840
ctcactactt ctggaatagc tcagaggcag aggcggcctc ggcctctgca taaataaaaa 3900
aaattagtca gccatggggc ggagaatggg cggaactggg cggagttagg ggcgggatgg 3960
gcggagttag gggcgggact atggttgctg actaattgag atgcatgctt tgcatacttc 4020
tgcctgctgg ggagcctggg gactttccac acctggttgc tgactaattg agatgcatgc 4080
tttgcatact tctgcctgct ggggagcctg gggactttcc acaccctcgt cgagctagct 4140
tcgtgaggct ccggtgcccg tcagtgggca gagcgcacat cgcccacagt ccccgagaag 4200
ttggggggag gggtcggcaa ttgaaccggt gcctagagaa ggtggcgcgg ggtaaactgg 4260
gaaagtgatg tcgtgtactg gctccgcctt tttcccgagg gtgggggaga accgtatata 4320
agtgcagtag tcgccgtgaa cgttcttttt cgcaacgggt ttgccgccag aacacaggta 4380
agtgccgtgt gtggttcccg cgggcctggc ctctttacgg gttatggccc ttgcgtgcct 4440
tgaattactt ccacctggct ccagtacgtg attcttgatc ccgagctgga gccaggggcg 4500
ggccttgcgc tttaggagcc ccttcgcctc gtgcttgagt tgaggcctgg cctgggcgct 4560
ggggccgccg cgtgcgaatc tggtggcacc ttcgcgcctg tctcgctgct ttcgataagt 4620
ctctagccat ttaaaatttt tgatgacctg ctgcgacgct ttttttctgg caagatagtc 4680
ttgtaaatgc gggccaggat ctgcacactg gtatttcggt ttttggggcc gcgggcggcg 4740
acggggcccg tgcgtcccag cgcacatgtt cggcgaggcg gggcctgcga gcgcggccac 4800
cgagaatcgg acgggggtag tctcaagctg gccggcctgc tctggtgcct ggcctcgcgc 4860
cgccgtgtat cgccccgccc tgggcggcaa ggctggcccg gtcggcacca gttgcgtgag 4920
cggaaagatg gccgcttccc ggccctgctc cagggggctc aaaatggagg acgcggcgct 4980
cgggagagcg ggcgggtgag tcacccacac aaaggaaagg ggcctttccg tcctcagccg 5040
tcgcttcatg tgactccacg gagtaccggg cgccgtccag gcacctcgat tagttctgga 5100
gcttttggag tacgtcgtct ttaggttggg gggaggggtt ttatgcgatg gagtttcccc 5160
acactgagtg ggtggagact gaagttaggc cagcttggca cttgatgtaa ttctccttgg 5220
aatttgccct ttttgagttt ggatcttggt tcattctcaa gcctcagaca gtggttcaaa 5280
gtttttttct tccatttcag gtgtcgtgaa cacgtggtcg cggccgcgcc gccaccatgg 5340
agacagacac actcctgcta tgggtactgc tgctctgggt tccaggttcc actggtgaca 5400
aaactcacac atgcccaccg tgcccagcac ctgaactcct gggaggaccg tcagtcttcc 5460
tcttcccccc aaaacccaag gacaccctca tgatctcccg gacccctgag gtcacatgcg 5520
tggtggtgga cgtgagccac gaagaccctg aggtcaagtt caactggtac gtggacggcg 5580

-continued

```
tggaggtgca taatgccaag acaaagccgc gggaggagca gtacaacagc acgtaccgtg   5640
tggtcagcgt cctcaccgtc ctgcaccagg actggctgaa tggcaaggag tacaagtgca   5700
aggtctccaa caaagccctc ccagccccca tcgagaaaac catctccaaa gccaaagggc   5760
agccccgaga accacaggtg tacaccctgc ccccatcccg cgatgagctg accaagaacc   5820
aggtcagcct gacctgcctg gtcaaaggct tctatcccag cgacatcgcc gtggagtggg   5880
agagcaatgg gcagccggag aacaactaca agaccacgcc tcccgtgttg gactccgacg   5940
gctccttctt cctctacagc aagctcaccg tggacaagag caggtggcag caggggaacg   6000
tcttctcatg ctccgtgatg catgaggctc tgcacaacca ctacacgcag aagagcctct   6060
ccctgtctcc gggtaaatga ctcgagagat ctggccggct gggcccgttt cgaaggtaag   6120
cctatcccta accctctcct cggtctcgat tctacgcgta ccggtcatca tcaccatcac   6180
cattgagttt aaacccgctg atcagcctcg actgtgcctt ctagttgcca gccatctgtt   6240
gtttgcccct cccccgtgcc ttccttgacc ctggaaggtg ccactcccac tgtcctttcc   6300
taataaaatg aggaaattgc atcgcattgt ctgagtaggt gtcattctat tctggggggt   6360
ggggtggggc aggacagcaa gggggaggat tgggaagaca atagcaggca tgctggggat   6420
gcggtgggct ctatggcttc tgaggcggaa agaaccagtg gcggtaatac ggttatccac   6480
agaatcaggg gataacgcag gaaagaacat gtgagcaaaa ggccagcaaa aggccaggaa   6540
ccgtaaaaag gccgcgttgc tggcgttttt ccataggctc cgcccccctg acgagcatca   6600
caaaaatcga cgctcaagtc agaggtggcg aaacccgaca ggactataaa gataccaggc   6660
gtttccccct agaagctccc tcgtgcgctc tcctgttccg accctgccgc ttaccggata   6720
cctgtccgcc tttctccctt cgggaagcgt ggcgctttct catagctcac gctgtaggta   6780
tctcagttcg gtgtaggtcg ttcgctccaa gctgggctgt gtgcacgaac cccccgttca   6840
gcccgaccgc tgcgccttat ccggtaacta tcgtcttgag tccaacccgg taagacacga   6900
cttatcgcca ctggcagcag ccactggtaa caggattagc agagcgaggt atgtaggcgg   6960
tgctacagag ttcttgaagt ggtggcctaa ctacggctac actagaagaa cagtatttgg   7020
tatctgcgct ctgctgaagc cagttacctt cggaaaaaga gttggtagct cttgatccgg   7080
caaacaaacc accgctggta gcggtggttt ttttgtttgc aagcagcaga ttacgcgcag   7140
aaaaaaagga tctcaagaag atcctttgat cttttctacg gggtctgacg ctcagtggaa   7200
cgaaaactca cgttaaggga ttttggtcat gacattaacc tataaaaata ggcgtatcac   7260
gaggcccttt cgtctcgcgc gtttcggtga tgacggtgaa aacctctgac acatgcagct   7320
cccggagacg gtcacagctt gtctgtaagc ggatgccggg agcagacaag cccgtcaggg   7380
cgcgtcagcg ggtgttggcg ggtgtcgggg ctggcttaac tatgcggcat cagagcagat   7440
tgtactgaga gtgcaccata tatgcggtgt gaaataccgc acagatgcgt aaggagaaaa   7500
taccgcatca ggcgccattc gccattcagg ctgcgcaact gttgggaagg gcgatcggtg   7560
cgggcctctt cgctattacg cca                                           7583

<210> SEQ ID NO 2
<211> LENGTH: 688
<212> TYPE: PRT
<213> ORGANISM: Artificial Sequence
<220> FEATURE:
<223> OTHER INFORMATION: pSYN-FIX-030
<220> FEATURE:
<221> NAME/KEY: SIGNAL
<222> LOCATION: (-46)..(-19)
      220>
```

```
<221> NAME/KEY: SIGNAL
<222> LOCATION: (-18)..(-1)
<220> FEATURE:
<221> NAME/KEY: mat_peptide
<222> LOCATION: (1)..(642)

<400> SEQUENCE: 2

Met Gln Arg Val Asn Met Ile Met Ala Glu Ser Pro Gly Leu Ile Thr
    -45                 -40                 -35
Ile Cys Leu Leu Gly Tyr Leu Leu Ser Ala Glu Cys Thr Val Phe Leu
-30                 -25                 -20                 -15

Asp His Glu Asn Ala Asn Lys Ile Leu Asn Arg Pro Lys Arg Tyr Asn
                -10                 -5                  -1  1

Ser Gly Lys Leu Glu Glu Phe Val Gln Gly Asn Leu Glu Arg Glu Cys
        5                   10                  15

Met Glu Glu Lys Cys Ser Phe Glu Glu Ala Arg Glu Val Phe Glu Asn
    20                  25                  30

Thr Glu Arg Thr Thr Glu Phe Trp Lys Gln Tyr Val Asp Gly Asp Gln
35                  40                  45                  50

Cys Glu Ser Asn Pro Cys Leu Asn Gly Gly Ser Cys Lys Asp Asp Ile
                55                  60                  65

Asn Ser Tyr Glu Cys Trp Cys Pro Phe Gly Phe Glu Gly Lys Asn Cys
            70                  75                  80

Glu Leu Asp Val Thr Cys Asn Ile Lys Asn Gly Arg Cys Glu Gln Phe
        85                  90                  95

Cys Lys Asn Ser Ala Asp Asn Lys Val Val Cys Ser Cys Thr Glu Gly
    100                 105                 110

Tyr Arg Leu Ala Glu Asn Gln Lys Ser Cys Glu Pro Ala Val Pro Phe
115                 120                 125                 130

Pro Cys Gly Arg Val Ser Val Ser Gln Thr Ser Lys Leu Thr Arg Ala
                135                 140                 145

Glu Thr Val Phe Pro Asp Val Asp Tyr Val Asn Ser Thr Glu Ala Glu
            150                 155                 160

Thr Ile Leu Asp Asn Ile Thr Gln Ser Thr Gln Ser Phe Asn Asp Phe
        165                 170                 175

Thr Arg Val Val Gly Gly Glu Asp Ala Lys Pro Gly Gln Phe Pro Trp
    180                 185                 190

Gln Val Val Leu Asn Gly Lys Val Asp Ala Phe Cys Gly Gly Ser Ile
195                 200                 205                 210

Val Asn Glu Lys Trp Ile Val Thr Ala Ala His Cys Val Glu Thr Gly
                215                 220                 225

Val Lys Ile Thr Val Val Ala Gly Glu His Asn Ile Glu Glu Thr Glu
            230                 235                 240

His Thr Glu Gln Lys Arg Asn Val Ile Arg Ile Ile Pro His His Asn
        245                 250                 255

Tyr Asn Ala Ala Ile Asn Lys Tyr Asn His Asp Ile Ala Leu Leu Glu
    260                 265                 270

Leu Asp Glu Pro Leu Val Leu Asn Ser Tyr Val Thr Pro Ile Cys Ile
275                 280                 285                 290

Ala Asp Lys Glu Tyr Thr Asn Ile Phe Leu Lys Phe Gly Ser Gly Tyr
                295                 300                 305

Val Ser Gly Trp Gly Arg Val Phe His Lys Gly Arg Ser Ala Leu Val
            310                 315                 320

Leu Gln Tyr Leu Arg Val Pro Leu Val Asp Arg Ala Thr Cys Leu Arg
        325                 330                 335
```

-continued

```
Ser Thr Lys Phe Thr Ile Tyr Asn Asn Met Phe Cys Ala Gly Phe His
    340                 345                 350

Glu Gly Gly Arg Asp Ser Cys Gln Gly Asp Ser Gly Gly Pro His Val
355                 360                 365                 370

Thr Glu Val Glu Gly Thr Ser Phe Leu Thr Gly Ile Ile Ser Trp Gly
                375                 380                 385

Glu Glu Cys Ala Met Lys Gly Lys Tyr Gly Ile Tyr Thr Lys Val Ser
            390                 395                 400

Arg Tyr Val Asn Trp Ile Lys Glu Lys Thr Lys Leu Thr Asp Lys Thr
        405                 410                 415

His Thr Cys Pro Pro Cys Pro Ala Pro Glu Leu Leu Gly Gly Pro Ser
    420                 425                 430

Val Phe Leu Phe Pro Pro Lys Pro Lys Asp Thr Leu Met Ile Ser Arg
435                 440                 445                 450

Thr Pro Glu Val Thr Cys Val Val Val Asp Val Ser His Glu Asp Pro
                455                 460                 465

Glu Val Lys Phe Asn Trp Tyr Val Asp Gly Val Glu Val His Asn Ala
            470                 475                 480

Lys Thr Lys Pro Arg Glu Glu Gln Tyr Asn Ser Thr Tyr Arg Val Val
        485                 490                 495

Ser Val Leu Thr Val Leu His Gln Asp Trp Leu Asn Gly Lys Glu Tyr
    500                 505                 510

Lys Cys Lys Val Ser Asn Lys Ala Leu Pro Ala Pro Ile Glu Lys Thr
515                 520                 525                 530

Ile Ser Lys Ala Lys Gly Gln Pro Arg Glu Pro Gln Val Tyr Thr Leu
                535                 540                 545

Pro Pro Ser Arg Asp Glu Leu Thr Lys Asn Gln Val Ser Leu Thr Cys
            550                 555                 560

Leu Val Lys Gly Phe Tyr Pro Ser Asp Ile Ala Val Glu Trp Glu Ser
        565                 570                 575

Asn Gly Gln Pro Glu Asn Asn Tyr Lys Thr Thr Pro Pro Val Leu Asp
    580                 585                 590

Ser Asp Gly Ser Phe Phe Leu Tyr Ser Lys Leu Thr Val Asp Lys Ser
595                 600                 605                 610

Arg Trp Gln Gln Gly Asn Val Phe Ser Cys Ser Val Met His Glu Ala
                615                 620                 625

Leu His Asn His Tyr Thr Gln Lys Ser Leu Ser Leu Ser Pro Gly Lys
            630                 635                 640


<210> SEQ ID NO 3
<211> LENGTH: 741
<212> TYPE: DNA
<213> ORGANISM: Artificial Sequence
<220> FEATURE:
<223> OTHER INFORMATION: Fc cassette from pSYN-FIX-030

<400> SEQUENCE: 3

atggagacag acacactcct gctatgggta ctgctgctct gggttccagg ttccactggt      60

gacaaaactc acacatgccc accgtgccca gcacctgaac tcctgggagg accgtcagtc     120

ttcctcttcc ccccaaaacc caaggacacc ctcatgatct cccggacccc tgaggtcaca     180

tgcgtggtgg tggacgtgag ccacgaagac cctgaggtca agttcaactg gtacgtggac     240

ggcgtggagg tgcataatgc caagacaaag ccgcgggagg agcagtacaa cagcacgtac     300

cgtgtggtca gcgtcctcac cgtcctgcac caggactggc tgaatggcaa ggagtacaag     360
```

```
tgcaaggtct ccaacaaagc cctcccagcc cccatcgaga aaaccatctc caaagccaaa    420

gggcagcccc gagaaccaca ggtgtacacc ctgcccccat cccgcgatga gctgaccaag    480

aaccaggtca gcctgacctg cctggtcaaa ggcttctatc ccagcgacat cgccgtggag    540

tgggagagca atgggcagcc ggagaacaac tacaagacca cgcctcccgt gttggactcc    600

gacggctcct tcttcctcta cagcaagctc accgtggaca agagcaggtg gcagcagggg    660

aacgtcttct catgctccgt gatgcatgag gctctgcaca accactacac gcagaagagc    720

ctctccctgt ctccgggtaa a                                              741
```

```
<210> SEQ ID NO 4
<211> LENGTH: 247
<212> TYPE: PRT
<213> ORGANISM: Artificial Sequence
<220> FEATURE:
<223> OTHER INFORMATION: Fc cassette from pSYN-FIX-030
<220> FEATURE:
<221> NAME/KEY: SIGNAL
<222> LOCATION: (-20)..(-1)
<220> FEATURE:
<221> NAME/KEY: mat_peptide
<222> LOCATION: (1)..(227)

<400> SEQUENCE: 4

Met Glu Thr Asp Thr Leu Leu Leu Trp Val Leu Leu Leu Trp Val Pro
-20                 -15                 -10                 -5
Gly Ser Thr Gly Asp Lys Thr His Thr Cys Pro Pro Cys Pro Ala Pro
            -1  1               5                   10

Glu Leu Leu Gly Gly Pro Ser Val Phe Leu Phe Pro Pro Lys Pro Lys
        15                  20                  25

Asp Thr Leu Met Ile Ser Arg Thr Pro Glu Val Thr Cys Val Val Val
    30                  35                  40

Asp Val Ser His Glu Asp Pro Glu Val Lys Phe Asn Trp Tyr Val Asp
45                  50                  55                  60

Gly Val Glu Val His Asn Ala Lys Thr Lys Pro Arg Glu Glu Gln Tyr
                65                  70                  75

Asn Ser Thr Tyr Arg Val Val Ser Val Leu Thr Val Leu His Gln Asp
            80                  85                  90

Trp Leu Asn Gly Lys Glu Tyr Lys Cys Lys Val Ser Asn Lys Ala Leu
        95                  100                 105

Pro Ala Pro Ile Glu Lys Thr Ile Ser Lys Ala Lys Gly Gln Pro Arg
    110                 115                 120

Glu Pro Gln Val Tyr Thr Leu Pro Pro Ser Arg Asp Glu Leu Thr Lys
125                 130                 135                 140

Asn Gln Val Ser Leu Thr Cys Leu Val Lys Gly Phe Tyr Pro Ser Asp
                145                 150                 155

Ile Ala Val Glu Trp Glu Ser Asn Gly Gln Pro Glu Asn Asn Tyr Lys
            160                 165                 170

Thr Thr Pro Pro Val Leu Asp Ser Asp Gly Ser Phe Phe Leu Tyr Ser
        175                 180                 185

Lys Leu Thr Val Asp Lys Ser Arg Trp Gln Gln Gly Asn Val Phe Ser
    190                 195                 200

Cys Ser Val Met His Glu Ala Leu His Asn His Tyr Thr Gln Lys Ser
205                 210                 215                 220

Leu Ser Leu Ser Pro Gly Lys
                225


<210> SEQ ID NO 5
```

<211> LENGTH: 5052
<212> TYPE: DNA
<213> ORGANISM: Artificial Sequence
<220> FEATURE:
<223> OTHER INFORMATION: B-Domain Deleted FVIIIFc

<400> SEQUENCE: 5
atgcaaatag agctctccac ctgcttcttt ctgtgccttt tgcgattctg ctttagtgcc 60
accagaagat actacctggg tgcagtggaa ctgtcatggg actatatgca aagtgatctc 120
ggtgagctgc ctgtggacgc aagatttcct cctagagtgc caaaatcttt tccattcaac 180
acctcagtcg tgtacaaaaa gactctgttt gtagaattca cggatcacct tttcaacatc 240
gctaagccaa ggccaccctg gatgggtctg ctaggtccta ccatccaggc tgaggtttat 300
gatacagtgg tcattacact taagaacatg gcttcccatc ctgtcagtct tcatgctgtt 360
ggtgtatcct actggaaagc ttctgaggga gctgaatatg atgatcagac cagtcaaagg 420
gagaaagaag atgataaagt cttccctggt ggaagccata catatgtctg gcaggtcctg 480
aaagagaatg gtccaatggc ctctgaccca ctgtgcctta cctactcata tctttctcat 540
gtggacctgg taaaagactt gaattcaggc ctcattggag ccctactagt atgtagagaa 600
gggagtctgg ccaaggaaaa gacacagacc ttgcacaaat ttatactact tttgctgta 660 tttgatgaag ggaaaagttg gcactcagaa acaaagaact ccttgatgca ggatagggat 720
gctgcatctg ctcgggcctg gcctaaaatg cacacagtca atggttatgt aaacaggtct 780
ctgccaggtc tgattggatg ccacaggaaa tcagtctatt ggcatgtgat tggaatgggc 840
accactcctg aagtgcactc aatattcctc gaaggtcaca catttcttgt gaggaaccat 900
cgccaggcgt ccttggaaat ctcgccaata actttcctta ctgctcaaac actcttgatg 960
gaccttggac agtttctact gttttgtcat atctcttccc accaacatga tggcatggaa 1020
gcttatgtca aagtagacag ctgtccagag gaaccccaac tacgaatgaa aaataatgaa 1080
gaagcggaag actatgatga tgatcttact gattctgaaa tggatgtggt caggtttgat 1140
gatgacaact ctccttcctt tatccaaatt cgctcagttg ccaagaagca tcctaaaact 1200
tgggtacatt acattgctgc tgaagaggag gactgggact atgctccctt agtcctcgcc 1260
cccgatgaca gaagttataa aagtcaatat ttgaacaatg gccctcagcg gattggtagg 1320
aagtacaaaa aagtccgatt tatggcatac acagatgaaa cctttaagac tcgtgaagct 1380
attcagcatg aatcaggaat cttgggacct ttactttatg gggaagttgg agacacactg 1440
ttgattatat ttaagaatca agcaagcaga ccatataaca tctaccctca cggaatcact 1500
gatgtccgtc ctttgtattc aaggagatta ccaaaaggtg taaaacattt gaaggatttt 1560
ccaattctgc caggagaaat attcaaatat aaatggacag tgactgtaga agatgggcca 1620
actaaatcag atcctcggtg cctgacccgc tattactcta gtttcgttaa tatggagaga 1680
gatctagctt caggactcat tggccctctc ctcatctgct acaaagaatc tgtagatcaa 1740
agaggaaacc agataatgtc agacaagagg aatgtcatcc tgttttctgt atttgatgag 1800
aaccgaagct ggtacctcac agagaatata caacgctttc tccccaatcc agctggagtg 1860
cagcttgagg atccagagtt ccaagcctcc aacatcatgc acagcatcaa tggctatgtt 1920
tttgatagtt tgcagttgtc agtttgtttg catgaggtgg catactggta cattctaagc 1980
attggagcac agactgactt cctttctgtc ttcttctctg gatatacctt caaacacaaa 2040
atggtctatg aagacacact caccctattc ccattctcag gagaaactgt cttcatgtcg 2100
atggaaaacc caggtctatg gattctgggg tgccacaact cagactttcg gaacagaggc 2160

```
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc catcaacggg aaataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata tataagagca gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga gacaagtgac agtacaggaa   3000
tttgctctgt tttcaccat ctttgatgag accaaaagct ggtacttcac tgaaaatatg   3060
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac actttttctg   3420
gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagccctttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata tttttaaccc tccaattatt gctcgataca tccgtttgca cccaactcat   3840
tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga aagtcacagg agtaactact cagggagtaa aatctctgct taccagcatg   4140
tatgtgaagg agttcctcat ctccagcagt caagatggcc atcagtggac tctctttttt   4200
cagaatggca aagtaaaggt tttcaggga aatcaagact ccttcacacc tgtggtgaac   4260
tctctagacc caccgttact gactcgctac cttcgaattc acccccagag ttgggtgcac   4320
cagattgccc tgaggatgga ggttctgggc tgcgaggcac aggacctcta cgacaaaact   4380
cacacatgcc caccgtgccc agctccagaa ctcctgggcg gaccgtcagt cttcctcttc   4440
cccccaaaac ccaaggacac cctcatgatc tcccggaccc ctgaggtcac atgcgtggtg   4500
```

```
gtggacgtga gccacgaaga ccctgaggtc aagttcaact ggtacgtgga cggcgtggag    4560

gtgcataatg ccaagacaaa gccgcgggag gagcagtaca acagcacgta ccgtgtggtc    4620

agcgtcctca ccgtcctgca ccaggactgg ctgaatggca aggagtacaa gtgcaaggtc    4680

tccaacaaag ccctcccagc ccccatcgag aaaaccatct ccaaagccaa agggcagccc    4740

cgagaaccac aggtgtacac cctgccccca tcccgggatg agctgaccaa gaaccaggtc    4800

agcctgacct gcctggtcaa aggcttctat cccagcgaca tcgccgtgga gtgggagagc    4860

aatgggcagc cggagaacaa ctacaagacc acgcctcccg tgttggactc cgacggctcc    4920

ttcttcctct acagcaagct caccgtggac aagagcaggt ggcagcaggg gaacgtcttc    4980

tcatgctccg tgatgcatga ggctctgcac aaccactaca cgcagaagag cctctccctg    5040

tctccgggta aa                                                        5052
```

<210> SEQ ID NO 6
<211> LENGTH: 1684
<212> TYPE: PRT
<213> ORGANISM: Artificial Sequence
<220> FEATURE:
<223> OTHER INFORMATION: B-Domain Deleted FVIIIFc
<220> FEATURE:
<221> NAME/KEY: SIGNAL
<222> LOCATION: (-19)..(-1)
<220> FEATURE:
<221> NAME/KEY: mat_peptide
<222> LOCATION: (1)..(1665)

<400> SEQUENCE: 6

```
Met Gln Ile Glu Leu Ser Thr Cys Phe Phe Leu Cys Leu Leu Arg Phe
            -15                 -10                  -5
Cys Phe Ser Ala Thr Arg Arg Tyr Tyr Leu Gly Ala Val Glu Leu Ser
 -1   1               5                  10

Trp Asp Tyr Met Gln Ser Asp Leu Gly Glu Leu Pro Val Asp Ala Arg
         15                  20                  25

Phe Pro Pro Arg Val Pro Lys Ser Phe Pro Phe Asn Thr Ser Val Val
 30                  35                  40                  45

Tyr Lys Lys Thr Leu Phe Val Glu Phe Thr Asp His Leu Phe Asn Ile
                 50                  55                  60

Ala Lys Pro Arg Pro Pro Trp Met Gly Leu Leu Gly Pro Thr Ile Gln
                 65                  70                  75

Ala Glu Val Tyr Asp Thr Val Val Ile Thr Leu Lys Asn Met Ala Ser
                 80                  85                  90

His Pro Val Ser Leu His Ala Val Gly Val Ser Tyr Trp Lys Ala Ser
                 95                 100                 105

Glu Gly Ala Glu Tyr Asp Asp Gln Thr Ser Gln Arg Glu Lys Glu Asp
110                 115                 120                 125

Asp Lys Val Phe Pro Gly Gly Ser His Thr Tyr Val Trp Gln Val Leu
                130                 135                 140

Lys Glu Asn Gly Pro Met Ala Ser Asp Pro Leu Cys Leu Thr Tyr Ser
                145                 150                 155

Tyr Leu Ser His Val Asp Leu Val Lys Asp Leu Asn Ser Gly Leu Ile
                160                 165                 170

Gly Ala Leu Leu Val Cys Arg Glu Gly Ser Leu Ala Lys Glu Lys Thr
                175                 180                 185

Gln Thr Leu His Lys Phe Ile Leu Leu Phe Ala Val Phe Asp Glu Gly
190                 195                 200                 205

Lys Ser Trp His Ser Glu Thr Lys Asn Ser Leu Met Gln Asp Arg Asp
                210                 215                 220
```

```
Ala Ala Ser Ala Arg Ala Trp Pro Lys Met His Thr Val Asn Gly Tyr
            225                 230                 235

Val Asn Arg Ser Leu Pro Gly Leu Ile Gly Cys His Arg Lys Ser Val
        240                 245                 250

Tyr Trp His Val Ile Gly Met Gly Thr Thr Pro Glu Val His Ser Ile
    255                 260                 265

Phe Leu Glu Gly His Thr Phe Leu Val Arg Asn His Arg Gln Ala Ser
270                 275                 280                 285

Leu Glu Ile Ser Pro Ile Thr Phe Leu Thr Ala Gln Thr Leu Leu Met
                290                 295                 300

Asp Leu Gly Gln Phe Leu Leu Phe Cys His Ile Ser Ser His Gln His
            305                 310                 315

Asp Gly Met Glu Ala Tyr Val Lys Val Asp Ser Cys Pro Glu Glu Pro
        320                 325                 330

Gln Leu Arg Met Lys Asn Asn Glu Glu Ala Glu Asp Tyr Asp Asp Asp
    335                 340                 345

Leu Thr Asp Ser Glu Met Asp Val Val Arg Phe Asp Asp Asp Asn Ser
350                 355                 360                 365

Pro Ser Phe Ile Gln Ile Arg Ser Val Ala Lys Lys His Pro Lys Thr
                370                 375                 380

Trp Val His Tyr Ile Ala Ala Glu Glu Glu Asp Trp Asp Tyr Ala Pro
            385                 390                 395

Leu Val Leu Ala Pro Asp Asp Arg Ser Tyr Lys Ser Gln Tyr Leu Asn
        400                 405                 410

Asn Gly Pro Gln Arg Ile Gly Arg Lys Tyr Lys Lys Val Arg Phe Met
    415                 420                 425

Ala Tyr Thr Asp Glu Thr Phe Lys Thr Arg Glu Ala Ile Gln His Glu
430                 435                 440                 445

Ser Gly Ile Leu Gly Pro Leu Leu Tyr Gly Glu Val Gly Asp Thr Leu
                450                 455                 460

Leu Ile Ile Phe Lys Asn Gln Ala Ser Arg Pro Tyr Asn Ile Tyr Pro
            465                 470                 475

His Gly Ile Thr Asp Val Arg Pro Leu Tyr Ser Arg Arg Leu Pro Lys
        480                 485                 490

Gly Val Lys His Leu Lys Asp Phe Pro Ile Leu Pro Gly Glu Ile Phe
    495                 500                 505

Lys Tyr Lys Trp Thr Val Thr Val Glu Asp Gly Pro Thr Lys Ser Asp
510                 515                 520                 525

Pro Arg Cys Leu Thr Arg Tyr Tyr Ser Ser Phe Val Asn Met Glu Arg
                530                 535                 540

Asp Leu Ala Ser Gly Leu Ile Gly Pro Leu Leu Ile Cys Tyr Lys Glu
            545                 550                 555

Ser Val Asp Gln Arg Gly Asn Gln Ile Met Ser Asp Lys Arg Asn Val
        560                 565                 570

Ile Leu Phe Ser Val Phe Asp Glu Asn Arg Ser Trp Tyr Leu Thr Glu
    575                 580                 585

Asn Ile Gln Arg Phe Leu Pro Asn Pro Ala Gly Val Gln Leu Glu Asp
590                 595                 600                 605

Pro Glu Phe Gln Ala Ser Asn Ile Met His Ser Ile Asn Gly Tyr Val
                610                 615                 620

Phe Asp Ser Leu Gln Leu Ser Val Cys Leu His Glu Val Ala Tyr Trp
            625                 630                 635
```

```
Tyr Ile Leu Ser Ile Gly Ala Gln Thr Asp Phe Leu Ser Val Phe Phe
        640                 645                 650

Ser Gly Tyr Thr Phe Lys His Lys Met Val Tyr Glu Asp Thr Leu Thr
    655                 660                 665

Leu Phe Pro Phe Ser Gly Glu Thr Val Phe Met Ser Met Glu Asn Pro
670                 675                 680                 685

Gly Leu Trp Ile Leu Gly Cys His Asn Ser Asp Phe Arg Asn Arg Gly
                690                 695                 700

Met Thr Ala Leu Leu Lys Val Ser Ser Cys Asp Lys Asn Thr Gly Asp
            705                 710                 715

Tyr Tyr Glu Asp Ser Tyr Glu Asp Ile Ser Ala Tyr Leu Leu Ser Lys
        720                 725                 730

Asn Asn Ala Ile Glu Pro Arg Ser Phe Ser Gln Asn Pro Pro Val Leu
    735                 740                 745

Lys Arg His Gln Arg Glu Ile Thr Arg Thr Thr Leu Gln Ser Asp Gln
750                 755                 760                 765

Glu Glu Ile Asp Tyr Asp Asp Thr Ile Ser Val Glu Met Lys Lys Glu
                770                 775                 780

Asp Phe Asp Ile Tyr Asp Glu Asp Glu Asn Gln Ser Pro Arg Ser Phe
            785                 790                 795

Gln Lys Lys Thr Arg His Tyr Phe Ile Ala Ala Val Glu Arg Leu Trp
        800                 805                 810

Asp Tyr Gly Met Ser Ser Ser Pro His Val Leu Arg Asn Arg Ala Gln
    815                 820                 825

Ser Gly Ser Val Pro Gln Phe Lys Lys Val Val Phe Gln Glu Phe Thr
830                 835                 840                 845

Asp Gly Ser Phe Thr Gln Pro Leu Tyr Arg Gly Glu Leu Asn Glu His
                850                 855                 860

Leu Gly Leu Leu Gly Pro Tyr Ile Arg Ala Glu Val Glu Asp Asn Ile
            865                 870                 875

Met Val Thr Phe Arg Asn Gln Ala Ser Arg Pro Tyr Ser Phe Tyr Ser
        880                 885                 890

Ser Leu Ile Ser Tyr Glu Glu Asp Gln Arg Gln Gly Ala Glu Pro Arg
    895                 900                 905

Lys Asn Phe Val Lys Pro Asn Glu Thr Lys Thr Tyr Phe Trp Lys Val
910                 915                 920                 925

Gln His His Met Ala Pro Thr Lys Asp Glu Phe Asp Cys Lys Ala Trp
                930                 935                 940

Ala Tyr Phe Ser Asp Val Asp Leu Glu Lys Asp Val His Ser Gly Leu
            945                 950                 955

Ile Gly Pro Leu Leu Val Cys His Thr Asn Thr Leu Asn Pro Ala His
        960                 965                 970

Gly Arg Gln Val Thr Val Gln Glu Phe Ala Leu Phe Phe Thr Ile Phe
    975                 980                 985

Asp Glu Thr Lys Ser Trp Tyr Phe Thr Glu Asn  Met Glu Arg Asn Cys
990                 995                 1000                1005

Arg Ala Pro Cys Asn  Ile Gln Met Glu Asp  Pro Thr Phe Lys Glu
                1010                1015                1020

Asn Tyr Arg Phe His  Ala Ile Asn Gly Tyr  Ile Met Asp Thr Leu
                1025                1030                1035

Pro Gly Leu Val Met  Ala Gln Asp Gln Arg  Ile Arg Trp Tyr Leu
                1040                1045                1050

Leu Ser Met Gly Ser  Asn Glu Asn Ile His  Ser Ile His Phe Ser
```

```
                1055                1060                1065

Gly His Val Phe Thr  Val Arg Lys Lys Glu  Glu Tyr Lys Met Ala
                1070                1075                1080

Leu Tyr Asn Leu Tyr  Pro Gly Val Phe Glu  Thr Val Glu Met Leu
                1085                1090                1095

Pro Ser Lys Ala Gly  Ile Trp Arg Val Glu  Cys Leu Ile Gly Glu
                1100                1105                1110

His Leu His Ala Gly  Met Ser Thr Leu Phe  Leu Val Tyr Ser Asn
                1115                1120                1125

Lys Cys Gln Thr Pro  Leu Gly Met Ala Ser  Gly His Ile Arg Asp
                1130                1135                1140

Phe Gln Ile Thr Ala  Ser Gly Gln Tyr Gly  Gln Trp Ala Pro Lys
                1145                1150                1155

Leu Ala Arg Leu His  Tyr Ser Gly Ser Ile  Asn Ala Trp Ser Thr
                1160                1165                1170

Lys Glu Pro Phe Ser  Trp Ile Lys Val Asp  Leu Leu Ala Pro Met
                1175                1180                1185

Ile Ile His Gly Ile  Lys Thr Gln Gly Ala  Arg Gln Lys Phe Ser
                1190                1195                1200

Ser Leu Tyr Ile Ser  Gln Phe Ile Ile Met  Tyr Ser Leu Asp Gly
                1205                1210                1215

Lys Lys Trp Gln Thr  Tyr Arg Gly Asn Ser  Thr Gly Thr Leu Met
                1220                1225                1230

Val Phe Phe Gly Asn  Val Asp Ser Ser Gly  Ile Lys His Asn Ile
                1235                1240                1245

Phe Asn Pro Pro Ile  Ile Ala Arg Tyr Ile  Arg Leu His Pro Thr
                1250                1255                1260

His Tyr Ser Ile Arg  Ser Thr Leu Arg Met  Glu Leu Met Gly Cys
                1265                1270                1275

Asp Leu Asn Ser Cys  Ser Met Pro Leu Gly  Met Glu Ser Lys Ala
                1280                1285                1290

Ile Ser Asp Ala Gln  Ile Thr Ala Ser Ser  Tyr Phe Thr Asn Met
                1295                1300                1305

Phe Ala Thr Trp Ser  Pro Ser Lys Ala Arg  Leu His Leu Gln Gly
                1310                1315                1320

Arg Ser Asn Ala Trp  Arg Pro Gln Val Asn  Asn Pro Lys Glu Trp
                1325                1330                1335

Leu Gln Val Asp Phe  Gln Lys Thr Met Lys  Val Thr Gly Val Thr
                1340                1345                1350

Thr Gln Gly Val Lys  Ser Leu Leu Thr Ser  Met Tyr Val Lys Glu
                1355                1360                1365

Phe Leu Ile Ser Ser  Ser Gln Asp Gly His  Gln Trp Thr Leu Phe
                1370                1375                1380

Phe Gln Asn Gly Lys  Val Lys Val Phe Gln  Gly Asn Gln Asp Ser
                1385                1390                1395

Phe Thr Pro Val Val  Asn Ser Leu Asp Pro  Pro Leu Leu Thr Arg
                1400                1405                1410

Tyr Leu Arg Ile His  Pro Gln Ser Trp Val  His Gln Ile Ala Leu
                1415                1420                1425

Arg Met Glu Val Leu  Gly Cys Glu Ala Gln  Asp Leu Tyr Asp Lys
                1430                1435                1440

Thr His Thr Cys Pro  Pro Cys Pro Ala Pro  Glu Leu Leu Gly Gly
                1445                1450                1455
```

-continued

```
Pro Ser Val Phe Leu  Phe Pro Pro Lys Pro  Lys Asp Thr Leu Met
                1460                 1465                 1470

Ile Ser Arg Thr Pro  Glu Val Thr Cys Val  Val Val Asp Val Ser
                1475                 1480                 1485

His Glu Asp Pro Glu  Val Lys Phe Asn Trp  Tyr Val Asp Gly Val
                1490                 1495                 1500

Glu Val His Asn Ala  Lys Thr Lys Pro Arg  Glu Glu Gln Tyr Asn
                1505                 1510                 1515

Ser Thr Tyr Arg Val  Val Ser Val Leu Thr  Val Leu His Gln Asp
                1520                 1525                 1530

Trp Leu Asn Gly Lys  Glu Tyr Lys Cys Lys  Val Ser Asn Lys Ala
                1535                 1540                 1545

Leu Pro Ala Pro Ile  Glu Lys Thr Ile Ser  Lys Ala Lys Gly Gln
                1550                 1555                 1560

Pro Arg Glu Pro Gln  Val Tyr Thr Leu Pro  Pro Ser Arg Asp Glu
                1565                 1570                 1575

Leu Thr Lys Asn Gln  Val Ser Leu Thr Cys  Leu Val Lys Gly Phe
                1580                 1585                 1590

Tyr Pro Ser Asp Ile  Ala Val Glu Trp Glu  Ser Asn Gly Gln Pro
                1595                 1600                 1605

Glu Asn Asn Tyr Lys  Thr Thr Pro Pro Val  Leu Asp Ser Asp Gly
                1610                 1615                 1620

Ser Phe Phe Leu Tyr  Ser Lys Leu Thr Val  Asp Lys Ser Arg Trp
                1625                 1630                 1635

Gln Gln Gly Asn Val  Phe Ser Cys Ser Val  Met His Glu Ala Leu
                1640                 1645                 1650

His Asn His Tyr Thr  Gln Lys Ser Leu Ser  Leu Ser Pro Gly Lys
                1655                 1660                 1665
```

<210> SEQ ID NO 7
<211> LENGTH: 741
<212> TYPE: DNA
<213> ORGANISM: Artificial Sequence
<220> FEATURE:
<223> OTHER INFORMATION: Fc Sequence

<400> SEQUENCE: 7

```
atggagacag acacactcct gctatgggta ctgctgctct gggttccagg ttccactggt     60

gacaaaactc acacatgccc accgtgccca gcacctgaac tcctgggagg accgtcagtc    120

ttcctcttcc ccccaaaacc caaggacacc ctcatgatct cccggacccc tgaggtcaca    180

tgcgtggtgg tggacgtgag ccacgaagac cctgaggtca agttcaactg gtacgtggac    240

ggcgtggagg tgcataatgc caagacaaag ccgcgggagg agcagtacaa cagcacgtac    300

cgtgtggtca gcgtcctcac cgtcctgcac caggactggc tgaatggcaa ggagtacaag    360

tgcaaggtct ccaacaaagc cctcccagcc cccatcgaga aaaccatctc caaagccaaa    420

gggcagcccc gagaaccaca ggtgtacacc ctgcccccat cccgcgatga gctgaccaag    480

aaccaggtca gcctgacctg cctggtcaaa ggcttctatc ccagcgacat cgccgtggag    540

tgggagagca atgggcagcc ggagaacaac tacaagacca cgcctcccgt gttggactcc    600

gacggctcct tcttcctcta cagcaagctc accgtggaca agagcaggtg gcagcagggg    660

aacgtcttct catgctccgt gatgcatgag gctctgcaca accactacac gcagaagagc    720

ctctccctgt ctccgggtaa a                                              741
```

<210> SEQ ID NO 8
<211> LENGTH: 247
<212> TYPE: PRT
<213> ORGANISM: Artificial Sequence
<220> FEATURE:
<223> OTHER INFORMATION: Fc chain
<220> FEATURE:
<221> NAME/KEY: SIGNAL
<222> LOCATION: (-20)..(-1)
<220> FEATURE:
<221> NAME/KEY: mat_peptide
<222> LOCATION: (-1)..(227)

<400> SEQUENCE: 8

```
Met Glu Thr Asp Thr Leu Leu Leu Trp Val Leu Leu Leu Trp Val Pro
-20                 -15                 -10                 -5
Gly Ser Thr Gly Asp Lys Thr His Thr Cys Pro Pro Cys Pro Ala Pro
            -1  1               5                   10

Glu Leu Leu Gly Gly Pro Ser Val Phe Leu Phe Pro Pro Lys Pro Lys
        15                  20                  25

Asp Thr Leu Met Ile Ser Arg Thr Pro Glu Val Thr Cys Val Val Val
    30                  35                  40

Asp Val Ser His Glu Asp Pro Glu Val Lys Phe Asn Trp Tyr Val Asp
45                  50                  55                  60

Gly Val Glu Val His Asn Ala Lys Thr Lys Pro Arg Glu Glu Gln Tyr
                65                  70                  75

Asn Ser Thr Tyr Arg Val Val Ser Val Leu Thr Val Leu His Gln Asp
            80                  85                  90

Trp Leu Asn Gly Lys Glu Tyr Lys Cys Lys Val Ser Asn Lys Ala Leu
        95                  100                 105

Pro Ala Pro Ile Glu Lys Thr Ile Ser Lys Ala Lys Gly Gln Pro Arg
    110                 115                 120

Glu Pro Gln Val Tyr Thr Leu Pro Pro Ser Arg Asp Glu Leu Thr Lys
125                 130                 135                 140

Asn Gln Val Ser Leu Thr Cys Leu Val Lys Gly Phe Tyr Pro Ser Asp
                145                 150                 155

Ile Ala Val Glu Trp Glu Ser Asn Gly Gln Pro Glu Asn Asn Tyr Lys
            160                 165                 170

Thr Thr Pro Pro Val Leu Asp Ser Asp Gly Ser Phe Phe Leu Tyr Ser
        175                 180                 185

Lys Leu Thr Val Asp Lys Ser Arg Trp Gln Gln Gly Asn Val Phe Ser
    190                 195                 200

Cys Ser Val Met His Glu Ala Leu His Asn His Tyr Thr Gln Lys Ser
205                 210                 215                 220

Leu Ser Leu Ser Pro Gly Lys
                225
```

<210> SEQ ID NO 9
<211> LENGTH: 7734
<212> TYPE: DNA
<213> ORGANISM: Artificial Sequence
<220> FEATURE:
<223> OTHER INFORMATION: Full Length FVIIIFc

<400> SEQUENCE: 9

```
atgcaaatag agctctccac ctgcttcttt ctgtgccttt tgcgattctg ctttagtgcc      60

accagaagat actacctggg tgcagtggaa ctgtcatggg actatatgca aagtgatctc     120

ggtgagctgc ctgtggacgc aagatttcct cctagagtgc caaaatcttt tccattcaac     180
```

```
acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg gcaggtcctg    480
aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggatagggat    720
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca aagtagacag ctgtccagag gaaccccaac tacgaatgaa aaataatgaa   1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctccctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc caggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctcccaga attcaagaca ccctagcact aggcaaaagc aatttaatgc caccacaatt   2340
ccagaaaatg acatagagaa gactgaccct tggtttgcac acagaacacc tatgcctaaa   2400
atacaaaatg tctcctctag tgatttgttg atgctcttgc gacagagtcc tactccacat   2460
gggctatcct tatctgatct ccaagaagcc aaatatgaga ctttttctga tgatccatca   2520
cctggagcaa tagacagtaa taacagcctg tctgaaatga cacacttcag gccacagctc   2580
```

-continued

```
catcacagtg gggacatggt atttacccct gagtcaggcc tccaattaag attaaatgag   2640
aaactgggga caactgcagc aacagagttg aagaaacttg atttcaaagt ttctagtaca   2700
tcaaataatc tgatttcaac aattccatca gacaatttgg cagcaggtac tgataataca   2760
agttccttag gacccccaag tatgccagtt cattatgata gtcaattaga taccactcta   2820
tttggcaaaa agtcatctcc ccttactgag tctggtggac ctctgagctt gagtgaagaa   2880
aataatgatt caaagttgtt agaatcaggt ttaatgaata gccaagaaag ttcatgggga   2940
aaaaatgtat cgtcaacaga gagtggtagg ttatttaaag ggaaaagagc tcatggacct   3000
gctttgttga ctaaagataa tgccttattc aaagttagca tctctttgtt aaagacaaac   3060
aaaacttcca ataattcagc aactaataga aagactcaca ttgatggccc atcattatta   3120
attgagaata gtccatcagt ctggcaaaat atattagaaa gtgacactga gtttaaaaaa   3180
gtgacacctt tgattcatga cagaatgctt atggacaaaa atgctacagc tttgaggcta   3240
aatcatatgt caaataaaac tacttcatca aaaaacatgg aaatggtcca acagaaaaaa   3300
gagggcccca ttccaccaga tgcacaaaat ccagatatgt cgttctttaa gatgctattc   3360
ttgccagaat cagcaaggtg gatacaaagg actcatggaa agaactctct gaactctggg   3420
caaggcccca gtccaaagca attagtatcc ttaggaccag aaaaatctgt ggaaggtcag   3480
aatttcttgt ctgagaaaaa caaagtggta gtaggaaagg gtgaatttac aaaggacgta   3540
ggactcaaag agatggtttt tccaagcagc agaaacctat ttcttactaa cttggataat   3600
ttacatgaaa ataatacaca caatcaagaa aaaaaaattc aggaagaaat agaaaagaag   3660
gaaacattaa tccaagagaa tgtagttttg cctcagatac atacagtgac tggcactaag   3720
aatttcatga agaacctttt cttactgagc actaggcaaa atgtagaagg ttcatatgac   3780
ggggcatatg ctccagtact tcaagatttt aggtcattaa atgattcaac aaatagaaca   3840
aagaaacaca cagctcattt ctcaaaaaaa ggggaggaag aaaacttgga aggcttggga   3900
aatcaaacca agcaaattgt agagaaatat gcatgcacca caaggatatc tcctaataca   3960
agccagcaga attttgtcac gcaacgtagt aagagagctt tgaaacaatt cagactccca   4020
ctagaagaaa cagaacttga aaaaaggata attgtggatg acacctcaac ccagtggtcc   4080
aaaaacatga aacatttgac ccCgagcacc ctcacacaga tagactacaa tgagaaggag   4140
aaaggggcca ttactcagtc tcccttatca gattgcctta cgaggagtca tagcatccct   4200
caagcaaata gatctccatt acccattgca aaggtatcat catttccatc tattagacct   4260
atatatctga ccagggtcct attccaagac aactcttctc atcttccagc agcatcttat   4320
agaaagaaag attctggggt ccaagaaagc agtcatttct tacaaggagc caaaaaaaat   4380
aacctttctt tagccattct aaccttggag atgactggtg atcaaagaga ggttggctcc   4440
ctggggacaa gtgccacaaa ttcagtcaca tacaagaaag ttgagaacac tgttctcccg   4500
aaaccagact tgcccaaaac atctggcaaa gttgaattgc ttccaaaagt tcacatttat   4560
cagaaggacc tattccctac ggaaactagc aatgggtctc ctggccatct ggatctcgtg   4620
gaagggagcc ttcttcaggg aacagaggga gcgattaagt ggaatgaagc aaacagacct   4680
ggaaaagttc cctttctgag agtagcaaca gaaagctctg caaagactcc ctccaagcta   4740
ttggatcctc ttgcttggga taaccactat ggtactcaga taccaaaaga agagtggaaa   4800
tcccaagaga agtcaccaga aaaaacagct tttaagaaaa aggataccat tttgtccctg   4860
aacgcttgtg aaagcaatca tgcaatagca gcaataaatg agggacaaaa taagcccgaa   4920
```

-continued

```
atagaagtca cctgggcaaa gcaaggtagg actgaaaggc tgtgctctca aaacccacca   4980
gtcttgaaac gccatcaacg ggaaataact cgtactactc ttcagtcaga tcaagaggaa   5040
attgactatg atgataccat atcagttgaa atgaagaagg aagattttga catttatgat   5100
gaggatgaaa atcagagccc ccgcagcttt caaaagaaaa cacgacacta ttttattgct   5160
gcagtggaga ggctctggga ttatgggatg agtagctccc cacatgttct aagaaacagg   5220
gctcagagtg gcagtgtccc tcagttcaag aaagttgttt tccaggaatt tactgatggc   5280
tcctttactc agcccttata ccgtggagaa ctaaatgaac atttgggact cctggggcca   5340
tatataagag cagaagttga agataatatc atggtaactt tcagaaatca ggcctctcgt   5400
ccctattcct tctattctag ccttatttct tatgaggaag atcagaggca aggagcagaa   5460
cctagaaaaa actttgtcaa gcctaatgaa accaaaactt acttttggaa agtgcaacat   5520
catatggcac ccactaaaga tgagtttgac tgcaaagcct gggcttattt ctctgatgtt   5580
gacctggaaa aagatgtgca ctcaggcctg attggacccc ttctggtctg ccacactaac   5640
acactgaacc ctgctcatgg gagacaagtg acagtacagg aatttgctct gtttttcacc   5700
atctttgatg agaccaaaag ctggtacttc actgaaaata tggaaagaaa ctgcagggct   5760
ccctgcaata tccagatgga agatcccact tttaaagaga attatcgctt ccatgcaatc   5820
aatggctaca taatggatac actacctggc ttagtaatgg ctcaggatca aaggattcga   5880
tggtatctgc tcagcatggg cagcaatgaa aacatccatt ctattcattt cagtggacat   5940
gtgttcactg tacgaaaaaa agaggagtat aaaatggcac tgtacaatct ctatccaggt   6000
gtttttgaga cagtggaaat gttaccatcc aaagctggaa tttggcgggt ggaatgcctt   6060
attggcgagc atctacatgc tgggatgagc acactttttc tggtgtacag caataagtgt   6120
cagactcccc tgggaatggc ttctggacac attagagatt ttcagattac agcttcagga   6180
caatatggac agtgggcccc aaagctggcc agacttcatt attccggatc aatcaatgcc   6240
tggagcacca aggagccctt ttcttggatc aaggtggatc tgttggcacc aatgattatt   6300
cacggcatca agacccaggg tgcccgtcag aagttctcca gcctctacat ctctcagttt   6360
atcatcatgt atagtcttga tgggaagaag tggcagactt atcgaggaaa ttccactgga   6420
accttaatgg tcttctttgg caatgtggat tcatctggga taaaacacaa tatttttaac   6480
cctccaatta ttgctcgata catccgtttg cacccaactc attatagcat tcgcagcact   6540
cttcgcatgg agttgatggg ctgtgattta aatagttgca gcatgccatt gggaatggag   6600
agtaaagcaa tatcagatgc acagattact gcttcatcct actttaccaa tatgtttgcc   6660
acctggtctc cttcaaaagc tcgacttcac ctccaaggga ggagtaatgc ctggagacct   6720
caggtgaata atccaaaaga gtggctgcaa gtggacttcc agaagacaat gaaagtcaca   6780
ggagtaacta ctcagggagt aaaatctctg cttaccagca tgtatgtgaa ggagttcctc   6840
atctccagca gtcaagatgg ccatcagtgg actctctttt ttcagaatgg caaagtaaag   6900
gtttttcagg gaaatcaaga ctccttcaca cctgtggtga actctctaga cccaccgtta   6960
ctgactcgct accttcgaat tcacccccag agttgggtgc accagattgc cctgaggatg   7020
gaggttctgg gctgcgaggc acaggacctc tacgacaaaa ctcacacatg cccaccgtgc   7080
ccagctccag aactcctggg cggaccgtca gtcttcctct tccccccaaa acccaaggac   7140
accctcatga tctcccggac ccctgaggtc acatgcgtgg tggtggacgt gagccacgaa   7200
gaccctgagg tcaagttcaa ctggtacgtg gacggcgtgg aggtgcataa tgccaagaca   7260
aagccgcggg aggagcagta caacagcacg taccgtgtgg tcagcgtcct caccgtcctg   7320
```

caccaggact ggctgaatgg caaggagtac aagtgcaagg tctccaacaa agccctccca 7380
gcccccatcg agaaaaccat ctccaaagcc aaagggcagc cccgagaacc acaggtgtac 7440
accctgcccc catcccggga tgagctgacc aagaaccagg tcagcctgac ctgcctggtc 7500
aaaggcttct atcccagcga catcgccgtg gagtgggaga gcaatgggca gccggagaac 7560
aactacaaga ccacgcctcc cgtgttggac tccgacggct ccttcttcct ctacagcaag 7620
ctcaccgtgg acaagagcag gtggcagcag gggaacgtct tctcatgctc cgtgatgcat 7680
gaggctctgc acaaccacta cacgcagaag agcctctccc tgtctccggg taaa 7734

<210> SEQ ID NO 10
<211> LENGTH: 2578
<212> TYPE: PRT
<213> ORGANISM: Artificial Sequence
<220> FEATURE:
<223> OTHER INFORMATION: Full Length FVIIIFc
<220> FEATURE:
<221> NAME/KEY: SIGNAL
<222> LOCATION: (-19)..(-1)
<220> FEATURE:
<221> NAME/KEY: mat_peptide
<222> LOCATION: (1)..(2559)

<400> SEQUENCE: 10

Met Gln Ile Glu Leu Ser Thr Cys Phe Phe Leu Cys Leu Leu Arg Phe
-15 -10 -5
Cys Phe Ser Ala Thr Arg Arg Tyr Tyr Leu Gly Ala Val Glu Leu Ser
-1 1 5 10

Trp Asp Tyr Met Gln Ser Asp Leu Gly Glu Leu Pro Val Asp Ala Arg
15 20 25

Phe Pro Pro Arg Val Pro Lys Ser Phe Pro Phe Asn Thr Ser Val Val
30 35 40 45

Tyr Lys Lys Thr Leu Phe Val Glu Phe Thr Asp His Leu Phe Asn Ile
50 55 60

Ala Lys Pro Arg Pro Pro Trp Met Gly Leu Leu Gly Pro Thr Ile Gln
65 70 75

Ala Glu Val Tyr Asp Thr Val Val Ile Thr Leu Lys Asn Met Ala Ser
80 85 90

His Pro Val Ser Leu His Ala Val Gly Val Ser Tyr Trp Lys Ala Ser
95 100 105

Glu Gly Ala Glu Tyr Asp Asp Gln Thr Ser Gln Arg Glu Lys Glu Asp
110 115 120 125

Asp Lys Val Phe Pro Gly Gly Ser His Thr Tyr Val Trp Gln Val Leu
130 135 140

Lys Glu Asn Gly Pro Met Ala Ser Asp Pro Leu Cys Leu Thr Tyr Ser
145 150 155

Tyr Leu Ser His Val Asp Leu Val Lys Asp Leu Asn Ser Gly Leu Ile
160 165 170

Gly Ala Leu Leu Val Cys Arg Glu Gly Ser Leu Ala Lys Glu Lys Thr
175 180 185

Gln Thr Leu His Lys Phe Ile Leu Leu Phe Ala Val Phe Asp Glu Gly
190 195 200 205

Lys Ser Trp His Ser Glu Thr Lys Asn Ser Leu Met Gln Asp Arg Asp
210 215 220

Ala Ala Ser Ala Arg Ala Trp Pro Lys Met His Thr Val Asn Gly Tyr
225 230 235

Val Asn Arg Ser Leu Pro Gly Leu Ile Gly Cys His Arg Lys Ser Val

-continued

```
        240                 245                 250

Tyr Trp His Val Ile Gly Met Gly Thr Thr Pro Glu Val His Ser Ile
    255                 260                 265

Phe Leu Glu Gly His Thr Phe Leu Val Arg Asn His Arg Gln Ala Ser
270                 275                 280                 285

Leu Glu Ile Ser Pro Ile Thr Phe Leu Thr Ala Gln Thr Leu Leu Met
                290                 295                 300

Asp Leu Gly Gln Phe Leu Leu Phe Cys His Ile Ser Ser His Gln His
            305                 310                 315

Asp Gly Met Glu Ala Tyr Val Lys Val Asp Ser Cys Pro Glu Glu Pro
        320                 325                 330

Gln Leu Arg Met Lys Asn Asn Glu Glu Ala Glu Asp Tyr Asp Asp Asp
    335                 340                 345

Leu Thr Asp Ser Glu Met Asp Val Val Arg Phe Asp Asp Asp Asn Ser
350                 355                 360                 365

Pro Ser Phe Ile Gln Ile Arg Ser Val Ala Lys Lys His Pro Lys Thr
                370                 375                 380

Trp Val His Tyr Ile Ala Ala Glu Glu Glu Asp Trp Asp Tyr Ala Pro
            385                 390                 395

Leu Val Leu Ala Pro Asp Asp Arg Ser Tyr Lys Ser Gln Tyr Leu Asn
        400                 405                 410

Asn Gly Pro Gln Arg Ile Gly Arg Lys Tyr Lys Lys Val Arg Phe Met
    415                 420                 425

Ala Tyr Thr Asp Glu Thr Phe Lys Thr Arg Glu Ala Ile Gln His Glu
430                 435                 440                 445

Ser Gly Ile Leu Gly Pro Leu Leu Tyr Gly Glu Val Gly Asp Thr Leu
                450                 455                 460

Leu Ile Ile Phe Lys Asn Gln Ala Ser Arg Pro Tyr Asn Ile Tyr Pro
            465                 470                 475

His Gly Ile Thr Asp Val Arg Pro Leu Tyr Ser Arg Arg Leu Pro Lys
        480                 485                 490

Gly Val Lys His Leu Lys Asp Phe Pro Ile Leu Pro Gly Glu Ile Phe
    495                 500                 505

Lys Tyr Lys Trp Thr Val Thr Val Glu Asp Gly Pro Thr Lys Ser Asp
510                 515                 520                 525

Pro Arg Cys Leu Thr Arg Tyr Tyr Ser Ser Phe Val Asn Met Glu Arg
                530                 535                 540

Asp Leu Ala Ser Gly Leu Ile Gly Pro Leu Leu Ile Cys Tyr Lys Glu
            545                 550                 555

Ser Val Asp Gln Arg Gly Asn Gln Ile Met Ser Asp Lys Arg Asn Val
        560                 565                 570

Ile Leu Phe Ser Val Phe Asp Glu Asn Arg Ser Trp Tyr Leu Thr Glu
    575                 580                 585

Asn Ile Gln Arg Phe Leu Pro Asn Pro Ala Gly Val Gln Leu Glu Asp
590                 595                 600                 605

Pro Glu Phe Gln Ala Ser Asn Ile Met His Ser Ile Asn Gly Tyr Val
                610                 615                 620

Phe Asp Ser Leu Gln Leu Ser Val Cys Leu His Glu Val Ala Tyr Trp
            625                 630                 635

Tyr Ile Leu Ser Ile Gly Ala Gln Thr Asp Phe Leu Ser Val Phe Phe
        640                 645                 650

Ser Gly Tyr Thr Phe Lys His Lys Met Val Tyr Glu Asp Thr Leu Thr
    655                 660                 665
```

```
Leu Phe Pro Phe Ser Gly Glu Thr Val Phe Met Ser Met Glu Asn Pro
670                 675                 680                 685

Gly Leu Trp Ile Leu Gly Cys His Asn Ser Asp Phe Arg Asn Arg Gly
                690                 695                 700

Met Thr Ala Leu Leu Lys Val Ser Ser Cys Asp Lys Asn Thr Gly Asp
            705                 710                 715

Tyr Tyr Glu Asp Ser Tyr Glu Asp Ile Ser Ala Tyr Leu Leu Ser Lys
        720                 725                 730

Asn Asn Ala Ile Glu Pro Arg Ser Phe Ser Gln Asn Ser Arg His Pro
    735                 740                 745

Ser Thr Arg Gln Lys Gln Phe Asn Ala Thr Thr Ile Pro Glu Asn Asp
750                 755                 760                 765

Ile Glu Lys Thr Asp Pro Trp Phe Ala His Arg Thr Pro Met Pro Lys
                770                 775                 780

Ile Gln Asn Val Ser Ser Ser Asp Leu Leu Met Leu Leu Arg Gln Ser
            785                 790                 795

Pro Thr Pro His Gly Leu Ser Leu Ser Asp Leu Gln Glu Ala Lys Tyr
        800                 805                 810

Glu Thr Phe Ser Asp Asp Pro Ser Pro Gly Ala Ile Asp Ser Asn Asn
    815                 820                 825

Ser Leu Ser Glu Met Thr His Phe Arg Pro Gln Leu His His Ser Gly
830                 835                 840                 845

Asp Met Val Phe Thr Pro Glu Ser Gly Leu Gln Leu Arg Leu Asn Glu
                850                 855                 860

Lys Leu Gly Thr Thr Ala Ala Thr Glu Leu Lys Lys Leu Asp Phe Lys
            865                 870                 875

Val Ser Ser Thr Ser Asn Asn Leu Ile Ser Thr Ile Pro Ser Asp Asn
        880                 885                 890

Leu Ala Ala Gly Thr Asp Asn Thr Ser Ser Leu Gly Pro Pro Ser Met
    895                 900                 905

Pro Val His Tyr Asp Ser Gln Leu Asp Thr Thr Leu Phe Gly Lys Lys
910                 915                 920                 925

Ser Ser Pro Leu Thr Glu Ser Gly Gly Pro Leu Ser Leu Ser Glu Glu
                930                 935                 940

Asn Asn Asp Ser Lys Leu Leu Glu Ser Gly Leu Met Asn Ser Gln Glu
            945                 950                 955

Ser Ser Trp Gly Lys Asn Val Ser Ser Thr Glu Ser Gly Arg Leu Phe
        960                 965                 970

Lys Gly Lys Arg Ala His Gly Pro Ala Leu Leu Thr Lys Asp Asn Ala
    975                 980                 985

Leu Phe Lys Val Ser Ile Ser Leu Leu Lys Thr  Asn Lys Thr Ser Asn
990                 995                 1000                1005

Asn Ser Ala Thr Asn  Arg Lys Thr His Ile  Asp Gly Pro Ser Leu
                1010                1015                1020

Leu Ile Glu Asn Ser  Pro Ser Val Trp Gln  Asn Ile Leu Glu Ser
                1025                1030                1035

Asp Thr Glu Phe Lys  Lys Val Thr Pro Leu  Ile His Asp Arg Met
                1040                1045                1050

Leu Met Asp Lys Asn  Ala Thr Ala Leu Arg  Leu Asn His Met Ser
                1055                1060                1065

Asn Lys Thr Thr Ser  Ser Lys Asn Met Glu  Met Val Gln Gln Lys
                1070                1075                1080
```

```
Lys Glu Gly Pro Ile  Pro Pro Asp Ala Gln  Asn Pro Asp Met Ser
                1085                 1090                 1095

Phe Phe Lys Met Leu  Phe Leu Pro Glu Ser  Ala Arg Trp Ile Gln
                1100                 1105                 1110

Arg Thr His Gly Lys  Asn Ser Leu Asn Ser  Gly Gln Gly Pro Ser
                1115                 1120                 1125

Pro Lys Gln Leu Val  Ser Leu Gly Pro Glu  Lys Ser Val Glu Gly
                1130                 1135                 1140

Gln Asn Phe Leu Ser  Glu Lys Asn Lys Val  Val Val Gly Lys Gly
                1145                 1150                 1155

Glu Phe Thr Lys Asp  Val Gly Leu Lys Glu  Met Val Phe Pro Ser
                1160                 1165                 1170

Ser Arg Asn Leu Phe  Leu Thr Asn Leu Asp  Asn Leu His Glu Asn
                1175                 1180                 1185

Asn Thr His Asn Gln  Glu Lys Lys Ile Gln  Glu Glu Ile Glu Lys
                1190                 1195                 1200

Lys Glu Thr Leu Ile  Gln Glu Asn Val Val  Leu Pro Gln Ile His
                1205                 1210                 1215

Thr Val Thr Gly Thr  Lys Asn Phe Met Lys  Asn Leu Phe Leu Leu
                1220                 1225                 1230

Ser Thr Arg Gln Asn  Val Glu Gly Ser Tyr  Asp Gly Ala Tyr Ala
                1235                 1240                 1245

Pro Val Leu Gln Asp  Phe Arg Ser Leu Asn  Asp Ser Thr Asn Arg
                1250                 1255                 1260

Thr Lys Lys His Thr  Ala His Phe Ser Lys  Lys Gly Glu Glu Glu
                1265                 1270                 1275

Asn Leu Glu Gly Leu  Gly Asn Gln Thr Lys  Gln Ile Val Glu Lys
                1280                 1285                 1290

Tyr Ala Cys Thr Thr  Arg Ile Ser Pro Asn  Thr Ser Gln Gln Asn
                1295                 1300                 1305

Phe Val Thr Gln Arg  Ser Lys Arg Ala Leu  Lys Gln Phe Arg Leu
                1310                 1315                 1320

Pro Leu Glu Glu Thr  Glu Leu Glu Lys Arg  Ile Ile Val Asp Asp
                1325                 1330                 1335

Thr Ser Thr Gln Trp  Ser Lys Asn Met Lys  His Leu Thr Pro Ser
                1340                 1345                 1350

Thr Leu Thr Gln Ile  Asp Tyr Asn Glu Lys  Glu Lys Gly Ala Ile
                1355                 1360                 1365

Thr Gln Ser Pro Leu  Ser Asp Cys Leu Thr  Arg Ser His Ser Ile
                1370                 1375                 1380

Pro Gln Ala Asn Arg  Ser Pro Leu Pro Ile  Ala Lys Val Ser Ser
                1385                 1390                 1395

Phe Pro Ser Ile Arg  Pro Ile Tyr Leu Thr  Arg Val Leu Phe Gln
                1400                 1405                 1410

Asp Asn Ser Ser His  Leu Pro Ala Ala Ser  Tyr Arg Lys Lys Asp
                1415                 1420                 1425

Ser Gly Val Gln Glu  Ser Ser His Phe Leu  Gln Gly Ala Lys Lys
                1430                 1435                 1440

Asn Asn Leu Ser Leu  Ala Ile Leu Thr Leu  Glu Met Thr Gly Asp
                1445                 1450                 1455

Gln Arg Glu Val Gly  Ser Leu Gly Thr Ser  Ala Thr Asn Ser Val
                1460                 1465                 1470

Thr Tyr Lys Lys Val  Glu Asn Thr Val Leu  Pro Lys Pro Asp Leu
```

```
                1475                1480                1485

Pro Lys Thr Ser Gly  Lys Val Glu Leu Leu  Pro Lys Val His Ile
                1490                1495                1500

Tyr Gln Lys Asp Leu  Phe Pro Thr Glu Thr  Ser Asn Gly Ser Pro
                1505                1510                1515

Gly His Leu Asp Leu  Val Glu Gly Ser Leu  Leu Gln Gly Thr Glu
                1520                1525                1530

Gly Ala Ile Lys Trp  Asn Glu Ala Asn Arg  Pro Gly Lys Val Pro
                1535                1540                1545

Phe Leu Arg Val Ala  Thr Glu Ser Ser Ala  Lys Thr Pro Ser Lys
                1550                1555                1560

Leu Leu Asp Pro Leu  Ala Trp Asp Asn His  Tyr Gly Thr Gln Ile
                1565                1570                1575

Pro Lys Glu Glu Trp  Lys Ser Gln Glu Lys  Ser Pro Glu Lys Thr
                1580                1585                1590

Ala Phe Lys Lys Lys  Asp Thr Ile Leu Ser  Leu Asn Ala Cys Glu
                1595                1600                1605

Ser Asn His Ala Ile  Ala Ala Ile Asn Glu  Gly Gln Asn Lys Pro
                1610                1615                1620

Glu Ile Glu Val Thr  Trp Ala Lys Gln Gly  Arg Thr Glu Arg Leu
                1625                1630                1635

Cys Ser Gln Asn Pro  Pro Val Leu Lys Arg  His Gln Arg Glu Ile
                1640                1645                1650

Thr Arg Thr Thr Leu  Gln Ser Asp Gln Glu  Glu Ile Asp Tyr Asp
                1655                1660                1665

Asp Thr Ile Ser Val  Glu Met Lys Lys Glu  Asp Phe Asp Ile Tyr
                1670                1675                1680

Asp Glu Asp Glu Asn  Gln Ser Pro Arg Ser  Phe Gln Lys Lys Thr
                1685                1690                1695

Arg His Tyr Phe Ile  Ala Ala Val Glu Arg  Leu Trp Asp Tyr Gly
                1700                1705                1710

Met Ser Ser Ser Pro  His Val Leu Arg Asn  Arg Ala Gln Ser Gly
                1715                1720                1725

Ser Val Pro Gln Phe  Lys Lys Val Val Phe  Gln Glu Phe Thr Asp
                1730                1735                1740

Gly Ser Phe Thr Gln  Pro Leu Tyr Arg Gly  Glu Leu Asn Glu His
                1745                1750                1755

Leu Gly Leu Leu Gly  Pro Tyr Ile Arg Ala  Glu Val Glu Asp Asn
                1760                1765                1770

Ile Met Val Thr Phe  Arg Asn Gln Ala Ser  Arg Pro Tyr Ser Phe
                1775                1780                1785

Tyr Ser Ser Leu Ile  Ser Tyr Glu Glu Asp  Gln Arg Gln Gly Ala
                1790                1795                1800

Glu Pro Arg Lys Asn  Phe Val Lys Pro Asn  Glu Thr Lys Thr Tyr
                1805                1810                1815

Phe Trp Lys Val Gln  His His Met Ala Pro  Thr Lys Asp Glu Phe
                1820                1825                1830

Asp Cys Lys Ala Trp  Ala Tyr Phe Ser Asp  Val Asp Leu Glu Lys
                1835                1840                1845

Asp Val His Ser Gly  Leu Ile Gly Pro Leu  Leu Val Cys His Thr
                1850                1855                1860

Asn Thr Leu Asn Pro  Ala His Gly Arg Gln  Val Thr Val Gln Glu
                1865                1870                1875
```

-continued

```
Phe Ala Leu Phe Phe  Thr Ile Phe Asp Glu  Thr Lys Ser Trp Tyr
                1880                 1885                 1890

Phe Thr Glu Asn Met  Glu Arg Asn Cys Arg  Ala Pro Cys Asn Ile
                1895                 1900                 1905

Gln Met Glu Asp Pro  Thr Phe Lys Glu Asn  Tyr Arg Phe His Ala
                1910                 1915                 1920

Ile Asn Gly Tyr Ile  Met Asp Thr Leu Pro  Gly Leu Val Met Ala
                1925                 1930                 1935

Gln Asp Gln Arg Ile  Arg Trp Tyr Leu Leu  Ser Met Gly Ser Asn
                1940                 1945                 1950

Glu Asn Ile His Ser  Ile His Phe Ser Gly  His Val Phe Thr Val
                1955                 1960                 1965

Arg Lys Lys Glu Glu  Tyr Lys Met Ala Leu  Tyr Asn Leu Tyr Pro
                1970                 1975                 1980

Gly Val Phe Glu Thr  Val Glu Met Leu Pro  Ser Lys Ala Gly Ile
                1985                 1990                 1995

Trp Arg Val Glu Cys  Leu Ile Gly Glu His  Leu His Ala Gly Met
                2000                 2005                 2010

Ser Thr Leu Phe Leu  Val Tyr Ser Asn Lys  Cys Gln Thr Pro Leu
                2015                 2020                 2025

Gly Met Ala Ser Gly  His Ile Arg Asp Phe  Gln Ile Thr Ala Ser
                2030                 2035                 2040

Gly Gln Tyr Gly Gln  Trp Ala Pro Lys Leu  Ala Arg Leu His Tyr
                2045                 2050                 2055

Ser Gly Ser Ile Asn  Ala Trp Ser Thr Lys  Glu Pro Phe Ser Trp
                2060                 2065                 2070

Ile Lys Val Asp Leu  Leu Ala Pro Met Ile  Ile His Gly Ile Lys
                2075                 2080                 2085

Thr Gln Gly Ala Arg  Gln Lys Phe Ser Ser  Leu Tyr Ile Ser Gln
                2090                 2095                 2100

Phe Ile Ile Met Tyr  Ser Leu Asp Gly Lys  Lys Trp Gln Thr Tyr
                2105                 2110                 2115

Arg Gly Asn Ser Thr  Gly Thr Leu Met Val  Phe Phe Gly Asn Val
                2120                 2125                 2130

Asp Ser Ser Gly Ile  Lys His Asn Ile Phe  Asn Pro Pro Ile Ile
                2135                 2140                 2145

Ala Arg Tyr Ile Arg  Leu His Pro Thr His  Tyr Ser Ile Arg Ser
                2150                 2155                 2160

Thr Leu Arg Met Glu  Leu Met Gly Cys Asp  Leu Asn Ser Cys Ser
                2165                 2170                 2175

Met Pro Leu Gly Met  Glu Ser Lys Ala Ile  Ser Asp Ala Gln Ile
                2180                 2185                 2190

Thr Ala Ser Ser Tyr  Phe Thr Asn Met Phe  Ala Thr Trp Ser Pro
                2195                 2200                 2205

Ser Lys Ala Arg Leu  His Leu Gln Gly Arg  Ser Asn Ala Trp Arg
                2210                 2215                 2220

Pro Gln Val Asn Asn  Pro Lys Glu Trp Leu  Gln Val Asp Phe Gln
                2225                 2230                 2235

Lys Thr Met Lys Val  Thr Gly Val Thr Thr  Gln Gly Val Lys Ser
                2240                 2245                 2250

Leu Leu Thr Ser Met  Tyr Val Lys Glu Phe  Leu Ile Ser Ser Ser
                2255                 2260                 2265
```

-continued

```
Gln Asp Gly His Gln  Trp Thr Leu Phe Phe  Gln Asn Gly Lys Val
                2270                 2275                 2280

Lys Val Phe Gln Gly  Asn Gln Asp Ser Phe  Thr Pro Val Val Asn
                2285                 2290                 2295

Ser Leu Asp Pro Pro  Leu Leu Thr Arg Tyr  Leu Arg Ile His Pro
                2300                 2305                 2310

Gln Ser Trp Val His  Gln Ile Ala Leu Arg  Met Glu Val Leu Gly
                2315                 2320                 2325

Cys Glu Ala Gln Asp  Leu Tyr Asp Lys Thr  His Thr Cys Pro Pro
                2330                 2335                 2340

Cys Pro Ala Pro Glu  Leu Leu Gly Gly Pro  Ser Val Phe Leu Phe
                2345                 2350                 2355

Pro Pro Lys Pro Lys  Asp Thr Leu Met Ile  Ser Arg Thr Pro Glu
                2360                 2365                 2370

Val Thr Cys Val Val  Val Asp Val Ser His  Glu Asp Pro Glu Val
                2375                 2380                 2385

Lys Phe Asn Trp Tyr  Val Asp Gly Val Glu  Val His Asn Ala Lys
                2390                 2395                 2400

Thr Lys Pro Arg Glu  Glu Gln Tyr Asn Ser  Thr Tyr Arg Val Val
                2405                 2410                 2415

Ser Val Leu Thr Val  Leu His Gln Asp Trp  Leu Asn Gly Lys Glu
                2420                 2425                 2430

Tyr Lys Cys Lys Val  Ser Asn Lys Ala Leu  Pro Ala Pro Ile Glu
                2435                 2440                 2445

Lys Thr Ile Ser Lys  Ala Lys Gly Gln Pro  Arg Glu Pro Gln Val
                2450                 2455                 2460

Tyr Thr Leu Pro Pro  Ser Arg Asp Glu Leu  Thr Lys Asn Gln Val
                2465                 2470                 2475

Ser Leu Thr Cys Leu  Val Lys Gly Phe Tyr  Pro Ser Asp Ile Ala
                2480                 2485                 2490

Val Glu Trp Glu Ser  Asn Gly Gln Pro Glu  Asn Asn Tyr Lys Thr
                2495                 2500                 2505

Thr Pro Pro Val Leu  Asp Ser Asp Gly Ser  Phe Phe Leu Tyr Ser
                2510                 2515                 2520

Lys Leu Thr Val Asp  Lys Ser Arg Trp Gln  Gln Gly Asn Val Phe
                2525                 2530                 2535

Ser Cys Ser Val Met  His Glu Ala Leu His  Asn His Tyr Thr Gln
                2540                 2545                 2550

Lys Ser Leu Ser Leu  Ser Pro Gly Lys
                2555


<210> SEQ ID NO 11
<211> LENGTH: 21
<212> TYPE: PRT
<213> ORGANISM: Artificial Sequence
<220> FEATURE:
<223> OTHER INFORMATION: Partial  B domain

<400> SEQUENCE: 11

Ser Phe Ser Gln Asn Ser Arg His Pro Ser Gln Asn Pro Pro Val Leu
1               5                   10                  15

Lys Arg His Gln Arg
            20


<210> SEQ ID NO 12
<211> LENGTH: 11
```

<212> TYPE: PRT
<213> ORGANISM: Artificial Sequence
<220> FEATURE:
<223> OTHER INFORMATION: albumin-binding peptide

<400> SEQUENCE: 12

```
Asp Ile Cys Leu Pro Arg Trp Gly Cys Leu Trp
1               5                   10
```

<210> SEQ ID NO 13
<211> LENGTH: 32
<212> TYPE: PRT
<213> ORGANISM: Artificial Sequence
<220> FEATURE:
<223> OTHER INFORMATION: CTP peptide

<400> SEQUENCE: 13

```
Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30
```

<210> SEQ ID NO 14
<211> LENGTH: 28
<212> TYPE: PRT
<213> ORGANISM: Artificial Sequence
<220> FEATURE:
<223> OTHER INFORMATION: CTP peptide

<400> SEQUENCE: 14

```
Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25
```

<210> SEQ ID NO 15
<211> LENGTH: 20
<212> TYPE: PRT
<213> ORGANISM: Artificial Sequence
<220> FEATURE:
<223> OTHER INFORMATION: PAS peptide

<400> SEQUENCE: 15

```
Ala Ser Pro Ala Ala Pro Ala Pro Ala Ser Pro Ala Ala Pro Ala Pro
1               5                   10                  15

Ser Ala Pro Ala
            20
```

<210> SEQ ID NO 16
<211> LENGTH: 20
<212> TYPE: PRT
<213> ORGANISM: Artificial Sequence
<220> FEATURE:
<223> OTHER INFORMATION: PAS peptide

<400> SEQUENCE: 16

```
Ala Ala Pro Ala Ser Pro Ala Pro Ala Ala Pro Ser Ala Pro Ala Pro
1               5                   10                  15

Ala Ala Pro Ser
            20
```

<210> SEQ ID NO 17
<211> LENGTH: 20
<212> TYPE: PRT
<213> ORGANISM: Artificial Sequence
<220> FEATURE:
<223> OTHER INFORMATION: PAS peptide

<400> SEQUENCE: 17

Ala Pro Ser Ser Pro Ser Pro Ser Ala Pro Ser Ser Pro Ser Pro Ala
1 5 10 15

Ser Pro Ser Ser
20

<210> SEQ ID NO 18
<211> LENGTH: 19
<212> TYPE: PRT
<213> ORGANISM: Artificial Sequence
<220> FEATURE:
<223> OTHER INFORMATION: PAS peptide

<400> SEQUENCE: 18

Ala Pro Ser Ser Pro Ser Pro Ser Ala Pro Ser Ser Pro Ser Pro Ala
1 5 10 15

Ser Pro Ser

<210> SEQ ID NO 19
<211> LENGTH: 20
<212> TYPE: PRT
<213> ORGANISM: Artificial Sequence
<220> FEATURE:
<223> OTHER INFORMATION: PAS peptide

<400> SEQUENCE: 19

Ser Ser Pro Ser Ala Pro Ser Pro Ser Ser Pro Ala Ser Pro Ser Pro
1 5 10 15

Ser Ser Pro Ala
20

<210> SEQ ID NO 20
<211> LENGTH: 24
<212> TYPE: PRT
<213> ORGANISM: Artificial Sequence
<220> FEATURE:
<223> OTHER INFORMATION: PAS peptide

<400> SEQUENCE: 20

Ala Ala Ser Pro Ala Ala Pro Ser Ala Pro Pro Ala Ala Ala Ser Pro
1 5 10 15

Ala Ala Pro Ser Ala Pro Pro Ala
20

<210> SEQ ID NO 21
<211> LENGTH: 20
<212> TYPE: PRT
<213> ORGANISM: Artificial Sequence
<220> FEATURE:
<223> OTHER INFORMATION: PAS peptide

<400> SEQUENCE: 21

Ala Ser Ala Ala Ala Pro Ala Ala Ala Ser Ala Ala Ala Ser Ala Pro
1 5 10 15

Ser Ala Ala Ala
20

POPULATION PHARMACOKINETICS TOOLS AND USES THEREOF

BACKGROUND OF THE INVENTION

Field of the Invention

The present invention is directed to computer based pharmacokinetics systems, such as, web-based pharmacokinetics systems, and their use to predict a dose and a dosing interval for a patient in need of a clotting factor therapy.

Background Art

While plasma-derived and recombinant clotting factor products allow hemophilia patients to live longer and healthier, hemophilia still remains one of the most costly and complex conditions to manage. The cost of clotting factor products exceeds $50,000 a year per patient. See Blankenship C. S., *Biotechnol. Healthc.* 2008, 5(4): 37-40. According to the National Heart, Lung, and Blood Institute, National Institute of Health (NIH), approximately 18,000 people in the U.S. have hemophilia, and 400 babies are born with the disease each year. Morbidity & Mortality: 2012 Chart Book on Cardiovascular, Lung and Blood Disease, page 5, National Heart, Lung, and Blood Institute, NIH. Due to its complexity, this chronic disease requires a special therapeutic management process for doctors, pharmacies, and patients. Clinicians often assess lifestyle, psychosocial requirements, and the home environment when evaluating a patient's or guardian's ability to provide adequate care.

In hemophilia, blood clotting is disturbed by a lack of certain plasma blood clotting factors. Hemophilia A, the most common form of hemophilia, is caused by Factor VIII deficiency. Hemophilia B is caused by decreased synthesis of Factor IX protein or synthesis of defective Factor IX having reduced activity. Treating hemophilia involves replacing missing or defective clotting factor with recombinant or plasma-derived FVIII or FIX. For patients who have developed antibodies against recombinant or plasma-derived FVIII or FIX, Factor VII can be used as a bypass therapy. Commercially available clotting factors are usually administered by peripheral intravenous injection. However, for patients with small veins or children who require frequent injections, clotting factors can be administered by a central venous access device. See Blankenship C. S., *Biotechnol. Healthc.* 2008, 5(4): 37-40.

Currently, three FIX products are approved by the Food and Drug Administration (FDA). The first, BENEFIX®, is a recombinant FIX product marketed by Pfizer. The second and third products are plasma-derived FIX products, ALPHANINE® marketed by Grifols and MONONINE® marketed by CSL Behring. According to their labels, BENEFIX® is supplied as a lyophilized powder in five different dosages: 250 IU, 500 IU, 1000 IU, 2000 IU, and 3000 IU. MONONINE® is supplied as a single dose vial with Sterile Water for Injection at 500 IU and 1000 IU. ALPHANINE is supplied in lyophilized form as single doses at 500 IU, 1000 IU, and 1500 IU. The FIX dose required for each patient is calculated based on the formula:

Number of factor IX IU required (IU)=Body Weight (kg)×Desired Factor IX Increase (% or IU/dL)×Reciprocal of Observed Recovery (IU/kg per IU/dL) (A)

Several Factor VIII products are also commercially available, which include recombinant FVIII products (ADVATE® and RECOMBINATE® marketed by Baxter, KOGENATE® FS marketed by Bayer, HELIXATE® FS marketed by CSL-Behring, and XYNTHA® and REFACTO® marketed by PFIZER) and Plasma-derived FVIII products (HEMOFIL-M® marketed by Baxter, MONARC-M® by American Red Cross, and MONOCLATE-P® marketed by CSL Behring). The required FVIII dose for each patient is calculated using the following formula:

Number of factor FVIII IU required (IU)=Body Weight (kg)×Desired Factor FVIII Increase (IU/dL or % of normal)×0.5(IU/kg per IU/dL) (B)

However, administering clotting factors can be complicated and costly for patients. The invention as described herein provides improved clotting factor-dosing methods.

BRIEF SUMMARY OF THE INVENTION

The present invention is directed to a method of estimating long-acting FIX dosing information individualized for a patient, the method comprising: a) receiving, by a computer-based system containing (i) the long-acting FIX population pharmacokinetic (popPK) model of Example 5 or 7 and (ii) a Bayesian estimation program, at least one of patient information and desired treatment outcome information, b) calculating, by the computer-based system, individualized long-acting FIX dosing information using the FIX popPK model, respectively, the Bayesian estimation program, and the received information, and c) outputting, by the computer-based system, the individualized dosing information.

Also disclosed is a method of estimating long-acting FVIII dosing information individualized for a patient, the method comprising: a) receiving, by a computer-based system containing (i) the long-acting FVIII popPK model of Example 9 or 11 or 16 and (ii) a Bayesian estimation program, at least one of patient information and desired treatment outcome information, b) calculating, by the computer-based system, individualized long-acting FVIII dosing information using the FVIII popPK model, respectively, the Bayesian estimation program, and the received information, and c) outputting, by the computer-based system, the individualized dosing information. Further disclosed is the method as described herein, further comprising selecting a dosing regimen based on the output individualized dosing information of (c) and administering the long-acting FIX polypeptide to the patient according to the selected dosing regimen. Also disclosed is the method as described herein, further comprising selecting a dosing regimen based on the output individualized dosing information of (c) and administering the long-acting FVIII polypeptide to the patient according to the selected dosing regimen.

Certain embodiments include a computer readable storage medium having instructions stored thereon that, when executed by a processor, causes the processor to perform the method as described herein.

Also disclosed is a system comprising a processor and a memory, the memory having instructions stored thereon that, when executed by the processor, cause the processor to perform the method as described herein.

Further disclosed is a method of estimating a long-acting FIX dosing regimen based on median popPK, the method comprising: a) receiving, by a computer-based system containing (i) the long-acting FIX popPK model of Example 5 or 7 and (ii) a Bayesian estimation program, at least one of patient information and desired treatment outcome information, b) calculating, by the computer-based system, median long-acting FIX PK information using the FIX popPK model, respectively, the Bayesian estimation program, and the received information, and c) outputting, by the computer-based system, the median PK information. Also disclosed is the method as described herein, further comprising selecting a dosing regimen based on the output median PK information of (c), and administering the long-acting FIX to a patient according to the selected dosing regimen.

Certain embodiments include a method of estimating a long-acting FVIII dosing regimen based on median popPK, the method comprising: a) receiving, by a computer-based system containing (i) the long-acting FVIII popPK model of Example 9 or 11 or 16 and (ii) a Bayesian estimation program, at least one of patient information and desired treatment outcome information, b) calculating, by the computer-based system, median long-acting FVIII PK information using the FVIII popPK model, respectively, the Bayesian estimation program, and the received information, and c) outputting, by the computer-based system, the median PK information. Also disclosed is the method as described herein, further comprising selecting a dosing regimen based on the output median PK information of (c), and administering the long acting FVIII to a patient according to the selected dosing regimen.

Certain embodiments include a computer readable storage medium having instructions stored thereon that, when executed by a processor, cause the processor to perform the method as described herein.

Also disclosed is a system comprising a processor and a memory, the memory having instructions stored thereon that, when executed by the processor, causes the processor to perform the method as described herein.

Some embodiments include a method of estimating individual patient PK of a long-acting FIX, the method comprising: (a) receiving, by a computer-based system containing (i) the long-acting FIX population pharmacokinetic (popPK) model of Example 5 or 7 and (ii) a Bayesian estimation program, individual long-acting FIX PK information, b) estimating, by the computer-based system, individualized patient PK information of a long-acting FIX using the FIX popPK model, the Bayesian estimation program, and the received information, and c) outputting, by the computer-based system, the individualized patient PK information. Also disclosed is the method as described herein, further comprising selecting a dosing regimen based on the output individualized patient PK information of (c), and administering the long-acting FIX to the patient according to the selected regimen.

Certain embodiments include a method of estimating individual patient PK of a long-acting FVIII, the method comprising: (a) receiving, by a computer-based system containing (i) the long-acting FVIII popPK model of Example 9 or 11 or 16 and a Bayesian estimation program, individual long-acting FVIII PK information, b) estimating, by the computer-based system, individualized patient PK information of a long-acting FVIII using the FVIII popPK model, the Bayesian estimation program, and the received information, and c) outputting, by the computer-based system, the individualized patient PK information. Also disclosed is the method as described herein, further comprising selecting a dosing regimen based on the output individualized patient PK information of (c), and administering the long-acting FVIII to the patient according to the selected regimen.

Some embodiments include a computer readable storage medium having instructions stored thereon that, when executed by a processor, causes the processor to perform the method as described herein.

Also disclosed is a system comprising a processor and a memory, the memory having instructions stored thereon that, when executed by the processor, cause the processor to perform the method as described herein.

Some embodiments include the method as described herein, wherein the desired treatment outcome information is desired rise in plasma FIX or FVIII level following dosing and the output information is dose for acute treatment.

Also disclosed is the method, wherein the desired treatment outcome information is desired dosing interval and the output information is dose for prophylaxis.

Some embodiments include the method as described herein, wherein the desired treatment outcome information is desired dose and the output information is interval for prophylaxis.

Also disclosed is the method as described herein, wherein (a) further comprises receiving, by the computer-based system, additional patient information.

Some embodiments include the method as described herein, wherein the patient information is age or body weight.

Some embodiments include a web-based method of estimating long-acting FIX dosing information individualized for a patient, the method comprising: (a) receiving, by one or more electronic devices, at least one of patient information and desired treatment outcome information, (b) transmitting, by a processing device, the at least one of patient information and desired treatment outcome information to a web-based application program accessible through a web server, wherein the application is programmed to implement a long-acting FIX population pharmacokinetic (popPK) model of Example 5 or 7 and a Bayesian estimation program, (c) receiving from the web based server and program, individualized dosing information calculated using the popPK model, the Bayesian estimation program, and the transmitted information of (b), and (d) outputting, by the one or more electronic devices, the individualized dosing information.

Also disclosed is a web-based method of estimating long-acting FVIII dosing information individualized for a patient, the method comprising: (a) receiving, by one or more electronic devices, at least one of patient information and desired treatment outcome information, (b) transmitting, by a processing device, the at least one of patient information and desired treatment outcome information to a web-based application program accessible through a web server, wherein the application is programmed to implement a long-acting FVIII popPK model of Example 9 or 11 or 16, and a Bayesian estimation program, (c) receiving from the web based server and program, individualized dosing information calculated using the popPK model, the Bayesian estimation program, and the transmitted information of (b), and (d) outputting, by the one or more electronic devices, the individualized dosing information.

Some embodiments include a web-based method of estimating long-acting FIX dosing information individualized for a patient, the method comprising: (a) receiving, by a processing device, at least one of patient information and desired treatment outcome information by a web-based application program accessible through a web server and programmed to implement a long-acting FIX population pharmacokinetic (popPK) model, and a Bayesian estimation program, wherein the received information is transmitted by one or more electronic devices, (b) calculating, by the web-based program, individualized long-acting FIX dosing information using the FIX popPK model, the Bayesian estimation program, and the received information, and (c) transmitting, by a processing device, the individualized calculated dosing information of (b) to one or more electronic devices for output of the information.

Also disclosed is a web-based method of estimating long-acting FVIII dosing information individualized for a patient, the method comprising: (a) receiving, by a processing device, at least one of patient information and desired treatment outcome information by a web-based application program accessible through a web server and programmed to implement a long-acting FVIII popPK model, and a Bayesian estimation program, wherein the received information is transmitted by one or more electronic devices, (b) calculating, by the web-based program, individualized long-acting FVIII dosing information using the FVIII popPK model of Example 9 or 11 or 16, the Bayesian estimation program, and the received information, and (c) transmitting, by a processing device, the individualized calculated dosing information of (b) to one or more electronic devices for output of the information. In some embodiments, the method as described herein further comprises selecting a dosing regimen based on the output individualized dosing information of (e) and administering the long-acting FIX to the patient according to the selected dosing regimen. In other embodiments, the method as described herein further comprises selecting a dosing regimen based on the output individualized dosing information of (e) and administering the long-acting FVIII to the patient according to the selected dosing regimen.

Some embodiments include the method as described herein, wherein the desired treatment outcome information is desired rise in plasma FIX activity level following dosing and the dosing output information is dose for acute treatment.

Also disclosed is the method as described herein, wherein the desired treatment outcome information is desired rise in plasma FVIII activity level following dosing and the dosing output information is dose for acute treatment.

Some embodiments include is the method as described herein, wherein the desired treatment outcome information is desired dosing interval and the dosing output information is dose for prophylaxis.

Also disclosed is the method as described herein, wherein, the desired treatment outcome information is desired dose and the dosing output information is interval for prophylaxis.

Some embodiments include a web-based method of estimating a long-acting FIX dosing regimen based on median FIX popPK, the method comprising: (a) receiving, by one or more electronic devices at least one of patient information and desired treatment outcome information, (b) transmitting, by a processing device, the at least one of patient information and desired treatment outcome information to a web-based application program accessible through a web server, wherein the application is programmed to implement a long-acting FIX population pharmacokinetic (popPK) model, such as that of Example 5 or 7, and a Bayesian estimation program, (c) receiving from the web based server and program, median long-acting FIX PK dosing information calculated using the FIX popPK model, respectively, the Bayesian estimation program, and the received information, and (d) outputting, by the one or more electronic devices, the median PK information.

Also disclosed is a web-based method of estimating a long-acting FVIII dosing regimen based on median FVIII popPK, the method comprising: (a) receiving, by one or more electronic devices at least one of patient information and desired treatment outcome information, (b) transmitting, by a processing device, the at least one of patient information and desired treatment outcome information to a web-based application program accessible through a web server, wherein the application is programmed to implement a long-acting FVIII population pharmacokinetic (popPK) model, such as that of Example 9 or 11 or 16, and a Bayesian estimation program, (c) receiving from the web based server and program, median long-acting FVII PK dosing information calculated using the FVIII popPK model, respectively, the Bayesian estimation program, and the received information, and (d) outputting, by the one or more electronic devices, the median PK information.

Some embodiments include a web-based method of estimating a long-acting FIX dosing regimen based on median FIX popPK, the method comprising: (a) receiving, by a processing device, at least one of patient information and desired treatment outcome information by a web-based application program accessible through a web server and programmed to implement a long-acting FIX popPK model, and a Bayesian estimation program, wherein the received information is transmitted by one or more electronic devices, (b) calculating, by the web-based program, individualized long-acting FIX dosing information using the FIX popPK model, the Bayesian estimation program, and the received information, and (c) transmitting, by a processing device, the individualized calculated dosing information of (b) to one or more electronic devices for output of the information.

Also disclosed is a web-based method of estimating a long-acting FVIII dosing regimen based on median FVIII popPK, the method comprising: (a) receiving, by a processing device, at least one of patient information and desired treatment outcome information by a web-based application program accessible through a web server and programmed to implement a long-acting FVIII population pharmacokinetic (popPK) model, and a Bayesian estimation program, wherein the received information is transmitted by one or more electronic devices, (b) calculating, by the web-based program, individualized long-acting FVIII dosing information using the FVIII popPK model, the Bayesian estimation program, and the received information, and (c) transmitting, by a processing device, the individualized calculated dosing information of (b) to one or more electronic devices for output of the information. Also disclosed is the method as described herein, further comprising selecting a dosing regimen based on the output median PK information of (e), and (f) administering the long-acting FIX to a patient according to the selected dosing regimen. Some embodiments include the method as described herein, further comprising selecting a dosing regimen based on the output median PK information of (e), and (f) administering the long-acting FVIII to a patient according to the selected dosing regimen.

Some embodiments include the method as described herein, wherein the desired treatment outcome information is desired rise in plasma FIX activity level following dosing and the dosing output information is dose for acute treatment. Some embodiments include the method as described herein, wherein the desired treatment outcome information is desired rise in plasma FVIII activity level following dosing and the dosing output information is dose for acute treatment. Also disclosed is the method as described herein, wherein the desired treatment outcome information is desired dosing interval and the dosing output information is dose for prophylaxis. Some embodiments include the method as described herein, wherein, the desired treatment outcome information is desired dose and the dosing output information is interval for prophylaxis.

Also disclosed is a web-based method of method of estimating individual patient PK of a long-acting FIX, the method comprising: (a) receiving, by one or more electronic devices, individual long-acting FIX PK information, (b) transmitting, by a processing device, the individual long-acting FIX PK information to a web-based application program accessible through a web server, wherein the application is programmed to implement a long-acting FIX population pharmacokinetic (popPK) model, such as that of Example 5 or 7, and a Bayesian estimation program, (c) receiving from the web-based server and program, individualized patient long-acting FIX PK information using the popPK model, the Bayesian estimation program, and the transmitted information of (b) and (d) outputting, by the one or more electronic devices, the individualized patient PK information.

Some embodiments include is a web-based method of estimating individual patient PK of a long-acting FVIII, the method comprising: (a) receiving, by one or more electronic devices, individual long-acting FVIII PK information, (b) transmitting, by a processing device, the individual long-acting FVIII PK information to a web-based application program accessible through a web server, wherein the application is programmed to implement a long-acting FVIII population pharmacokinetic (popPK) model, such as that of Example 9 or 11 or 16, and a Bayesian estimation program, (c) receiving from the web-based server and program, individualized patient long-acting FVIII PK information using the popPK model, the Bayesian estimation program, and the transmitted information of (b) and (d) outputting, by the one or more electronic devices, the individualized patient PK information.

Also disclosed is a web-based method of estimating individual patient PK of a long-acting FIX, the method comprising: (a) receiving, of individual long-acting FIX PK information by a web-based application program accessible through a web server and programmed to implement a long-acting FIX population pharmacokinetic (popPK) model, such as that of Example 5 or 7, and a Bayesian estimation program, wherein the received information is transmitted by one or more electronic devices, (b) calculating by the web-based program, individualized patient PK information of a long-acting FIX using the FIX popPK model, the Bayesian estimation program and the received information, and (c) transmitting, by a processing device, the estimated individualized patient long-acting FIX PK information of (b) to one or more one or more electronic devices, for output of the information.

Some embodiments include web-based method of estimating individual patient PK of a long-acting FVIII, the method comprising: (a) receiving, of individual long-acting FVIII PK information by a web-based application program accessible through a web server and programmed to implement a long-acting FVIII popPK model, such as that of Example 9 or 11 or 16, and a Bayesian estimation program, wherein the received information is transmitted by one or more electronic devices, (b) calculating by the web-based program, individualized patient PK information of a long-acting FVIII using the FVIII popPK model, the Bayesian estimation program and the received information, and (c) transmitting, by a processing device, the estimated individualized patient long-acting FVIII PK information of (b) to one or more one or more electronic devices, for output of the information.

In certain embodiments, the method as described herein further comprises selecting a dosing regimen based on the output estimated patient PK information of (e), and administering the long-acting FIX to the patient according to the selected regimen. In other embodiments, the method as described herein further comprises selecting a dosing regimen based on the output estimated patient PK information of (e), and administering the long-acting FVIII to the patient according to the selected regimen.

Some embodiments include the method as described herein, further comprising selecting a dosing regimen based on the output estimated patient PK information of (e), and administering the long-acting FIX to the patient according to the selected regimen.

In certain embodiments, the method as described herein further comprises selecting a dosing regimen based on the output estimated patient PK information of (e), and administering the long-acting FVIII to the patient according to the selected regimen.

Some embodiments include a web-based method of estimating individual patient PK of a long-acting FIX, the method comprising: (a) receiving, by one or more electronic devices, information regarding individual body weight and (i) desired rise of plasma factor activity level following the dose or (ii) desired dose or desired dose interval, (b) transmitting, by a processing device, the information of (a) to a web-based application program accessible through a web server, wherein the application is programmed to implement a long-acting FIX population pharmacokinetic (popPK) model, such as that of Example 5 or 7, and a Bayesian estimation program, (c) receiving from the web based server and program, individualized patient PK information of a long-acting FIX calculated using the popPK model, the Bayesian estimation program, and the transmitted information of (b), and (d) outputting, by the one or more electronic devices, the estimated patient PK information.

Also included is a web-based method of estimating individual patient PK of a long-acting FVIII, the method comprising: (a) receiving, by one or more electronic devices, information regarding individual body weight and (i) desired rise of plasma factor activity level following the dose or (ii) desired dose or desired dose interval, (b) transmitting, by a processing device, the information of (a) to a web-based application program accessible through a web server, wherein the application is programmed to implement a long-acting FVIII popPK model, such as that of Example 9 or 11 or 16, and a Bayesian estimation program, (c) receiving from the web based server and program, individualized patient PK information of a long-acting FVIII calculated using the popPK model, the Bayesian estimation program, and the transmitted information of (b), and (d) outputting, by the one or more electronic devices, the estimated patient PK information.

Some embodiments include a web-based method of estimating individual patient PK of a long-acting FIX, the method comprising: (a) receiving, by one or more electronic devices, information regarding individual body weight and (i) desired rise of plasma factor activity level following the dose or (ii) desired dose or desired dose interval, (b) transmitting, by a processing device, the information of (a) to a web-based application program accessible through a web server, wherein the application is programmed to implement a long-acting FIX population pharmacokinetic (popPK) model, such as that of Example 5 or 7, and a Bayesian estimation program, (c) receiving from the web based server and program, individualized patient PK information of the long-acting FIX calculated using the popPK model, the Bayesian estimation program, and the transmitted information of (b), and (d) outputting, by the one or more electronic devices, the estimated patient PK information.

Some embodiments include a web-based method of estimating individual patient PK of a long-acting FVIII, the method comprising: (a) receiving, by one or more electronic devices, information regarding individual body weight and (i) desired rise of plasma factor activity level following the dose or (ii) desired dose or desired dose interval, (b) transmitting, by a processing device, the information of (a) to a web-based application program accessible through a web server, wherein the application is programmed to implement a long-acting FVIII popPK model, such as that of Example 9 or 11 or 16, and a Bayesian estimation program, (c) receiving from the web based server and program, individualized patient PK information of the long-acting FVIII calculated using the popPK model, the Bayesian estimation program, and the transmitted information of (b), and (d) outputting, by the one or more electronic devices, the estimated patient PK information.

In other embodiments, the method as described herein further comprises selecting a dosing regimen based on the output estimated patient PK information of (e), and administering the long-acting FIX to the patient according to the selected regimen. Some embodiments include the method as described herein, further comprising selecting a dosing regimen based on the output estimated patient PK information of (e), and administering the long-acting FIX to the patient according to the selected regimen. Also included is the method as described herein, wherein (a) further comprises receiving, by the electronic device, patient information and (b) further comprises transmitting, by a processing device, the patient information to the web-based application program.

Some embodiments include the method as described herein, wherein (a) further comprises receiving information by the electronic device information relating to diagnostic (baseline) factor level, dosing history, actual dose, actual time of PK sampling or factor activity level, and (b) further comprises transmitting, by a processing device, the information to the web-based application program.

Also disclosed is the method as described herein, wherein the individualized patient PK includes a PK curve or a PK parameter selected from incremental recovery (Cmax/Dose), mean residence time, terminal $t_{1/2}$, clearance, Vss and AUC/Dose.

Some embodiments include the method as described herein, wherein the information is desired rise in plasma FIX activity level following dosing and the dosing output information is dose for acute treatment.

Also disclosed is the method as described herein, wherein the information is desired rise in plasma FVIII activity level following dosing and the dosing output information is dose for acute treatment.

Some embodiments include the method as described herein, wherein the information is desired dose and the dosing output information is dose for prophylaxis.

Also disclosed is the method as described herein, wherein, the information is desired dose interval and the dosing output information is interval for prophylaxis.

Some embodiments include the method as described herein, wherein, the electronic device is selected from a digital pen, a smart phone, a tablet computer, a personal digital assistant, a handheld computer, a laptop computer, a scanner, a camera, and a fax machine.

Also disclosed is a computer readable storage medium having instructions stored thereon that, when executed by a processor, cause the processor to estimate a long-acting FIX dosing information individualized for a patient, wherein the computer-based system comprises (i) a long-acting FIX population pharmacokinetic (popPK) model of Example 5 or 7 and (ii) a Bayesian estimation program.

Some embodiments include a computer readable storage medium having instructions stored thereon that, when executed by a processor, cause the processor to estimate a long-acting FVIII dosing information individualized for a patient, wherein the computer-based system comprises (i) a long-acting FVIII population pharmacokinetic (popPK) model of Example 9 or 11 or 16 and (ii) a Bayesian estimation program.

Also disclosed is a system comprising a processor and a memory, the memory having instructions stored thereon that, when executed by the processor, cause the processor to estimate a long-acting FIX dosing information individualized for a patient, wherein the memory comprises (i) a long-acting FIX population pharmacokinetic (popPK) model of Example 5 or 7 and (ii) a Bayesian estimation program and wherein the system receives at least one of patient information and desired treatment outcome information, calculates individualized long-acting FIX dosing information using the popPK model, the Bayesian estimation program, and the received information, and outputting the individualized dosing information.

Some embodiments include a system comprising a processor and a memory, the memory having instructions stored thereon that, when executed by the processor, cause the processor to estimate a long-acting FVIII dosing information individualized for a patient, wherein the memory comprises (i) a long-acting FVIII population pharmacokinetic (popPK) model of Example 9 or 11 or 16 and (ii) a Bayesian estimation program and wherein the system receives at least one of patient information and desired treatment outcome information, calculates individualized long-acting FVIII dosing information using the popPK model, the Bayesian estimation program, and the received information, and outputting the individualized dosing information.

Also disclosed is a method of treating a bleeding episode comprising administering to a subject in need thereof a therapeutic dose of a clotting factor at a dosing interval, wherein the dose and dosing interval are calculated using a web-based application that is accessible through a web server, wherein the application is programmed to implement a clotting factor population pharmacokinetic (popPK) model and a Bayesian estimation program to calculate the dose and dosing interval.

Also disclosed is a method of treating a bleeding episode comprising (1) calculating a therapeutic dose of a clotting factor and a dosing interval of the clotting factor for a subject in need thereof using a web-based application that is accessible through a web server, wherein the application is programmed to implement a clotting factor population pharmacokinetic (popPK) model and a Bayesian estimation program to calculate the dose and dosing interval and (2) administering the clotting factor at the calculated dose and the dosing interval to the subject.

In some embodiments, the method further comprises entering individual clotting factor pharmacokinetic information.

In some embodiments, the method further comprises, optionally contemporaneously, updating the popPK model based on the individual clotting factor pharmacokinetic information.

In some embodiments, the application continuously updates the popPK model based on newly input clotting factor pharmacokinetic information.

In some embodiments, the method further comprises, before the calculating, inputting a body weight of the subject.

In some embodiments, the method further comprises inputting a rise of clotting factor plasma activity level desired following the administrating ("desired rise of clotting factor plasma activity level").

Also disclosed is the method as described herein, wherein the clotting factor is long-acting. Also disclosed is the method as described herein, wherein the long-acting clotting factor is rFVIIIFc or rFIXFc.

In some embodiments, the method further comprises, before the calculating, inputting the subject's age. Also disclosed is the method, as described herein, wherein the subject is less than 6 years old, equal to or greater than 6 years old and less than 12 years old, less than 12 years old, or equal to or greater than 12 years old.

Also disclosed is the method, as described herein, wherein the long-acting clotting factor is rFVIIIFc and the method further comprises, before the calculating, inputting the subject's Von Willebrand Factor (VWF) level.

In some embodiments, the method further comprises, before the calculating, measuring a clotting factor activity level in plasma at various time points after an initial dose of the clotting factor, wherein individual subject clotting factor pharmacokinetic information is, optionally contemporaneously, calculated based on the clotting factor activity level.

In some embodiments, the method, further comprises, before the measuring, administering an initial dose of the clotting factor.

Also disclosed is the method, as described herein wherein the initial dose is a fixed interval dose.

In some embodiments of the method herein, the clotting factor popPK model is updated, optionally contemporaneously, and is, optionally immediately, available through the web server.

In some embodiments, the clotting factor popPK model is updated, optionally immediately, after the individual subject clotting factor pharmacokinetic information is added to the application and wherein an updated clotting factor popPK model is available for a next use.

Some embodiments include a web-based method of, optionally contemporaneously, improving the predictive accuracy of clotting factor dosing information, the method comprising: (a) accessing a web-based application accessible through a web server, the application comprising a dataset comprising clotting factor population pharmacokinetic (popPK) information, (b) inputting individual subject clotting factor pharmacokinetic information into the application to create a new dataset, and (c) calculating, using the application, a clotting factor popPK model using the new dataset.

Also disclosed is the method as described herein, wherein the calculating is performed automatically or upon request.

Also disclosed is the method as described herein, wherein the popPK model is used to create a dosing regimen for clotting factor administration to a subject in need thereof.

In some embodiments, the method further comprises administering to the subject a clotting factor according to the regimen.

Also disclosed is the method as described herein, wherein the clotting factor is long-acting.

Also disclosed is the method as described herein, wherein the long-acting clotting factor is rFVIIIFc or rFIXFc.

Also disclosed is the method as described herein, wherein (a) the clotting factor is rFVIIIFc and the popPK model includes one or more parameters selected from the group consisting of the parameters in Example 9, 11, and 16 (Table 18, 24, 25, or 33), or (b) the clotting factor is rFIXFc and the popPK model includes one or more parameters selected from the group consisting of the parameters in Example 5 or 7 (Table 10, 13, or 14). Also disclosed is the method as described herein, wherein the clotting factor is rFVIIIFc and the popPK model is generated as disclosed in Examples 9, 11, 16, or any combinations thereof. Also disclosed is the method as described herein, wherein one or more parameters for the popPK model are selected from the group consisting of the parameters in Table 18, 24, 25, 33, and any combinations thereof. Also disclosed is the method as described herein, wherein the clotting factor is rFIXFc and the popPK model is generated as disclosed in Example 5, 7, or both. Also disclosed is the method as described herein, wherein one or more parameters for the popPK model are selected from the group consisting of the parameters in Table 10, 13, 14, and any combinations thereof.

Some embodiments include a system for producing an improved clotting factor regimen to be administered to a subject in need thereof, the system comprising a web-based application accessible through a web server, wherein the application comprises: (a) a first dataset comprising clotting factor population pharmacokinetic (popPK) information, (b) a second dataset comprising the first dataset and individual clotting factor pharmacokinetic information of a subject, and (c) a first regimen for a subject in need thereof calculated by the application using the dataset of (b), wherein the first regimen has improved predictive accuracy in comparison to a second regimen calculated by the application using the dataset of (a).

Also disclosed is the system, as described herein, wherein the application continuously updates a popPK model based on newly input clotting factor pharmacokinetic information. 122. Also disclosed is the system as described herein, wherein the individual clotting factor pharmacokinetic information of (b) is from the subject of (c) or is from a subject different from the subject of (c).

Some embodiments include a method of producing an improved clotting factor regimen for administration to a subject in need thereof, the method comprising: (a) accessing a web-based application accessible through a web server, the application comprising a first dataset comprising clotting factor population pharmacokinetic (popPK) information, (b) inputting individual clotting factor pharmacokinetic information into the application to create a second dataset, (c) calculating the regimen for the subject in need thereof using the dataset of (b), wherein the calculated regimen has improved predictive accuracy in comparison to a regimen calculated from the dataset of (a), and (d) recording the calculated regimen.

Also disclosed is the method as described herein, which comprises recording the calculated regimen on a computer readable storage medium.

Also disclosed is the method as described herein, wherein the individual clotting factor pharmacokinetic information of (b) is from the subject of (c).

Also disclosed is the method as described herein, wherein the individual clotting factor pharmacokinetic information of (b) is from a subject different from the subject of (c).

The method may further comprises producing the recorded regimen.

The method may further comprise administering the regimen to the subject of (c)

Also disclosed is the method as described herein, wherein the calculating is performed automatically or upon request.

Also disclosed is the system or method described herein, wherein the dataset includes data from the popPK model in Examples 9, 11, 16, or any combinations thereof. Also disclosed is the system or method described herein, wherein the data include one or more parameters for the popPK model selected from the group consisting of the parameters in Table 18, 24, 25, 33, and any combinations thereof. Also disclosed is the system or method described herein, wherein the dataset includes data from the popPK model in Example 5, 7, or both. Also disclosed is the system or method described herein, wherein the data include one or more parameters for the popPK model selected from the group consisting of the parameters in Table 10, 13, 14, and any combinations thereof.

Some embodiments include a method of administering rFVIIIFc to a subject in need thereof, comprising administering to the subject a therapeutic dose of rFVIIIFc at a dosing interval greater than one times longer than the dosing interval required for an equivalent amount of FVIII, wherein the subject is <6 years old or 6 to <12 years old, and wherein the therapeutic dose has at least one pharmacokinetic property, expressed in arithmetic mean with 95% confidence interval, selected from the group consisting of: a terminal half-life of 12.67 (11.23, 14.11) hours, a terminal half-life of 14.88 (11.98, 17.77) hours, a clearance of 3.60 (3.13, 4.07) mL/h/kg, a clearance of 2.78 (2.44, 3.13) mL/h/kg, an incremental recovery of 1.92 (1.80, 2.04) IU/dL per IU/kg, an incremental recovery of 2.44 (2.07, 2.80) IU/dL per IU/kg, a mean recovery time of 17.24 (15.40, 19.07) hours, a recovery time of 20.90 (17.06, 24.74) hours, a volume of distribution at steady state of 58.58 (54.90, 62.27) mL/kg, a volume of distribution at steady state of 52.13 (45.25, 59.01) mL/kg, a dose normalized area under the concentration-time curve of 30.04 (26.45, 33.63) IU*h/dL per IU/kg, and a dose normalized area under the concentration-time curve of 41.87 (34.00, 49.75) IU*h/dL per IU/kg for the older cohort.

Also disclosed is the method as described herein, the medium as described herein, or the system as described herein, wherein the long-acting FIX polypeptide comprises a FIX portion and a second portion.

Some embodiments include the method as described herein, wherein the long-acting FVIII polypeptide comprises a FVIII portion and a second portion. Also disclosed is the method as described herein, wherein the second portion is albumin or a fragment thereof or an immunoglobulin constant region or a portion thereof. Some embodiments include the method as described herein, wherein the immunoglobulin constant region or a portion thereof comprises a neonatal Fc receptor (FcRn) or an Fc domain.

Some embodiments include the method as described herein, wherein the second portion comprises a human Fc. Also disclosed is the method as described herein, wherein the second portion comprises a mutant Fc.

Also disclosed is the method as described herein, wherein the long-acting FIX polypeptide or the long-acting FVIII polypeptide is in the form of a hybrid comprising a second polypeptide in association with said chimeric polypeptide, wherein said second polypeptide comprises a FcRn BP.

Some embodiments include the method as described herein, wherein the Factor IX is a human Factor IX. Also disclosed is the method as described herein, wherein the FIX is a mutant Factor IX. Some embodiments include the method as described herein, wherein said Factor VIII is human Factor VIII. Also disclosed is the method as described herein, wherein said Factor VIII has a full or partial deletion of the B domain.

BRIEF DESCRIPTION OF DRAWINGS/FIGURES

FIG. 1 shows FIXFc study design and CONSORT chart. Efficacy data that were collected outside of the efficacy period were not included in the efficacy analyses. *PK subgroup dosed with rFIX followed by PK assessment and washout (greater than or equal to 5 days) prior to rFIXFc dosing for PK evaluation. rFIX sampling was done as follows: pre-injection, 10 (±2) min, 1 hour (±15 min), 3 hr (±15 min), 6 hr (±15 min), 24 (±2) hr, 48 (±2) hr, 72 (43) hr, and 96 (±3) hr (4 d) from the start of the injection. rFIXFc sampling was done as follows: pre-injection, 10 (±2) min, 1 hour (±15 min), 3 hr (±15 min), 6 hr (±15 min), 24 (±2) hr, 48 (±2) hr, 96 (±3) hr (4 d), 144 (±3) hr (6 d), 168 (±3) hr (7 d), 192 (±3) hr (8 d), and 240 (±3) hr (10 d) from the start of the injection. Infusion was within 10 minutes. Blood samples were collected over 96 hours for each subject. A repeat PK assessment of rFIXFc was also performed at Week 26. ED=exposure day; PK=pharmacokinetics.

FIGS. 2A-C show study design for phase ½a (B) and phase 3 (C) clinical trials of a long-acting FIXFc polypeptide (i.e., rFIXFc). FIG. 2C shows rFIXFc sampling schemes.

FIG. 3 shows a summary of Arm 1 sequential dosing and PK sampling of a long-acting FIX polypeptide (i.e., rFIXFc).

FIG. 4 shows a diagram of three-compartment pharmacokinetic model of a long-acting FIX polypeptide (i.e., rFIXFc). IV intravenous $V_1$ volume of compartment 1, $V_2$ volume of compartment 2, $V_3$ volume of compartment 3, $Q_2$ inter-compartmental clearance between compartments 1 and 2, $Q_3$ inter-compartmental clearance between compartments 1 and 2.

FIG. 5A shows pairwise comparison of baseline and repeat pharmacokinetics CL estimates for the base model with IOV for a long-acting FIX polypeptide (i.e., rFIXFc). FIG. 5B shows pairwise comparison of baseline and repeat pharmacokinetics $V_1$ estimates for the base model with IOV. Dashed line represents the mean. CL clearance, IOV inter-occasion variability, PK pharmacokinetic, $V_1$ volume of compartment 1.

FIG. 6 shows individual PK parameters versus body weight (BW) of a long-acting FIX polypeptide (i.e., rFIXFc).

FIGS. 7A-D show goodness-of-fit plots of the final model of FIX activity predicted by the population or individual PK model compared to observed FIX activity. The solid line is the unit line; dashed line represents the linear regression line in (FIG. 7A) and (FIG. 7B) and the LOESS smoother in (FIG. 7C) and (FIG. 7D); DV is observed FIX activity (adjusted for baseline activity and residual decay) and unit is IU/dL (%); PRED is the population FIX activity prediction and unit is IU/dL; IPRED is the individual FIX activity prediction and unit is IU/dL; CWRES is conditional weighted residual; TIME is the time after dose and unit is hour. DV is dependent variable.

FIGS. 8A-D show Visual Predictive Check (VPC) plots of the population PK model for 50 IU/kg or 100 IU/kg doses of a long-acting FIX polypeptide (i.e., rFIXFc). Visual predictive check for the final model derived from the modeling dataset (8A and 8B), and the model derived from the full dataset (8C and 8D). The solid and dashed lines are $10^{th}$, $50^{th}$ and $90^{th}$ percentiles of the observation (solid) and simulation (dashed), respectively. FIGS. 8A and 8C represent dose groups of 50 IU/kg. FIGS. 8B and 8D represent dose groups of 100 IU/kg.

Figure 12:
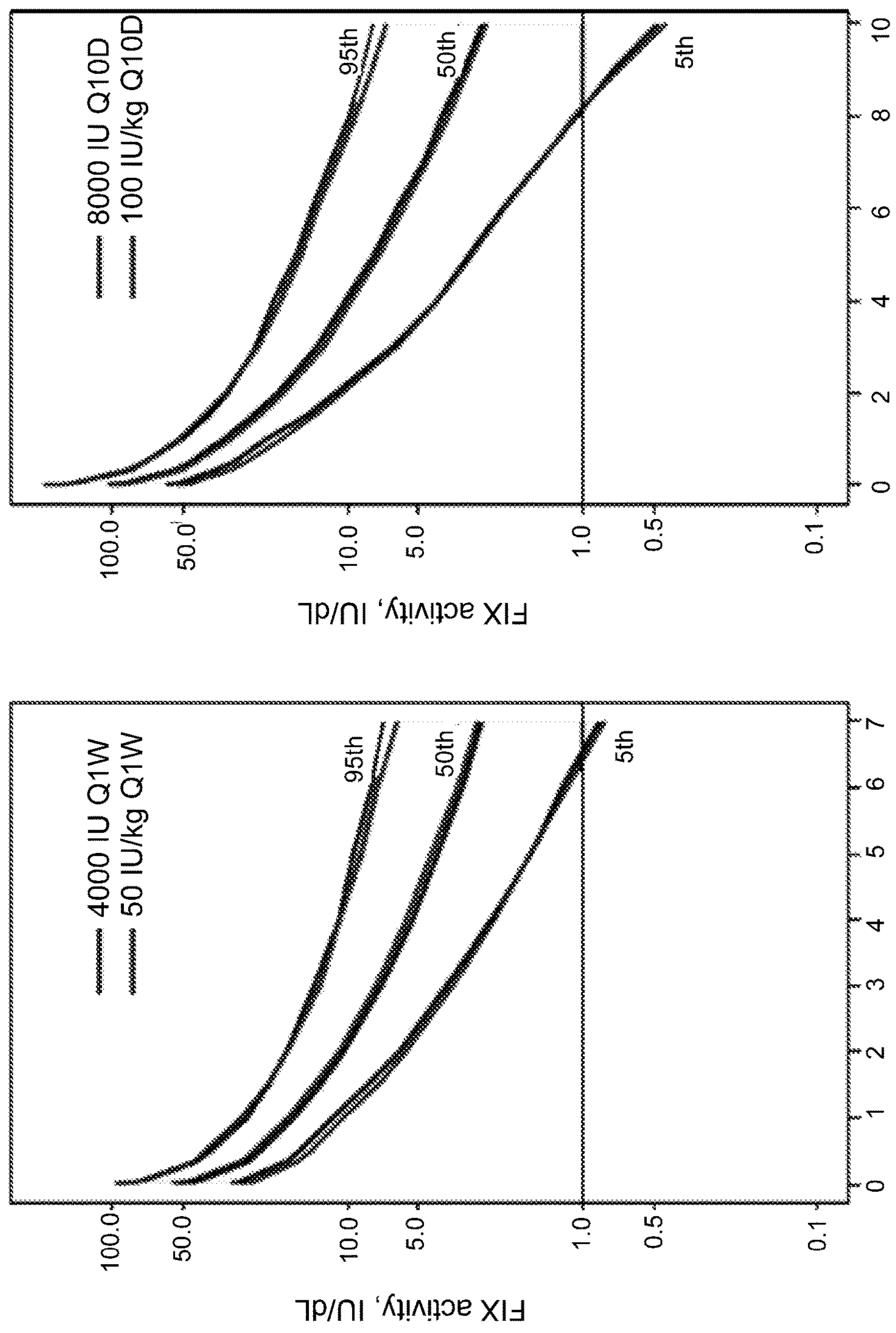

FIG. 12 shows a simulation of steady-state FIX activity vs. time profile for a long-acting FIX polypeptide (i.e., rFIXFc) comparing 50 IU/kg vs 4000 IU once weekly and 100 IU/kg vs 8000 IU every 10 days in 5th to 95th percentile of the population.

FIG. 13 shows a proposed output for individual PK assessment of a long-acting FIX polypeptide (i.e., rFIXFc) or a long-acting FVIII polypeptide (i.e., rFVIIIFc).

Figure 14:
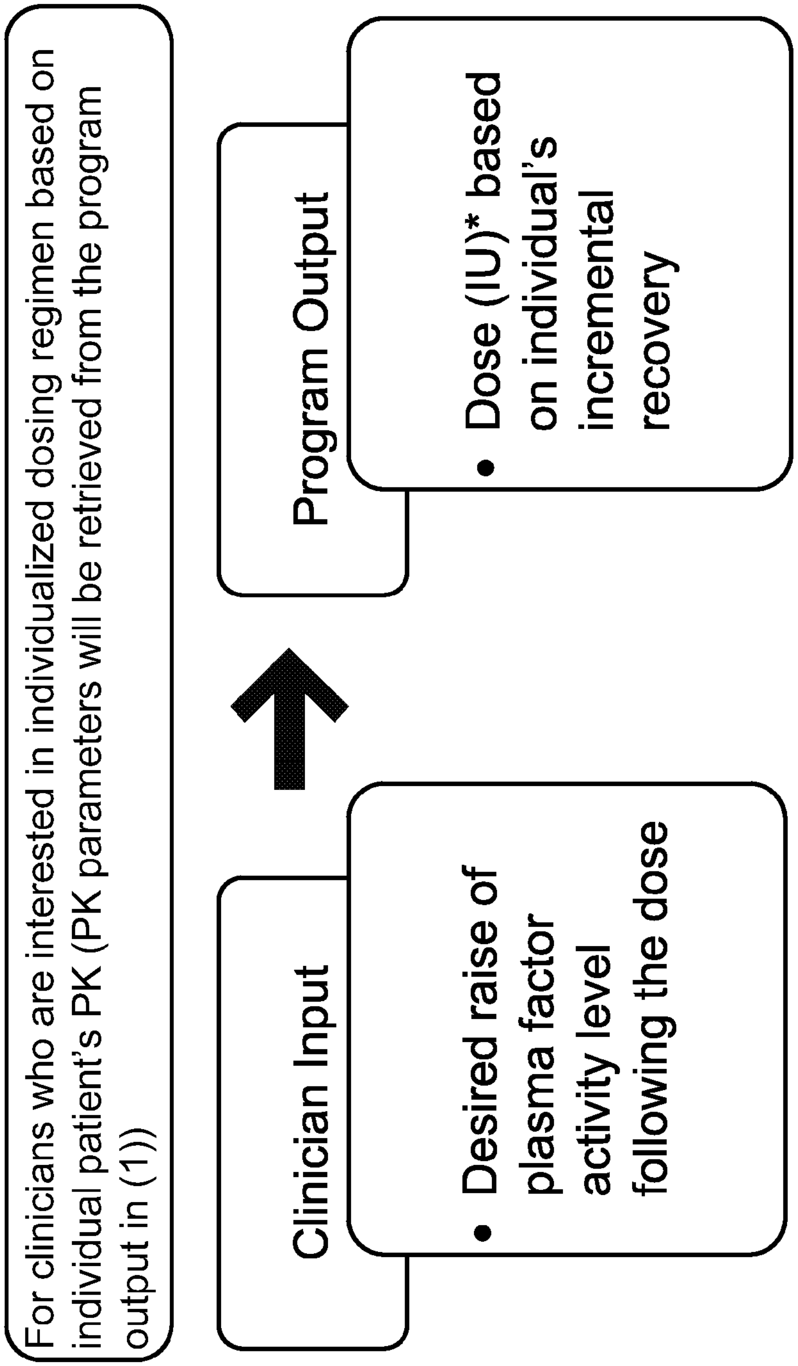

FIG. 14 shows a proposed output for individualized dosing regimen selection for episodic treatment of a long-acting FIX polypeptide (i.e., rFIXFc) or a long-acting FVIII polypeptide (i.e., rFVIIIFc).

Figure 15:
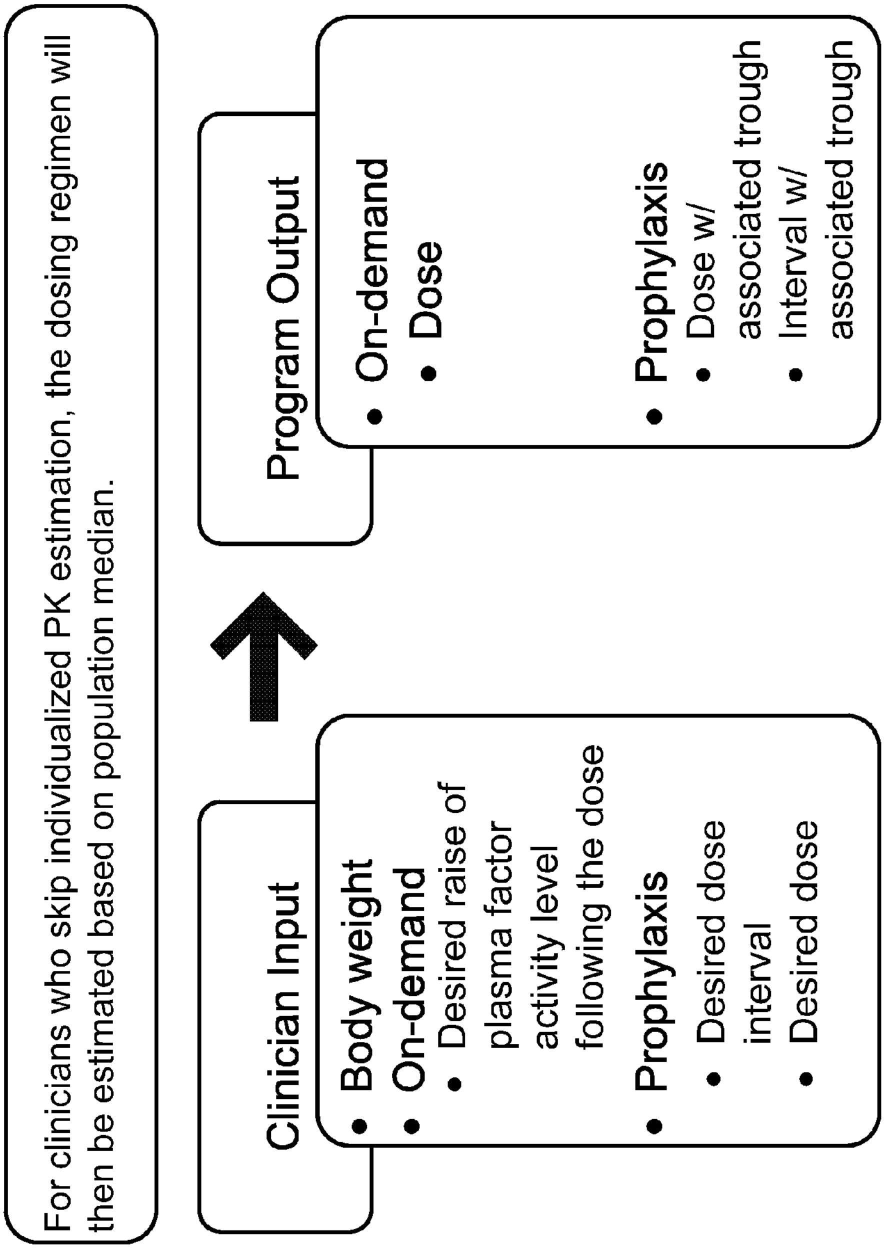

FIG. 15 shows a proposed output for dosing regimen selections without individualized PK assessment of a long-acting FIX polypeptide (i.e., rFIXFc) or a long-acting FVIII polypeptide (i.e., rFVIIIFc).

FIG. 16 shows another proposed output for dosing regimen selections without individualized PK assessment of a long-acting FIX polypeptide (i.e., rFIXFc).

Figure 17:
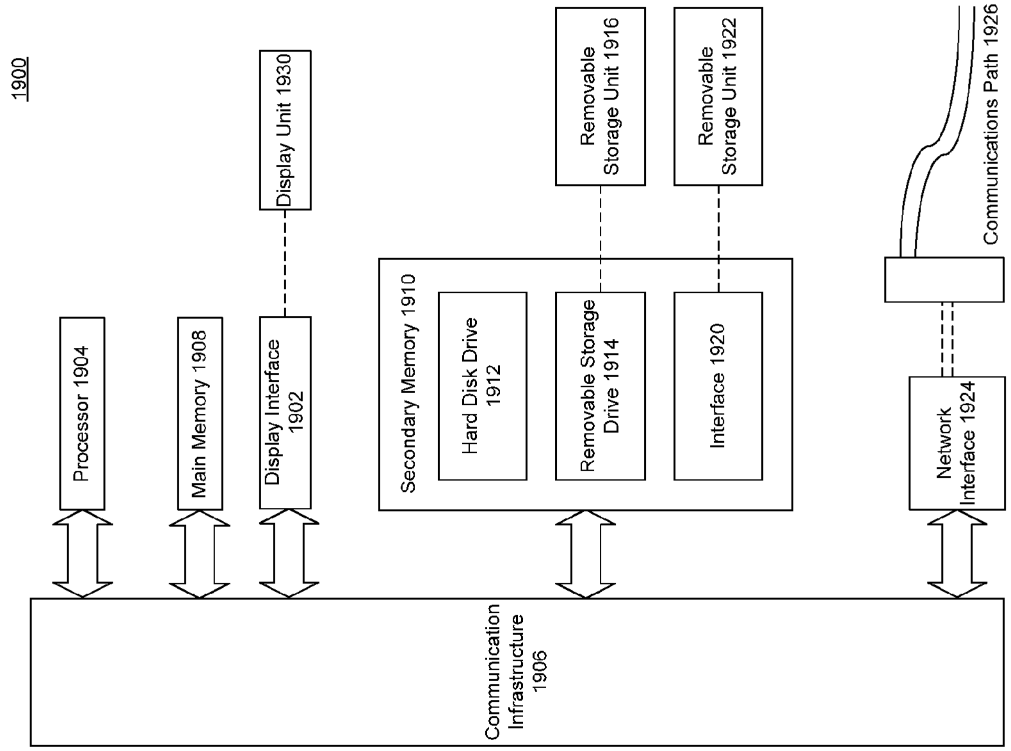

FIG. 17 shows an example computer system that can be used in embodiments for a long-acting FIX polypeptide (i.e., rFIXFc) or a long-acting FVIII polypeptide (i.e., rFVIIIFc).

Figure 18:
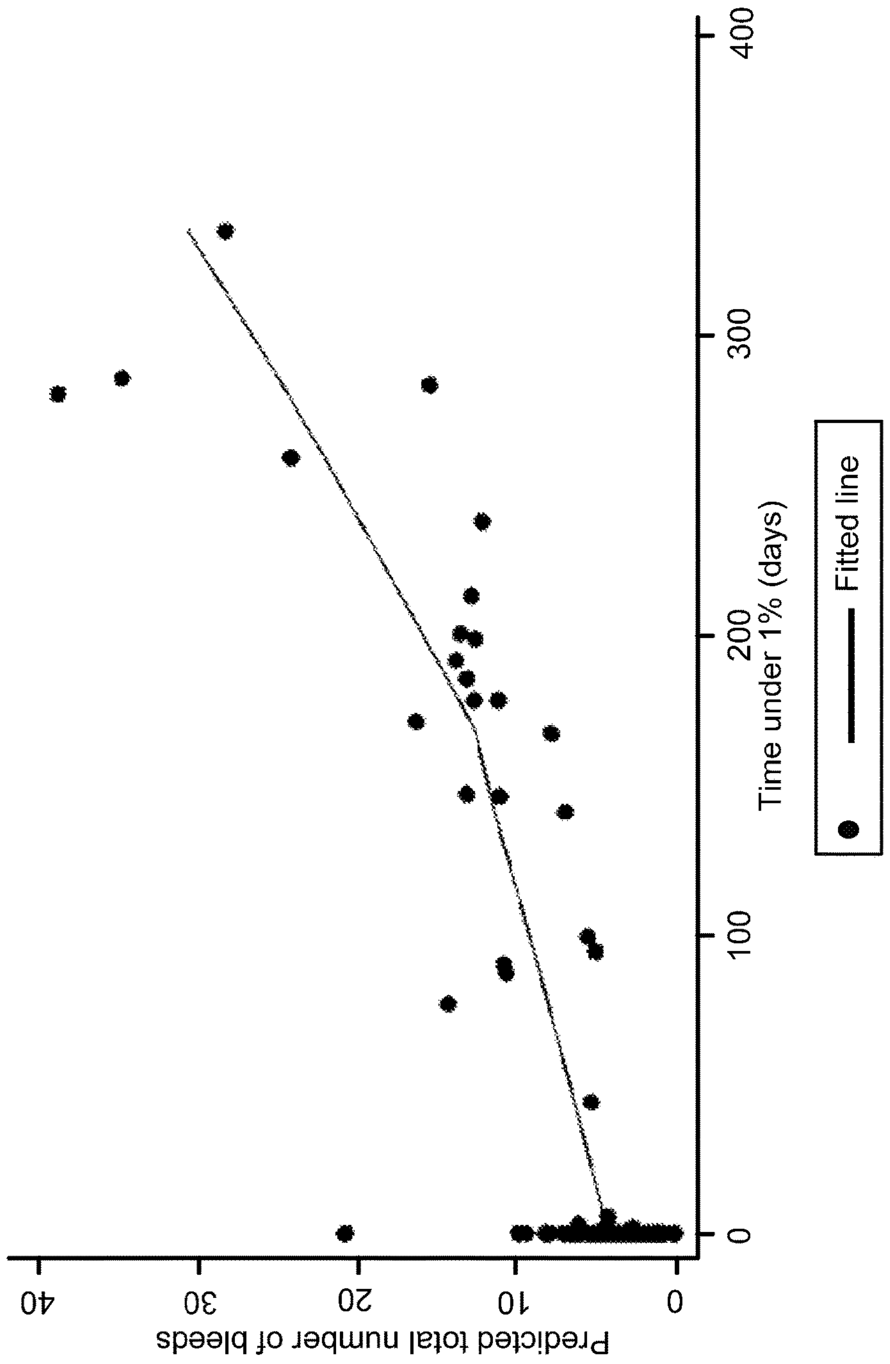

FIG. 18 shows a graph plotting the predicted total number of bleeds vs. time under 1% FIX activity level of a long-acting FIX polypeptide (i.e., rFIXFc).

Figure 19:
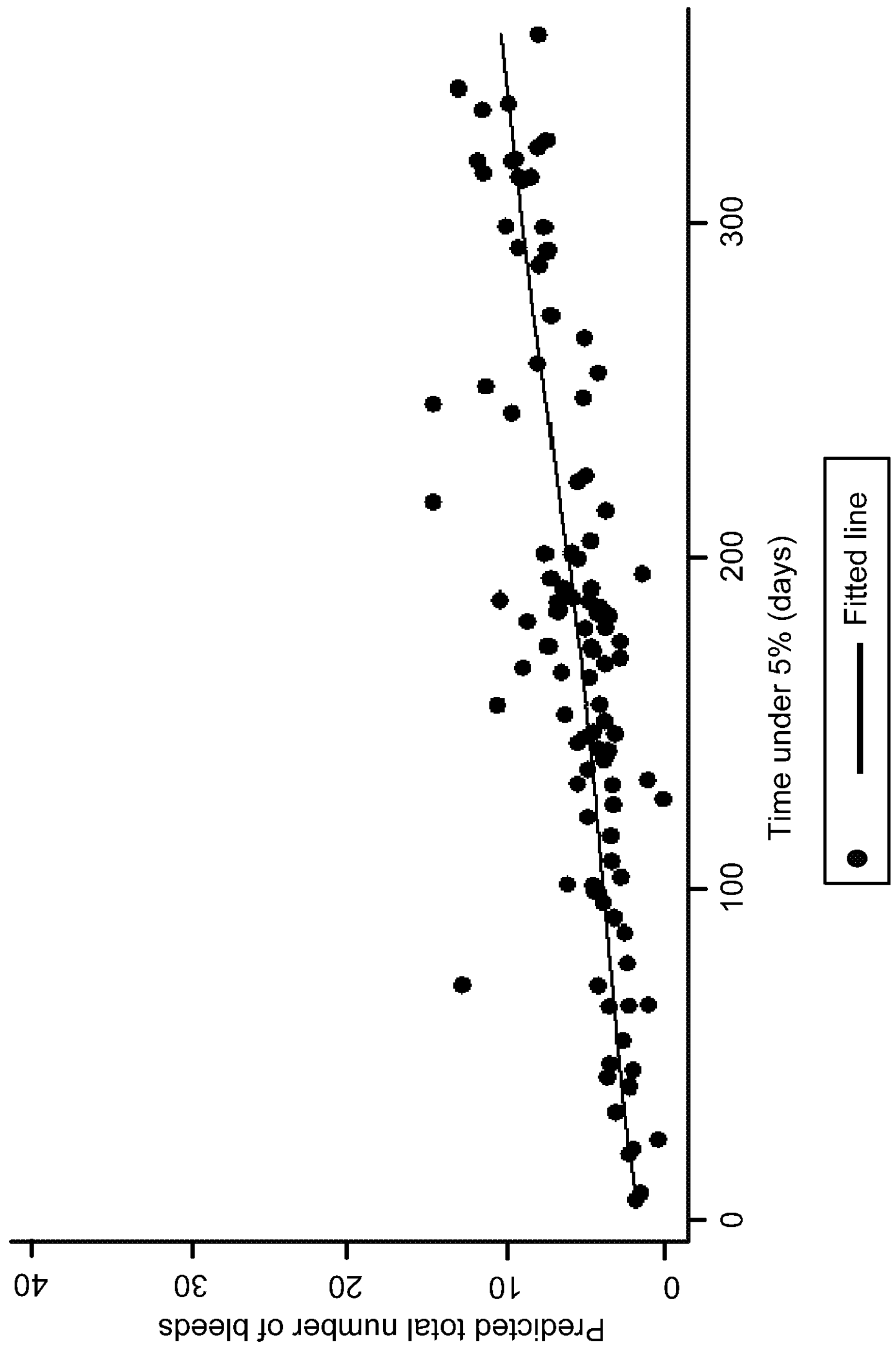

FIG. 19 shows a graph plotting the predicted total number of bleeds vs. time under 5% FIX activity level of a long-acting FIX polypeptide (i.e., rFIXFc).

Figure 20:
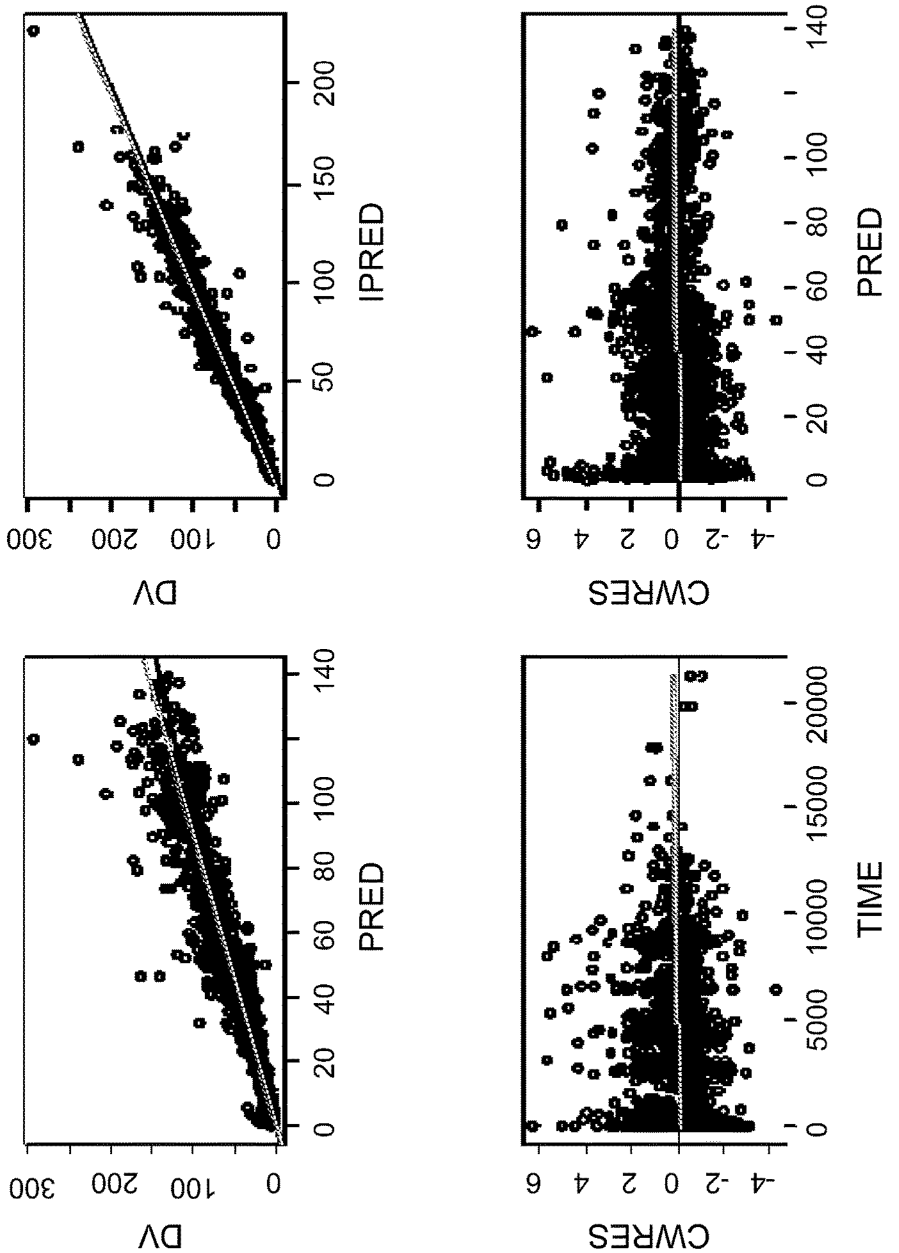

FIG. 20 shows goodness-of-fit plots for the full dataset model of a long-acting FIX polypeptide (i.e., rFIXFc). The solid line is the unit line; dashed line represents the linear regression line in (A) and (B) and the LOESS smoother in (C) and (D); DV is observed FIX activity (adjusted for baseline activity and residual decay) and unit is IU/dL (%); PRED is the prediction by population PK parameter estimates and unit is IU/dL; IPRED is the prediction by individual PK parameter estimates and unit is IU/dL; CWRES is conditional weighted residual; TIME unit is hour; and DV is dependent variable.

FIG. 21 shows details on the design of the sequential PK subgroup (Arm 1) dosing and PK sampling of a long-acting FVIII polypeptide (i.e., rFVIIIFc).

Figure 22:
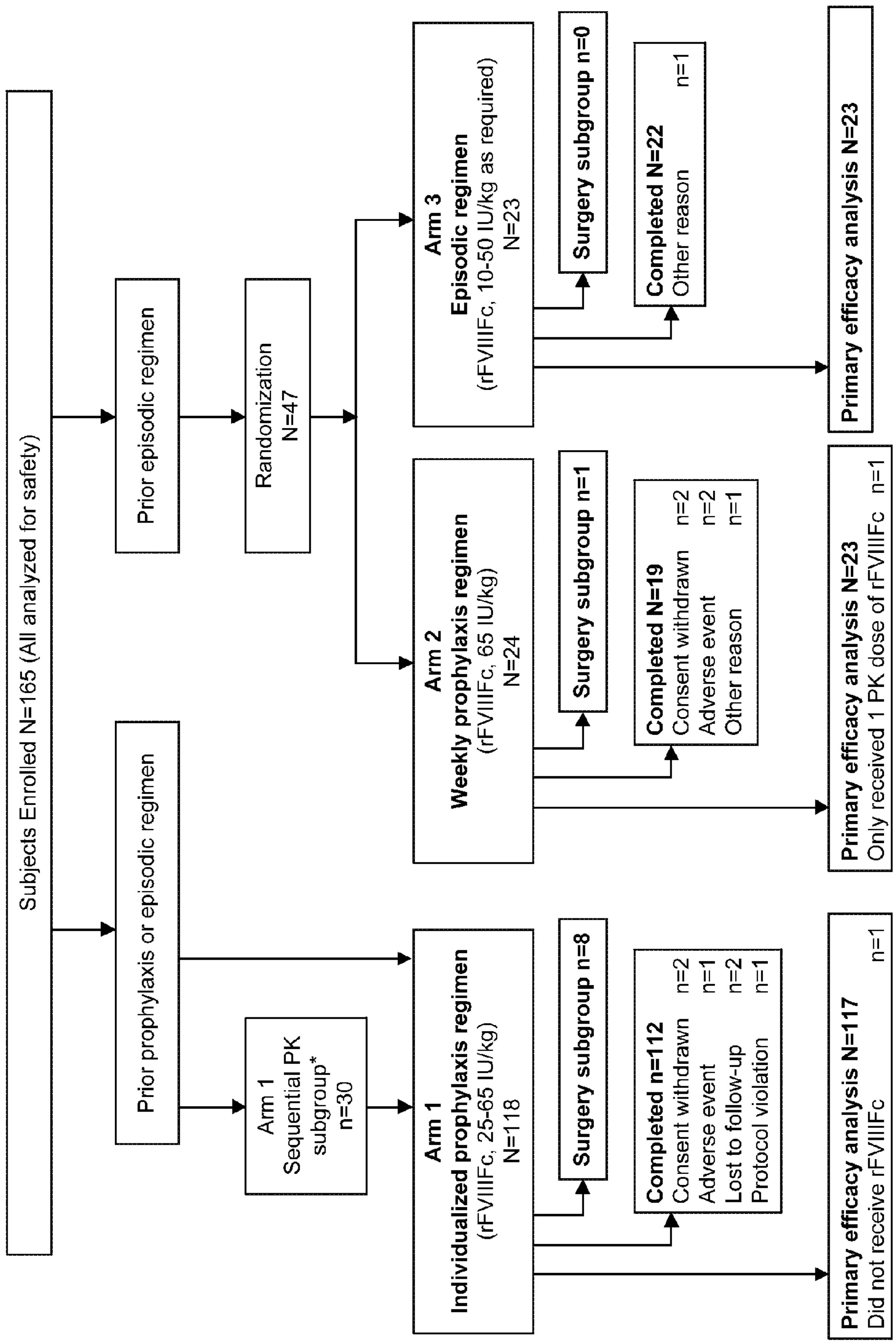

FIG. 22 shows patient disposition enrolled in the A-LONG study (N=165) for a long-acting FVIII polypeptide.

Figure 23:
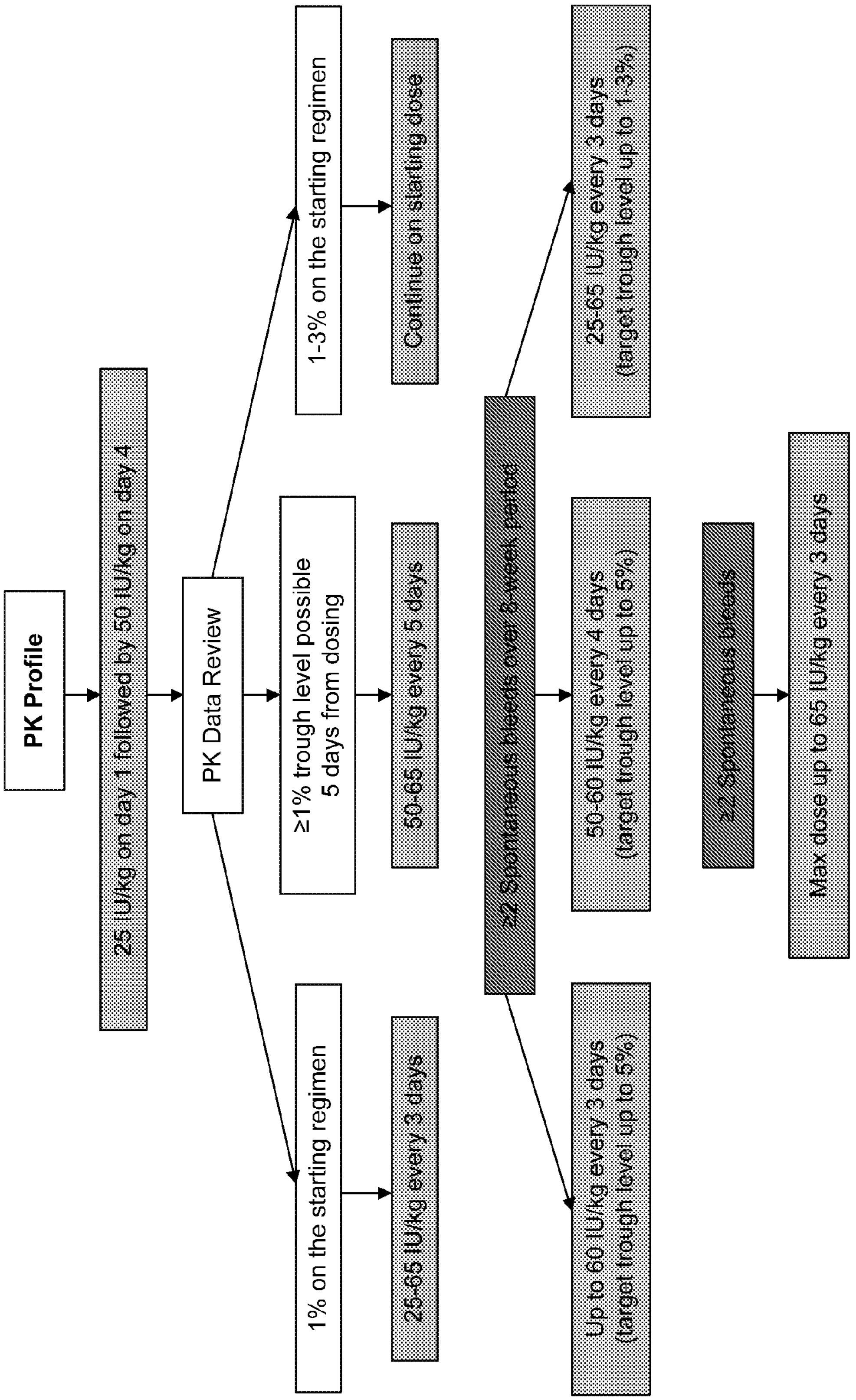

FIG. 23 shows dose modification in Arm 1 (individualized prophylaxis) for a long-acting FVIII polypeptide.

Figure 24:
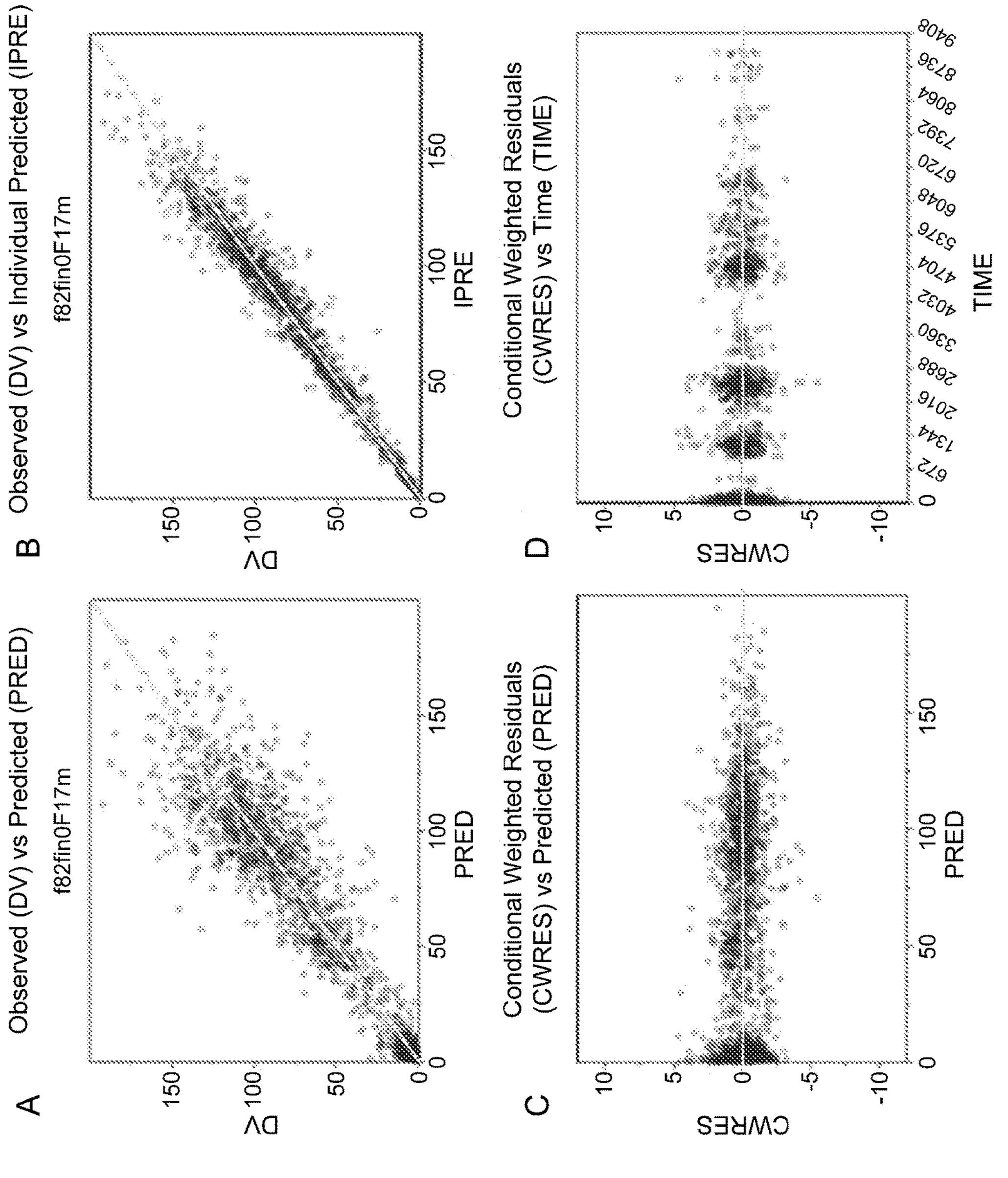

FIGS. 24A-D show goodness of fit diagnostic plots for the two-compartment model of pharmacokinetics of long-acting rFVIIIFc. FIG. 24A shows observed (DV) v. predicted (PRED). FIG. 24B shows observed (DV) v. individual predicted (IPRE). FIG. 24C shows conditional weighted residuals (CWRES) v. Predicted (PRED). FIG. 24D shows conditional weighted residuals (CWRES) v. Time (TIME).

Figure 25:
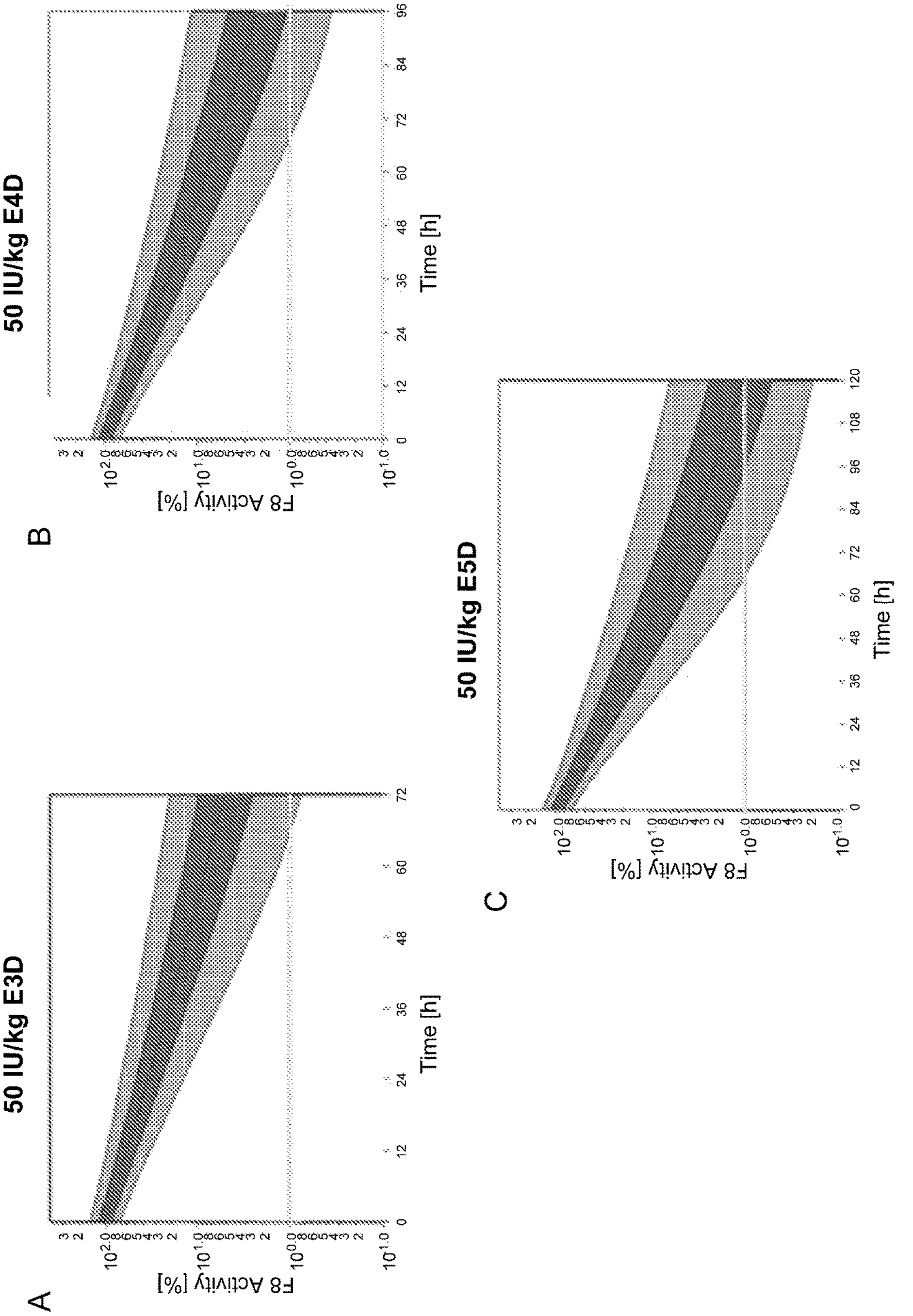

FIGS. 25A-C show the predicted steady-state activity profiles of selected rFVIIIFc prophylaxis dosing regimens. The line in the middle represents the median; the dark shaded area covers the 25th to 75th percentiles; the light shaded area covers the 5th to 95th percentiles.

FIG. 25A shows a dosing regimen of 50 IU/kg at every 3 days. FIG. 25B shows a dosing regimen of 50 IU/kg at every 4 days. FIG. 25C shows a dosing regimen of 50 IU/kg at every 5 days.

Figure 26:
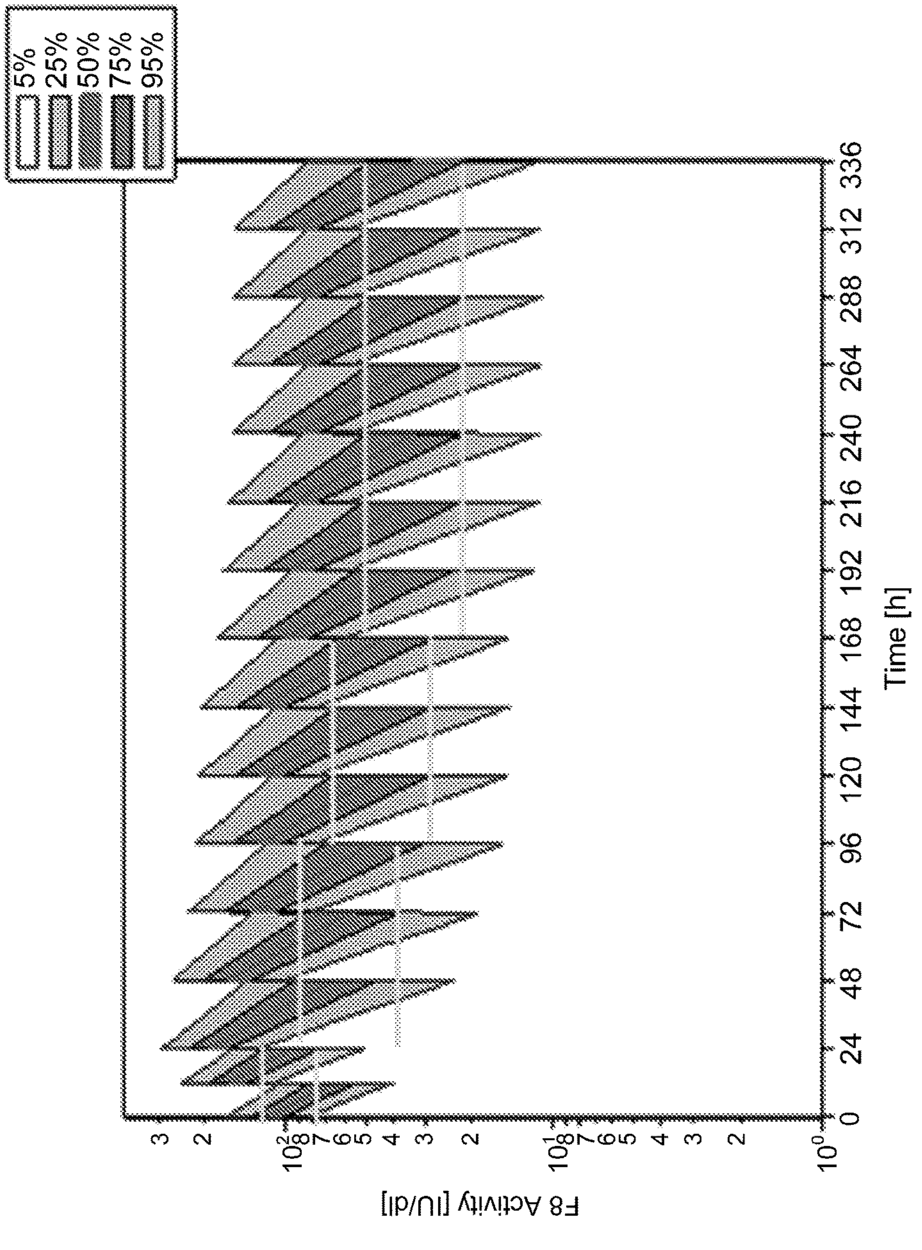

FIG. 26 shows the predicted FVIII activity for the hypothetical perioperative dosing regimen in Table 21 for a long-acting FVIII polypeptide (i.e., rFVIIIFc). The middle line shows the 50 percentile. The light shaded areas represent the 5th to 25th percentile and 75th to 95th percentile. The dark shaded areas represent the 25th to 50th percentile and the 50th to 75th percentile.

Figure 27:
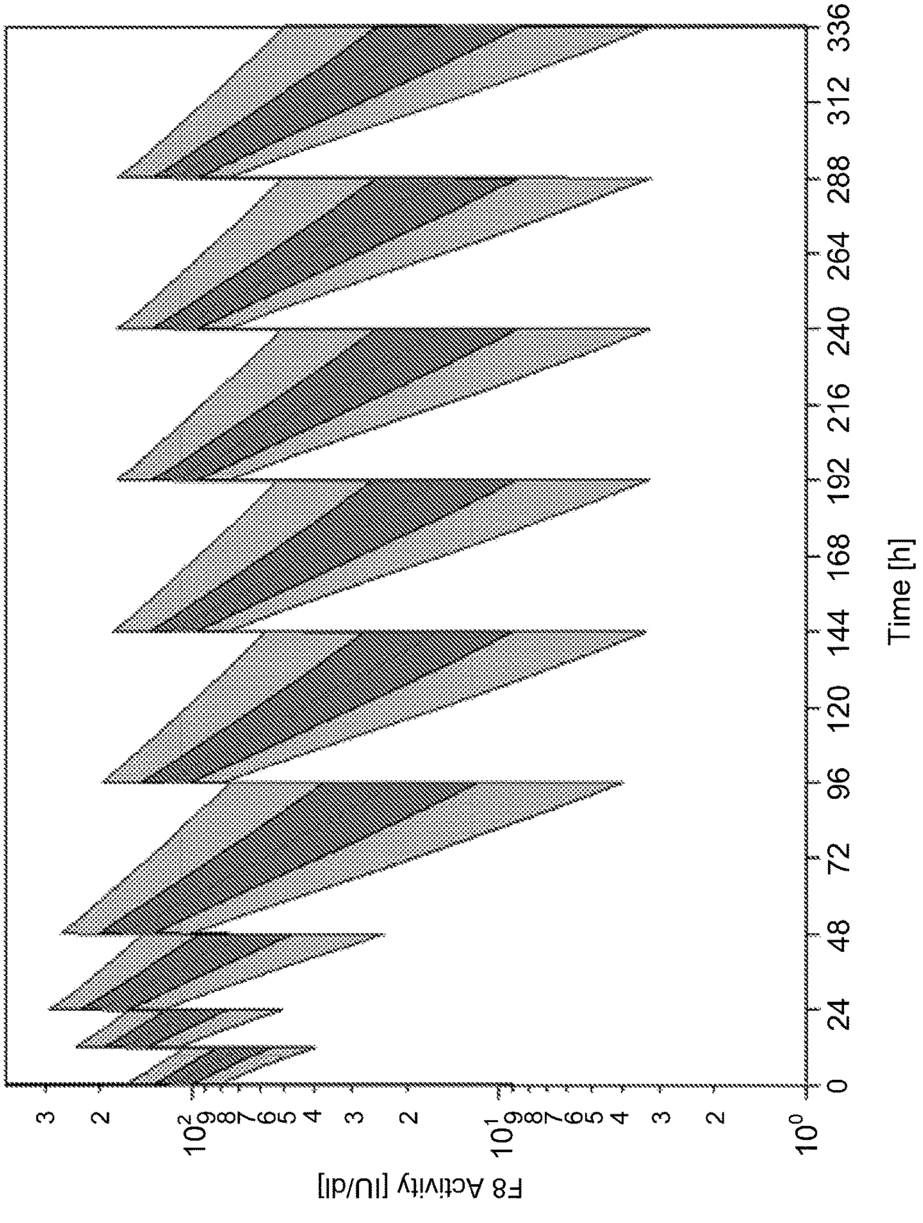

FIG. 27 shows the predicted FVIII activity for the hypothetical perioperative dosing regimen in Table 22 for a long-acting FVIII polypeptide (i.e., rFVIIIFc).

Figure 28:
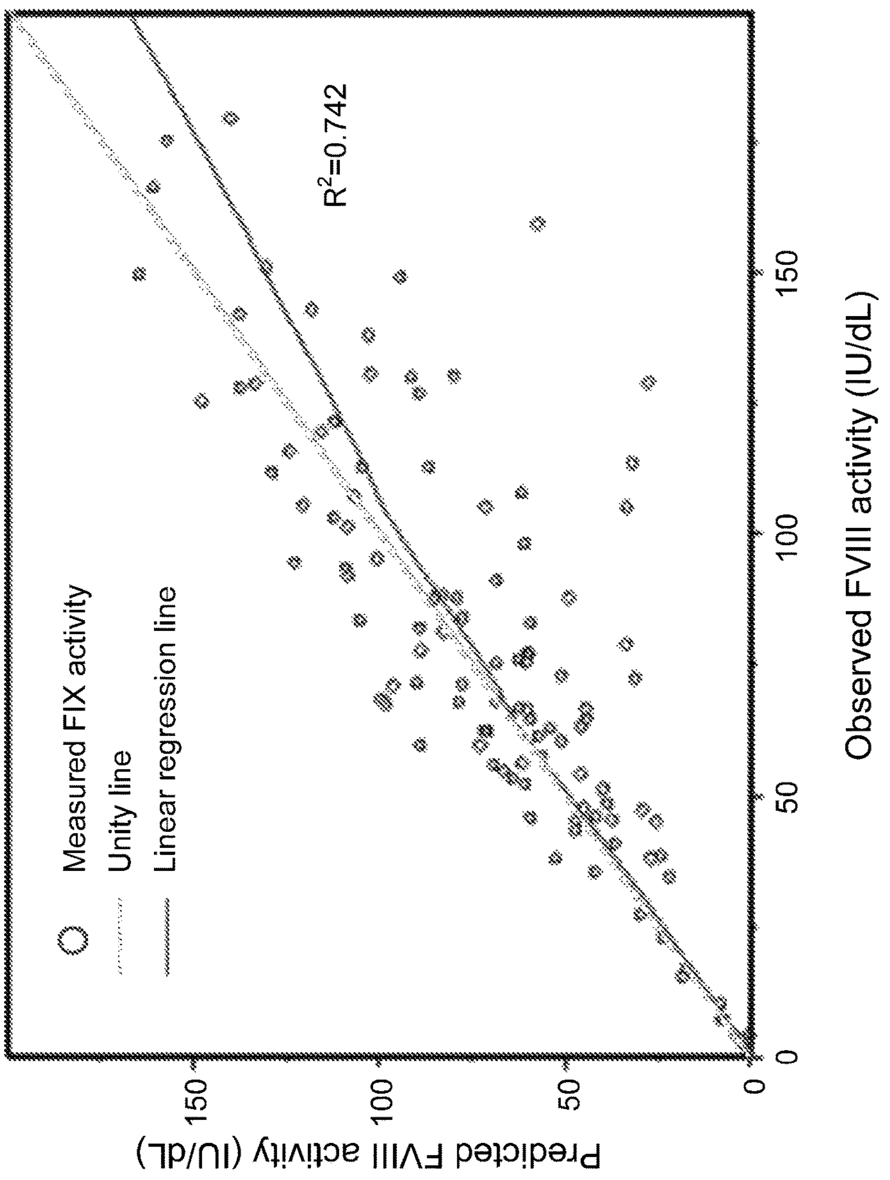

FIG. 28 is a representative plot comparing the simulated and observed FVIII activities within the first 21 days after the first rFVIIIFc surgical dose (n=13; 9 major surgeries, 4 minor surgeries). The upper line represents the line of identity (unity line); the lower line (linear regression line) is the nonparametric fit of the data.

FIG. 29 shows another proposed output for dosing regimen selections without individualized PK assessment for a long-acting FVIII polypeptide.

FIG. 30A-D show the goodness of fit diagnostics of the final model for rFVIIIFc.

Figure 30:
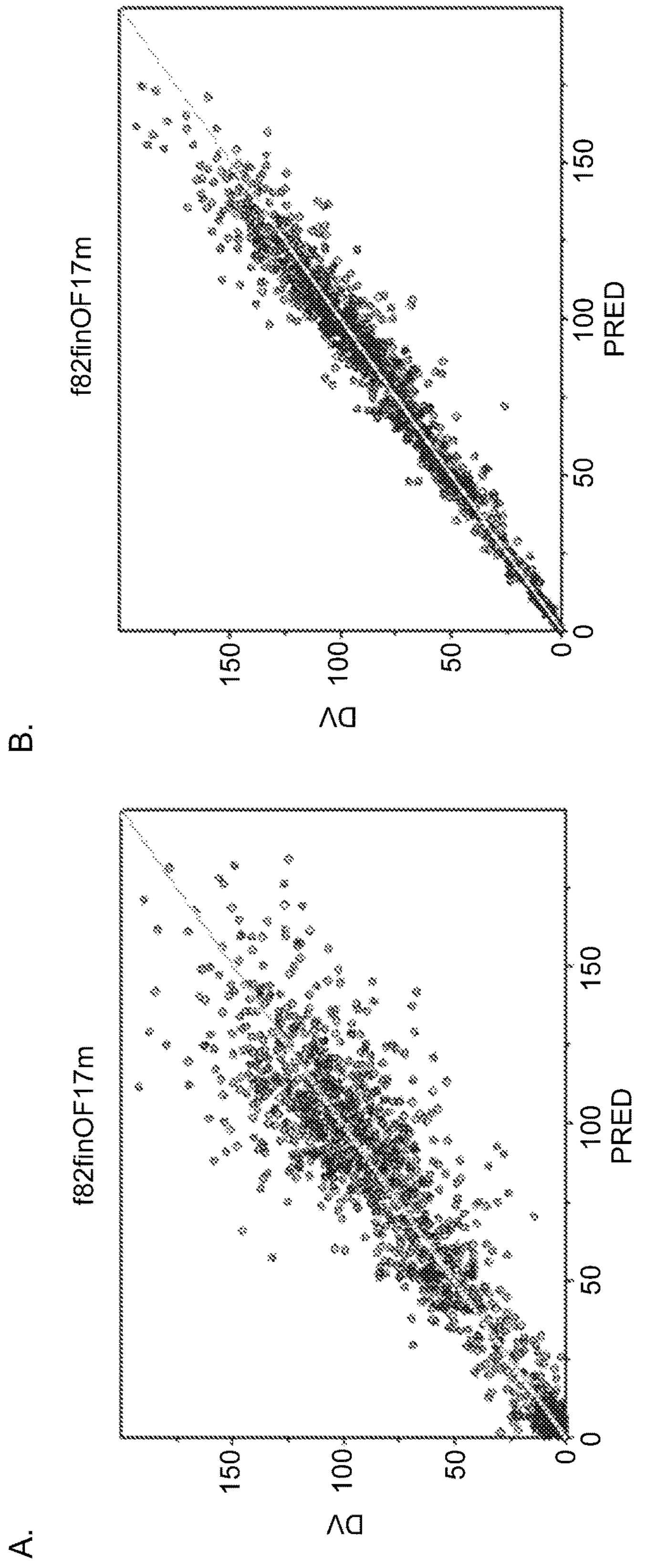
Figure 30:
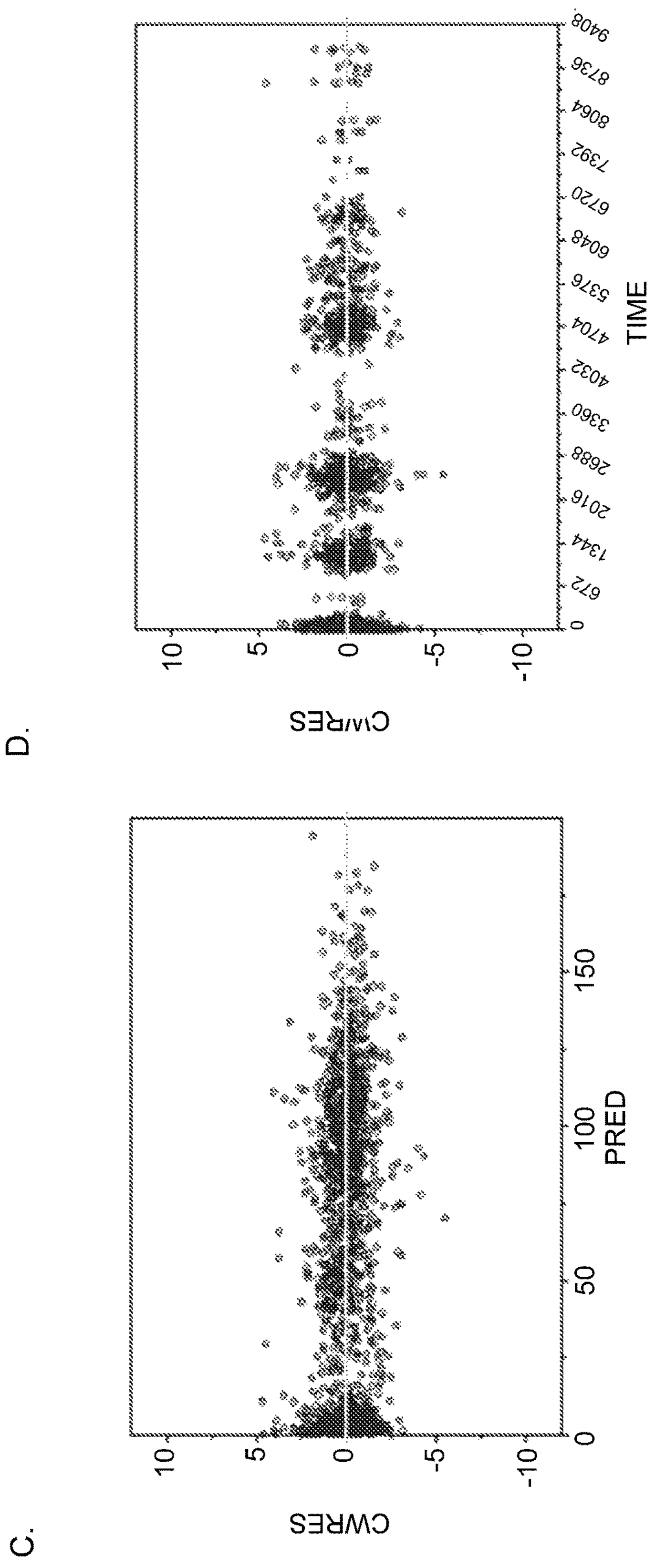

FIG. 30A shows Observed (DV) vs Predicted (PRED), and FIG. 30B shows Observed (DV) vs Individual Predicted (IPRE). FIG. 30C shows Conditional Weighted Residuals (CWRES) vs Predicted (PRED) for a long-acting FVIII polypeptide (i.e., rFVIIIFc), and FIG. 30D shows Conditional Weighted Residuals (CWRES) vs Time (TIME) for a long-acting FVIII polypeptide (i.e., rFVIIIFc).

Figure 31:
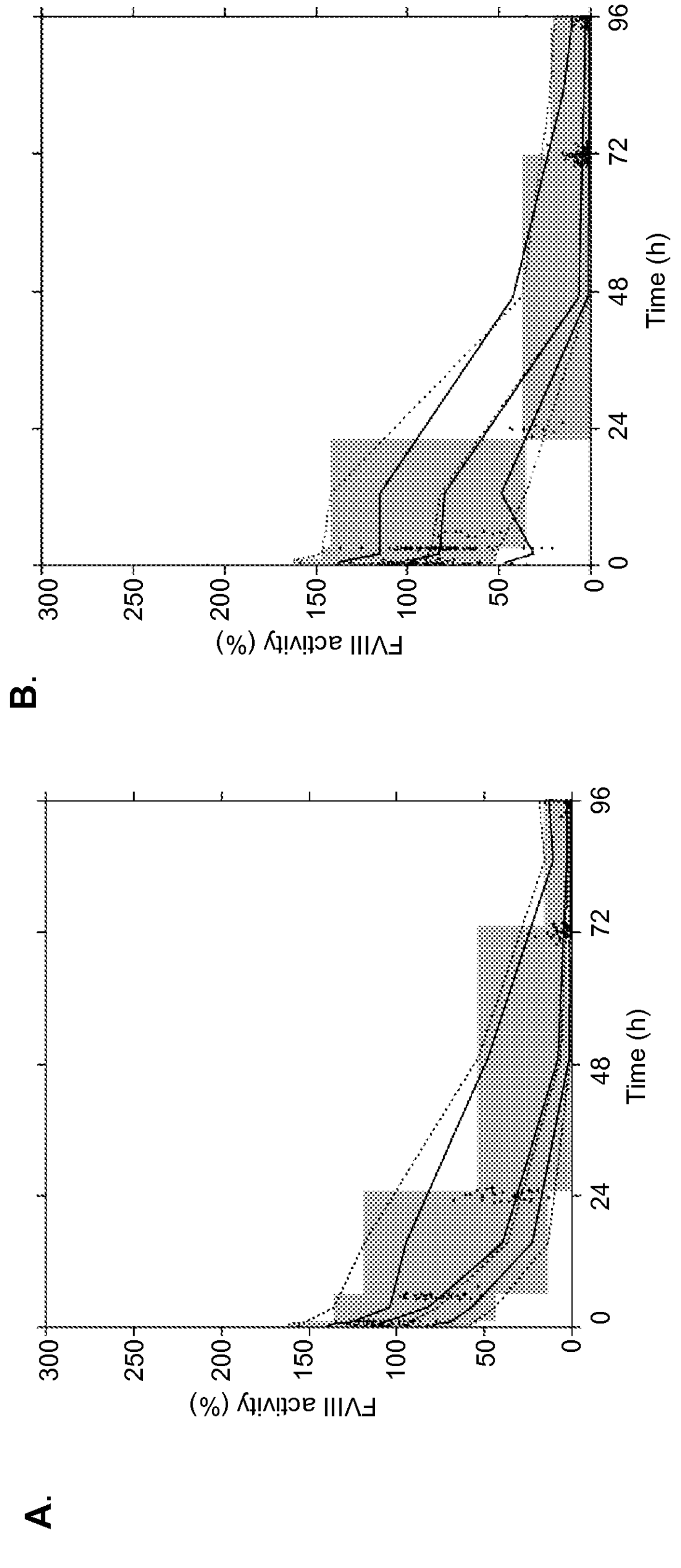
Figure 31:
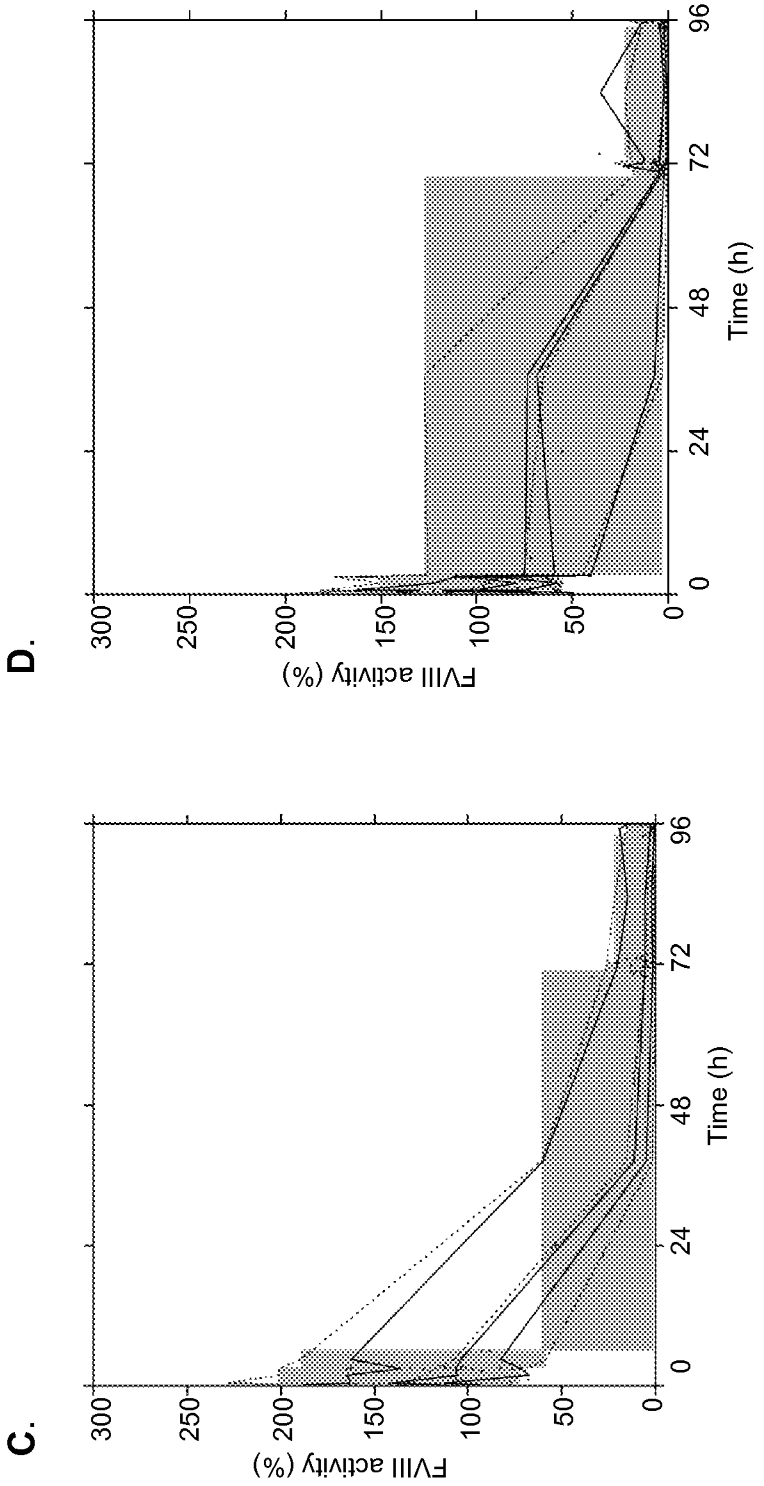
Figure 31:
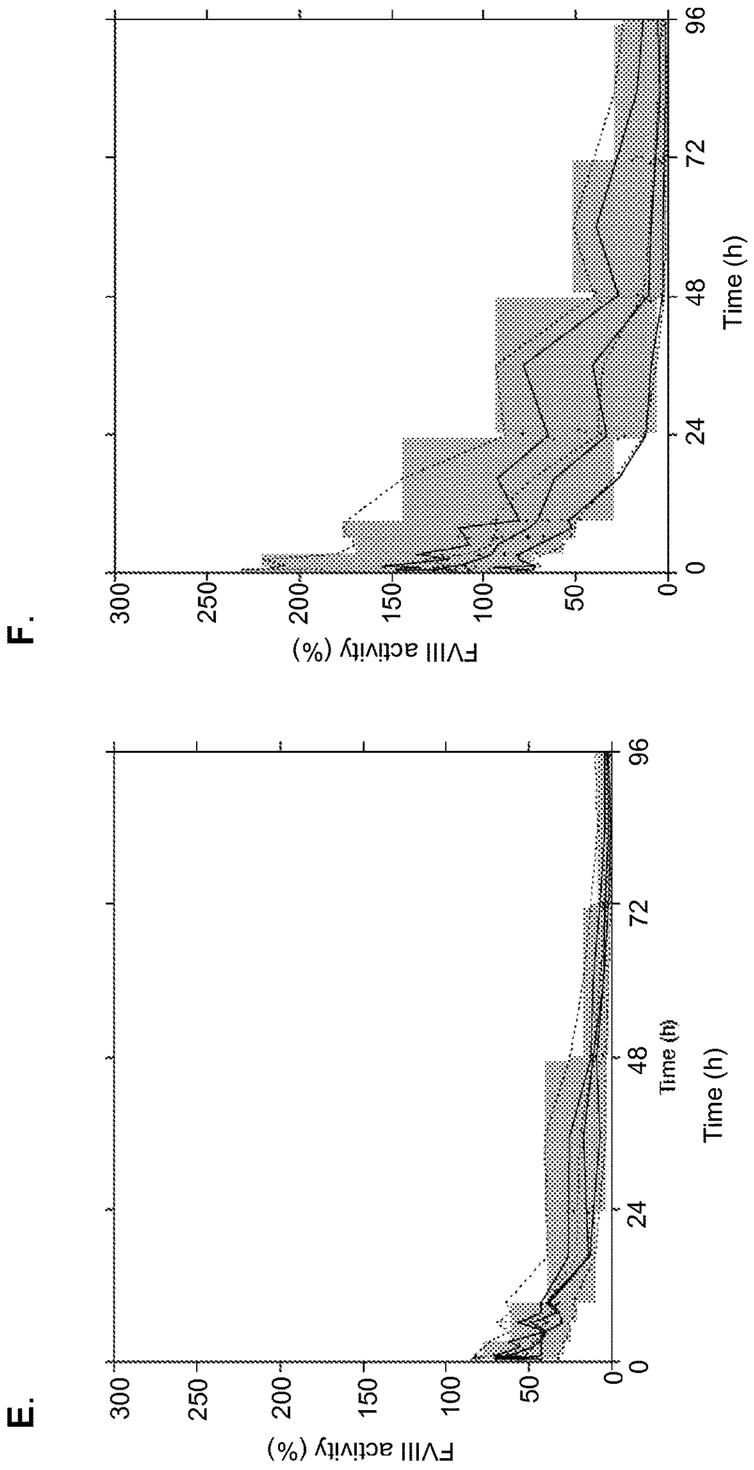

FIG. 31A shows the visual predictive check (VPC) results (Baseline PK profiles) of the final model for Arm 1 sequential PK group. FIG. 31B shows the visual predictive check (VPC) results (Baseline PK profiles) of the final model for Arm 1 non-sequential PK group. For FIGS. 31A and 31B, the 5th, 50th (median), and 95th percentiles of simulated data are represented by the dotted lines and gray shaded area, while the 5th, 50th (median), and 95th percentiles of the observed data are presented as solid lines and solid circles. FIG. 31C shows VPC results (Baseline PK profiles) of the final model for Arm 2 (phase 3 study) rFVIIIFc. FIG. 31D shows VPC results (Baseline PK profiles) of the final model for Arm 3 (phase 3 study) rFVIIIFc. FIG. 31E shows VPC results (Baseline PK profiles) of the final model for Cohort A (phase ½a study) rFVIIIFc. FIG. 31F shows VPC results (Baseline PK profiles) of the final model for Cohort B (phase ½a study) rFVIIIFc. For FIGS. 31C-F, the 5th, 50th (median), and 95th percentiles of simulated data are represented by the dotted lines and gray shaded area, while the 5th, $50^{th}$, and 95th percentiles of the observed data are presented as solid lines and solid circles.

Figure 32:
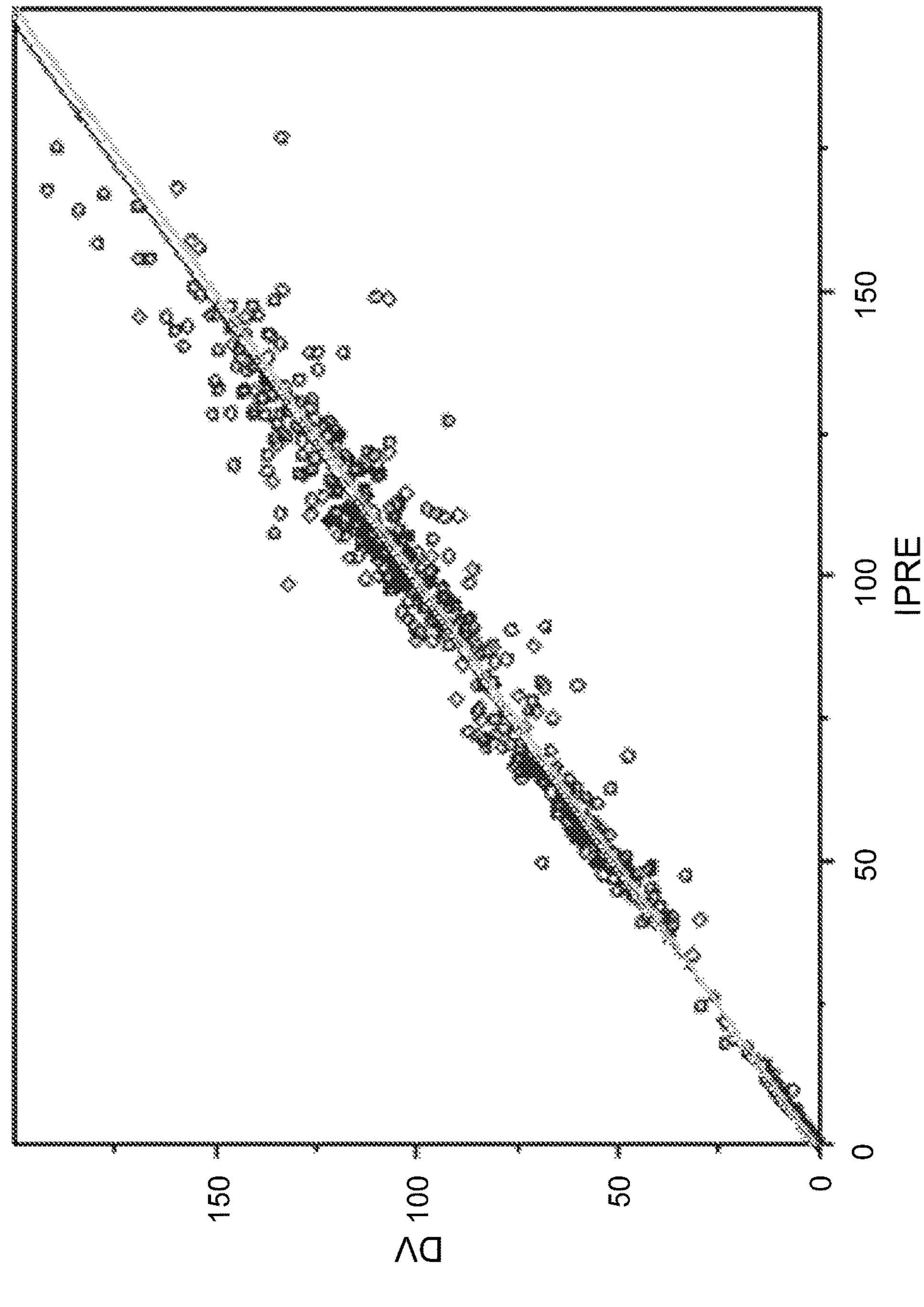

FIG. 32 shows the external validation of the rFVIIIFc model. Observed (DV) vs Individual Predicted (IPRE) values from the validation set only.

FIG. 33A-B shows the goodness of fit diagnostics of the base model for ADVATE®. FIG. 33A shows Observed (DV) vs Individual Predicted (IPRE); FIG. 33B shows Conditional Weighted Residuals (CWRES) vs Predicted (PRED).

Figure 34:
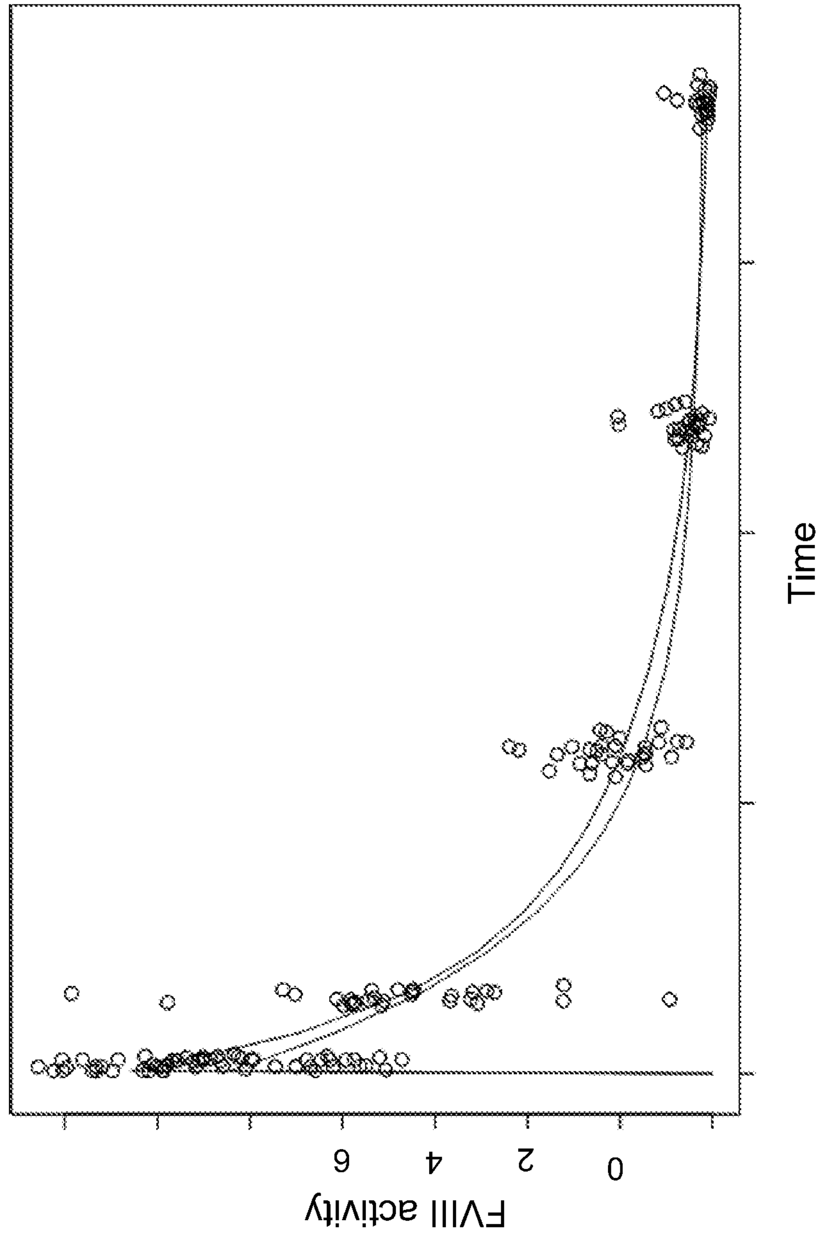

FIG. 34 shows an ADVATE® model comparison. The lower line in the graph is the current model; the upper line is the model reported by Bjorkman et al. Superimposed are the ADVATE® activity data from the Phase 3 study dataset.

Figure 35:
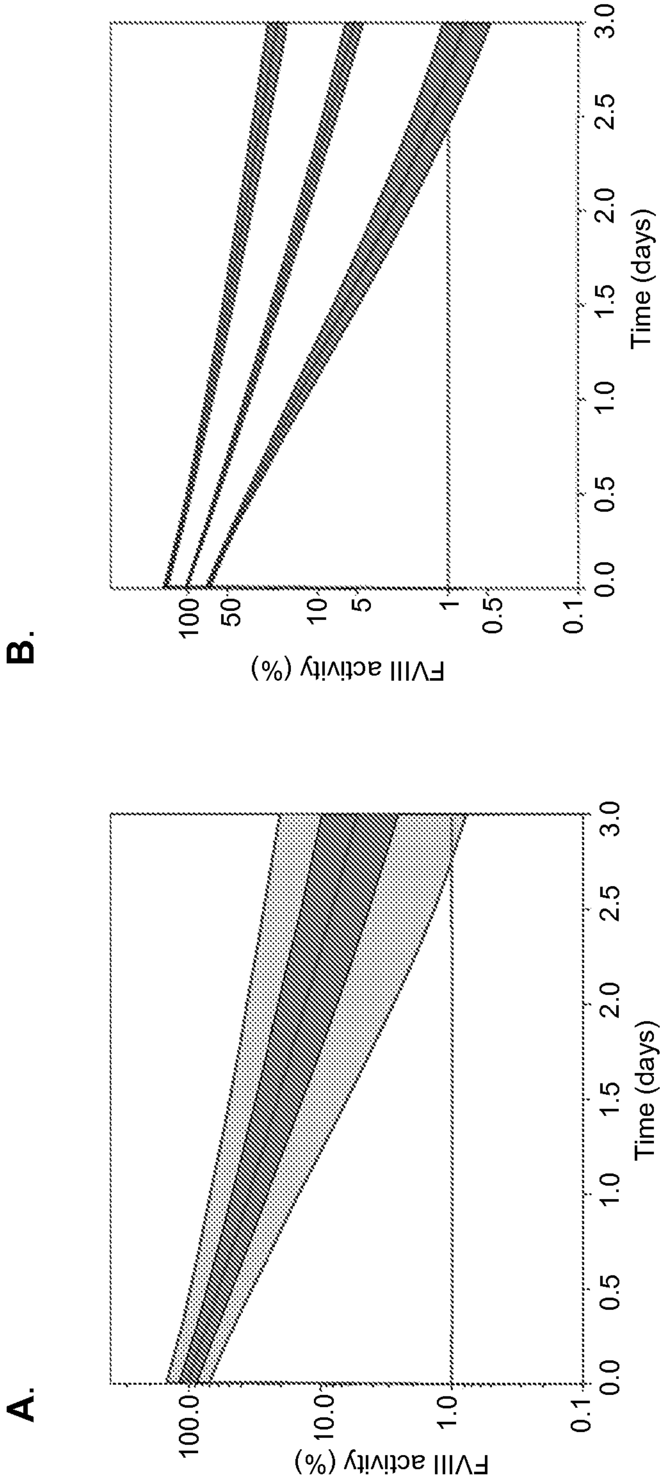
Figure 35:
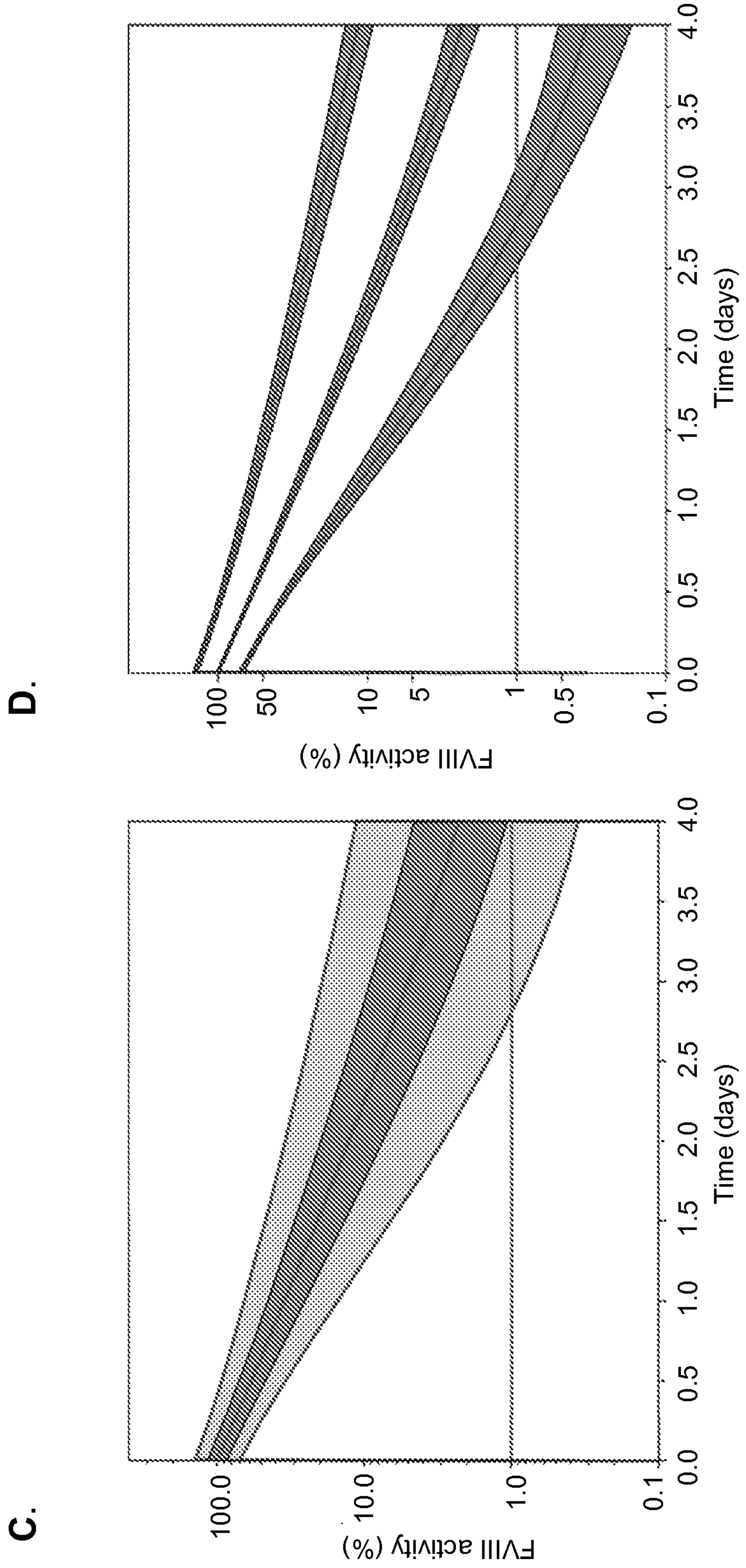
Figure 35:
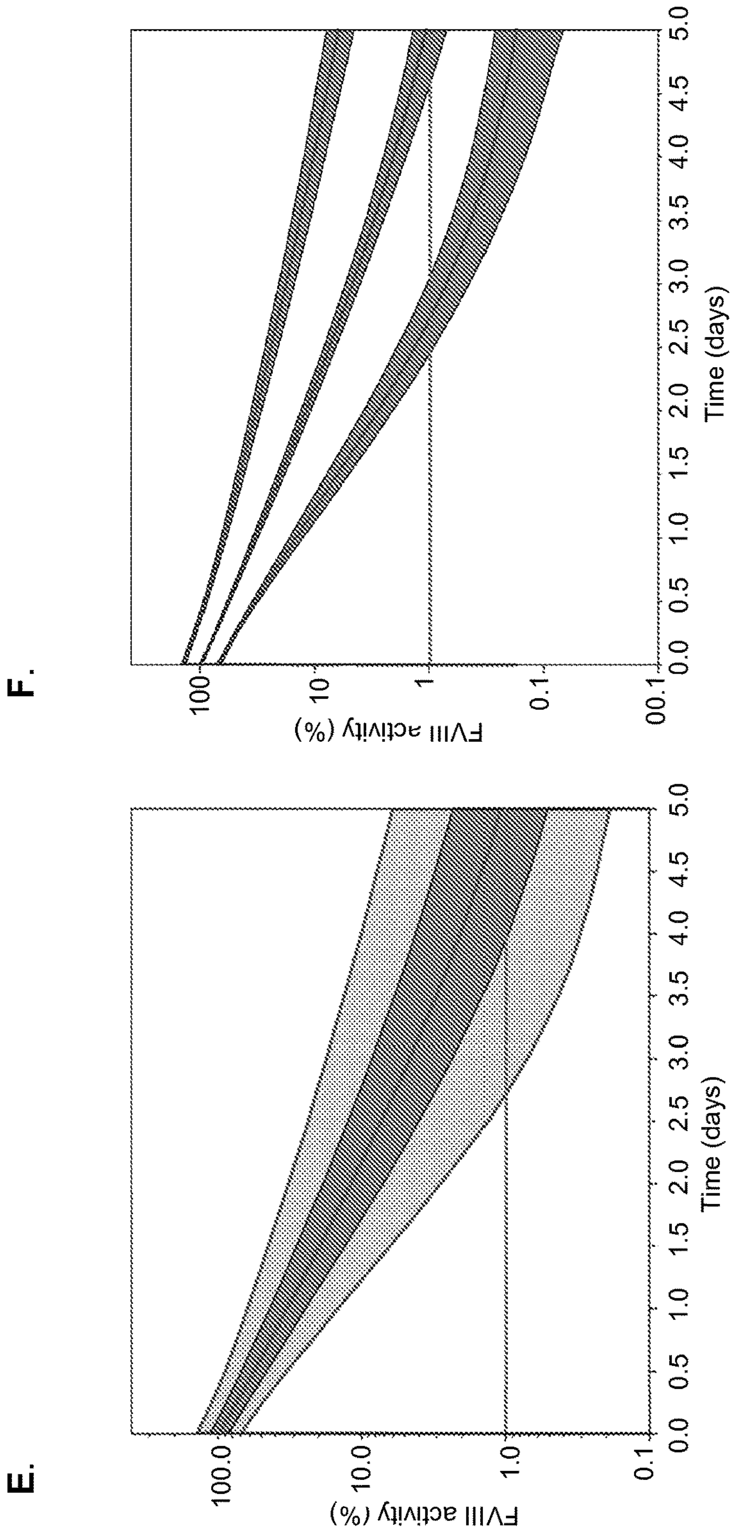
Figure 35:
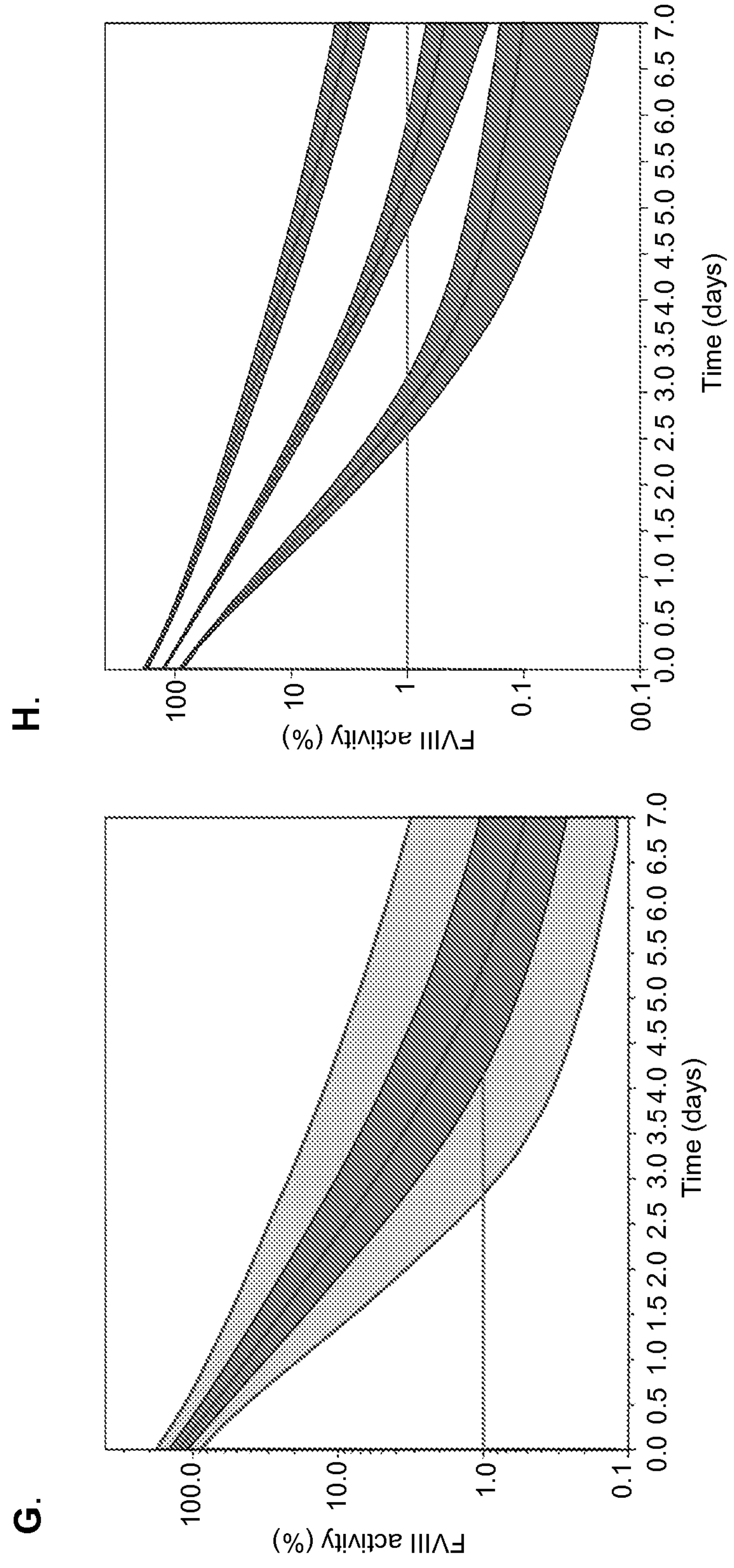

FIG. 35A-H show steady state activity profiles of selected rFVIII prophylaxis dosing regimens. FIG. 35A shows 50 IU/dL E3D without uncertainty; FIG. 35B shows 50 IU/dL E3D with uncertainty; FIG. 35C shows 50 IU/dL E4D without uncertainty; FIG. 35D shows 50 IU/dL E4D with uncertainty; FIG. 35E shows 50 IU/dL E5D without uncertainty; FIG. 35F shows 50 IU/dL E5D with uncertainty; FIG. 35G shows 65 IU/dL QW without uncertainty; FIG. 35H shows 65 IU/dL QW with uncertainty. In FIGS. 35A, 35C, 35E, and 35G, the solid line is the predicted median activity, the dark grey shaded region covers the 25th to 75th percentiles of the predicted activity and the light grey shaded region covers the 5th to 95th percentiles of the predicted activity. In FIGS. 35B, 35D, 35F, and 35H, the middle line is the predicted median activity with the 90% confidence interval around the predictions represented by the grey shaded region. The upper and the lower lines represent the 5th and 95th percentiles of the predicted activity, respectively, along with the corresponding 90% confidence intervals represented by the grey shaded regions.

Figure 36:
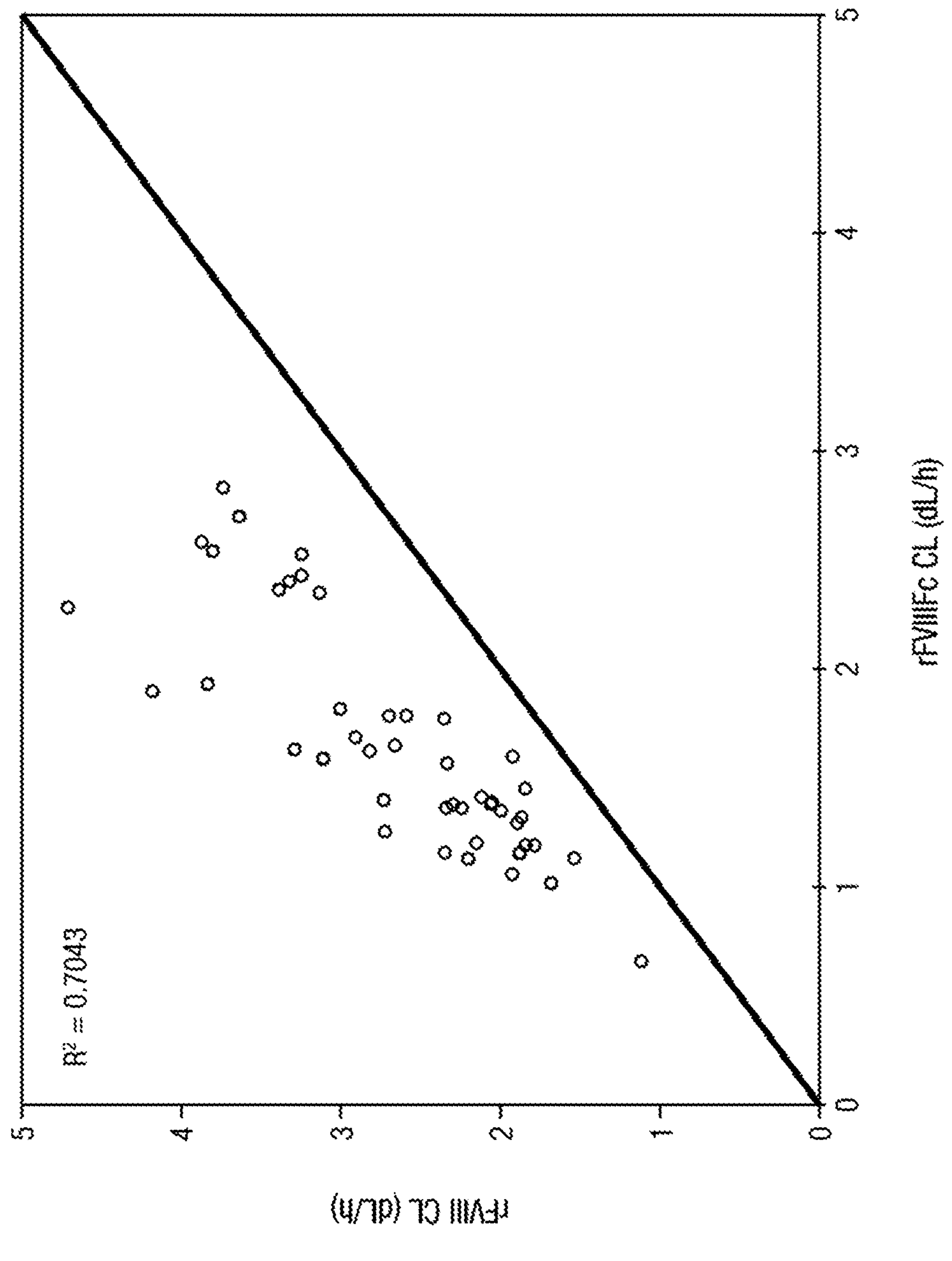
Figure 36:
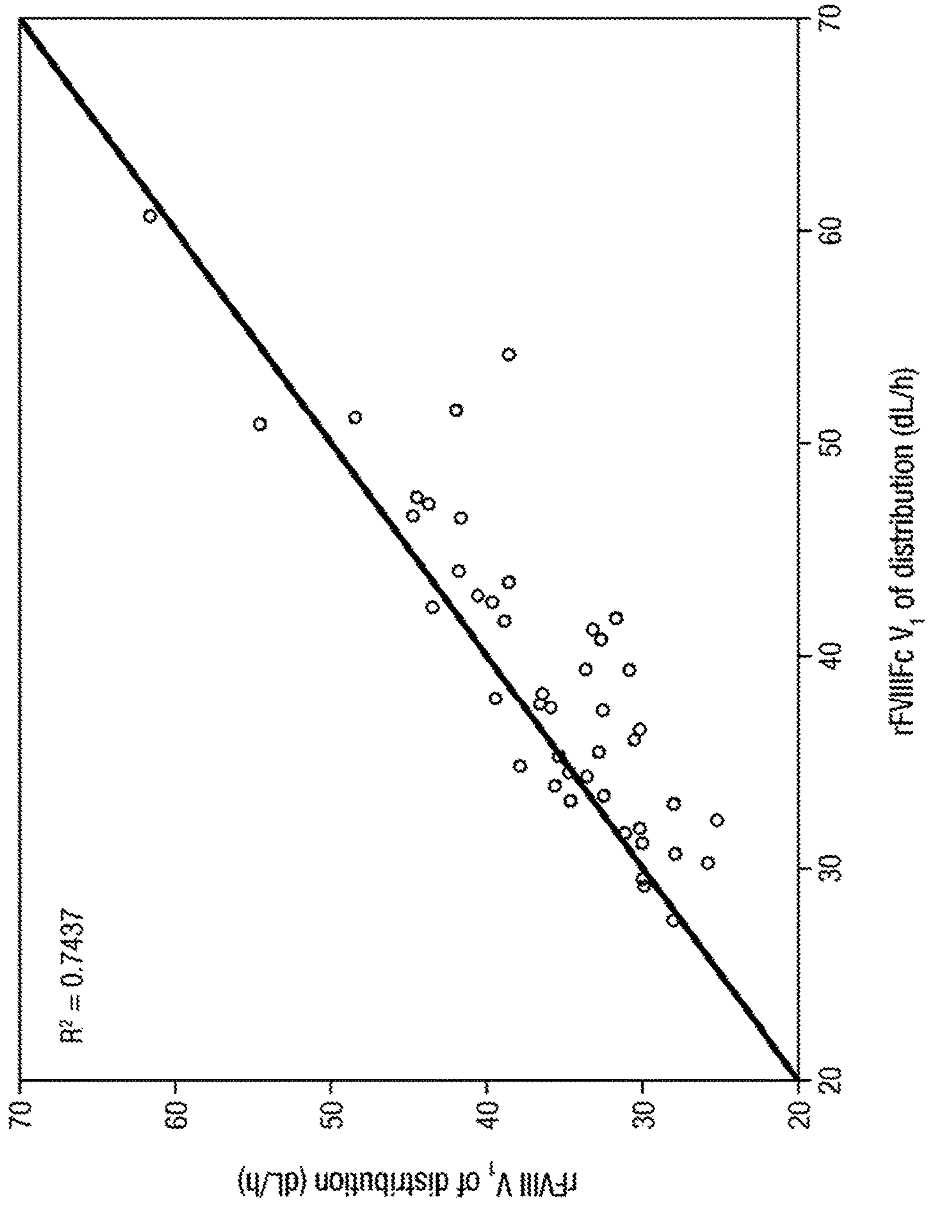
Figure 36:
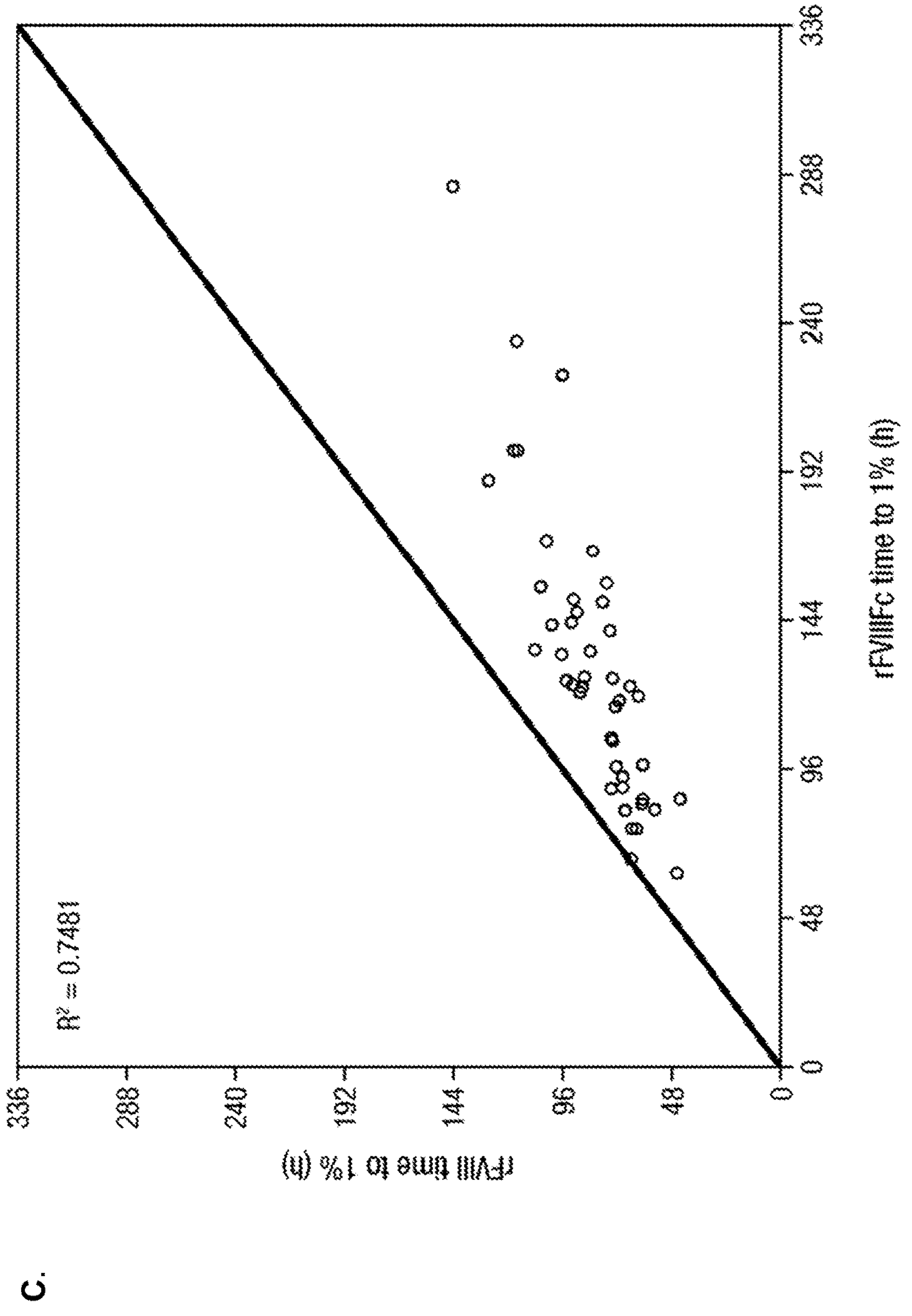

FIGS. 36A-C show a comparison of individual Bayesian parameter estimates for rFVIII and rFVIIIFc. FIG. 36A: Clearance (CL)—Each point represents one individual. Both agents were administered at a nominal dose of 50 IU/kg. FIG. 36B: Central Volume (Vs)—each point represents one individual. The solid line is the identity line. Both agents were administered at a nominal dose of 50 IU/kg. FIG. 36C: Time to 1 IU/dL (Time 1%)—each point represents one individual. The solid line is the identity line. Both agents were administered at a nominal dose of 50 IU/kg.

Figure 37:
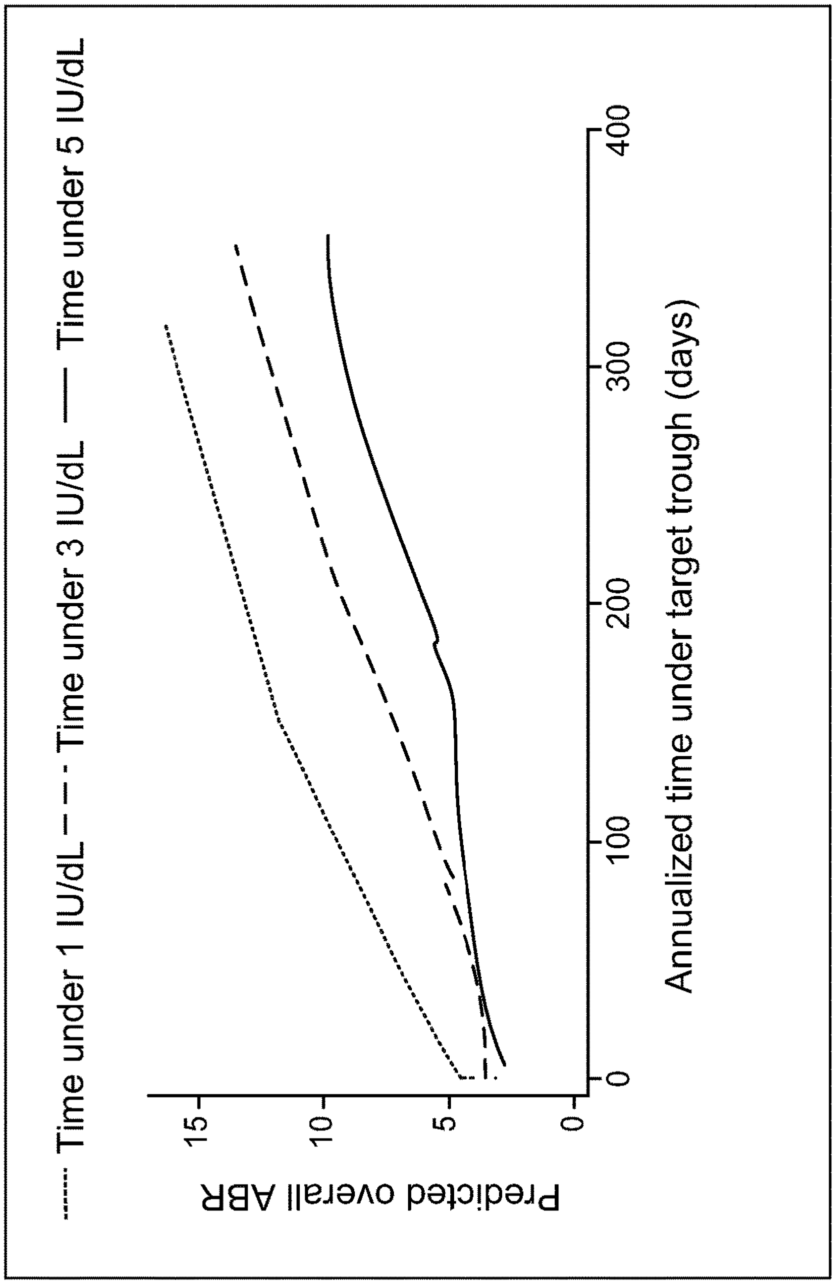

FIG. 37 shows the predicted annualized bleeding rate (ABR) correlated with time under the target trough FVIII levels of 1, 3, and 5 IU/dL.

Figure 38:
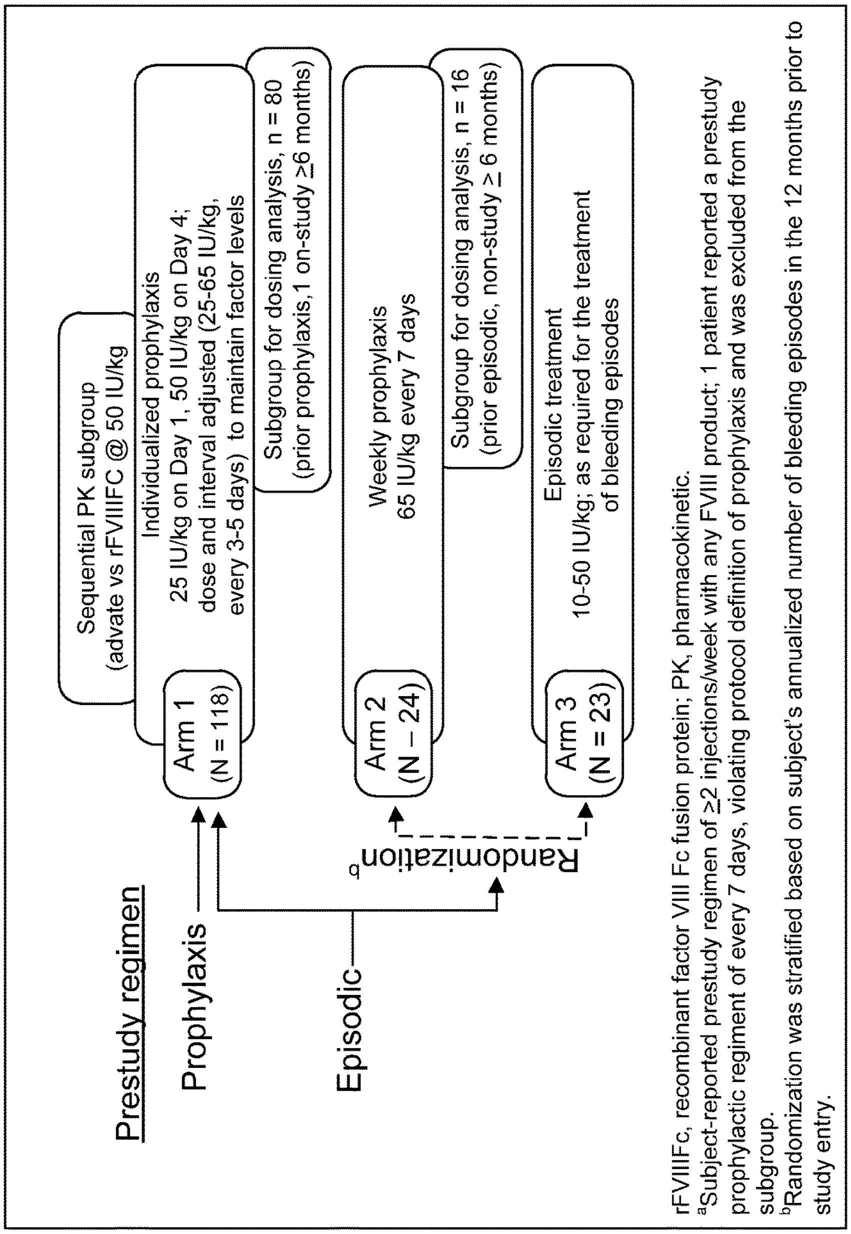

FIG. 38 shows A-LONG study design for a long-acting FVIII polypeptide (i.e., rFVIIIFc).

Figure 39:
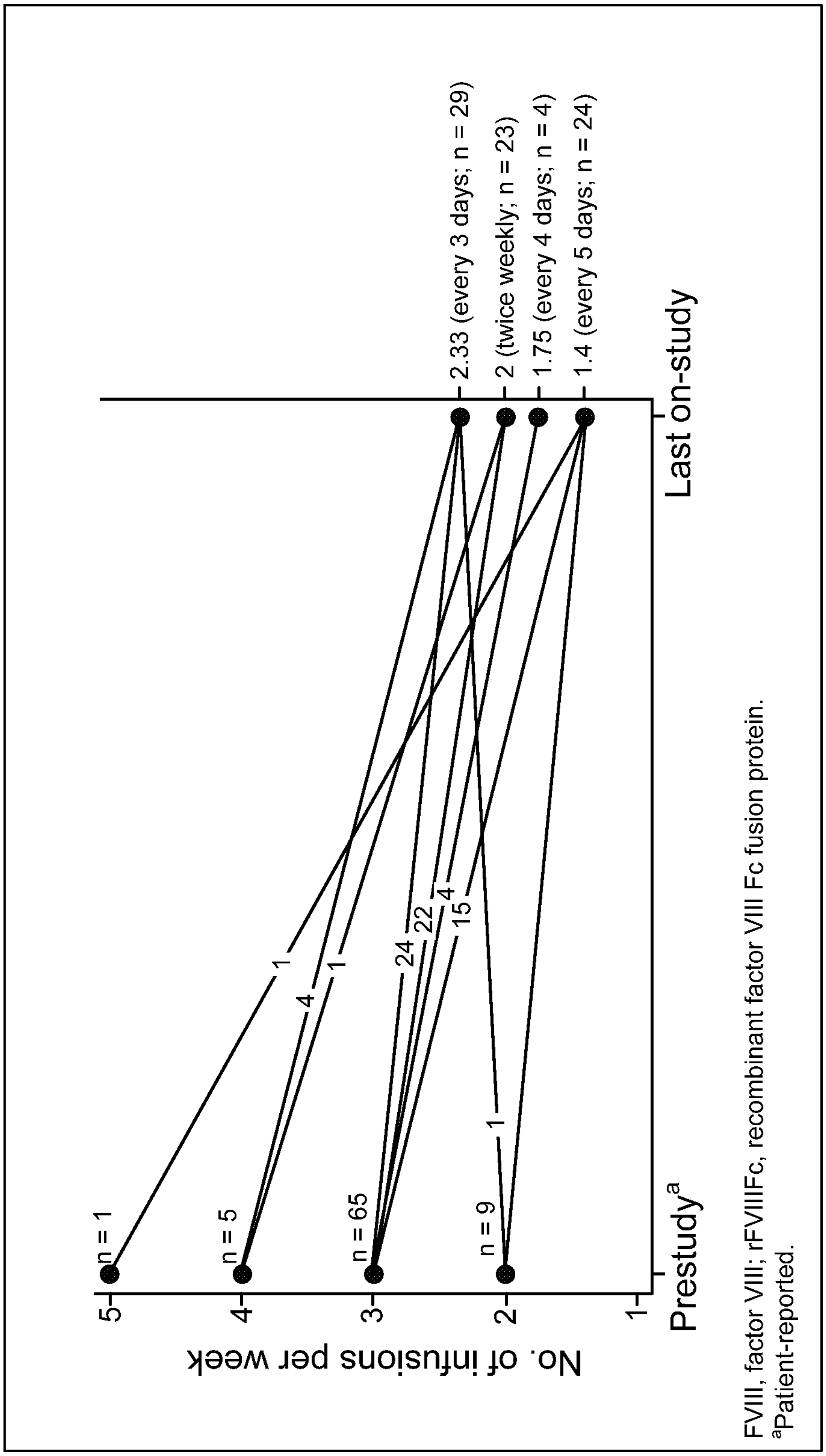

FIG. 39 shows comparison of the number of prophylactic infusions for FVIII (prestudy) and rFVIIIFc (on-study) in Arm-1 subjects.

Figure 40:
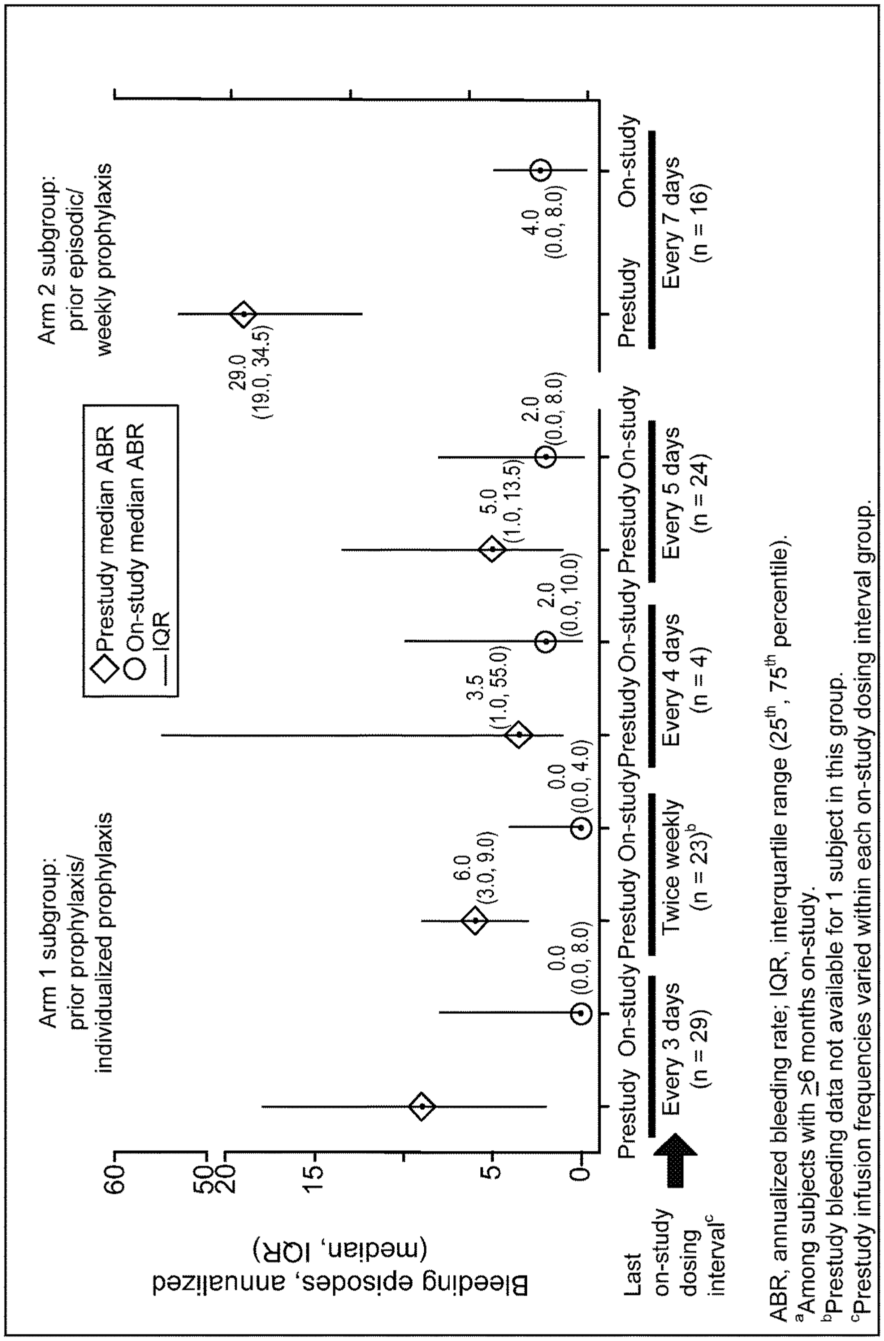

FIG. 40 shows comparison of patient-reported, 12 month, prestudy bleeding events and on-study ABR (last 3 months); stratified by last on-study dosing interval.

FIG. 41 shows simulated dosing regiments: predicted proportion of individuals with steady-state FVIII trough levels above 5 IU/dL (1%).

Figure 42:
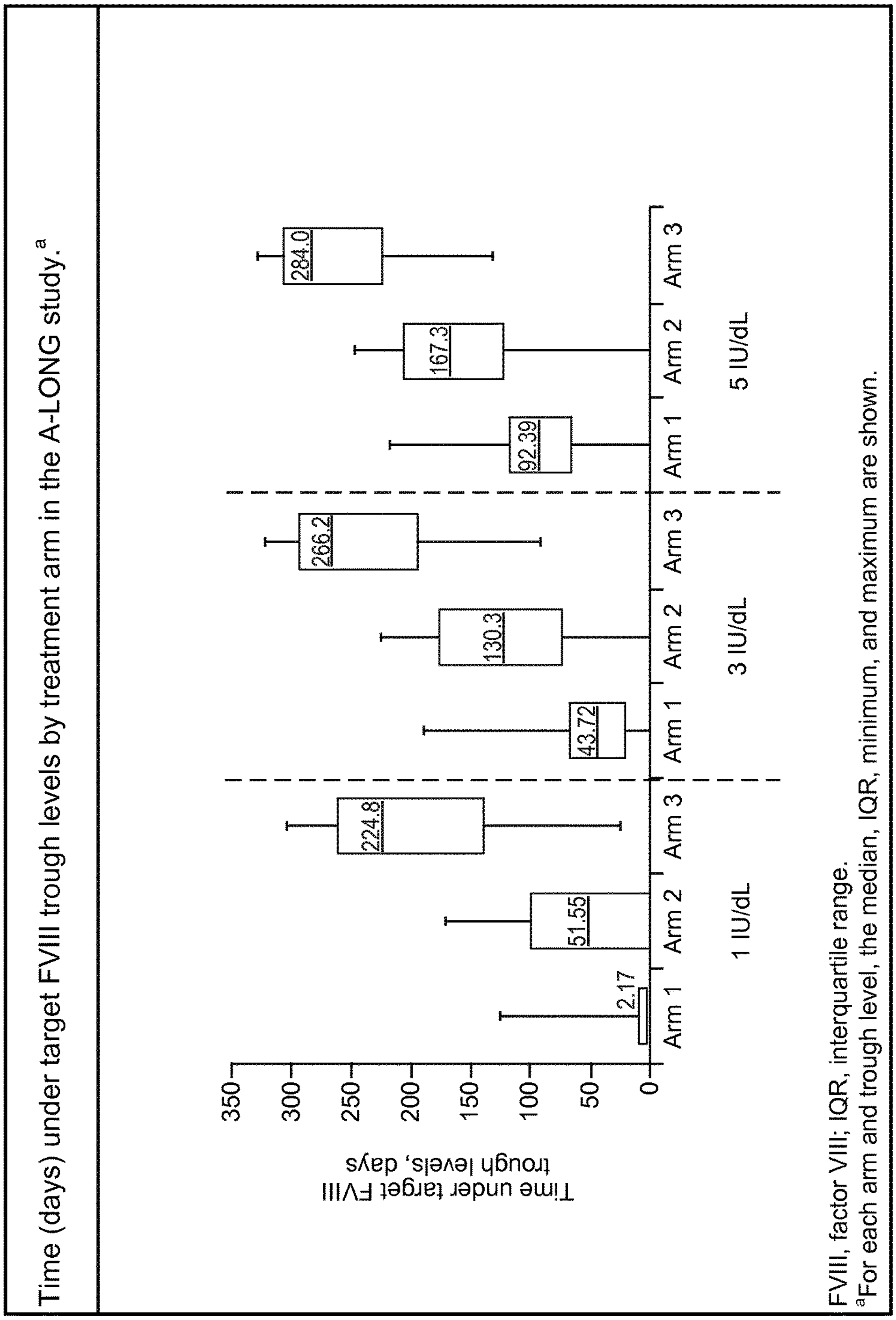

FIG. 42 shows time (days) under target FVIII trough levels by treatment arm in the A-LONG study.

FIG. 43 shows predicted ABR versus time under target trough FVIII levels of 1, 3, and 5 IU/dL, based on (A) the unadjusted NBR model and (B) the adjusted NBR model.

Figure 44:
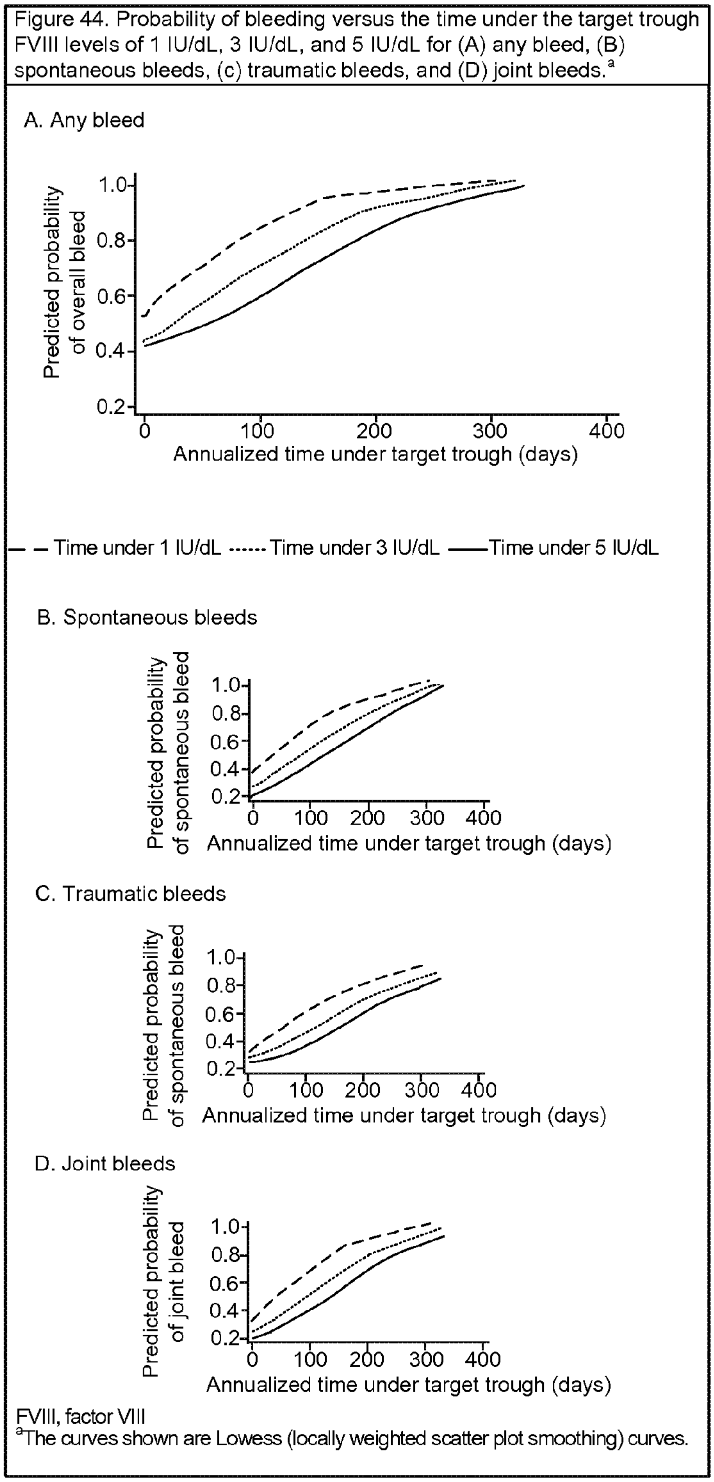

FIG. 44 shows probability of bleeding versus the time under the target trough FVIII levels of 1, 3, and 5 IU/dL for (A) any bleed, (B) spontaneous bleeds, (C) traumatic bleeds, and (D) joint bleeds.

Figure 45:
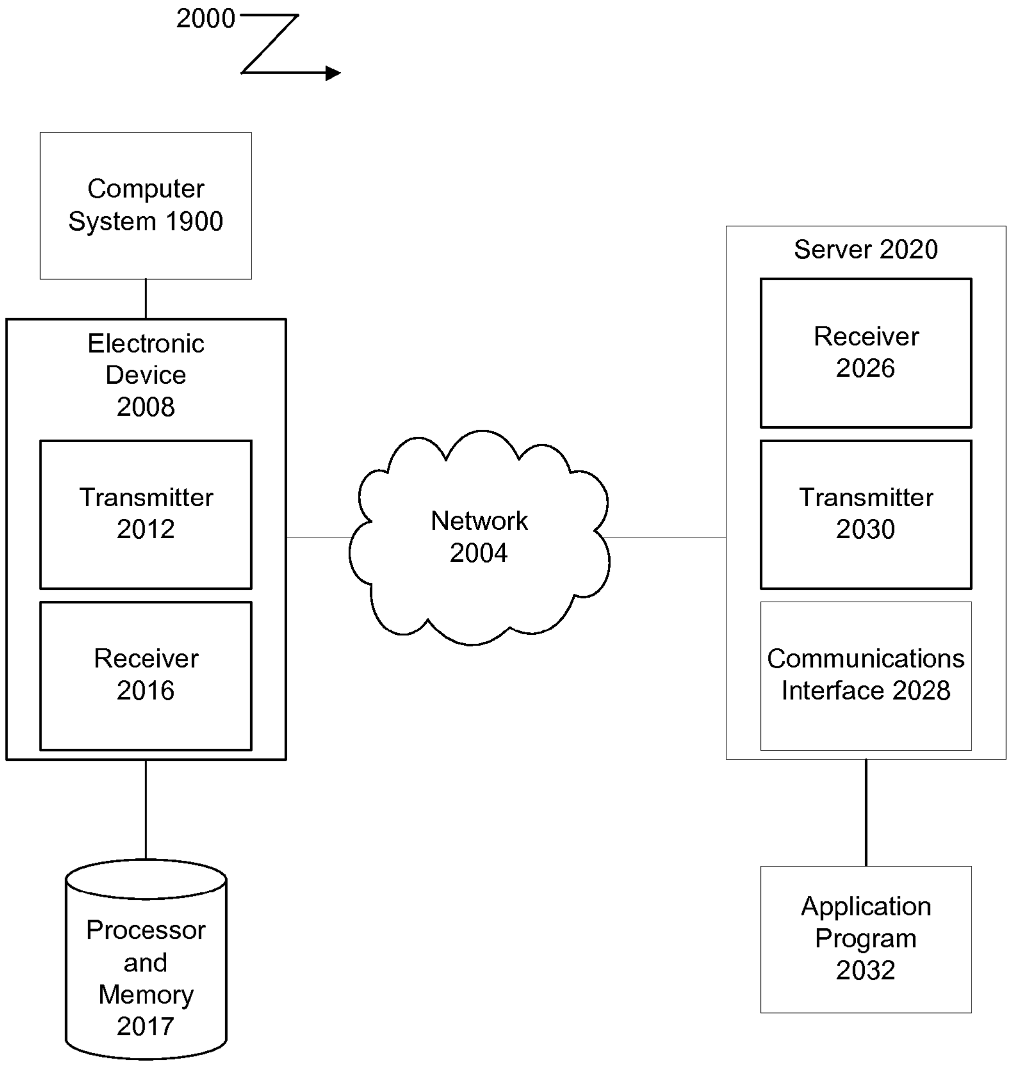
Figure 46A:
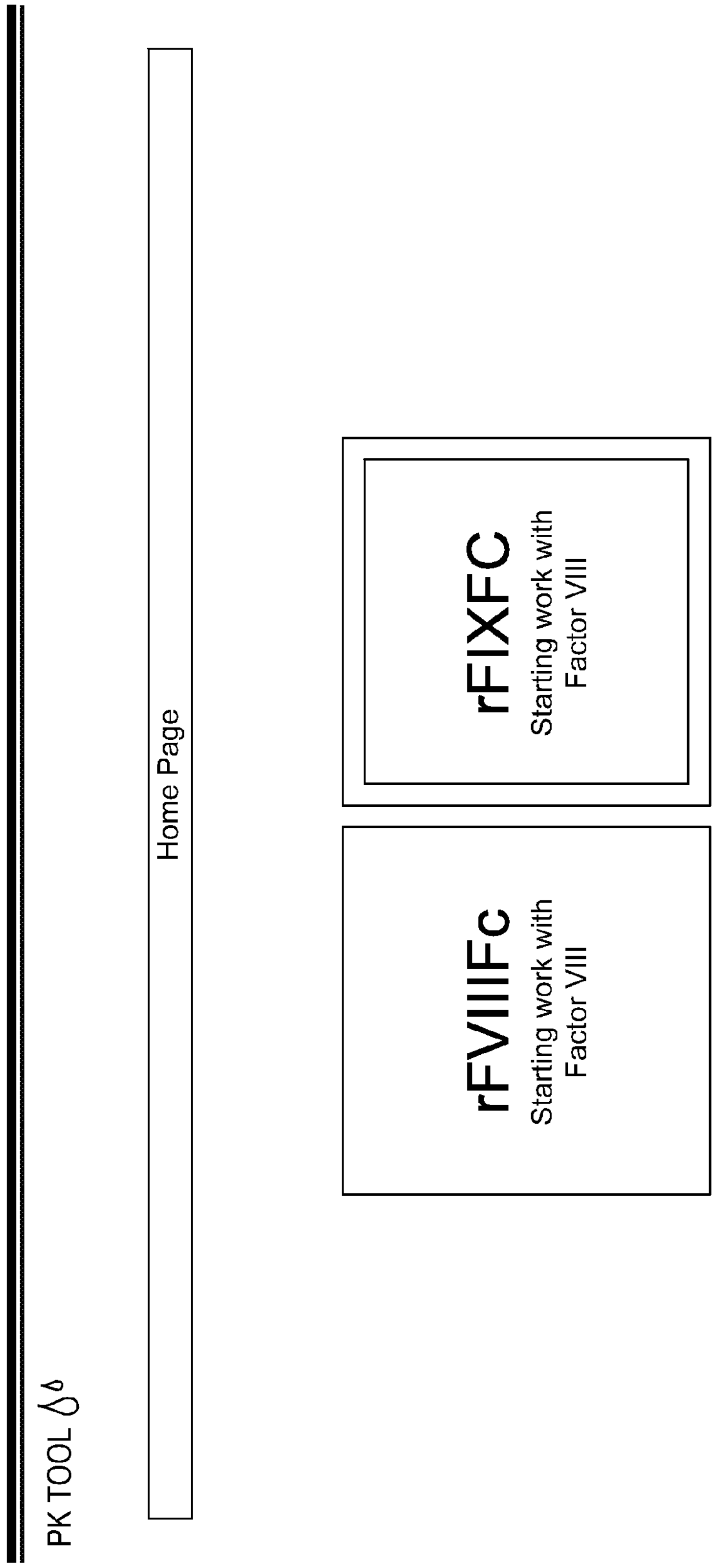
Figure 46B:
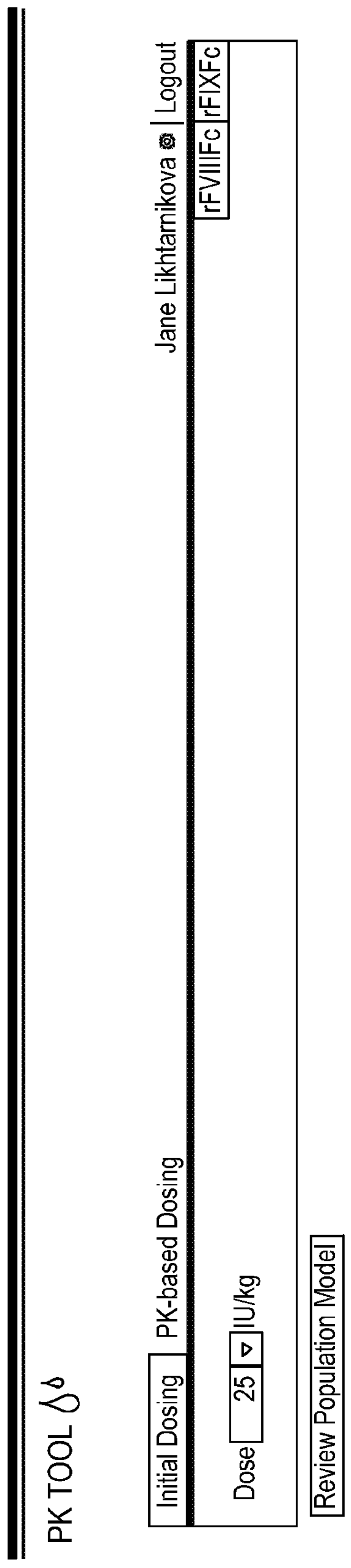
Figure 46C:
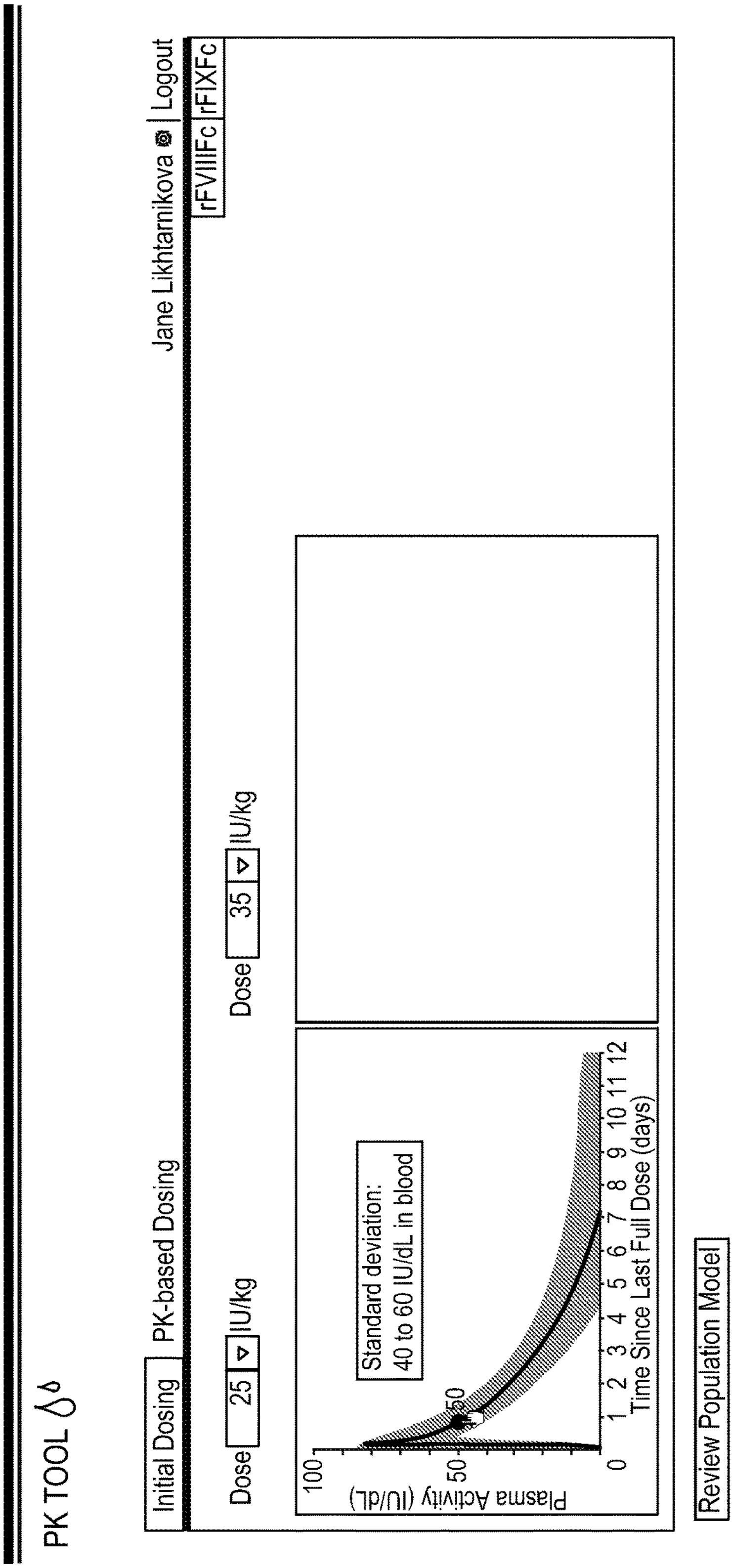
Figure 46D:
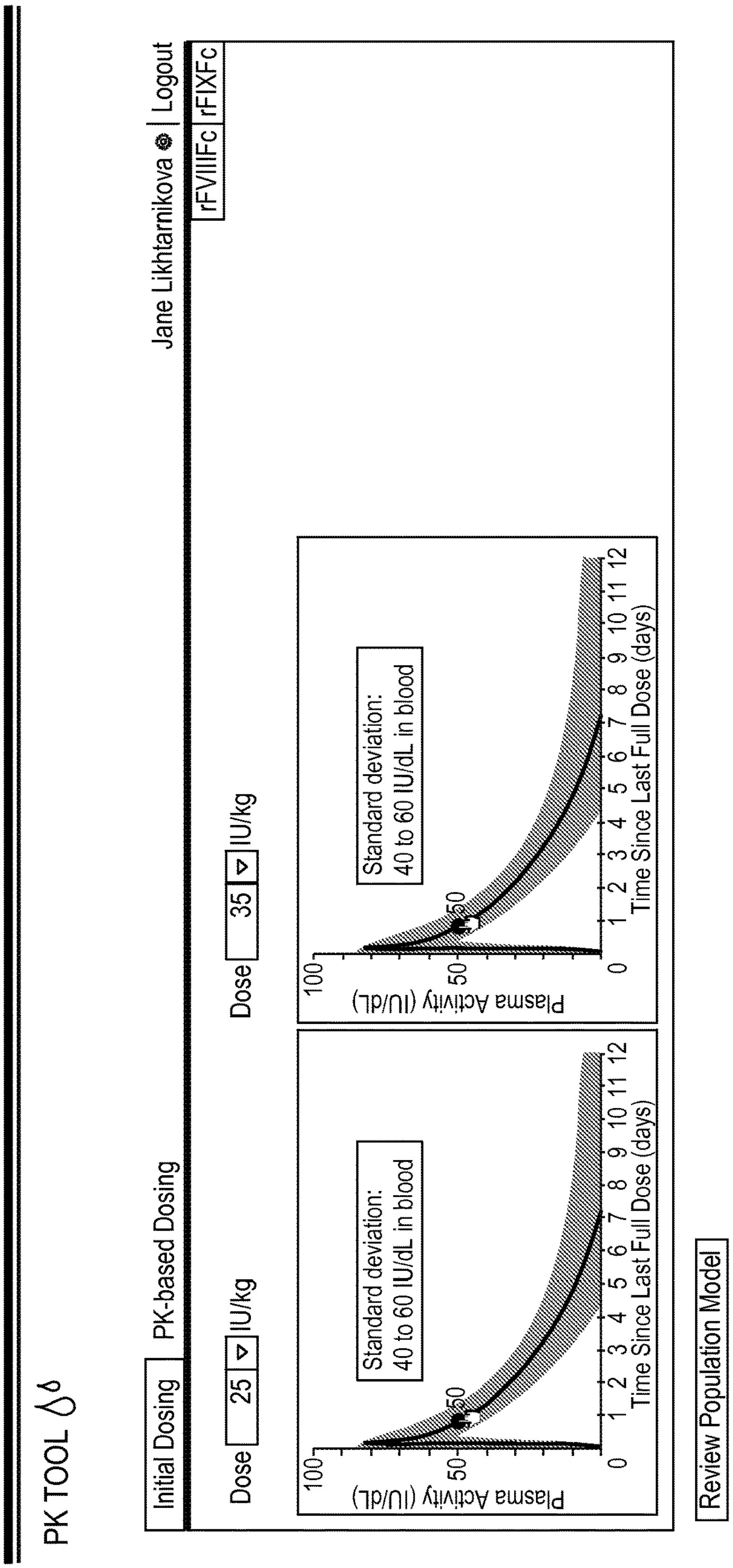
Figure 46F:
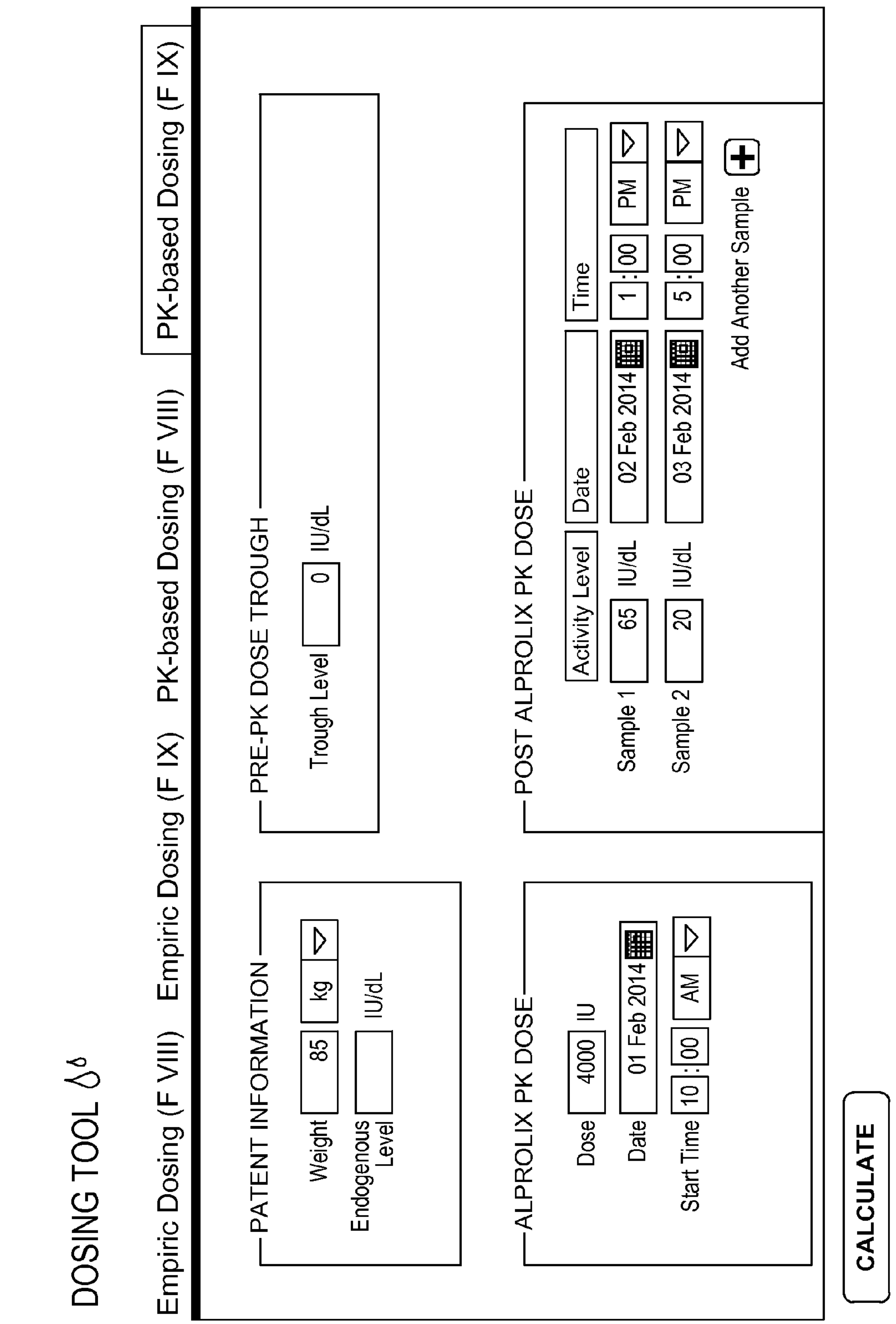
Figure 46G:
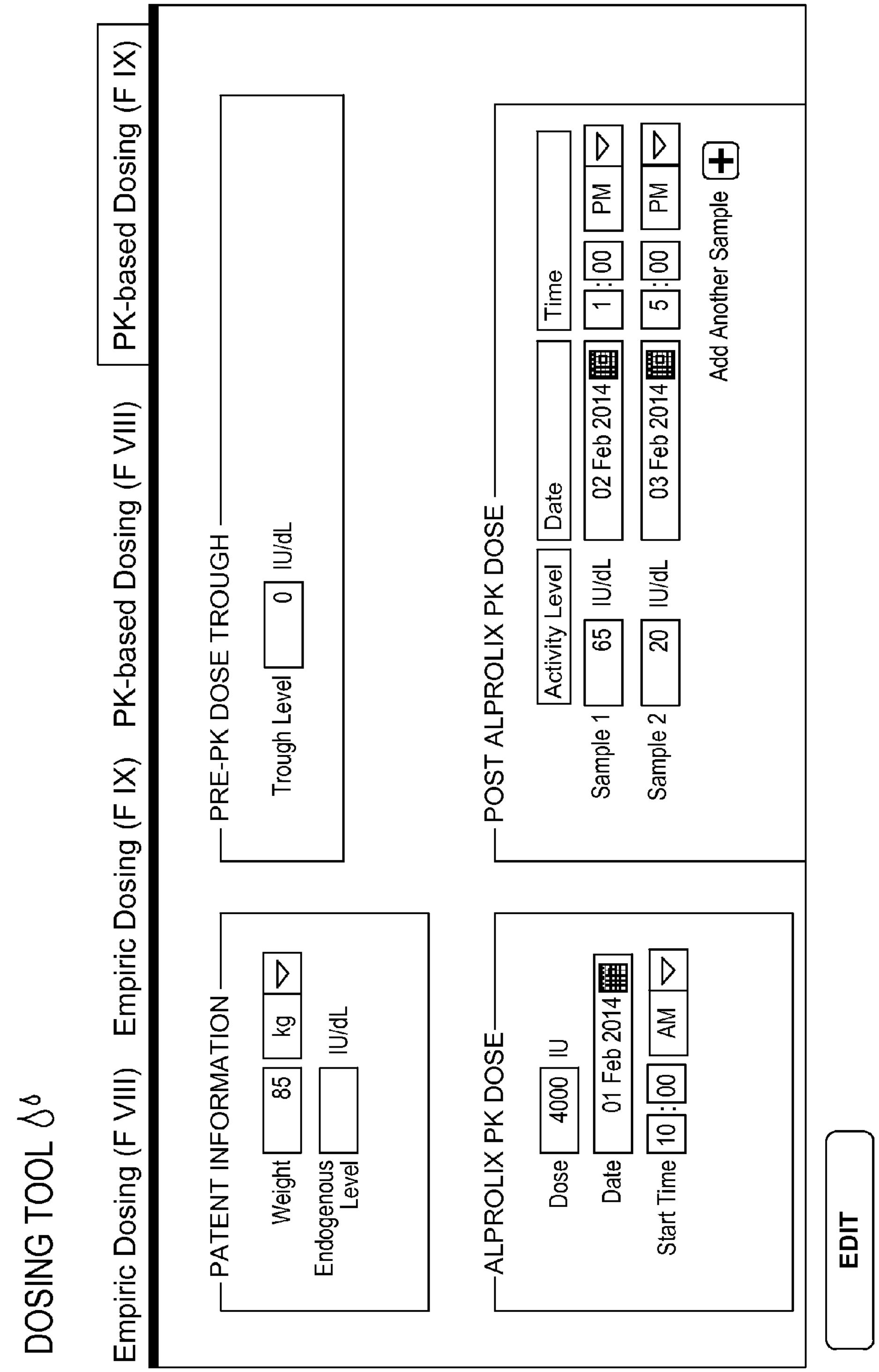
Figure 46H:
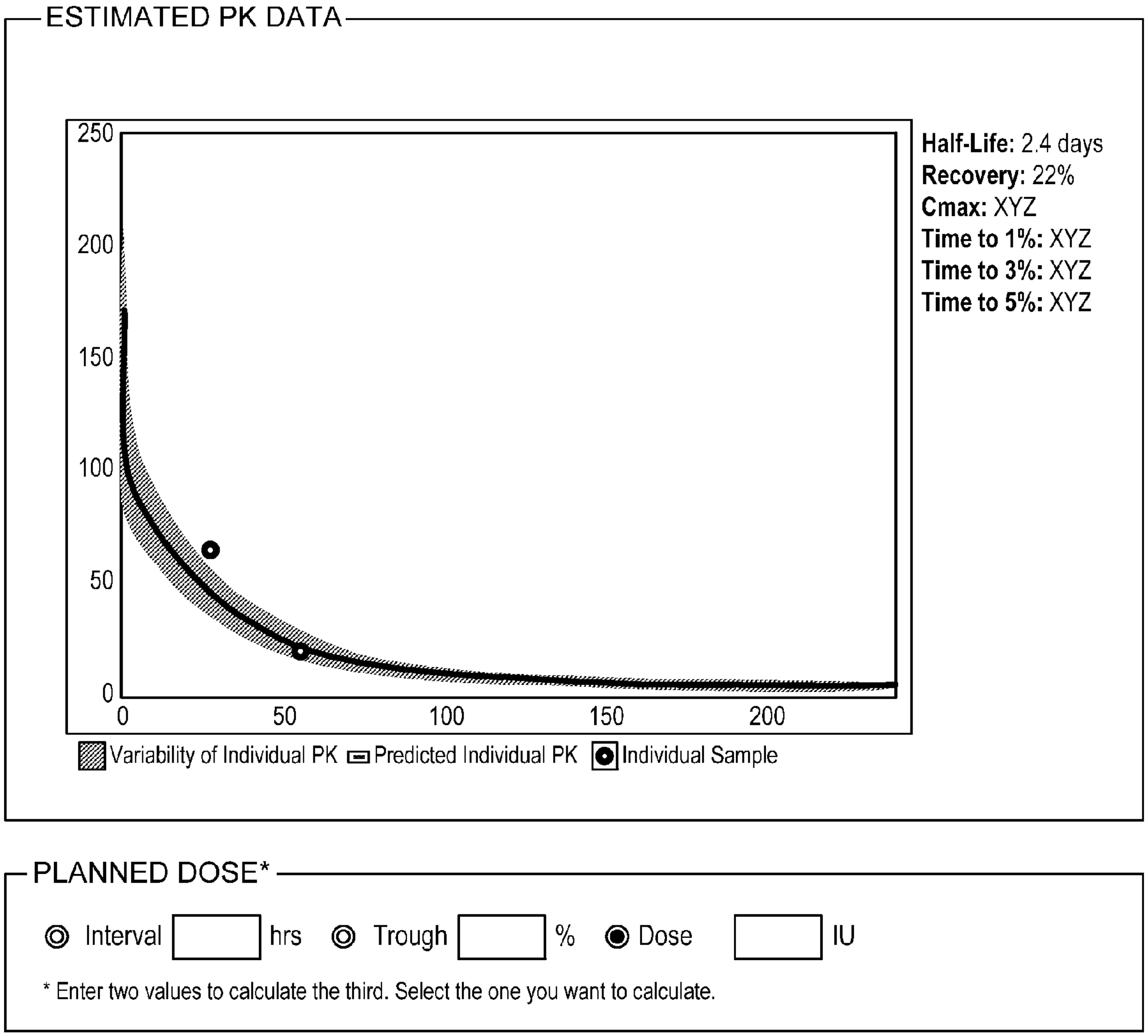
Figure 46I:
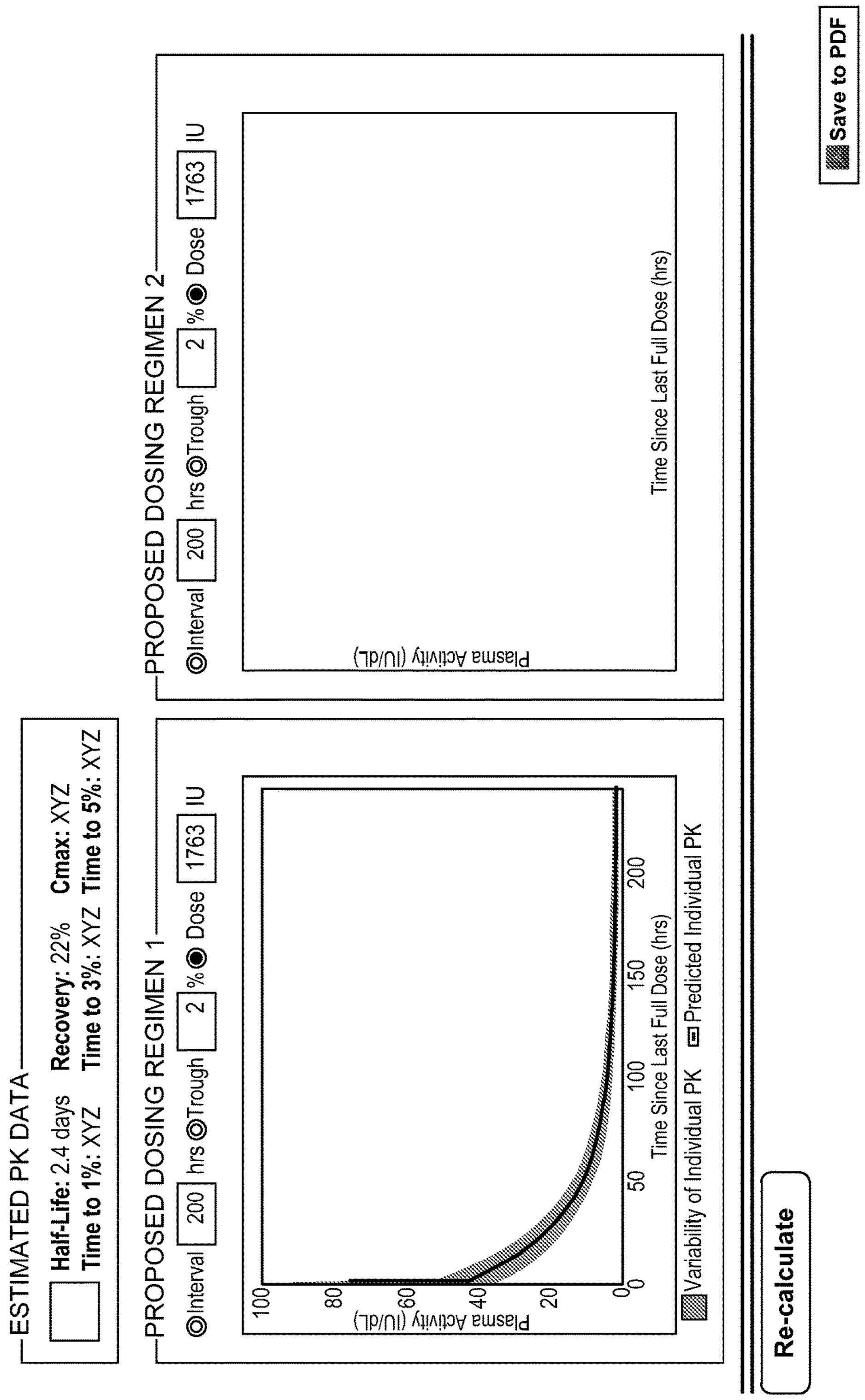
Figure 46J:
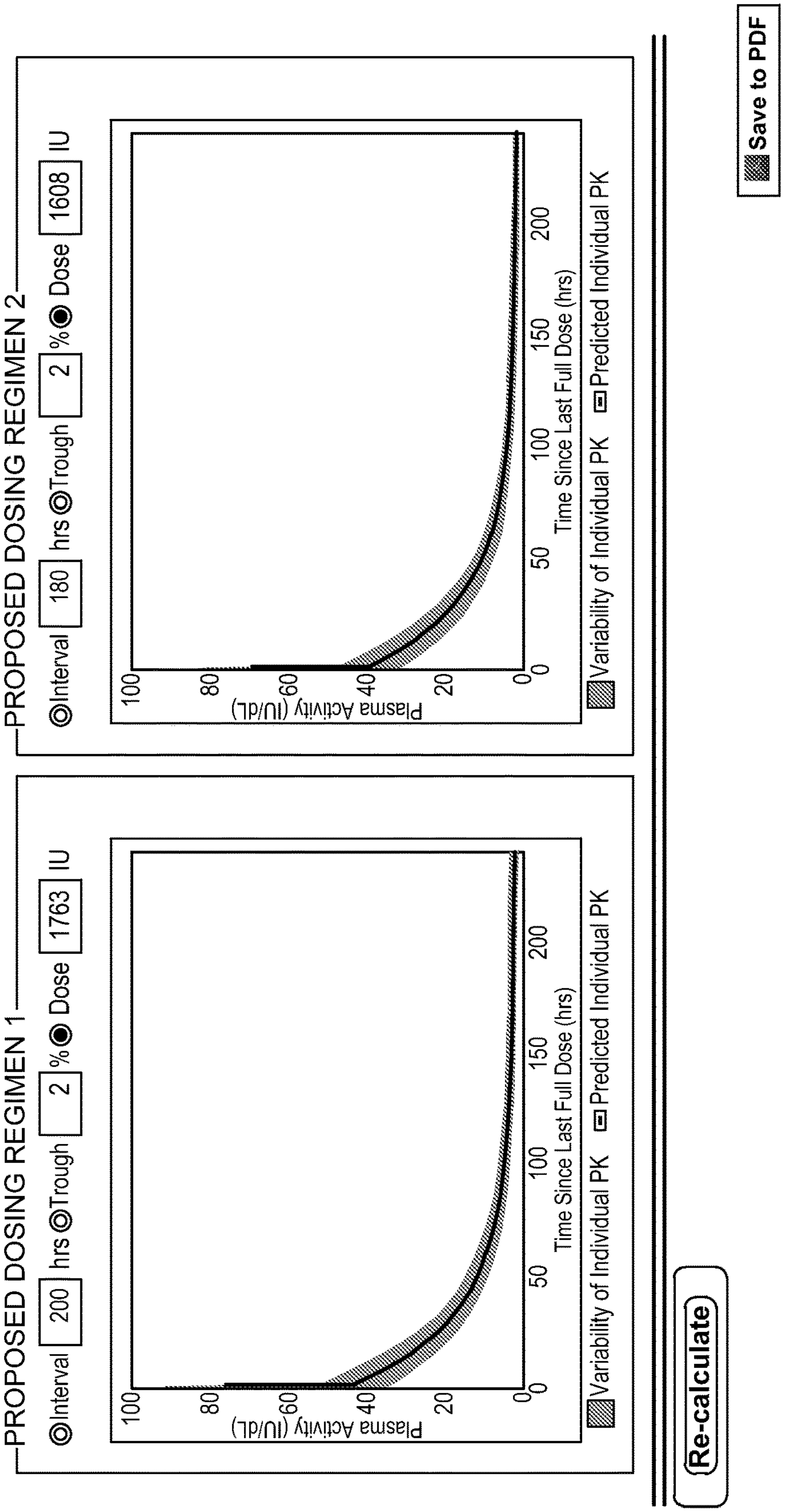

FIG. 45 shows a block diagram of an exemplary network-based system 2000 for obtaining an estimated patient individualized dosing information, patient individualized PK information, and patient median PK information.

FIGS. 46A to 46J shows exemplary screen shots of the pharmacokinetic tool (e.g., web-based application) for calculating individual dosing information.

Figure 47B:
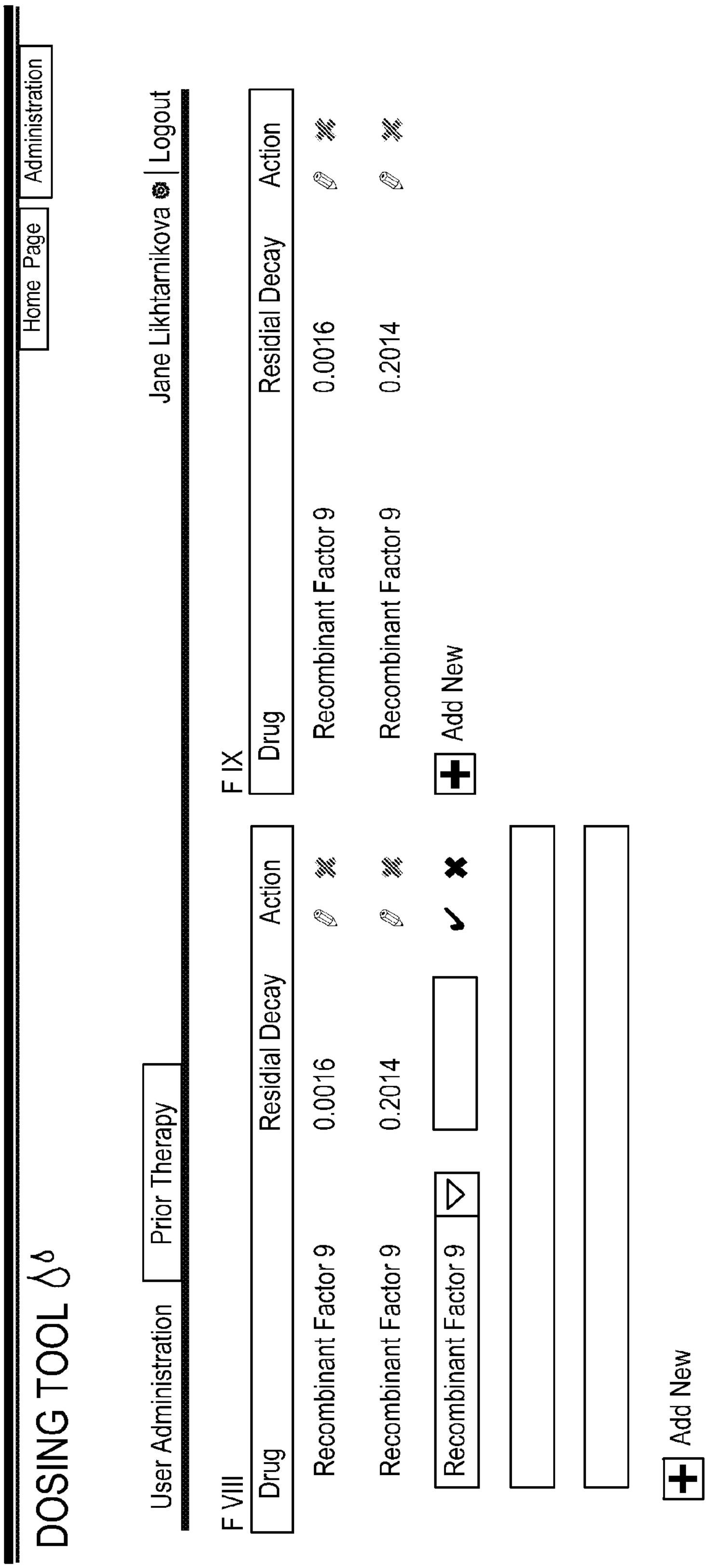

FIGS. 47A to 47B shows exemplary screen shots for inputting user administration (A) and prior therapy information (B).

DETAILED DESCRIPTION OF THE INVENTION

The present invention provides a computer-based system, e.g., web-based system for estimating individual patient PK of a long-acting FIX protein or a long-acting FVIII protein for treatment of hemophilia, e.g., Hemophilia B or Hemophilia A or a method of estimating individual patient PK of a long-acting FIX protein or a long-acting FVIII protein using the computer-based system, e.g., web-based system.

I. Definitions

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "polypeptide," "peptide" and "protein" are used interchangeably and refer to a polymeric compound comprised of covalently linked amino acid residues.

The term "polynucleotide" and "nucleic acid" are used interchangeably and refer to a polymeric compound comprised of covalently linked nucleotide residues. Polynucleotides can be DNA, cDNA, RNA, single stranded, or double stranded, vectors, plasmids, phage, or viruses. Polynucleotides include those in Table 33 or Table 35, which encode the polypeptides of Table 34 or Table 36, respectively. Polynucleotides also include fragments of the polynucleotides of Table 33 or Table 35, e.g., those that encode fragments of the polypeptides of Table 34 or Table 36, such as the Factor IX, Factor VIII, Fc, signal sequence, propeptide, 6His and other fragments of the polypeptides of Table 34 or Table 36.

The term "administering," as used herein, means to or prescribe or give a pharmaceutically acceptable a long-acting FIX polypeptide or a long-acting FVIII polypeptide of the invention to a subject via a pharmaceutically acceptable route. Examples of routes of administration include, but are not limited to, intravenous, e.g., intravenous injection and intravenous infusion, e.g., via central venous access. Additional routes of administration include subcutaneous, intramuscular, oral, nasal, and pulmonary administration, preferably subcutaneous. A long-acting FIX polypeptide or a long-acting FVIII polypeptide (a FIX or FVIII chimeric or hybrid proteins) can be administered as part of a pharmaceutical composition comprising at least one excipient. Advantages of the present invention include: improved regimen compliance; reduced break through bleeds; increased protection of joints from bleeds; prevention of joint damage; reduced morbidity; reduced mortality; prolonged protection from bleeding; decreased thrombotic events; and improved quality of life.

The term "chimeric polypeptide," as used herein, means a polypeptide that includes within it at least two polypeptides (or portions thereof such as subsequences or peptides) from different sources. Chimeric polypeptides can include two, three, four, five, six, seven, or more polypeptides or portions thereof from different sources, such as different genes, different cDNAs, or different animal or other species. Chimeric polypeptides can include one or more linkers joining the different polypeptides or portions thereof. Thus, the polypeptides or portions thereof can be joined directly or they can be joined indirectly, via linkers, or both, within a single chimeric polypeptide. Chimeric polypeptides can include additional peptides such as signal sequences and sequences such as 6His and FLAG that aid in protein purification or detection. In addition, chimeric polypeptides can have amino acid or peptide additions to the N- and/or C-termini. Exemplary chimeric polypeptides of the invention are Factor IX-FcRn BP chimeric polypeptides, e.g., FIXFc in SEQ ID NO: 2 (Table 34) or Factor VIII-FcRn BP chimeric polypeptides, e.g., FVIIIFc in SEQ ID NO: 10 (Table 36).

Factor IX or Factor VIII coagulant activity is expressed as International Unit(s) (IU). Several assays are available for measuring Factor IX activity, including the one stage clotting assay (activated partial thromboplastin time; aPTT), thrombin generation time (TGA) and rotational thromboelastometry (ROTEM®).

"Dosing interval," as used herein, means the amount of time that elapses between multiple doses being administered to a subject. Dosing interval can thus be indicated as ranges. The dosing interval in the methods of the invention using a chimeric FIX-FcRn BP, e.g., a chimeric FIX-Fc can be at least about one and one-half to eight times longer than the dosing interval required for an equivalent amount (in IU/kg) of said Factor IX without the FcRn BP, e.g., Fc portion (i.e., a polypeptide consisting of said FIX). Dosing interval can thus be indicated as ranges. The dosing interval in the methods of the invention using a chimeric FVIII-FcRn BP, e.g., a chimeric FVIII-Fc can be at least about one and one-half to eight times longer than the dosing interval required for an equivalent amount (in IU/kg) of said Factor VIII without the FcRn BP, e.g., Fc portion (i.e., a polypeptide consisting of said FVIII).

The term "dosing frequency" as used herein refers to the frequency of administering doses of a long-acting FIX polypeptide or a long-acting FVIII polypeptide in a given time. Dosing frequency can be indicated as the number of doses per a given time, e.g., once a week or once in two weeks.

The term "bleeding episode" as used herein is given a standardized definition: A bleeding episode starts from the first sign of a bleed, and ends 72 hours after the last treatment for the bleeding, within which any symptoms of bleeding at the same location, or injections less than or equal to 72 hours apart, is considered the same bleeding episode. See Blanchette V. (2006) *Haemophilia* 12:124-7. As used herein, any injection to treat the bleeding episode, taken more than 72 hours after the preceding one, is considered the first injection to treat a new bleeding episode at the same location. Likewise, any bleeding at a different location is considered a separate bleeding episode regardless of time from the last injection.

The term "prophylaxis of one or more bleeding episode" or "prophylactic treatment" as used herein means administering a long-acting FIX polypeptide or a long-acting FVIII polypeptide in multiple doses to a subject over a course of time to increase the level of Factor IX or Factor VIII activity in a subject's plasma. In one embodiment, "prophylaxis of one or more bleeding episode" indicates use of a long-acting FIX polypeptide or a long-acting FVIII polypeptide to prevent or inhibit occurrence of one or more spontaneous or uncontrollable bleeding or bleeding episodes or to reduce the frequency of one or more spontaneous or uncontrollable bleeding or bleeding episodes. In another embodiment, the increased FIX or FVIII activity level is sufficient to decrease the incidence of spontaneous bleeding or to prevent bleeding in the event of an unforeseen injury. Prophylactic treatment decreases or prevents bleeding episodes, for example, those described under on-demand treatment. Prophylactic treatment can be individualized, as discussed under "dosing interval", e.g., to compensate for inter-subject variability.

The term "about once a week" as used herein means approximate number, and "about once a week" can include every seven days t two days, i.e., every five days to every nine days. The dosing frequency of "once a week" thus can be every five days, every six days, every seven days, every eight days, or every nine days.

The term "individualized interval prophylaxis" as used herein means use of a long-acting FIX polypeptide or a long-acting FVIII polypeptide for an individualized dosing interval or frequency to prevent or inhibit occurrence of one or more spontaneous and/or uncontrollable bleeding or bleeding episodes or to reduce the frequency of one or more spontaneous and/or uncontrollable bleeding or bleeding episodes. In one embodiment, the "individualized interval" includes every 10 days ±3 days, i.e. every seven days to every 13 days. The dosing frequency of the "individualized interval prophylaxis" thus can be ever three days, every seven days, every eight days, every nine days, every ten days, every 11 days, every 12 days, or every 13 days.

The term "on-demand treatment," as used herein, means treatment that is intended to take place over a short course of time and is in response to an existing condition, such as a bleeding episode, or a perceived short term need such as planned surgery. The "on-demand treatment" is used interchangeably with "episodic" treatment. Conditions that can require on-demand treatment include a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. Bleeding episodes other than these are also included. The subject can be in need of surgical prophylaxis, peri-operative management, or treatment for surgery. Such surgeries include minor surgery, major surgery, tooth extraction, tonsillectomy, other dental/thoraco-facial surgeries, inguinal herniotomy, synovectomy, total knee replacement, other joint replacement, craniotomy, osteosynthesis, trauma surgery, intracranial surgery, intra-abdominal surgery, intrathoracic surgery. Surgeries other than these are also included.

Additional conditions that can require on-demand treatment include minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Additional reasons for on-demand treatment include the need for peri-operative management for surgery or dental extraction, major surgery, extensive oral surgery, urologic surgery, hernia surgery, orthopedic surgery such as replacement of knee, hip, or other major joint.

The term "treatment" or "treating" as used herein means amelioration or reduction of one or more symptoms of bleeding diseases or disorders including, but not limited to, hemophilia B. In one embodiment, "treatment of" or "treating" a bleeding disease or disorder includes prevention of one or more symptoms of a bleeding disease or disorder. In a bleeding disease or disorder caused by a FIX deficiency (e.g., a low baseline FIX activity) or a FVIII deficiency, the term "treatment" or "treating" means a FIX or FVIII replacement therapy. By administering a long-acting FIX polypeptide or a long-acting FVIII polypeptide to a subject, the subject can achieve and/or maintain a plasma trough level of a FIX or FVIII activity at about 1 IU/dl or above 1 IU/dl. In other embodiments, "treatment" or "treating" means reduction of the frequency of one or more symptoms of bleeding diseases or disorders, e.g., spontaneous or uncontrollable bleeding episodes. "Treatment," however, need not be a cure.

The term "perioperative management" as used herein means use of a long-acting FIX polypeptide or a long-acting FVIII polypeptide before, concurrently with, or after an operative procedure, e.g., a surgical operation. The use for "perioperative management" of one or more bleeding episode includes surgical prophylaxis before (i.e., preoperative), during (i.e., intraoperative), or after (i.e., postoperative) a surgery to prevent one or more bleeding or bleeding episode or reducing or inhibiting spontaneous and/or uncontrollable bleeding episodes before, during, and after a surgery.

Pharmacokinetic (PK) parameters include the terms above and the following terms, which have their ordinary meaning in the art, unless otherwise indicated. Some of the terms are explained in more detail in the Examples. PK parameters can be based on FIX or FVIII antigen level (often denoted parenthetically herein as "antigen") or FIX or FVIII activity level (often denoted parenthetically herein as "activity"). In the literature, PK parameters are often based on FIX or FVIII activity level due to the presence in the plasma of some subjects of endogenous, inactive FIX or FVIII, which interferes with the ability to measure administered (i.e., exogenous) FIX or FVIII using antibody against FIX or FVIII, respectively. However, when FIX or FVIII is administered as part of a fusion or hybrid protein containing a heterologous polypeptide such as an FcRn BP, administered (i.e., exogenous) FIX or FVIII antigen can be accurately measured using antibody to the heterologous polypeptide. In addition, certain PK parameters can be based on model predicted data (often denoted parenthetically herein as "model predicted") or on observed data (often denoted parenthetically herein as "observed"), and preferably are based on observed data.

"Baseline," as used herein, is the lowest measured plasma Factor IX or FVIII level in a subject prior to administering a dose. The Factor IX or FVIII plasma levels can be measured at two time points prior to dosing: at a screening visit and immediately prior to dosing. Alternatively, (a) the baseline in subjects whose pretreatment FIX or FVIII activity is <1%, who have no detectable FIX or FVIII antigen, and have nonsense genotypes can be defined as 0%, (b) the baseline for subjects with pretreatment FIX or FVIII activity <1% and who have detectable FIX or FVIII antigen can be set at 0.5%, (c) the baseline for subjects whose pretreatment FIX or FVIII activity is between 1-2% is Cmin (the lowest activity throughout the PK study), and (d) the baseline for subjects whose pretreatment FIX or FVIII activity is ≥22% can be set at 2%. Activity above the baseline pre-dosing can be considered residue drug from prior treatment, and can be decayed to baseline and subtracted from the PK data following long-acting FIX polypeptide or long-acting FVIII polypeptide dosing.

"$T_{1/2\beta}$" or "$T_{1/2\ beta}$" or "Beta HL," as used herein, is half-life associated with elimination phase, $t_{1/2\beta}$=(ln 2)/elimination rate constant associated with the terminal phase. The $T_{1/2\ beta}$ can be measured by FIX or FVIII activity or by FIX or FVIII antigen level in plasma. The $T_{1/2\ beta}$ based on activity is shown as $T_{1/2\ beta}$ (activity), and the $T_{1/2\ beta}$ based on the FIX or FVIII antigen level can be shown as $T_{1/2\ beta}$ (antigen). Both $T_{1/2\ beta}$ (activity) and $T_{1/2\ beta}$ (antigen) can be shown as ranges or a geometric mean.

"Trough," as used herein, is the lowest plasma Factor IX or FVIII activity level reached after administering a dose of chimeric polypeptide of the invention or another Factor IX or FVIII molecule and before the next dose is administered, if any. Trough is used interchangeably herein with "threshold." Baseline Factor IX or FVIII levels are subtracted from measured Factor IX or FVIII levels to calculate the trough level.

The term "annualized bleeding rate" ("ABR) as used herein refers to the number of bleeding episodes (including spontaneous and traumatic bleeds) experienced by a subject during a defined time period, extrapolated to 1 year. For example two bleeds in six months would indicate an ABR of four. The median ABR provides a single number to describe all subjects, indicating that half of the subjects had individual ABRs less than or equal to the median and half had ABRs greater than or equal to the median. For example, an ABR can be calculated according to the following formula:

$$\text{Annualized bleeding rate} = \frac{\text{Number of bleeding episodes during the efficacy period}}{\text{Total number of days during the efficacy period}} \times 365.25 \quad \text{(C)}$$

The population pharmacokinetic modeling terms used herein (e.g., model, modeling, validation, dataset) have their ordinary and customary meaning in the field of pharmacokinetics.

"Immediately," as used herein in reference to updating a popPK model, means that the model is updated as soon as the application performs necessary modeling computations to arrive at an updated model. Thus, "immediately," may reasonably differ in duration of time depending on the hardware and software on which the application is running.

"Contemporaneously," as used herein in reference to updating, calculating, and improving, means shortly after the user has input the information needed to update the popPK model or to calculate the pharmacokinetic information, preferably during the same session in which the user has input the information.

"Subject," as used herein means a human. Subject as used herein includes an individual who is known to have at least one incidence of uncontrolled bleeding episodes, who has been diagnosed with a disease or disorder associated with uncontrolled bleeding episodes, e.g., a bleeding disease or disorder, e.g., hemophilia A or hemophilia B, who are susceptible to uncontrolled bleeding episodes, e.g., hemophilia, or any combinations thereof. Subjects can also include an individual who is in danger of one or more uncontrollable bleeding episodes prior to a certain activity, e.g., a surgery, a sport activity, or any strenuous activities. The subject can have a baseline FIX or FVIII activity less than 1%, less than 0.5%, less than 2%, less than 2.5%, less than 3%, or less than 4%. Subjects also include pediatric humans. Pediatric human subjects are birth to 20 years, preferably birth to 18 years, birth to 16 years, birth to 15 years, birth to 12 years, birth to 11 years, birth to 6 years, birth to 5 years, birth to 2 years, and 2 to 11 years of age.

"Therapeutic dose," "dose," "effective dose," or "dosing amount" as used herein, means a dose that achieves a plasma trough level of a FIX or FVIII activity at least about 1 IU/dl or above 1 IU/dl in the subject administered with the long-acting FIX polypeptide or the long-acting FVIII polypeptide. For the purpose of this invention, in one embodiment, the "dose" refers to the amount of the doses that a plasma trough level of a FIX or FVIII activity is maintained at least about 1 IU/dl or above 1 IU/dl, at least about 2 IU/dl or above 2 IU/dl, at least about 3 IU/dl or above 3 IU/dl, at least about 4 IU/dl or above 4 IU/dl, or at least about 5 IU/dl or above 5 IU/dl throughout the administration of the long-acting FIX polypeptide or the long-acting FVIII polypeptide. In another embodiment, the "dose" reduces or decreases frequency of bleeding or bleeding disorder. In other embodiments, the "dose" stops on-going, uncontrollable bleeding or bleeding episodes. In still other embodiments, the "dose" prevents spontaneous bleeding or bleeding episodes in a subject susceptible to such spontaneous bleeding or bleeding episodes. The "dose" or "therapeutic dose" need not cure hemophilia.

"Variant," as used herein, refers to a polynucleotide or polypeptide differing from the original polynucleotide or polypeptide, but retaining essential properties thereof e.g., Factor IX coagulant activity or Fc (FcRn binding) activity. Generally, variants are overall closely similar, and, in many regions, identical to the original polynucleotide or polypeptide. Variants include polypeptide and polynucleotide fragments, deletions, insertions, and modified versions of original polypeptides.

II. Methods, Systems, and Storage Medium for Estimating Patient Individualized Dosing Information, Patient Individualized PK Information, and Patient Median PK Information—Long-Acting FIX Polypeptide The invention includes a method of estimating a long-acting FIX dosing information individualized for a patient, the method comprising: (a) receiving, by a computer-based system containing the long-acting FIX population pharmacokinetic (popPK) model of Example 5 or 7, e.g., Table 10, 13, or 14, and, optionally, a Bayesian estimation program, at least one of patient information and desired treatment outcome information, (b) calculating, by the computer-based system, individualized long-acting FIX dosing information using the popPK model, the optional Bayesian estimation program, and the received information, and (c) outputting, by the computer-based system, the individualized dosing information.

In some embodiments, the method also comprises selecting a dosing regimen based on the output individualized dosing information of (c) and administering the long-acting FIX polypeptide to the patient according to the selected dosing regimen.

In some embodiments, the desired treatment outcome information is desired rise in plasma FIX activity level following dosing and the output information is dose for acute treatment.

In some embodiments, the desired treatment outcome information is desired dosing interval and the output information is dose for prophylaxis.

In some embodiments, the desired treatment outcome information is desired dose and the output information is interval for prophylaxis.

The invention also includes a method of estimating a long-acting FIX dosing regimen based on median popPK, the method comprising: (a) receiving, by a computer-based system containing the long-acting FIX popPK model of Example 5 or 7, e.g., Table 10, 13, or 14, and, optionally, a Bayesian estimation program, at least one of patient information and desired treatment outcome information, (b) calculating, by the computer-based system, median long-acting FIX PK information using the popPK model, the optional Bayesian estimation program, and the received information, and (c) outputting, by the computer-based system, the median PK information.

In some embodiments, the method also comprises selecting a dosing regimen based on the output median PK information of (c), and administering the long-acting FIX polypeptide to a patient according to the selected dosing regimen.

The invention also includes a method of estimating individual patient long-acting FIX PK, the method comprising: (a) receiving, by a computer-based system containing the long-acting FIX population pharmacokinetic (popPK) model of Example 5 or 7, e.g., Table 10, 13, or 14, and, optionally, a Bayesian estimation program, individual long-acting FIX PK information, (b) estimating, by the computer-based system, individualized patient long-acting FIX PK information using the popPK model, the optional Bayesian estimation program, and the received information, and (c) outputting, by the computer-based system, the individualized patient PK information.

In some embodiments, the method also comprises selecting a dosing regimen based on the output individualized patient PK information of (c), and administering the long-acting FIX polypeptide to the patient according to the selected regimen.

In some embodiments (a) further comprises receiving, by the computer-based system, patient information.

In some embodiments the patient information is age, e.g., 12 and older, or body weight. Additional patient information includes diagnostic (baseline) FIX level, PK determinations, time of PK sampling, dosing history if PK samples were taken from multiple doses, actual dose, FIX activity level, etc.

In some embodiments, desired treatment outcome information is, e.g., desired PK or desired regimen outcome, e.g., desired rise in plasma FIX activity level following dose, desired dosing interval, and desired dose.

In some embodiments, output information is, e.g., PK curve, PK parameter such as incremental recovery (Cmax/dose), mean residence time, terminal t½, clearance, Vss, AUC/dose, doses and associated troughs, and intervals and associated troughs.

For example, for assessing individualized patient PK, the system can recommend that the user input 2-3 optimized PK sampling time points. In this case, system output can include PK curve and one or more selected PK parameters, e.g., incremental recovery (Cmax/Dose), mean residence time, terminal t½, clearance, Vss, AUC, and time to 1 or X %, etc. e.g., FIG. 12.

As additional examples, to select an individualized dosing regimen using the output individual PK parameters discussed in the preceding paragraph, (i) the dose selected for acute treatment can be based on user input of the desired rise in plasma FIX activity level following the dose, (ii) the dose selected for prophylaxis can be based on user input of the desired dosing interval, or (iii) the selected interval for prophylaxis can be based on user input for the desired dose. In the first case, the system can output the dose (IU) based in the patient's incremental recovery, e.g., FIG. 14. In the second case, system output can be a table of doses and associated troughs, e.g., x IU/kg, 1% trough, y IU/kg, 2% trough, etc. e.g., FIG. 15, top. In the third case, system output can be a table of intervals and associated troughs, e.g., x days, 1% trough, y IU/kg, 2% trough, etc., e.g., FIG. 15, bottom.

The user may wish to use the system without inputting any individualized PK data. In this case, the dosing output would be based on the population median rather than being individualized for the particular patient. E.g., FIG. 15. In this way, the user inputs, e.g., body weight and age, and (i) the desired rise in plasma FIX activity level following the dose, (ii) the desired dose interval for prophylaxis, or (iii) the desired dose for prophylaxis. In the first case, the system can output the dose. In the second case, the system can output the dose and associated trough, e.g., Table 6. In the third case, the system can output the interval and associated trough, e.g., Table 7.

In some embodiments, the system is compliant with patient privacy laws. In some embodiments, the system is encrypted, e.g., with SSL. In some embodiments, input patient information is made anonymous.

In some embodiments, the system includes a user help function.

The method can be carried out by, e.g., a physician, a nurse, or another healthcare practitioner.

Additional embodiments include a computer readable storage medium having instructions stored thereon that, when executed by a processor, cause the processor to perform any of the methods or processes described herein.

Additional embodiments include a system comprising a processor and a memory, the memory having instructions stored thereon that, when executed by the processor, cause the processor to perform any of the above methods.

The user of the system or computer readable storage medium, can be, e.g., a physician, a nurse, or another healthcare practitioner.

For additional embodiments of these aspects of the invention, see Examples 5 and 7, and the Figures discussed therein.

Additional embodiments include a computer readable storage medium having instructions stored thereon that, when executed by a processor, cause the processor to perform any of the methods or processes described herein.

In some embodiments, the system is web-based.

According to one embodiment, the invention includes a web-based method of estimating a long-acting FIX dosing information individualized for a patient, the method comprising: (a) receiving, by one or more electronic devices, at least one of patient information and desired treatment outcome information, (b) transmitting, by a processing device, the at least one of patient information and desired treatment outcome information to a web-based application program accessible through a web server, wherein the application is programmed to implement a long-acting FIX population pharmacokinetic (popPK) model, such as that of Example 5 or 7, e.g., Table 10, 13, or 14, and, optionally, a Bayesian estimation program, (c) receiving from the web based server and program, individualized dosing information calculated using the popPK model, the optional Bayesian estimation program, and the transmitted information of (b), and (d) outputting, by the one or more electronic devices, the individualized dosing information. In some embodiments, the method also comprises selecting a dosing regimen based on the output individualized dosing information of (d) and administering the long-acting FIX polypeptide to the patient according to the selected dosing regimen.

In some embodiments, the patient information includes body weight. In some embodiments, the desired treatment outcome information is desired rise in plasma FIX activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating a long-acting FIX dosing information individualized for a patient, wherein the method comprises: (a) receiving, by a processing device, at least one of patient information and desired treatment outcome information by a web-based application program accessible through a web server and programmed to implement a long-acting FIX population pharmacokinetic (popPK) model, and a Bayesian estimation program, and the received information, and (c) transmitting, by a processing device, the individualized calculated dosing information of (b) to one or more electronic devices for output of the information. In some embodiments, the method also comprises selecting a dosing regimen based on the output individualized dosing information transmitted in (c) and administering the long-acting FIX to the patient according to the selected dosing regimen.

In some embodiments, the patient information includes body weight. In some embodiments, the desired treatment outcome information is desired rise in plasma FIX activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating a long-acting FIX dosing information individualized for a patient, the method comprising: (a) receiving, by an electronic device, at least one of patient information and desired treatment outcome, (b) transmitting, by a processing device, the individual long-acting FIX PK information to outcome information to a web-based application program accessible through a web server, and programmed to implement a long-acting FIX population pharmacokinetic (popPK) model, such as that of Example 5 or 7, e.g., Table 10, 13, or 14, and, optionally, a Bayesian estimation program, (c) calculating, by the web-based program, individualized long-acting FIX dosing information using the popPK model, and. Optionally a Bayesian estimation program, and the received information, (d) transmitting, by a processing device, the individualized calculated dosing information of (c) to one or more one or more electronic devices, and (e) outputting, by the one or more electronic devices, the individualized dosing information. In some embodiments, the method also comprises selecting a dosing regimen based on the output individualized dosing information of (e) and administering the long-acting FIX polypeptide to the patient according to the selected dosing regimen. In some embodiments, the method also comprises selecting a dosing regimen based on the output individualized dosing information in (e) and administering the long-acting FIX polypeptide to the patient according to the selected dosing regimen.

In some embodiments, the patient information includes body weight. In some embodiments, the desired treatment outcome information is desired rise in plasma FIX activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating a long-acting FIX dosing regimen based on median popPK, the method comprising: (a) receiving, by one or more electronic devices at least one of patient information and desired treatment outcome information, (b) transmitting, by a processing device, the at least one of patient information and desired treatment outcome information to a web-based application program accessible through a web server, wherein the application is programmed to implement a long-acting FIX population pharmacokinetic (popPK) model, such as that of Example 5 or 7, e.g., Table 10, 13, or 14, and a Bayesian estimation program, (c) receiving from the web based server and program, median long-acting FIX PK dosing information calculated using the popPK model, the Bayesian estimation program, and the received information, and (d) outputting, by the one or more electronic devices, the median PK information. In some embodiments, the method also comprises selecting a dosing regimen based on the output median PK information of (e), and (f) administering the long-acting FIX polypeptide to a patient according to the selected dosing regimen. In some embodiments, the method also comprises selecting a dosing regimen based on the output individualized dosing information output in (d) and administering the long-acting FIX polypeptide to the patient according to the selected dosing regimen.

In some embodiments, the patient information includes body weight. In some embodiments, the desired treatment outcome information is desired rise in plasma FIX activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating a long-acting FIX dosing regimen based on median popPK, that comprises: (a) receiving, by a processing device, at least one of patient information and desired treatment outcome information by a web-based application program accessible through a web server and programmed to implement a long-acting FIX population pharmacokinetic (popPK) model, and a Bayesian estimation program, wherein the received information is transmitted by one or more electronic devices, (b) calculating, by the web-based program, individualized long-acting FIX dosing information using the popPK model, the Bayesian estimation program, and the received information, and (c) transmitting, by a processing device, the individualized calculated dosing information of (b) to one or more electronic devices for output of the information. In some embodiments, the method also comprises selecting a dosing regimen based on the output individualized dosing information transmitted in (c) and administering the long-acting FIX polypeptide to the patient according to the selected dosing regimen.

In some embodiments, the desired treatment outcome information is desired rise in plasma FIX activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating individual patient long-acting FIX PK, the method comprising: (a) receiving, by one or more electronic devices, individual long-acting FIX PK information, (b) transmitting, by a processing device, the individual long-acting FIX PK information to a web-based application program accessible through a web server, wherein the application is programmed to implement a long-acting FIX population pharmacokinetic (popPK) model, such as that of Example 5 or 7, e.g., Table 10, 13, or 14, and a Bayesian estimation program, (c) receiving from the web-based server and program, individualized patient long-acting FIX PK information using the popPK model, the Bayesian estimation program, and the transmitted information of (b) and (d) outputting, by the one or more electronic devices, the individualized patient PK information. In some embodiments the patient information is age or body weight. In some embodiments, the method also comprises selecting a dosing regimen based on the individualized patient PK information output in (d) and administering the long-acting FIX polypeptide to the patient according to the selected dosing regimen.

The invention also includes a web-based method of estimating a long-acting FIX dosing regimen based on median popPK, the method comprising: (a) receiving, by one or more electronic devices at least one of patient information and desired treatment outcome information, (b) transmitting, by a processing device, the at least one of patient information and desired treatment outcome information to a web-based application program accessible through a web server, wherein the application is programmed to implement a long-acting FIX population pharmacokinetic (popPK) model, such as that of Example 5 or 7, e.g., Table 10, 13, or 14, and, optionally, a Bayesian estimation program, (c) receiving from the web based server and program, median long-acting FIX PK dosing information calculated using the popPK model, the optional Bayesian estimation program, and the received information, and (d) outputting, by the one or more electronic devices, the median PK information. In some embodiments, the method also comprises selecting a dosing regimen based on the output median PK information of (d), and (f) administering long-acting FIX to a patient according to the selected dosing regimen.

In some embodiments, the desired treatment outcome information is desired rise in plasma FIX activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating individual patient long-acting FIX PK, the method comprising: (a) receiving, by one or more electronic devices, individual long-acting FIX PK information, (b) transmitting, by a processing device, the individual long-acting FIX PK information to a web-based application program accessible through a web server, wherein the application is programmed to implement a long-acting FIX population pharmacokinetic (popPK) model, such as that of Example 5 or 7, e.g., Table 10, 13, or 14, and, optionally, a Bayesian estimation program, (c) receiving from the web-based server and program, individualized patient long-acting FIX PK information calculated using the popPK model, the optional Bayesian estimation program, and the transmitted information of (b) and (d) outputting, by the one or more electronic devices, the calculated patient PK information. In some embodiments, the method also comprises selecting a dosing regimen based on the output calculated patient PK information of (d) and administering the long-acting FIX polypeptide to the patient according to the selected dosing regimen.

In particular embodiments, the individual long-acting FIX PK information includes 2-3 PK sampling time points. In some embodiments, the individual long-acting FIX PK information includes one or more of patient body weight, diagnostic (baseline) factor level, dosing history if PK samples were taken from multiple doses, actual dose, actual time of PK sampling, factor activity level and patient body weight.

In some embodiments the output individualized patient PK includes a PK curve or a PK parameter selected from incremental recovery (Cmax/Dose), mean residence time, terminal $t_{1/2}$, clearance, Vss and AUC/Dose. In some embodiments, the desired treatment outcome information based on the individual patient's PK is desired rise in plasma FIX activity level following dosing and the output information is dose for acute treatment.

The invention also includes a web-based method of estimating individual patient long-acting FIX PK, the method comprising: (a) receiving, of individual long-acting FIX PK information by a web-based application program accessible through a web server, and programmed to implement a long-acting FIX population pharmacokinetic (popPK) model, such as that of Example 5 or 7, e.g., Table 10, 13, or 14, and, optionally, a Bayesian estimation program, wherein the received information is transmitted by one or more electronic devices (b) estimating, by the web-based program, individualized patient long-acting FIX PK information using the popPK model, the optional Bayesian estimation program, and the received information, and (c) transmitting, by a processing device, the estimated individualized patient long-acting FIX PK information of (b) to one or more one or more electronic devices for output of the individualized patient PK information. In some embodiments, the method also comprises selecting a dosing regimen based on the transmitted patient PK information in (c) and administering the long-acting FIX polypeptide to the patient according to the selected dosing regimen.

In particular embodiments, the individual long-acting FIX PK information includes 2-3 PK sampling time points. In some embodiments, the individual long-acting FIX PK information includes one or more of patient body weight, diagnostic (baseline) factor level, dosing history if PK samples were taken from multiple doses, actual dose, actual time of PK sampling, factor activity level and patient body weight.

In some embodiments the output individualized patient PK includes a PK curve or a PK parameter selected from incremental recovery (Cmax/Dose), mean residence time, terminal $t_{1/2}$, clearance, Vss and AUC/Dose. In some embodiments, the desired treatment outcome information based on the individual patient's PK is desired rise in plasma FIX activity level following dosing and the output information is dose for acute treatment.

The invention also includes a web-based method of estimating individual patient long-acting FIX PK, the method comprising: (a) receiving, by one or more electronic devices, individual long-acting FIX PK information, (b) transmitting, by a processing device, the individual long-acting FIX PK information to a web-based application program accessible through a web server, and programmed to implement a long-acting FIX population pharmacokinetic (popPK) model, such as that of Example 5 or 7, e.g., Table 10, 13, or 14, and, optionally, a Bayesian estimation program, (c) estimating, by the web-based program, individualized patient long-acting FIX PK information using the popPK model, the optional Bayesian estimation program, and the received information, (d) transmitting, by a processing device, the estimated individualized patient long-acting FIX PK information of (c) to one or more one or more electronic devices, and (e) outputting, by the one or more electronic devices, the individualized patient PK information. In some embodiments, the method also comprises selecting a dosing regimen based on the transmitted patient PK information of (d) and administering the long-acting FIX polypeptide to the patient according to the selected dosing regimen.

In particular embodiments, the individual long-acting FIX PK information includes 2-3 PK sampling time points. In some embodiments, the individual long-acting FIX PK information includes one or more of patient body weight, diagnostic (baseline) factor level, dosing history if PK samples were taken from multiple doses, actual dose, actual time of PK sampling, factor activity level and patient body weight.

In some embodiments the output individualized patient PK includes a PK curve or a PK parameter selected from incremental recovery (Cmax/Dose), mean residence time, terminal t½, clearance, Vss and AUC/Dose. In some embodiments, the desired treatment outcome information based on the individual patient's PK is desired rise in plasma FIX activity level following dosing and the output information is dose for acute treatment.

In another embodiment, the invention includes a web-based method of estimating individual patient long-acting FIX PK, the method comprising: (a) receiving, by one or more electronic devices, information regarding individual body weight and (i) desired rise of plasma factor activity level following the dose or (ii) desired dose or desired dose interval, (b) transmitting, by a processing device, the information of (a) to a web-based application program accessible through a web server, wherein the application is programmed to implement a long-acting FIX population pharmacokinetic (popPK) model, such as that of Example 5 or 7, e.g., Table 10, 13, or 14, and a Bayesian estimation program, (c) receiving from the web based server and program, individualized patient long-acting FIX PK information calculated using the popPK model, the Bayesian estimation program, and the transmitted information of (b), and (d) outputting, by the one or more electronic devices, the estimated patient PK information. In some embodiments, the method also comprises selecting a dosing regimen based on the output estimated patient PK information output of (d), and administering the long-acting FIX polypeptide to the patient according to the selected regimen.

In some embodiments (a) further comprises receiving, by the electronic device patient information and (b) further comprises transmitting, by a processing device, the patient information to the web-based application program. In some embodiments (a) further comprises receiving information, by the electronic device information relating to diagnostic (baseline) factor level, dosing history (if PK samples were taken from multiple doses), actual dose, actual time of PK sampling or factor activity level and (b) further comprises transmitting, by a processing device, the information to the web-based application program. In some embodiments the individualized patient PK includes a PK curve or a PK parameter selected from incremental recovery (Cmax/Dose), mean residence time, terminal tin, clearance, Vss and AUC/Dose.

In another embodiment, the invention includes a web-based method of estimating individual patient long-acting FIX PK, that comprises: (a) receiving information regarding individual body weight and (i) desired rise of plasma factor activity level following the dose or (ii) desired dose or desired dose interval, wherein the received information is transmitted by one or more electronic devices, (c) estimating, by the web-based program, individualized patient long-acting FIX PK information using the popPK model, the Bayesian estimation program, and the received information, based on population median, and (c) transmitting, by a processing device, the estimated patient PK information of (b) to one or more electronic devices for output of the information. In some embodiments, the method also comprises selecting a dosing regimen based on the estimated patient PK information transmitted in (c), and administering the long-acting FIX polypeptide to the patient according to the selected regimen.

In some embodiments (a) further comprises receiving, by the electronic device additional patient information and (b) further comprises transmitting, by a processing device, the additional patient information to the web-based application program. In some embodiments (a) further comprises receiving information, by the electronic device information relating to diagnostic (baseline) factor level, dosing history (if PK samples were taken from multiple doses), actual dose, actual time of PK sampling or factor activity level and (b) further comprises transmitting, by a processing device, the information to the web-based application program.

In another embodiment, the invention includes a web-based method of estimating individual patient long-acting FIX PK, the method comprising: (a) receiving, by one or more electronic devices, patient information regarding individual body weight and (i) desired rise of plasma factor activity level following the dose or (ii) desired dose or desired dose interval, (b) transmitting, by a processing device, the information of (a) to a web-based application program accessible through a web server, and programmed to implement a long-acting FIX population pharmacokinetic (popPK) model, such as that of Example 5 or 7, e.g., Table 10, 13, or 14, and, optionally, a Bayesian estimation program. (c) estimating, by the web-based program, individualized patient long-acting FIX PK information using the popPK model, the optional Bayesian estimation program, and the received information, based on population medium, (d) transmitting, by a processing device, the estimated patient PK information of (c) to one or more electronic devices, and (e) outputting, by the one or more electronic devices, the estimated patient PK information. In some embodiments, the method also comprises selecting a dosing regimen based on the estimated patient PK information of (c), and administering long-acting FIX to the patient according to the selected regimen.

In some embodiments, a processor (processing device) is an electronic device. In some embodiments, the electronic device is selected from a digital pen, a smart phone, a tablet computer, a personal digital assistant, a handheld computer, a laptop computer, a point-of-sale transaction device, a scanner, a camera, and a fax machine.

In some embodiments (a) further comprises receiving, by the electronic device patient information and (b) further comprises transmitting, by a processing device, the patient information to the web-based application program. In some embodiments (a) further comprises receiving information, by the electronic device information relating to diagnostic (baseline) factor level, dosing history (if PK samples were taken from multiple doses), actual dose, actual time of PK sampling or factor activity level and (b) further comprises transmitting, by a processing device, the information to the web-based application program. In some embodiments the individualized patient PK includes a PK curve or a PK parameter selected from incremental recovery (Cmax/Dose), mean residence time, terminal $t_{1/2}$, clearance, Vss and AUC/Dose.

In some embodiments, the electronic device is selected from a digital pen, a smart phone, a tablet computer, a personal digital assistant, a handheld computer, a laptop computer, a point-of-sale transaction device, a scanner, a camera, and a fax machine.

The electronic device can be a general-purpose computer with a processor, local memory, display, and one or more computer input devices such as a keyboard, a mouse and/or a joystick. Alternatively, the electronic device can be a specialized computing device such as, for example, a mobile handset. The electronic device communicates with one or more network-based (e.g., web-based) application programs over one or more networks, such as the Internet. Similar to the electronic device, the network-based (e.g., web-based) application program can be implemented using any general-purpose computer capable of serving data to the electronic device.

Each of the client, authority, or transmitter may be implemented on any electronic device. Such electronic device can include, but is not limited to, a personal computer, mobile device such as a mobile phone, workstation, embedded system, game console, television, set-top box, or any other computing device. Further, an electronic device can include, but is not limited to, a device having a processor and memory for executing and storing instructions. Software may include one or more applications and an operating system. Hardware can include, but is not limited to, a processor, memory and graphical user interface display. The electronic device may also have multiple processors and multiple shared or separate memory components. For example, the electronic device may be a clustered computing environment or server farm.

Network 116 can be any network or combination of networks that can carry data communication, and may be referred to herein as a computer network. Such network 116 can include, but is not limited to, a local area network, medium area network, and/or wide area network such as the Internet. Network 116 can support protocols and technology including, but not limited to, World Wide Web protocols and/or services. Intermediate web servers, gateways, or other servers may be provided between components of system 100 depending upon a particular application or environment.

III. Method System, and Storage Medium for Estimating Patient Individualized Dosing Information, Patient Individualized PK Information, and Patient Median PK Information—FVIII The invention also includes a method of estimating a long-acting FVIII dosing information individualized for a patient, the method comprising: (a) receiving, by a computer-based system containing the long-acting FVIII population pharmacokinetic (popPK) model of Example 9 or 11 or 16, e.g., Table 18, 24, 25, or 33, and, optionally, a Bayesian estimation program, at least one of patient information and desired treatment outcome information, (b)

calculating, by the computer-based system, individualized long-acting FVIII dosing information using the popPK model, the optional Bayesian estimation program, and the received information, and (c) outputting, by the computer-based system, the individualized dosing information.

In some embodiments, the method also comprises selecting a dosing regimen based on the output individualized dosing information of (c) and administering the long-acting FVIII polypeptide to the patient according to the selected dosing regimen.

In some embodiments, the desired treatment outcome information is desired rise in plasma FVIII activity level following dosing and the output information is dose for acute treatment.

In some embodiments, the desired treatment outcome information is desired dosing interval and the output information is dose for prophylaxis.

In some embodiments, the desired treatment outcome information is desired dose and the output information is interval for prophylaxis.

The invention also includes a method of estimating a long-acting FVIII dosing regimen based on median popPK, the method comprising: (a) receiving, by a computer-based system containing the long-acting FVIII popPK model of Example 9 or 11 or 16, e.g., Table 18, 24, 25, or 33, and, optionally, a Bayesian estimation program, at least one of patient information and desired treatment outcome information, (b) calculating, by the computer-based system, median long-acting FVIII PK information using the popPK model, the optional Bayesian estimation program, and the received information, and (c) outputting, by the computer-based system, the median PK information.

In some embodiments, the method also comprises selecting a dosing regimen based on the output median PK information of (c), and administering the long-acting FVIII polypeptide to a patient according to the selected dosing regimen.

The invention also includes a method of estimating individual patient long-acting FVIII PK, the method comprising: (a) receiving, by a computer-based system containing the long-acting FVIII population pharmacokinetic (popPK) model of Example 9 or 11 or 16, e.g., Table 18, 24, 25, or 33, and, optionally, a Bayesian estimation program, individual long-acting FVIII PK information, (b) estimating, by the computer-based system, individualized patient long-acting FVIII PK information using the popPK model, the optional Bayesian estimation program, and the received information, and (c) outputting, by the computer-based system, the individualized patient PK information.

In some embodiments, the method also comprises selecting a dosing regimen based on the output individualized patient PK information of (c), and administering the long-acting FVIII polypeptide to the patient according to the selected regimen.

In some embodiments (a) further comprises receiving, by the computer-based system, patient information.

In some embodiments the patient information is age, e.g., 12 and older, Von Willebrand Factor, hematocrit, or body weight. Additional patient information includes diagnostic (baseline) FVIII level, PK determinations, time of PK sampling, dosing history if PK samples were taken from multiple doses, actual dose, FVIII activity level, etc.

In some embodiments, desired treatment outcome information is, e.g., desired PK or desired regimen outcome, e.g., desired rise in plasma FVIII activity level following dose, desired dosing interval, and desired dose.

In some embodiments, output information is, e.g., PK curve, PK parameter such as incremental recovery (Cmax/dose), mean residence time, terminal t½, clearance, Vss, AUC/dose, doses and associated troughs, and intervals and associated troughs.

For example, for assessing individualized patient PK, the system can recommend that the user input 2-3 optimized PK sampling time points. In this case, system output can include PK curve and one or more selected PK parameters, e.g., incremental recovery (Cmax/Dose), mean residence time, terminal t½, clearance, Vss, AUC, and time to 1 or X %, etc., e.g., FIG. 14.

As additional examples, to select an individualized dosing regimen using the output individual PK parameters discussed in the preceding paragraph, (i) the dose selected for acute treatment can be based on user input of the desired rise in plasma FVIII activity level following the dose, (ii) the dose selected for prophylaxis can be based on user input of the desired dosing interval, or (iii) the selected interval for prophylaxis can be based on user input for the desired dose. In the first case, the system can output the dose (IU) based in the patient's incremental recovery, e.g., FIG. 14. In the second case, system output can be a table of doses and associated troughs, e.g., x IU/kg, 1% trough, y IU/kg, 2% trough, etc. e.g., FIG. 15, top. In the third case, system output can be a table of intervals and associated troughs, e.g., x days, 1% trough, y IU/kg, 2% trough, etc., e.g., FIG. 15, bottom.

The user may wish to use the system without inputting any individualized PK data. In this case, the dosing output would be based on the population median rather than being individualized for the particular patient. E.g., FIG. 15. In this way, the user inputs, e.g., body weight and age, and (i) the desired rise in plasma FVIII activity level following the dose, (ii) the desired dose interval for prophylaxis, or (iii) the desired dose for prophylaxis. In the first case, the system can output the dose. In the second case, the system can output the dose and associated trough. E.g., Table 19 In the third case, the system can output the interval and associated trough. E.g., Table 20.

In some embodiments, the system is compliant with patient privacy laws. In some embodiments, the system is encrypted, e.g., with SSL. In some embodiments, input patient information is made anonymous.

In some embodiments, the system includes a user help function.

The method can be carried out by, e.g., a physician, a nurse, or another healthcare practitioner.

Additional embodiments include a computer readable storage medium having instructions stored thereon that, when executed by a processor, cause the processor to perform any of the above methods.

Additional embodiments include a system comprising a processor and a memory, the memory having instructions stored thereon that, when executed by the processor, cause the processor to perform any of the above methods.

The user of the system or computer readable storage medium, can be, e.g., a physician, a nurse, or another healthcare practitioner.

For additional embodiments of these aspects of the invention, see Examples 9, 10, and 11 and the Figures discussed therein.

In some embodiments, the system is web-based.

According to one embodiment, the invention includes a web-based method of estimating a long-acting FVII dosing information individualized for a patient, the method comprising: (a) receiving, by one or more electronic devices, at least one of patient information and desired treatment outcome information, (b) transmitting, by a processing device, the at least one of patient information and desired treatment outcome information to a web-based application program accessible through a web server, wherein the application is programmed to implement a long-acting FVIII population pharmacokinetic (popPK) model, such as that of Example 9 or 11 or 16, e.g., Table 18, 24, 25, or 33, and, optionally, a Bayesian estimation program, (c) receiving from the web based server and program, individualized dosing information calculated using the popPK model, the optional Bayesian estimation program, and the transmitted information of (b), and (d) outputting, by the one or more electronic devices, the individualized dosing information. In some embodiments, the method also comprises selecting a dosing regimen based on the output individualized dosing information of (d) and administering the long-acting FVIII polypeptide to the patient according to the selected dosing regimen.

In some embodiments, the patient information includes body weight. In some embodiments, the desired treatment outcome information is desired rise in plasma FVIII activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating a long-acting FVIII dosing information individualized for a patient, wherein the method comprises: (a) receiving, by a processing device, at least one of patient information and desired treatment outcome information by a web-based application program accessible through a web server and programmed to implement a long-acting FVIII population pharmacokinetic (popPK) model, and a Bayesian estimation program, and the received information, and (c) transmitting, by a processing device, the individualized calculated dosing information of (b) to one or more electronic devices for output of the information. In some embodiments, the method also comprises selecting a dosing regimen based on the output individualized dosing information transmitted in (c) and administering the long-acting FVIII polypeptide to the patient according to the selected dosing regimen.

In some embodiments, the patient information includes body weight. In some embodiments, the desired treatment outcome information is desired rise in plasma FVIII activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating a long-acting FVIII dosing information individualized for a patient, the method comprising: (a) receiving, by an electronic device, at least one of patient information and desired treatment outcome, (b) transmitting, by a processing device, the individual long-acting FVIII PK information to outcome information to a web-based application program accessible through a web server, and programmed to implement a long-acting FVIII population pharmacokinetic (popPK) model, such as that of Example 9 or 11 or 16, e.g., Table 18, 24, 25, or 33, and, optionally, a Bayesian estimation program, (c) calculating, by the web-based program, individualized long-acting FVIII dosing information using the popPK model, and optionally a Bayesian estimation program, and the received information, (d) transmitting, by a processing device, the individualized calculated dosing information of (c) to one or more one or more electronic devices, and (e) outputting, by the one or more electronic devices, the individualized dosing information. In some embodiments, the method also comprises selecting a dosing regimen based on the output individualized dosing information of (e) and administering the long-acting FVIII polypeptide to the patient according to the selected dosing regimen. In some embodiments, the method also comprises selecting a dosing regimen based on the output individualized dosing information in (e) and administering the long-acting FVIII polypeptide to the patient according to the selected dosing regimen.

In some embodiments, the patient information includes body weight. In some embodiments, the desired treatment outcome information is desired rise in plasma FVIII activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis The invention also includes a web-based method of estimating a long-acting FVIII dosing regimen based on median popPK, the method comprising: (a) receiving, by one or more electronic devices at least one of patient information and desired treatment outcome information, (b) transmitting, by a processing device, the at least one of patient information and desired treatment outcome information to a web-based application program accessible through a web server, wherein the application is programmed to implement a long-acting FVIII population pharmacokinetic (popPK) model, such as that of Example 9 or 11 or 16, e.g., Table 18, 24, 25, or 33, and a Bayesian estimation program, (c) receiving from the web based server and program, median long-acting FVIII PK dosing information calculated using the popPK model, the Bayesian estimation program, and the received information, and (d) outputting, by the one or more electronic devices, the median PK information. In some embodiments, the method also comprises selecting a dosing regimen based on the output median PK information of (e), and (f) administering the long-acting FVIII polypeptide to a patient according to the selected dosing regimen. In some embodiments, the method also comprises selecting a dosing regimen based on the output individualized dosing information output in (d) and administering the long-acting FVIII polypeptide to the patient according to the selected dosing regimen.

In some embodiments, the patient information includes body weight. In some embodiments, the desired treatment outcome information is desired rise in plasma FVIII activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating a long-acting FVIII dosing regimen based on median popPK, that comprises: (a) receiving, by a processing device, at least one of patient information and desired treatment outcome information by a web-based application program accessible through a web server and programmed to implement a long-acting FVIII population pharmacokinetic (popPK) model, and a Bayesian estimation program, wherein the received information is transmitted by one or more electronic devices, (b) calculating, by the web-based program, individualized long-acting FVIII dosing information using the popPK model, the Bayesian estimation program, and the received information, and (c) transmitting, by a processing device, the individualized calculated dosing information of (b) to one or more electronic devices for output of the information. In some embodiments, the method also comprises selecting a dosing regimen based on the output individualized dosing information transmitted in (c) and administering the long-acting FVIII polypeptide to the patient according to the selected dosing regimen.

In some embodiments, the desired treatment outcome information is desired rise in plasma FVIII activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating individual patient long-acting FVIII PK, the method comprising: (a) receiving, by one or more electronic devices, individual long-acting FVIII PK information, (b) transmitting, by a processing device, the individual long-acting FVIII PK information to a web-based application program accessible through a web server, wherein the application is programmed to implement a long-acting FVIII population pharmacokinetic (popPK) model, such as that of Example 9 or 11 or 16, e.g., Table 18, 24, 25, or 33, and a Bayesian estimation program, (c) receiving from the web-based server and program, individualized patient long-acting FVIII PK information using the popPK model, the Bayesian estimation program, and the transmitted information of (b) and (d) outputting, by the one or more electronic devices, the individualized patient PK information. In some embodiments the patient information is age or body weight. In some embodiments, the method also comprises selecting a dosing regimen based on the individualized patient PK information output in (d) and administering the long-acting FVIII polypeptide to the patient according to the selected dosing regimen.

The invention also includes a web-based method of estimating a long-acting FVIII dosing regimen based on median popPK, the method comprising: (a) receiving, by one or more electronic devices at least one of patient information and desired treatment outcome information, (b) transmitting, by a processing device, the at least one of patient information and desired treatment outcome information to a web-based application program accessible through a web server, wherein the application is programmed to implement a long-acting FVIII population pharmacokinetic (popPK) model, such as that of Example 9 or 11 or 16, e.g., Table 18, 24, 25, or 33, and, optionally, a Bayesian estimation program, (c) receiving from the web based server and program, median long-acting FVIII PK dosing information calculated using the popPK model, the optional Bayesian estimation program, and the received information, and (d) outputting, by the one or more electronic devices, the median PK information. In some embodiments, the method also comprises selecting a dosing regimen based on the output median PK information of (d), and (f) administering the long-acting FVIII polypeptide to a patient according to the selected dosing regimen.

In some embodiments, the desired treatment outcome information is desired rise in plasma FVIII activity level following dosing and the output information is dose for acute treatment. In some embodiments, the desired treatment outcome information is desired dosing interval and the output information is dose for prophylaxis. In some embodiments, the desired treatment outcome information is desired dose and the output information is interval for prophylaxis.

The invention also includes a web-based method of estimating individual patient long-acting FVIII PK, the method comprising: (a) receiving, by one or more electronic devices, individual long-acting FVIII PK information, (b) transmitting, by a processing device, the individual long-acting FVIII PK information to a web-based application program accessible through a web server, wherein the application is programmed to implement a long-acting FVIII population pharmacokinetic (popPK) model, such as that of Example 9 or 11 or 16, e.g., Table 18, 24, 25, or 33, and, optionally, a Bayesian estimation program, (c) receiving from the web-based server and program, individualized patient long-acting FVIII PK information calculated using the popPK model, the optional Bayesian estimation program, and the transmitted information of (b) and (d) outputting, by the one or more electronic devices, the calculated patient PK information. In some embodiments, the method also comprises selecting a dosing regimen based on the output calculated patient PK information of (d) and administering the long-acting FVIII polypeptide to the patient according to the selected dosing regimen.

In particular embodiments, the individual long-acting FVIII PK information includes 2-3 PK sampling time points. In some embodiments, the individual long-acting FVIII PK information includes one or more of patient body weight, diagnostic (baseline) factor level, dosing history if PK samples were taken from multiple doses, actual dose, actual time of PK sampling, factor activity level and patient body weight.

In some embodiments the output individualized patient PK includes a PK curve or a PK parameter selected from incremental recovery (Cmax/Dose), mean residence time, terminal t½, clearance, Vss and AUC/Dose. In some embodiments, the desired treatment outcome information based on the individual patient's PK is desired rise in plasma FIX activity level following dosing and the output information is dose for acute treatment.

The invention also includes a web-based method of estimating individual patient long-acting FVIII PK, the method comprising: (a) receiving, of individual long-acting FVIII PK information by a web-based application program accessible through a web server, and programmed to implement a long-acting FVIII population pharmacokinetic (popPK) model, such as that of Example 9 or 11 or 16, e.g., Table 18, 24, 25, or 33, and, optionally, a Bayesian estimation program, wherein the received information is transmitted by one or more electronic devices (b) estimating, by the web-based program, individualized patient long-acting FVIII PK information using the popPK model, the optional Bayesian estimation program, and the received information, and (c) transmitting, by a processing device, the estimated individualized patient long-acting FVIII PK information of (b) to one or more one or more electronic devices for output of the individualized patient PK information. In some embodiments, the method also comprises selecting a dosing regimen based on the transmitted patient PK information in (c) and administering the long-acting FVIII polypeptide to the patient according to the selected dosing regimen.

In particular embodiments, the individual long-acting FVIII PK information includes 2-3 PK sampling time points. In some embodiments, the individual long-acting FVIII PK information includes one or more of patient body weight, diagnostic (baseline) factor level, dosing history if PK samples were taken from multiple doses, actual dose, actual time of PK sampling, factor activity level and patient body weight.

In some embodiments the output individualized patient PK includes a PK curve or a PK parameter selected from incremental recovery (Cmax/Dose), mean residence time, terminal t½, clearance, Vss and AUC/Dose. In some embodiments, the desired treatment outcome information based on the individual patient's PK is desired rise in plasma FVIII activity level following dosing and the output information is dose for acute treatment.

The invention also includes a web-based method of estimating individual patient long-acting FVIII PK, the method comprising: (a) receiving, by one or more electronic devices, individual long-acting FVIII PK information, (b) transmitting, by a processing device, the individual long-acting FVIII PK information to a web-based application program accessible through a web server, and programmed to implement a long-acting FVIII population pharmacokinetic (popPK) model, such as that of Example 9 or 1 or 16, e.g., Table 18, 24, 25, or 33, and, optionally, a Bayesian estimation program, (c) estimating, by the web-based program, individualized patient long-acting FVIII PK information using the popPK model, the optional Bayesian estimation program, and the received information, (d) transmitting, by a processing device, the estimated individualized patient long-acting FVIII PK information of (c) to one or more one or more electronic devices, and (e) outputting, by the one or more electronic devices, the individualized patient PK information. In some embodiments, the method also comprises selecting a dosing regimen based on the transmitted patient PK information of (d) and administering the long-acting FVIII polypeptide to the patient according to the selected dosing regimen.

In particular embodiments, the individual long-acting FVIII PK information includes 2-3 PK sampling time points. In some embodiments, the individual long-acting FVIII PK information includes one or more of patient body weight, diagnostic (baseline) factor level, dosing history if PK samples were taken from multiple doses, actual dose, actual time of PK sampling, factor activity level and patient body weight.

In some embodiments the output individualized patient PK includes a PK curve or a PK parameter selected from incremental recovery (Cmax/Dose), mean residence time, terminal t½, clearance, Vss and AUC/Dose. In some embodiments, the desired treatment outcome information based on the individual patient's PK is desired rise in plasma FVIII activity level following dosing and the output information is dose for acute treatment.

In another embodiment, the invention includes a web-based method of estimating individual patient long-acting FVIII PK, the method comprising: (a) receiving, by one or more electronic devices, information regarding individual body weight and (i) desired rise of plasma factor activity level following the dose or (ii) desired dose or desired dose interval, (b) transmitting, by a processing device, the information of (a) to a web-based application program accessible through a web server, wherein the application is programmed to implement a long-acting FVIII population pharmacokinetic (popPK) model, such as that of Example 9 or 11 or 16, e.g., Table 18, 24, 25, or 33, and a Bayesian estimation program, (c) receiving from the web based server and program, individualized patient long-acting FVIII PK information calculated using the popPK model, the Bayesian estimation program, and the transmitted information of (b), and (d) outputting, by the one or more electronic devices, the estimated patient PK information. In some embodiments, the method also comprises selecting a dosing regimen based on the output estimated patient PK information output of (d), and administering the long-acting FVIII polypeptide to the patient according to the selected regimen.

In some embodiments (a) further comprises receiving, by the electronic device patient information and (b) further comprises transmitting, by a processing device, the patient information to the web-based application program. In some embodiments (a) further comprises receiving information, by the electronic device information relating to diagnostic (baseline) factor level, dosing history (if PK samples were taken from multiple doses), actual dose, actual time of PK sampling or factor activity level and (b) further comprises transmitting, by a processing device, the information to the web-based application program. In some embodiments the individualized patient PK includes a PK curve or a PK parameter selected from incremental recovery (Cmax/Dose), mean residence time, terminal t½, clearance, Vss and AUC/Dose.

In another embodiment, the invention includes a web-based method of estimating individual patient long-acting FVIII PK, that comprises: (a) receiving information regarding individual body weight and (i) desired rise of plasma factor activity level following the dose or (ii) desired dose or desired dose interval, wherein the received information is transmitted by one or more electronic devices, (c) estimating, by the web-based program, individualized patient long-acting FVIII PK information using the popPK model, the Bayesian estimation program, and the received information, based on population median, and (c) transmitting, by a processing device, the estimated patient PK information of (b) to one or more electronic devices for output of the information. In some embodiments, the method also comprises selecting a dosing regimen based on the estimated patient PK information transmitted in (c), and administering the long-acting FVIII polypeptide to the patient according to the selected regimen.

In some embodiments (a) further comprises receiving, by the electronic device additional patient information and (b) further comprises transmitting, by a processing device, the additional patient information to the web-based application program. In some embodiments (a) further comprises receiving information, by the electronic device information relating to diagnostic (baseline) factor level, dosing history (if PK samples were taken from multiple doses), actual dose, actual time of PK sampling or factor activity level and (b) further comprises transmitting, by a processing device, the information to the web-based application program.

In another embodiment, the invention includes a web-based method of estimating individual patient long-acting FVIII PK, the method comprising: (a) receiving, by one or more electronic devices, patient information regarding individual body weight and (i) desired rise of plasma factor activity level following the dose or (ii) desired dose or desired dose interval, (b) transmitting, by a processing device, the information of (a) to a web-based application program accessible through a web server, and programmed to implement a long-acting FVIII population pharmacokinetic (popPK) model, such as that of Example 9 or 11 or 16, e.g., Table 18, 24, 25, or 33, and, optionally, a Bayesian estimation program, (c) estimating, by the web-based program, individualized patient long-acting FVIII PK information using the popPK model, the optional Bayesian estimation program, and the received information, based on population medium, (d) transmitting, by a processing device, the estimated patient PK information of (c) to one or more electronic devices, and (e) outputting, by the one or more electronic devices, the estimated patient PK information. In some embodiments, the method also comprises selecting a dosing regimen based on the estimated patient PK information of (c), and administering the long-acting FVIII polypeptide to the patient according to the selected regimen.

In some embodiments, a processor (processing device) is an electronic device. In some embodiments, the electronic device is selected from a digital pen, a smart phone, a tablet computer, a personal digital assistant, a handheld computer, a laptop computer, a point-of-sale transaction device, a scanner, a camera, and a fax machine.

In some embodiments (a) further comprises receiving, by the electronic device patient information and (b) further comprises transmitting, by a processing device, the patient information to the web-based application program. In some embodiments (a) further comprises receiving information, by the electronic device information relating to diagnostic (baseline) factor level, dosing history (if PK samples were taken from multiple doses), actual dose, actual time of PK sampling or factor activity level and (b) further comprises transmitting, by a processing device, the information to the web-based application program. In some embodiments the individualized patient PK includes a PK curve or a PK parameter selected from incremental recovery (Cmax/Dose), mean residence time, terminal t½, clearance, Vss and AUC/Dose.

In some embodiments, the electronic device is selected from a digital pen, a smart phone, a tablet computer, a personal digital assistant, a handheld computer, a laptop computer, a point-of-sale transaction device, a scanner, a camera, and a fax machine.

The electronic device can be a general-purpose computer with a processor, local memory, display, and one or more computer input devices such as a keyboard, a mouse and/or a joystick. Alternatively, the electronic device can be a specialized computing device such as, for example, a mobile handset. The electronic device communicates with one or more network-based (e.g., web-based) application programs over one or more networks, such as the Internet. Similar to the electronic device, the network-based (e.g., web-based) application program can be implemented using any general-purpose computer capable of serving data to the electronic device.

Each of the client, authority, or transmitter may be implemented on any electronic device. Such electronic device can include, but is not limited to, a personal computer, mobile device such as a mobile phone, workstation, embedded system, game console, television, set-top box, or any other computing device. Further, an electronic device can include, but is not limited to, a device having a processor and memory for executing and storing instructions. Software may include one or more applications and an operating system. Hardware can include, but is not limited to, a processor, memory and graphical user interface display. The electronic device may also have multiple processors and multiple shared or separate memory components. For example, the electronic device may be a clustered computing environment or server farm.

Network 116 can be any network or combination of networks that can carry data communication, and may be referred to herein as a computer network. Such network 116 can include, but is not limited to, a local area network, medium area network, and/or wide area network such as the Internet. Network 116 can support protocols and technology including, but not limited to, World Wide Web protocols and/or services. Intermediate web servers, gateways, or other servers may be provided between components of system 100 depending upon a particular application or environment.

In one embodiment of the present invention, the web-based application allows contemporaneously updating the popPK model based on the individual clotting factor pharmacokinetic information. In another embodiment, the web-based application continuously updates the popPK model based on newly input clotting factor pharmacokinetic information. By contemporaneously updating the popPK model based on the individual clotting factor pharmacokinetic information and/or by continuously updating the popPK model, the user of the application can have an access to the most updated popPK model, thereby obtaining the most accurate dosing information from the web-based application system. In addition, the web-based application allows the user to pool a large amount of information quickly and utilize the information in order to calculate the dosing information of the subject. This type of pooling and analyzing a large amount of information quickly and efficiently for the next user is not available routinely and by human hand.

IV. Exemplary Computing Environments for FVIII and FIX

Various modeling techniques, dosage calculations, and estimations described herein can be implemented by software, firmware, hardware, or a combination thereof. FIG. 17 illustrates an example computer system 1900 in which the embodiments, or portions thereof, can be implemented as computer-readable code. In one embodiment, for long-acting FIX polypeptide, the modeling of Examples 5 and 7, and/or the patient treatment simulation of Example 6 can be implemented in system 1900. In another embodiment, for long-acting FVIII polypeptide, the modeling of Examples 9 and 11, and/or the patient treatment simulation of Example 10 can be implemented in system 1900.

Computer system 1900 includes one or more processors, such as processor 1904. Processor 1904 is connected to a communication infrastructure 1906 (for example, a bus or network).

Computer system 1900 also includes a main memory 1908, preferably random access memory (RAM), and may also include a secondary memory 1910. In accordance with implementations, user interface data may be stored, for example and without limitation, in main memory 1908. Main memory 1908 may include, for example, cache, and/or static and/or dynamic RAM. Secondary memory 1910 may include, for example, a hard disk drive and/or a removable storage drive. Removable storage drive 1914 may include a floppy disk drive, a magnetic tape drive, an optical disk drive, a flash memory, or the like. The removable storage drive 1914 reads from and/or writes to removable storage unit 1916 in a well-known manner. Removable storage unit 1916 may include a floppy disk, magnetic tape, optical disk, etc. which is read by and written to by removable storage drive 1914. As will be appreciated by persons skilled in the relevant art(s), removable storage unit 1916 includes a computer readable storage medium having stored therein computer software and/or data.

Computer system 1900 may also include a display interface 1902. Display interface 1902 may be adapted to communicate with display unit 1930. Display unit 1930 may include a computer monitor or similar means for displaying graphics, text, and other data received from main memory 1908 via communication infrastructure 1906. In alternative implementations, secondary memory 1910 may include other similar means for allowing computer programs or other instructions to be loaded into computer system 1900. Such means may include, for example, a removable storage unit 1922 and an interface 1920. Examples of such means may include a program cartridge and cartridge interface (such as that found in video game devices), a removable memory chip (such as an EPROM, or PROM) and associated socket, and other removable storage units 1922 and interfaces 1920 which allow software and data to be transferred from the removable storage unit 1922 to computer system 1900.

Computer system 1900 may also include a communications interface 1924. Communications interface 1924 allows software and data to be transferred between computer system 1900 and external devices. Communications interface 1924 may include a modem, a network interface (such as an Ethernet card), a communications port, a PCMCIA slot and card, or the like. Software and data transferred via communications interface 1924 are in the form of signals which may be electronic, electromagnetic, optical, or other signals capable of being received by communications interface 1924. These signals are provided to communications interface 1924 via a communications path 1926. Communications path 1926 carries signals and may be implemented using wire or cable, fiber optics, a phone line, a cellular phone link, an RF link or other communications channels.

In this document, the term "computer readable storage medium" is used to generally refer to non-transitory storage media such as removable storage unit 1916, removable storage unit 1922, and a hard disk installed in hard disk drive 1912. Computer readable storage medium can also refer to one or more memories, such as main memory 1908 and secondary memory 1910, which can be memory semiconductors (e.g. DRAMs, etc.). These computer program products are means for providing software to computer system 1900.

Computer programs (also called computer control logic) are stored in main memory 1908 and/or secondary memory 1910. Computer programs may also be received via communications interface 1924 and stored on main memory 1908 and/or secondary memory 1910. Such computer programs, when executed, enable computer system 1900 to implement embodiments as discussed herein. In particular, the computer programs, when executed, enable processor 1904 to implement processes of the present disclosure, such as certain methods discussed above. Accordingly, such computer programs represent controllers of the computer system 1900. Where embodiments use software, the software may be stored in a computer program product and loaded into computer system 1900 using removable storage drive 1914, interface 1920, or hard drive 1912.

Embodiments may be directed to computer program products comprising software stored on any computer readable medium. Such software, when executed in one or more data processing device, causes a data processing device(s) to operate as described herein. Embodiments may employ any computer useable or readable medium. Examples of computer readable storage media include, but are not limited to, non-transitory primary storage devices (e.g., any type of random access memory), and non-transitory secondary storage devices (e.g., hard drives, floppy disks, CD ROMS, ZIP disks, tapes, magnetic storage devices, and optical storage devices, MEMS, nano-technological storage device, etc.). Other computer readable media include communication mediums (e.g., wired and wireless communications networks, local area networks, wide area networks, intranets, etc.).

FIG. 45 illustrates an example of a network-based system 2000 for a long-acting FIX polypeptide or a long-acting FVIII polypeptide, in which the embodiments, or portions thereof, can be implemented as computer-readable code. In one embodiment, for long-acting FIX polypeptide, the modeling of Examples 5 and 7, and/or the patient treatment simulation of Example 6 can be implemented in system 2000. In another embodiment, for long-acting FVIII polypeptide, the modeling of Examples 9 and 11, and/or the patient treatment simulation of Example 10 can be implemented in system 2000.

Network-based system 2000 includes network 2004 that can be any network or combination of networks that can carry data communication, and may be referred to herein as a computer network. Such network 2004 can include, but is not limited to, a local area network, medium area network, and/or wide area network such as the Internet. Network 2004 can support protocols and technology including, but not limited to, World Wide Web protocols and/or services. Intermediate web servers, gateways, or other servers may be provided between components of system 2000 depending upon a particular application or environment.

FIG. 45 shows a block diagram of an exemplary network-based system 2000 for obtaining an estimated patient individualized dosing information, patient individualized PK information, and patient median PK information. System 2000 includes an electronic device 2008 that can communicate over network 2004. Electronic device 2008 includes a transmitting engine 2012, and receiving engine 2016. Transmitting engine 2012 may transmit messages over network 2004. For example, transmitting engine 2012 may transmit information associated with dosing information individualized for a patient. Receiving engine 2016 may receive messages over network 2004 (e.g., from server 2020). For example, receiving engine 2016 may receive a response associated with individualized calculated dosing information transmitted over network 2004 by server 2020.

Electronic device 2008 can include computer system 1900 and can include, but is not limited to, a personal computer, mobile device such as a mobile phone, workstation, embedded system, game console, television, set-top box, or any other computing device. Further, electronic device 2008 can include, but is not limited to, a device having a processor and memory 2017 for executing and storing instructions.

Server 2020 is web-based or fixed (physical) and includes a receiving engine 2026 and a communications interface 2028. Receiving engine 2026 may receive messages over network 2004 (e.g., from electronic device 2008) and communicate the received message to application program 2032. In one embodiment, application program 2032 can be web-based or computer-based and is programmed to implement a long-acting FIX population pharmacokinetic (popPK) model such as that of Example 5 or 7, and, optionally, a Bayesian estimation program. In another embodiment, application program 2032 is web-based or computer-based and is programmed to implement a long-acting FVIII population pharmacokinetic (popPK) model such as that of Example 9 or 11 or 16, and, optionally, a Bayesian estimation program. Output of application program 2032 may be communicated by communications interface 2028 over network 2004. For example, transmitting engine 2030 may transmit output information associated with dosing information individualized for a patient over network 2004 to electronic device 2008.

V. Administering Long-Acting FIX Polypeptide

The present invention further comprises administering a dose of a long-acting FIX polypeptide to a human subject in need thereof at a dosing interval, wherein the dose and/or the dosing interval is identified by the web-based or computer based program. Administration of the long-acting FIX polypeptide is a replacement therapy by adding a recombinant FIX to a subject with FIX deficiency. Administration of the long-acting FIX polypeptide can reduce or prevent a number of bleeding or bleeding episodes in the subject.

The subject for the methods of the invention includes those in need of control or prevention of bleeding or bleeding episodes. The subject can be bleeding at the time of administration or be expected to be bleeding, or can be susceptible to bleeding in minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Such subjects also include those in need of peri-operative management, such as management of bleeding associated with surgery or dental extraction. In one embodiment, the subject is in need of prophylaxis of one or more bleeding episodes. In another embodiment, the subject is in need of individualized interval prophylaxis. In other embodiments, the subject is in need of on-demand treatment of one or more bleeding episodes. In still other embodiments, the subject is in need of perioperative management of one or more bleeding episodes.

The present invention also identifies the appropriate dosing amount and the dosing interval that can treat or prevent one or more bleeding episodes. Administration of the appropriate dosing amount for the dosing interval can achieve a plasma trough level of a FIX activity at least about 1 IU/dl or above 1 IU/dl during the interval in a subject administered with a long-acting FIX polypeptide. In one embodiment, the invention includes a dosing amount (or ranges of the dosing amount) and a dosing interval (or ranges of the dosing interval) that can maintain a plasma trough level of a FIX activity at least about 1 IU/dl (1%) or above 1 IU/dl (1%), at least about 2 IU/dl (2%) or above 2 IU/dl (2%), at least about 3 IU/dl (3%) or above 3 IU/dl (3%), at least about 4 IU/dl (4%) or above 4 IU/dl (4%), or at least about 5 IU/dl (5%) or above 5 IU/di (5%) throughout the interval. In another embodiment, a dosing amount (or ranges of the dosing amount) and a dosing interval (or ranges of the dosing interval) that reduces or decreases frequency of bleeding or bleeding disorder. In other embodiments, the dosing amount (or ranges of the dosing amount) and the dosing interval (or ranges of the dosing interval) of a long-acting FIX polypeptide stops on-going, uncontrollable bleeding or bleeding episodes in a subject administered with the dosing amount during the dosing interval. In still other embodiments, the dosing amount (or ranges of the dosing amount) and the dosing interval (or ranges of the dosing interval) of a long-acting FIX polypeptide prevents spontaneous bleeding or bleeding episodes in a subject susceptible to such spontaneous bleeding or bleeding episodes. Various dosing amounts and dosing intervals are described in International Appl. No. PCT/US2011/043569 filed Jul. 11, 2011 and published as WO 2012/006624 on Jan. 12, 2012, which is incorporated herein by reference in its entirety.

The doses that can be used in the methods of the invention are about 10 IU/kg to about 200 IU/kg, about 10 IU/kg to about 180 IU/kg, or about 25 IU/kg to about 200 IU/kg. In one embodiment, the dose of a long-acting FIX polypeptide is about 10 IU/kg to about 50 IU/kg, about 10 IU/kg to about 100 IU/kg, about 25 IU/kg to about 75 IU/kg, about 25 IU/kg to about 100 IU/kg, about 25 IU/kg to about 125 IU/kg, about 25 IU/kg to about 150 IU/kg, about 25 IU/kg to about 50 IU/kg, about 50 IU/kg to about 100 IU/kg, about 50 IU/kg to about 150 IU/kg, about 100 IU/kg to about 150 IU/kg, about 150 IU/kg to about 200 IU/kg, or any combinations thereof.

The dosing interval can, alternatively, be an individualized interval that is determined for each subject based on the population pharmacokinetic data or other information about that subject. The individualized dose/dosing interval combination can be the same as those for fixed interval regimens in the preceding paragraphs, or can differ. The regimen can initially be at a fixed dosing interval, and then it can change to an individualized dosing interval.

In some embodiments, a dose of a long-acting FIX polypeptide is an amount sufficient for individualized interval prophylaxis of a bleeding episode. In one example, the individualized interval is every nine days, every 10 days, every 11 days, every 12 days, every 13 days, every 14 days, every 15 days, every 16 days, every 17 days, every 18 days, every 19 days or two times monthly.

In some embodiments, a dose of a long-acting FIX polypeptide is sufficient for on-demand treatment of one or more bleeding episodes. The doses for the on-demand treatment can vary depending on the various factors, e.g., subject's baseline FIX activity, subject's body weight, subject's likelihood of experiencing bleeding episode, and etc. In one example, the doses for the on-demand treatment can be about 10 to about 50, about 15 to about 100, about 20 to about 100, about 20 to about 50, about 50 to about 100, about 10, about 20, about 40, about 50, and about 100 IU/kg.

In certain embodiments, a dosing amount and a dosing interval combination for a subject is 20 IU/kg once weekly, 40 IU/kg once weekly, 50 IU/kg once weekly, 100 IU/kg every 10 days, and 100 IU/kg every two weeks (or twice monthly). In one embodiment, a dosing frequency for a long-acting FIX polypeptide is about every two weeks or twice monthly. In another embodiment, the dosing frequency is every 7 days for 25-50 IU/kg, every 10-13 days for 50-100 IU/kg, or every 14 days for 100-150 IU/kg. The interval (or frequency) and dose are determined such that the combination of interval (or frequency) and dose will result in a trough level of at least about 1-5 or at least about 1-3, or at least about 1, at least about 2, at least about 3 IU/dl FIX activity in the subject.

In some embodiments of the invention, an annualized bleeding rate (ABR) of a bleeding episode is controlled by the present methods. For example, the dosing amount and dosing interval can be administered to reduce or decrease an annualized bleeding rate to a certain level. In one embodiment, administration of a long-acting FIX polypeptide at a dose and a dosing interval for prophylaxis of a bleeding episode results in an annual bleeding rate of less than 2, less than 2.5, less than 3, less than 3.5, less than 4, less than 4.5, less than 5, less than 5.5, less than 6, less than 6.5, less than 7, less than 7.5, less than 8, less than 8.5, less than 9, less than 9.5, or less than 10. For example, ABR of weekly prophylaxis of a bleeding episode can be 2.95.

The long-acting FIX polypeptide of the invention can provide a half-life, e.g., $T_{1/2\ beta}$ (activity) or $T_{1/2\ beta}$ (antigen), that is longer than wild-type FIX (e.g., a polypeptide consisting of amino acids 1 to 415 of SEQ ID NO: 2; BENEFIX®; or pdFIX). In one embodiment, a $T_{1/2\ beta}$ (activity) of a long-acting FIX polypeptide is at least about 40 hours, at least about 45 hours, at least about 50 hours, at least about 55 hours, at least about 60 hours, at least about 65 hours, at least about 70 hours, at least about 75 hours, at least about 80 hours, at least about 85 hours, at least about 90 hours, at least about 95 hours, at least about 100 hours, at least about 105 hours, at least about 110 hours, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, or at least about 193 hours.

In some embodiments, the $T_{1/2\ beta}$ (activity) of a long-acting FIX polypeptide is expressed as a mean. For example, a mean of the $T_{1/2\ beta}$ (activity) of a long-acting FIX polypeptide is at least about 76 hours, at least about 77 hours, at least about 78 hours, at least about 79 hours, at least about 80 hours, at least about 81 hours, at least about 82 hours, at least about 83 hours, at least about 84 hours, at least about 85 hours, at least about 86 hours, at least about 87 hours, at least about 88 hours, at least about 89 hours, at least about 90 hours, at least about 91 hours, or at least about 92 hours. In a specific embodiment, a mean of the $T_{1/2\ beta}$ (activity) of a long-acting FIX polypeptide is 82 hours.

In other embodiments, the $T_{1/2\ beta}$ (activity) of a long-acting FIX polypeptide is shown as a comparison to a $T_{1/2\ beta}$ (activity) of wild-type mature FIX. In one example, the mean of the $T_{1/2\ beta}$ (activity) is at least about 2.0 fold higher than wild-type mature FIX (a polypeptide consisting of amino acids 1 to 415 of SEQ ID NO: 2, BENEFIX®, or pdFIX). In another example, the mean of the $T_{1/2\ beta}$ (activity) is at least about 2.0 fold, at least about 2.1 fold, at least about 2.2 fold, at least about 2.3 fold, at least about 2.4 fold, at least about 2.5 fold, at least about 2.6 fold, at least about 2.7 fold, at least about 2.8 fold, at least about 2.9 fold, at least about 3.0 fold, at least about 3.1 fold, or at least about 3.2 fold higher than wild-type mature FIX (a polypeptide consisting of amino acids 1 to 415 of SEQ ID NO: 2, BENEFIX®, or pdFIX).

In certain embodiments of the invention, the method of the invention further comprises measuring a baseline FIX activity of a subject prior to the initial administration of a long-acting FIX polypeptide. Measuring of a baseline FIX activity can employ any known clotting assays in the art, e.g., one step aPTT assay, two step chromogenic assay, ROTEM, TGA, or etc.

In some embodiments, the method of the invention further comprises measuring a $T_{1/2beta}$ (activity) or $T_{1/2beta}$ (antigen) of the long-acting FIX polypeptide in the subject after administration of a long-acting FIX polypeptide.

Long-Acting FIX Polypeptide

A long-acting FIX polypeptide useful for the invention is a chimeric polypeptide comprising a FIX polypeptide and a second portion. In one embodiment, the second portion comprises albumin or an FcRn binding partner. Non-limiting examples for the second portion is described elsewhere herein. In certain embodiments, the long-acting FIX is a fusion protein comprising a single molecule of human recombinant coagulation FIX (rFIX) covalently linked to the dimeric Fc domain of immunoglobulin G1 (IgG1) with no intervening sequence. The FIX polypeptide of the invention comprises a functional Factor IX polypeptide in its normal role in coagulation, unless otherwise specified. Thus, the FIX polypeptide includes variant polypeptides that are functional and the polynucleotides that encode such functional variant polypeptides. In one embodiment, the FIX polypeptides are the human, bovine, porcine, canine, feline, and murine FIX polypeptides. The full length polypeptide and polynucleotide sequences of FIX are known, as are many functional variants, e.g., fragments, mutants and modified versions. FIX polypeptides include full-length FIX, full-length FIX minus Met at the N-terminus, full-length FIX minus the signal sequence, mature FIX (minus the signal sequence and propeptide), and mature FIX with an additional Met at the N-terminus. FIX can be made by recombinant means ("recombinant Factor IX" or "rFIX"), i.e., it is not naturally occurring or derived from plasma.

A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses FIX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International publication number WO 08/118507 A2, which is herein incorporated by reference in its entirety, discloses FIX mutants that exhibit increased clotting activity at page 5, line 14 to page 6, line 5. International publication number WO 09/051717 A2, which is herein incorporated by reference in its entirety, discloses FIX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant FIX molecules that have an increased number of glycosylation sites, which result in an increased half-life, at page 4, line 26 to page 12, line 6. International publication number WO 09/140015 A2, which is herein incorporated by reference in its entirety, discloses functional FIX mutants that an increased number of Cys residues, which can be used for polymer (e.g., PEG) conjugation, at page 11, paragraph [0043] to page 13, paragraph [0053]. The FIX polypeptides described in International Application No. PCT/US2011/043569 filed Jul. 11, 2011 and published as WO 2012/006624 on Jan. 12, 2012 are also incorporated herein by reference in its entirety.

In addition, hundreds of non-functional mutations in FIX have been identified in hemophilia subjects, many of which are disclosed in Table 5, at pages 11-14 of International publication number WO 09/137254 A2, which is herein incorporated by reference in its entirety. Such non-functional mutations are not included in the invention, but provide additional guidance for which mutations are more or less likely to result in a functional FIX polypeptide.

In one embodiment, the Factor IX (or Factor IX portion of a chimeric polypeptide) can be at least 70%, at least 80%, at least 85%, at least 90%, at least 95%, at least 96%, at least 97%, at least 98%, at least 99%, or 100% identical to a FIX amino acid sequence shown in Table 34A without a signal sequence and propeptide sequence (amino acids 1 to 415 of SEQ ID NO: 2), or alternatively, with a propeptide sequence, or with a propeptide and signal sequence (full length FIX).

A long-acting FIX polypeptide can be a hybrid FIX polypeptide. Hybrid FIX polypeptide means a combination of a FIX chimeric polypeptide with a second polypeptide. The chimeric polypeptide and the second polypeptide in a hybrid can be associated with each other via non-covalent protein-protein interactions, such as charge-charge or hydrophobic interactions. The chimeric polypeptide and the second polypeptide in a hybrid can be associated with each other via covalent bond(s) such as disulfide bonds. The chimeric peptide and the second peptide can be associated with each other via more than one type of bond, such as non-covalent and disulfide bonds. Hybrids are described in WO 2004/101740, WO 2005/001025, U.S. Pat. Nos. 7,404,956, 7,348,004, and WO 2006/074199, each of which is incorporated herein by reference in its entirety. The second polypeptide can be a second copy of the same chimeric polypeptide or it can be a non-identical chimeric polypeptide. In other embodiments, the second polypeptide is a polypeptide comprising an FcRn BP, e.g., Fc. In some embodiments, the chimeric polypeptide is a Factor IX-FcRn BP, e.g., Factor IX-Fc chimeric polypeptide, and the second polypeptide consists essentially of Fc. See, e.g., Table 34 (SEQ ID NOs: 2 and 4). See, e.g., U.S. Pat. No. 7,404,956, which is incorporated herein by reference in its entirety.

VI. Administering Long-Acting FVIII Polypeptide

The present invention further comprises administering a dose of a long-acting FVIII polypeptide to a human subject in need thereof at a dosing interval, wherein the dose and/or the dosing interval is identified by the web-based or computer based program. Administration of the long-acting FVIII polypeptide is a replacement therapy by adding a recombinant FVIII to a subject with FVIII deficiency. Administration of the long-acting FVIII polypeptide can reduce or prevent a number of bleeding or bleeding episodes in the subject.

Treatment of hemophilia A is a replacement therapy targeting restoration of FVIII activity to 1 to 5% of normal levels to prevent spontaneous bleeding (Mannucci, P. M. et al., *N. Engl. J. Med.* 344:1773-9 (2001), herein incorporated by reference in its entirety).

In one embodiment, the long-acting FVIII polypeptide is administered at a dosing interval of every three days or longer. In another embodiment, the effective dose is between about 20 IU/kg and about 90 IU/kg. In other embodiments, the effective dose is 20-30 IU/kg, 30-40 IU/kg, 40-50 IU/kg, 50-60 IU/kg, 60-70 IU/kg, 70-80 IU/kg, or 80-90 IU/kg.

In certain embodiments, administration of a long-acting FVIII polypeptide is for individualized (tailored) prophylaxis and results in an ABR of less than about 5.5, less than about 5.4, less than about 5.3, less than about 5.2, less than about 5.1, less than about 5.0, less than about 4.9, less than about 4.8, less than about 4.7, less than about 4.6, or less than about 4.5.

In some embodiments, administration of a long-acting FVIII polypeptide is for weekly prophylaxis and results in an ABR of less than about 9.0, less than about 8.9, less than about 8.8, less than about 8.7, less than about 8.6, less than about 8.5, or less than about 8.4.

In other embodiments, administration of a long-acting FVIII polypeptide is for episodic or on-demand treatment and results in an ABR of less than about 55, less than about 54, less than about 53, less than about 52, less than about 51, less than about 50, less than about 49, less than about 48, or less than about 47.

In some embodiments, the effective dose for individualized prophylaxis, weekly prophylaxis, or episodic treatment is a fixed dose or a stratified dose. In one aspect, the fixed dose is about 2,000 IU per dose, about 2,500 IU per dose, about 3,000 IU per dose, about 3,500 IU per dose, or about 4,000 IU per dose.

The dosing interval suitable for administration of a long-acting FVIII polypeptide can be at least about one and one-half times longer than the dosing interval required for an equivalent dose of the Factor VIII without the non-Factor VIII portion (a polypeptide consisting of the Factor VIII portion).

The dosing interval can be at least about one and one-half to six times longer, one and one-half to five times longer, one and one-half to four times longer, one and one-half to three times longer, or one and one-half to two times longer, than the dosing interval required for an equivalent dose of the Factor VIII without the non-Factor VIII portion (a polypeptide consisting of the Factor VIII portion), e.g., without the Fc portion. The dosing interval can be at least about one and one-half, two, two and one-half, three, three and one-half, four, four and one-half, five, five and one-half or six times longer than the dosing interval required for an equivalent dose of the Factor VIII without the non-Factor VIII portion (a polypeptide consisting of the Factor VIII portion), e.g., without the Fe portion. The dosing interval can be about every three, four, five, six, seven, eight, nine, ten, eleven, twelve, thirteen, or fourteen days or longer.

The dosing interval can be at least about one and one-half to 5, one and one-half 2, 3, 4, or 5 days or longer.

The methods of the invention can be practiced on a subject in need of prophylactic treatment or on-demand treatment.

The bleeding condition can be caused by a blood coagulation disorder. A blood coagulation disorder can also be referred to as a coagulopathy. In one example, the blood coagulation disorder, which can be treated with a pharmaceutical composition of the current disclosure, is hemophilia. In another example, the blood coagulation disorder that can be treated with a pharmaceutical composition of the present disclosure is hemophilia A.

In some embodiments, the type of bleeding associated with the bleeding condition is selected from hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, and bleeding in the illiopsoas sheath.

In other embodiments, the subject suffering from bleeding condition is in need of treatment for surgery, including, e.g., surgical prophylaxis or peri-operative management. In one example, the surgery is selected from minor surgery and major surgery. Exemplary surgical procedures include tooth extraction, tonsillectomy, inguinal herniotomy, synovectomy, craniotomy, osteosynthesis, trauma surgery, intracranial surgery, intra-abdominal surgery, intrathoracic surgery, joint replacement surgery (e.g., total knee replacement, hip replacement, and the like), heart surgery, and caesarean section.

Long-Acting FVIII Polypeptide

A "B domain" of Factor VIII, as used herein, is the same as the B domain known in the art that is defined by internal amino acid sequence identity and sites of proteolytic cleavage by thrombin, e.g., residues Ser741-Arg1648 of full length mature human factor VIII. The other human factor VIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. The locations of the boundaries for all of the domains, including the B domains, for porcine, mouse and canine factor VIII are also known in the art. In one embodiment, the B domain of Factor VIII is deleted ("B domain deleted factor VIII" or "BDD FVIII"). An example of a BDD FVIII is REFACTO® (recombinant BDD FVIII), which has the same sequence as the Factor VIII portion of the sequence in Table 36A(i) (amino acids 1 to 1457 of SEQ ID NO: 6 or 20 to 1457 of SEQ ID NO: 10). In another embodiment, the B domain deleted Factor VIII contains an intact intracellular processing site, which corresponds to Arginine at residue 754 of B domain deleted Factor VIII, which corresponds to Arginine residue 773 of SEQ ID NO: 6, or residue 1648 of full-length Factor VIII, which corresponds to Arginine residue 1667 of SEQ ID NO: 10. The sequence residue numbers used herein without referring to any SEQ ID Numbers correspond to the Factor VIII sequence without the signal peptide sequence (19 amino acids) unless otherwise indicated. For example, S743/Q1638 of full-length Factor VIII corresponds to S762/Q1657 of SEQ ID NO: 10 due to the 19 amino acid signal peptide sequence. In other embodiments, the B domain deleted FVIII comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In some embodiments, the amino acid substituted at the amino acid position corresponding to Arginine 1645 is a different amino acid from the amino acid substituted at the amino acid position corresponding to Arginine 1648. In certain embodiments, the substitution or mutation is an amino acid other than arginine, e.g., alanine.

A "B domain deleted factor VIII" can have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted factor VIII of the present invention has a deletion disclosed at col. 2, lines 26-51 and examples 5-8 of U.S. Pat. No. 5,789,203 (also U.S. Pat. No. 6,060,447, 5,595,886, and 6,228,620). In some embodiments, a B domain deleted factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and Table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted factor VIII has a deletion of most of the B domain, but still contains amino-terminal sequences of the B domain that are essential for in vivo proteolytic processing of the primary translation product into two polypeptide chain (i.e., intracellular processing site), as disclosed in WO 91/09122, which is incorporated herein by reference in its entirety. In some embodiments, a B domain deleted factor VIII is constructed with a deletion of amino acids 747-1638, i.e., virtually a complete deletion of the B domain. Hoeben R. C., et al. *J. Biol. Chem.* 265 (13): 7318-7323 (1990), incorporated herein by reference in its entirety. A B domain deleted factor VIII can also contain a deletion of amino acids 771-1666 or amino acids 868-1562 of factor VIII. Meulien P., et al. *Protein Eng.* 2(4): 301-6 (1988), incorporated herein by reference in its entirety. Additional B domain deletions that are part of the invention include, e.g., deletion of amino acids 982 through 1562 or 760 through 1639 (Toole et al., *Proc. Natl. Acad. Sci. U.S.A.* 83:5939-5942 (1986)), 797 through 1562 (Eaton et al., *Biochemistry* 25:8343-8347 (1986)), 741 through 1646 (Kaufman (PCT published application No. WO 87/04187)), 747-1560 (Sarver et al., *DNA* 6:553-564 (1987)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. In some embodiments, B domain deleted FVIII comprises a partial deletion in B domain, i.e., having 21 amino acids from B domain (i.e., SFSQNSRHPSQNPPVLKRHQR, which is SEQ ID NO: 11) disclosed in US Publication No. 20100286067 and US Publication No. US 20120093840, both of which are incorporated herein by reference in their entireties. Each of the foregoing deletions can be made in any Factor VIII sequence. Each of the foregoing deletions can be made in any Factor VIII sequence.

In one embodiment, the B domain deleted Factor VIII portion in the long-acting FVIII polypeptide is processed into two chains connected (or associated) by a metal bond, the first chain comprising a heavy chain (A1-A2-partial B) and a second chain comprising a light chain (A3-C1-C2). In another embodiment, the B domain deleted Factor VIII portion is a single chain Factor VIII. The single chain Factor VIII can comprise an intracellular processing site, which corresponds to Arginine at residue 754 of B domain deleted Factor VIII (residue 773 of SEQ ID NO: 6) or at residue 1648 of full-length Factor VIII (residue 1657 of SEQ ID NO: 10).

The metal bond between the heavy chain and the light chain can be any metal known in the art. For example, the metals useful for the invention can be a divalent metal ion. The metals that can be used to associate the heavy chain and light chain include, but not limited to, $Ca^{2+}$, $Mn^{2+}$, or $Cu^{2+}$. Fatouros et al., *Intern. J. Pharm.* 155(1): 121-131 (1997); Wakabayashi et al., *JBC.* 279(13): 12677-12684 (2004).

The long-acting FVIII polypeptide can comprise a sequence at least 60%, 70%, 80%, 90%, 95%, 96%, 97%, 98%, 99%, or 100% identical to the Factor VIII and Fc amino acid sequence shown in Table 36A(i) without a signal sequence (amino acids 20 to 1684 of SEQ ID NO: 6) or at least 60%, 70%, 80%, 90%, 95%, 96%, 97%, 98%, 99%, or 100% identical to the Factor VIII and Fc amino acid sequence shown in Table 36A(i) with a signal sequence (amino acids 1 to 1684 of SEQ ID NO: 6), wherein the sequence has Factor VIII activity. The Factor VIII activity can be measured by activated Partial Thromboplastin Time (aPPT) assay, chromogenic assay, or other known methods. The chimeric polypeptide can comprise a sequence identical to the Factor VIII and Fc amino acid sequence shown in Table 36A(i) without a signal sequence (amino acids 20 to 1684 of SEQ ID NO: 6) or identical to the Factor VIII and Fc amino acid sequence shown in Table 36A(i) with a signal sequence (amino acids 1 to 1684 of SEQ ID NO: 6).

The Factor VIII polypeptide as used herein is functional factor VIII polypeptide in its normal role in coagulation, unless otherwise specified. Thus, the term Factor VIII includes variant polypeptides that are functional. Factor VIII proteins can be the human, porcine, canine, and murine factor VIII proteins. As described in the Background Art section, the full length polypeptide and polynucleotide sequences are known, as are many functional fragments, mutants and modified versions. Examples of human factor VIII sequences are shown as subsequences in SEQ ID NOs: 6 or 10 (Table 36). Factor VIII polypeptides include, e.g., full-length factor VIII, full-length factor VIII minus Met at the N-terminus, mature factor VIII (minus the signal sequence), mature factor VIII with an additional Met at the N-terminus, and/or factor VIII with a full or partial deletion of the B domain. Factor VIII variants include B domain deletions, whether partial or full deletions.

A great many functional factor VIII variants are known, as is discussed above and below. In addition, hundreds of nonfunctional mutations in factor VIII have been identified in hemophilia patients, and it has been determined that the effect of these mutations on factor VIII function is due more to where they lie within the 3-dimensional structure of factor VIII than on the nature of the substitution (Cutler et al., *Hum. Mutat.* 19:274-8 (2002)), incorporated herein by reference in its entirety. In addition, comparisons between factor VIII from humans and other species have identified conserved residues that are likely to be required for function (Cameron et al., Thromb. Haemost. 79:317-22 (1998); U.S. Pat. No. 6,251,632), incorporated herein by reference in its entirety.

The human factor VIII gene was isolated and expressed in mammalian cells (Toole, J. J., et al., *Nature* 312:342-347 (1984); Gitschier, J., et al., *Nature* 312:326-330 (1984); Wood, W. I., et al., *Nature* 312:330-337 (1984); Vehar, G. A., et al., *Nature* 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, discloses a recombinant DNA method for producing factor VIII in mammalian host cells and purification of human factor VIII. Human factor VIII expression in CHO (Chinese hamster ovary) cells and BHK (baby hamster kidney cells) has been reported. Human factor VIII has been modified to delete part or all of the B domain (U.S. Pat. Nos. 4,994,371 and 4,868,112, each of which is incorporated herein by reference in its entirety), and replacement of the human factor VIII B domain with the human factor V B domain has been performed (U.S. Pat. No. 5,004,803, incorporated herein by reference in its entirety). The cDNA sequence encoding human factor VIII and predicted amino acid sequence are shown in SEQ ID NOs: 1 and 2, respectively, of US Application Publ. No. 2005/0100990, incorporated herein by reference in its entirety.

U.S. Pat. No. 5,859,204, Lollar, J. S., incorporated herein by reference in its entirety, reports functional mutants of factor VIII having reduced antigenicity and reduced immunoreactivity. U.S. Pat. No. 6,376,463, Lollar, J. S., incorporated herein by reference in its entirety, also reports mutants of factor VIII having reduced immunoreactivity. US Application Publ. No. 2005/0100990, Saenko et al., incorporated herein by reference in its entirety, reports functional mutations in the A2 domain of factor VIII.

A number of functional factor VIII molecules, including B-domain deletions, are disclosed in the following U.S. Pat. Nos. 6,316,226 and 6,346,513, both assigned to Baxter, U.S. Pat. No. 7,041,635 assigned to In2Gen; U.S. Pat. Nos. 5,789,203, 6,060,447, 5,595,886, and 6,228,620 assigned to Chiron; U.S. Pat. Nos. 5,972,885 and 6,048,720 assigned to Biovitrum, U.S. Pat. Nos. 5,543,502 and 5,610,278 assigned to Novo Nordisk; U.S. Pat. No. 5,171,844 assigned to Immuno Ag; U.S. Pat. No. 5,112,950 assigned to Transgene S.A.; U.S. Pat. No. 4,868,112 assigned to Genetics Institute, each of which is incorporated herein by reference in its entirety.

The porcine factor VIII sequence is published, (Toole, J. J., et al., *Proc. Natl. Acad. Sci. USA* 83:5939-5942 (1986)), incorporated herein by reference in its entirety, and the complete porcine cDNA sequence obtained from PCR amplification of factor VIII sequences from a pig spleen cDNA library has been reported (Healey, J. F. et al., *Blood* 88:4209-4214 (1996), incorporated herein by reference in its entirety). Hybrid human/porcine factor VIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine factor VII and a chimeric factor VIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain deleted porcine Factor VIII.

The Factor VIII (or Factor VIII portion of a chimeric polypeptide) can be at least 60%, 70%, 80%, 90%, 95%, 96%, 97%, 98%, 99%, or 100% identical to a Factor VIII amino acid sequence shown in Table 36 without a signal sequence (amino acids 20 to 1457 of SEQ ID NO: 6; and amino acids 20 to 2351 of SEQ ID NO: 10), wherein the Factor VIII portion has Factor VIII activity. The Factor VIII (or Factor VIII portion of a chimeric polypeptide) can be identical to a Factor VIII amino acid sequence shown in Table 36 without a signal sequence (amino acids 20 to 1457 of SEQ ID NO: 6; and amino acids 20 to 2351 of SEQ ID NO: 10).

The Factor VIII (or Factor VIII portion of a chimeric polypeptide) can be at least 60%, 70%, 80%, 90%, 95%, 96%, 97%, 98%, 99%, or 100% identical to a Factor VIII amino acid sequence shown in Table 36 with a signal sequence (amino acids 1 to 1457 of SEQ ID NO: 6 and amino acids 1 to 2351 of SEQ ID NO: 10), wherein the Factor VIII portion has Factor VIII activity. The Factor VIII (or Factor VIII portion of a chimeric polypeptide) can be identical to a Factor VIII amino acid sequence shown in Table 36 with a signal sequence (amino acids 1 to 1457 of SEQ ID NO: 6 and amino acids 1 to 2351 of SEQ ID NO: 10).

As stated above, polypeptide variants include, e.g., modified polypeptides. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation (Mei et al., *Blood* 116:270-79 (2010), which is incorporated herein by reference in its entirety), proteolytic processing, phosphorylation, prenylation, racemization, selenoylation, sulfation, transfer-RNA mediated addition of amino acids to proteins such as arginylation, and ubiquitination. In some embodiments, Factor VIII is modified, e.g., pegylated, at any convenient location. In some embodiments, Factor VIII is pegylated at a surface exposed amino acid of Factor VIII, e.g., a surface exposed cysteine, which can be an engineered cysteine. Id.

The long-acting FVIII polypeptide used herein can comprise processed Factor VIII or single chain Factor VIII or a combination thereof. "Processed Factor VIII," as used herein means Factor VIII that has been cleaved at Arginine 1648 (for full-length Factor VIII) or Arginine 754 (for B-domain deleted Factor VIII), i.e., intracellular processing site. Due to the cleavage at the intracellular processing site, processed Factor VIII comprises two polypeptide chains, the first chain being a heavy chain and the second chain being a light chain. For example, the processed Factor VIII-Fc fusion protein (i.e., Heavy chain and Light chain fused to Fc) run at approximately 90 kDa and 130 kDa on a non-reducing SDS-PAGE, respectively, and 90 kDa and 105 kDa on a reducing SDS-PAGE, respectively. Therefore, in one embodiment, at least about 50%, about 60%, about 70%, about 75%, about 80%, about 85%, about 900/%, about 95%, about 96%, about 97%, about 98%, about 99%, or about 100% of the Factor VIII portion in the long-acting FVIII polypeptide is processed Factor VIII. In another embodiment, about 50%, about 60%, about 70%, about 75%, about 80%, about 85%, about 90%, about 95%, about 96%, about 97%, about 98%, about 99%, or about 100% of the Factor VIII portion in the long-acting FVIII polypeptide is processed Factor VIII. In a particular embodiment, the long-acting FVIII polypeptide comprising processed Factor VIII is purified (or isolated) from the chimeric polypeptide comprising single chain Factor VIII, and at least about 75%, about 80%, about 85%, about 90%, about 95%, about 96%, about 97%/*, about 98%, about 99%, or about 100% of the Factor VIII portion in the long-acting FVIII polypeptide is processed Factor VIII. In some embodiments, the long-acting FVIII polypeptide comprises about 15% to 25% of single chain FVIII polypeptide and about 75% to about 85% of processed FVIII polypeptide.

"Single chain Factor VIII," "SC Factor VIII," or "SCFVIII" as used herein means Factor VIII that has not been cleaved at the Arginine site (residue 1648 for full-length Factor VIII (i.e., residue 1667 of SEQ ID NO: 10) or residue 754 for B-domain deleted Factor VIII (i.e., residue 773 of SEQ ID NO: 6). Therefore, single chain Factor VIII in the long-acting FVIII polypeptide used herein comprises a single chain. In one embodiment, the single chain Factor VIII contains an intact intracellular processing site. In another embodiment, the single chain Factor VIII of the invention comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In other embodiments, the amino acid substituted at the amino acid position corresponding to Arginine 1645 is a different amino acid from the amino acid substituted at the amino acid position corresponding to Arginine 1648. In certain embodiments, the substitution or mutation is an amino acid other than arginine, e.g., isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, histidine, ornithine, pyrrolysine, or taurine. The single chain Factor VIII-Fc fusion protein can run at approximately 220 kDa on a non-reducing SDS-PAGE and at approximately 195 kDa on a reducing SDS-PAGE.

The Factor VIII portion in the long-acting FVIII polypeptide used herein has Factor VIII activity. Factor VIII activity can be measured by any known methods in the art. For example, one of those methods can be a chromogenic assay. The chromogenic assay mechanism is based on the principles of the blood coagulation cascade, where activated Factor VIII accelerates the conversion of Factor X into Factor Xa in the presence of activated Factor IX, phospholipids and calcium ions. The Factor Xa activity is assessed by hydrolysis of a p-nitroanilide (pNA) substrate specific to Factor Xa. The initial rate of release of p-nitroaniline measured at 405 nM is directly proportional to the Factor Xa activity and thus to the Factor VIII activity in the sample. The chromogenic assay is recommended by the Factor VIII and Factor IX Subcommittee of the Scientific and Standardization Committee (SSC) of the International Society on Thrombosis and Hemostasis (ISTH). Since 1994, the chromogenic assay has also been the reference method of the European Pharmacopoeia for the assignment of FVIII concentrate potency. Thus, in one embodiment, the long-acting FVIII polypeptide comprising single chain Factor VIII has Factor VIII activity comparable to a long-acting FVIII polypeptide comprising processed Factor VIII (e.g., a chimeric polypeptide consisting essentially of or consisting of two Fe portions and processed Factor VIII, wherein said processed Factor VIII is fused to one of the two Fc portions), when the Factor VIII activity is measured in vitro by a chromogenic assay.

Second Portion

In some embodiments, the long-acting FIX or FVIII polypeptide comprises a FIX or FVIII portion and a non-FIX portion or a non-Factor VIII portion, respectively, e.g., a heterologous moiety. In one embodiment, the heterologous moiety is capable of extending in vivo or in vitro half-life of the FIX or FVIII polypeptide. Exemplary non-FIX or FVIII portions include, e.g., Fc, albumin, a PAS sequence, transferrin, CTP (28 amino acid C-terminal peptide (CTP) of human chorionic gonadotropin (hCG) with its 4 O-glycans), polyethylene glycol (PEG), hydroxyethyl starch (HES), albumin binding polypeptide, albumin-binding small molecules, or any combination thereof. Exemplary long-acting FVIII polypeptides of the invention include, e.g., Factor VIII-Fc polypeptides, Factor VIII-albumin polypeptides, Factor VIII-PAS polypeptides, Factor VIII-transferrin polypeptides, Factor VIII-CTP polypeptides, Factor VIII-PEG polypeptides, Factor VIII-HES polypeptides, Factor VIII-albumin binding polypeptide polypeptides, or Factor VII-albumin-binding small molecule polypeptides. Exemplary long-acting FIX polypeptides of the invention include, e.g., Factor IX-Fc polypeptides, Factor IX-albumin polypeptides, Factor IX-PAS polypeptides, Factor IX-transferrin polypeptides, Factor IX-CTP polypeptides, Factor IX-PEG polypeptides, Factor IX-HES polypeptides, Factor IX-albumin binding polypeptide polypeptides, or Factor IX-albumin-binding small molecule polypeptides.

In one embodiment, the second portion fused to FIX or FVIII is an FcRn binding partner. In another embodiment, an FcRn binding partner fused to FIX or FVIII is an Fc fragment. An FcRn binding partner is any molecule that can be specifically bound by the FcRn receptor with consequent active transport by the FcRn receptor of the FcRn binding partner. Thus, the term Fc includes any variants of IgG Fc that are functional. The region of the Fc portion of IgG that binds to the FcRn receptor has been described based on X-ray crystallography (Burmeister et al., *Nature* 372:379 (1994), incorporated herein by reference in its entirety). The major contact area of the Fc with the FcRn is near the junction of the CH2 and CH3 domains. Fc-FcRn contacts are all within a single Ig heavy chain. The FcRn binding partners include, e.g., whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological Interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al., *J. Exp. Med.* 180: 2377 (1994), incorporated herein by reference in its entirety.) An Fc can comprise the CH2 and CH3 domains of an immunoglobulin with or without the hinge region of the immunoglobulin. Exemplary Fc variants are provided in WO 2004/101740 and WO 2006/074199, incorporated herein by reference in its entirety.

Fc (or Fc portion of a chimeric polypeptide) can contain one or more mutations, and combinations of mutations.

Fc (or Fc portion of a chimeric polypeptide) can contain mutations conferring increased half-life such as M252Y, S254T, T256E, and combinations thereof, as disclosed in Oganesyan et al., *Mol. Immunol.* 46:1750 (2009), which is incorporated herein by reference in its entirety; H433K, N434F, and combinations thereof, as disclosed in Vaccaro et al., *Nat. Biotechnol.* 23:1283 (2005), which is incorporated herein by reference in its entirety; the mutants disclosed at pages 1-2, paragraph [0012], and Examples 9 and 10 of US 2009/0264627 A1, which is incorporated herein by reference in its entirety; and the mutants disclosed at page 2, paragraphs [0014] to [0021] of US 20090163699 A1, which is incorporated herein by reference in its entirety.

Fc (or Fc portion of a chimeric polypeptide) can also include, e.g., the following mutations: The Fc region of IgG can be modified according to well recognized procedures such as site directed mutagenesis and the like to yield modified IgG or Fc fragments or portions thereof that will be bound by FcRn. Such modifications include, e.g., modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine other amino acids can be substituted for the wildtype amino acids at the positions specified above. Mutations can be introduced singly into Fc giving rise to more than one hundred FcRn binding partners distinct from native Fc. Additionally, combinations of two, three, or more of these individual mutations can be introduced together, giving rise to hundreds more FcRn binding partners. Certain of these mutations can confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety). Additionally, at least three human Fc gamma receptors appear to recognize a binding site on IgG within the lower hinge region, generally amino acids 234-237. Therefore, another example of new functionality and potential decreased immunogenicity can arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII which mediate various effector functions will not bind to IgG1 when such mutations have been introduced (Ward and Ghetie, *Therapeutic Immunology* 2:77 (1995), which is incorporated herein by reference in its entirety; and Armour et al., *Eur. J. Immunol.* 29:2613 (1999), which is incorporated herein by reference in its entirety). As a further example of new functionality arising from mutations described above affinity for FcRn can be increased beyond that of wild type in some instances. This increased affinity can reflect an increased "on" rate, a decreased "off" rate or both an increased "on" rate and a decreased "off" rate. Mutations believed to impart an increased affinity for FcRn include, e.g., T256A, T307A, E380A, and N434A (Shields et al., *J. Biol. Chem.* 276:6591 (2001), which is incorporated herein by reference in its entirety).

The Fc (or Fc portion of a chimeric polypeptide) can be at least 60%, 70%, 80%, 90%, 95%, 96%, 97%, 98%, 99%, or 100% identical to the Fc amino acid sequence shown in Table 36 (amino acids 1458 to 1684 of SEQ ID NO: 6 or amino acids 2352 to 2578 of SEQ ID NO: 10). The Fc (or Fc portion of a chimeric polypeptide) can be identical to the Fc amino acid sequence shown in Table 36 (amino acids 1458 to 1684 of SEQ ID NO: 6 and amino acids 2352 to 2578 of SEQ ID NO: 10).

As discussed above, exemplary long-acting polypeptides also include FIX or FVIII fused to one or more albumin polypeptides, albumin binding polypeptides, or albumin-binding small molecules. In one embodiment, the albumin is human albumin. The albumin or albumin binding protein can be fused to either the N-terminal end of FIX or FVIII or to the C-terminal end of FIX or FVIII or inserted between two amino acids in FIX or FVIII. Examples of albumin, e.g., fragments thereof, that can be used in the present invention are known. e.g., U.S. Pat. No. 7,592,010; 6,686,179; and Schulte, *Thrombosis Res.* 124 Suppl. 2:S6-S8 (2009), each of which is incorporated herein by reference in its entirety.

The albumin binding polypeptides can compromise, without limitation, bacterial albumin-binding domains, albumin-binding peptides, or albumin-binding antibody fragments that can bind to albumin. Domain 3 from streptococcal protein G, as disclosed by Kraulis et al., *FEBS Lett.* 378: 190-194 (1996) and Linhult et al., *Protein Sci.* 11:206-213 (2002) is an example of a bacterial albumin-binding domain. Examples of albumin-binding peptides include a series of peptides having the core sequence DICLPRWGCLW (SEQ ID NO: 12). See, e.g., Dennis et al., *J. Biol. Chem.* 2002, 277: 35035-35043 (2002). Examples of albumin-binding antibody fragments are disclosed in Muller and Kontermann, *Curr. Opin. Mol. Ther.* 9:319-326 (2007); Rooverset et al., *Cancer Immunol. Immunother.* 56:303-317 (2007), and Holt et al., *Prot. Eng. Design Sci.,* 21:283-288 (2008), which are incorporated herein by reference in their entireties.

In certain aspects, a recombinant FIX or FVIII polypeptide of the invention comprises at least one attachment site for a non-polypeptide small molecule, variant, or derivative that can bind to albumin thereof. An example of such albumin binding moieties is 2-(3-maleimidopropanamido)-6-(4-(4-iodophenyl)butanamido)hexanoate ("Albu" tag) as disclosed by Trusselet et al., *Bioconjugate Chem.* 20:2286-2292 (2009).

As discussed above, exemplary long-acting polypeptides also include FIX or FVIII fused to at least one C-terminal peptide (CTP) of the β subunit of human chorionic gonadotropin or fragment, variant, or derivative thereof. The CTP can be fused to FIX or FVIII either the N-terminal end of FIX or FVIII or to the C-terminal end of FIX or FVIII or inserted between two amino acids in FIX or FVIII. One or more CTP peptides fused to or inserted into a recombinant protein is known to increase the in vivo half-life of that protein. See, e.g., U.S. Pat. No. 5,712,122, incorporated by reference herein in its entirety. Exemplary CTP peptides include DPRFQDSSSSKAPPPSLPSPSRLPGPSDTPIL (SEQ ID NO: 13) or SSSSKAPPPSLPSPSRLPGPSDTPILPQ. (SEQ ID NO: 14). See, e.g., U.S. Patent Application Publication No. US 2009/0087411 A1, incorporated by reference.

As discussed above, exemplary long-acting polypeptides also include FIX or FVIII fused to at least one PAS sequence or fragment, variant, or derivative thereof. The PAS sequence can be fused to either the N-terminal end of FIX or FVIII or to the C-terminal end of FIX or FVIII or inserted between two amino acids in FVIII. A PAS peptide or PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. An amino acid polymer also can form random coil conformation when residues other than alanine, serine, and proline are added as a minor constituent in the PAS sequence. By "minor constituent" is meant that that amino acids other than alanine, serine, and proline can be added in the PAS sequence to a certain degree, e.g., up to about 12%, i.e., about 12 of 100 amino acids of the PAS sequence, up to about 10%, up to about 9%, up to about 8%, about 6%, about 5%, about 4%, about 3%, i.e. about 2%, or about 1%, of the amino acids. The amino acids different from alanine, serine and proline can be selected from the group consisting of Arg, Asn, Asp, Cys, Gin, Glu, Gly, His, Ile, Leu, Lys, Met, Phe, Thr, Trp, Tyr, and Val. Under physiological conditions, a PAS peptide forms a random coil conformation and thereby can mediate an increased in vivo and/or in vitro stability to a recombinant protein of the invention, and has procoagulant activity.

Non-limiting examples of the PAS peptides include ASPAAPAPASPAAPAPSAPA (SEQ ID NO: 15), AAPASPAPAAPSAPAPAAPS (SEQ ID NO: 16), APSSPSPSAPSSPSPASPSS (SEQ ID NO: 17), APSSPSPSAPSSPSPASPS (SEQ ID NO: 18), SSPSAPSPSSPASPSPSSPA (SEQ ID NO: 19), AASPAAPSAPPAAASPAAPSAPPA (SEQ ID NO: 20), ASAAAPAAASAAASAPSAAA (SEQ ID NO: 21) or any variants, derivatives, fragments, or combinations thereof. Additional examples of PAS sequences are known from, e.g., US Pat. Publ. No. 2010/0292130 A1 and PCT Appl. Publ. No. WO 2008/155134 A1. European issued patent EP2173890.

As discussed above, exemplary long-acting polypeptides also include FIX or FVIII fused to at least one transferrin peptide or fragment, variant, or derivative thereof. At least one transferrin peptide can be fused to either the N-terminal end of FIX or FVIII or to the C-terminal end of FIX or FVIII or inserted between two amino acids in FIX or FVII. Any transferrin can be fused to or inserted into a recombinant FIX or FVIII protein of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM039847 and S95936 (www.ncbi.nlm.nih.gov), all of which are herein incorporated by reference in their entirety.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., *Trends Pharmacol. Sci.* 23:206-209 (2002)). Transferrin fusion proteins have been studied for half-life extension, targeted deliver for cancer therapies, oral delivery and sustained activation of proinsulin (Brandsma et al., *Biotechnol. Adv.,* 29: 230-238 (2011); Bai et al., *Proc. Natl. Acad. Sci. USA* 102:7292-7296 (2005); Kim et al., *J. Pharmacol. Exp. Ther.,* 334:682-692 (2010); Wang et al., J. Controlled Release 155:386-392 (2011)).

As discussed above, exemplary long-acting polypeptides also include FIX or FVIII fused to at least one polyethylene glycol (PEG) moieties.

PEGylated FVIII can refer to a conjugate formed between FIX or FVIII and at least one polyethylene glycol (PEG) molecule. PEG is commercially available in a large variety of molecular weights and average molecular weight ranges. Typical examples of PEG average molecular weight ranges include, but are not limited to, about 200, about 300, about 400, about 600, about 1000, about 1300-1600, about 1450, about 2000, about 3000, about 3000-3750, about 3350, about 3000-7000, about 3500-4500, about 5000-7000, about 7000-9000, about 8000, about 10000, about 8500-11500, about 16000-24000, about 35000, about 40000, about 60000, and about 80000 daltons. These average molecular weights are provided merely as examples and are not meant to be limiting in any way.

A recombinant long-acting FIX or FVIII protein of the invention can be PEGylated to include mono- or poly- (e.g., 2-4) PEG moieties. PEGylation can be carried out by any of the PEGylation reactions known in the art. Methods for preparing a PEGylated protein product will generally include (i) reacting a polypeptide with polyethylene glycol (such as a reactive ester or aldehyde derivative of PEG) under conditions whereby the peptide of the invention becomes attached to one or more PEG groups; and (ii) obtaining the reaction product(s). In general, the optimal reaction conditions for the reactions will be determined case by case based on known parameters and the desired result.

There are a number of PEG attachment methods available to those skilled in the art, for example Malik F et al., *Exp. Hematol.* 20:1028-35 (1992); Francis, Focus on Growth Factors 3(2):4-10 (1992); European Pat. Pub. Nos. EP0401384, EP0154316, and EP0401384; and International Pat. Appl. Pub. Nos. WO92/16221 and WO95/34326. As a non-limiting example, FIX or FVIII variants can contain cysteine substitutions in one or more insertion sites in FIX or FVIII, and the cysteines can be further conjugated to PEG polymer. See Mei et al., *Blood* 116:270-279 (2010) and U.S. Pat. No. 7,632,921, which are incorporated herein by reference in their entireties.

As discussed above, exemplary long-acting polypeptides also include FIX or FVIII fused to at least one hydroxyethyl starch (HES) polymer. HES is a derivative of naturally occurring amylopectin and is degraded by alpha-amylase in the body. HES exhibits advantageous biological properties and is used as a blood volume replacement agent and in hemodilution therapy in the clinics. See, e.g., Sommermeyer et al., *Krankenhauspharmazie* 8:271-278 (1987); and Weidler et al., *Arzneim.-Forschung/Drug Res.* 41: 494-498 (1991).

HES is mainly characterized by the molecular weight distribution and the degree of substitution. HES has a mean molecular weight (weight mean) of from 1 to 300 kD, from 2 to 200 kD, from 3 to 100 kD, or from 4 to 70 kD. Hydroxyethyl starch can further exhibit a molar degree of substitution of from 0.1 to 3, from 0.1 to 2, from 0.1 to 0.9, or from 0.1 to 0.8, and a ratio between C2:C6 substitution in the range of from 2 to 20 with respect to the hydroxyethyl groups. HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. There are a number of HES attachment methods available to those skilled in the art, e.g., the same PEG attachment methods described above.

Pharmaceutical Composition

A long-acting FIX polypeptide or a long-acting FVIII polypeptide can be formulated as a pharmaceutical composition. The pharmaceutical composition can be formulated for administration to humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Various methods of formulating the invention is well known in the art.

A long-acting FIX polypeptide or a long-acting FVIII polypeptide can be formulated as a pharmaceutical composition or formulation. In certain formulations provided herein, a long-acting FIX polypeptide or a long-acting FVIII polypeptide is formulated as a sterile, preservative-free, non-pyrogenic, lyophilized, white to off-white powder to cake, for intravenous (IV) administration. The formulation can be provided in a single-use vial.

In certain embodiments the first container of a pharmaceutical kit provided herein is a glass vial comprising a rubber stopper. In certain embodiments, the second container a pharmaceutical kit provided herein is a syringe body, associated with a plunger. In certain embodiments, the syringe is a pre-filled syringe containing the diluent. In certain embodiments, a pharmaceutical kit provided herein further comprises an adaptor to connect the glass vial to the syringe body. In certain embodiments a pharmaceutical kit provided herein further comprises infusion tubing associated with a needle to be connected to the syringe, suitable for intravenous infusion.

In certain embodiments, a desired dose of a long-acting FIX polypeptide or a long-acting FVIII polypeptide can be achieved through the use of one pharmaceutical kit as provided herein. In certain embodiments, more than one pharmaceutical kit can be used to achieve a desired dose. Provided herein is a method of combining or pooling the formulations contained in two or more pharmaceutical kits as provided herein in order to achieve a desired dose.

The pharmaceutical composition of the invention can be formulated as a liquid formulation, lyophilized powder, or suspension. A container comprising the pharmaceutical compositions can be a vial, a cartridge, or a syringe. In a particular embodiment, a syringe comprising the pharmaceutical composition is a dual chamber syringe.

In certain embodiments, the pharmaceutical composition of the invention or the reconstitution solution for the lyophilized powder comprises a preservative in an amount sufficient to provide antimicrobial activity. Pharmaceutically acceptable preservatives that are useful for pharmaceutical composition are well known in the art. For example, examples of the pharmaceutically acceptable preservatives include, but are not limited to, phenol, m-cresol, benzyl alcohol, chlorobutanol, methyl paraben, propylparaben, phenoxyethanol, any other pharmaceutically acceptable preservative, and any combinations thereof. In a particular embodiment, the preservative is benzyl alcohol. In some embodiments, the pharmaceutical composition comprises benzyl alcohol at a concentration between 0.5% and 0.9%.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Example 1. Product Description rFIXFc is a long-acting, fully recombinant fusion protein consisting of human coagulation Factor IX (FIX) covalently linked to the Fc domain of human immunoglobulin G1 (IgG1). The Factor IX portion of rFIXFc has a primary amino acid sequence that is identical to the $Thr^{148}$ allelic form of plasma derived Factor IX and has structural and functional characteristics similar to endogenous Factor IX. The Fc domain of rFIXFc contains the hinge, CH2 and CH3 regions of IgG1. rFIXFc contains 869 amino acids with a molecular weight of approximately 98 kilodaltons.

rFIXFc is produced by recombinant DNA technology in a human embryonic kidney (HEK) cell line, which has been extensively characterized. The cell line expresses rFIXFc into a defined cell culture medium that does not contain any proteins derived from animal or human sources. rFIXFc is purified by a series of chromatography steps that does not require use of a monoclonal antibody. The process includes multiple viral clearance steps including 15 nm virus-retaining nano-filtration. No human or animal additives are used in the cell culture, purification, and formulation processes.

Example 2. Dosage and Method of Administration/Method of Calculating Initial Estimated Dose rFIXFc is long-acting anti-hemophilic factor (recombinant) indicated in adults and children (≥12 years) with hemophilia B (congenital Factor IX deficiency) for, e.g., control and prevention of bleeding episodes, routine prophylaxis to prevent or reduce the frequency of bleeding episodes, and perioperative management (surgical prophylaxis).

Dosing of rFIXFc, formulated as described in Example 1, can be estimated as described in this example, but can also be determined by standard tests such as FIX activity assays described elsewhere herein.

1 IU of rFIXFc per kg body weight is expected to increase the circulating level of Factor IX by 1% [IU/dL]. rFIXFc has been shown to have a prolonged circulating half-life.

No dose adjustment for recovery is generally required. Since subjects can vary in their pharmacokinetic (e.g., half-life, in vivo recovery) and clinical responses to rFIXFc, the expected in vivo peak increase in Factor IX level expressed as IU/dL (or % of normal) or the required dose can be estimated using the following formulas:

$$\text{IU/dL (or \% of normal)} = [\text{Total Dose (IU)/body weight (kg)}] \times \text{recovery (IU/dL per IU/kg)} \quad (D)$$

OR $$\text{Dose (IU)} = \text{body weight (kg)} \times \text{Desired Factor IX Rise (IU/dL or \% of normal)} \times \text{reciprocal of recovery (IU/kg per IU/dL)} \quad (E)$$

The following table (Table 1) can be used to guide dosing in bleeding episodes:

TABLE 1

Guide to rFIXFc Dosing for Treatment of Bleeding

| Severity of Bleed | Factor IX Level Required (IU/dL or % of normal) | Dose (IU/kg)/ Frequency of Doses (hrs) |
|---|---|---|
| Minor and Moderate<br>For example: joint, superficial muscle/no neurovascular compromise (except iliopsoas), superficial soft tissue, mucous membranes | 30-60 | 30-60 IU/kg<br>Repeat every 48 hours if there is further evidence of bleeding |
| Major<br>For example: iliopsoas and deep muscle with neurovascular injury, or substantial blood loss, retroperitoneum, CNS | 80-120 | For repeat dosing, follow guidelines for major surgery [see Table 2] |

Adapted from: Roberts and Eberst, WFH 2008, and WFH 2012

Subsequent dosage and duration of treatment depends on the individual clinical response, the severity of the Factor IX deficiency, and the location and extent of bleeding.

The following table (Table 2) can be used to guide dosing for and perioperative management (surgical prophylaxis):

TABLE 2

Guide to rFIXFc Dosing for Perioperative Management (Surgical Prophylaxis)*

| Type of Surgery | Initial Factor IX Level Required (IU/dL or % of normal) | Dose (IU/kg)/ Frequency of Doses (hrs) |
|---|---|---|
| Minor<br>Minor operations including uncomplicated dental extraction | 50 to 80 | 50-80 IU/kg<br>A single infusion may be sufficient. Repeat as needed after 24-48 hours. |
| Major | 60 to 120 (initial level)<br>Days 1-3: maintain level 40-60%<br>Days 4-6: maintain level 30-50%<br>Days 7-14: maintain level 20-40% | 100 IU/kg (initial dose)<br>A repeat dose at 80 IU/kg should be considered after 6-10 hours and then every 24 hours for the first 3 days.<br>Based on the long half-life of rFIXFc, the dose may be reduced and frequency of dosing in the post-surgical setting may be extended after day 3 to every 48 hours. |

Adapted from: Roberts and Eberst, WFH 2008, and WFH 2012
*See Pharmacokinetics (Example 5 below)

For routine prophylaxis, the recommended starting regimens are either: 50 IU/kg once weekly, or 100 IU/kg once every 10-14 days. Either regimen can be adjusted based on subject response.

rFIXFc is contraindicated in subjects who have manifested severe hypersensitivity reactions, including anaphylaxis, to the product or its components.

The clinical response to rFIXFc may vary. If bleeding is not controlled with the recommended dose, the plasma level of Factor IX can be determined, and a sufficient dose of rFIXFc can be administered to achieve a satisfactory clinical response. If the subject's plasma Factor IX level fails to increase as expected or if bleeding is not controlled after rFIXFc administration, the subject's plasma can be tested for the presence of an inhibitor, e.g., neutralizing antibodies. Subjects using rFIXFc can be monitored for the development of Factor IX inhibitors by appropriate clinical observations and laboratory tests known to those of ordinary skill in the art.

Subject's plasma can be monitored for Factor IX activity levels by performing, e.g., the one-stage clotting assay to confirm adequate Factor IX levels have been achieved and maintained, when clinically indicated. Subject's plasma can further be monitored for the development of Factor IX inhibitors.

Example 3. The Clinical Implications of Population Pharmacokinetics of rFIXFc in Routine Prophylaxis, Control of Bleeding and Perioperative Management for Hemophilia B Subjects Background:

Clinical dosing of factor IX (FIX) in treatment of hemophilia B is well established based on empirical practice and clinical outcomes. Since pharmacokinetics (PK) of FIX activity is the surrogate efficacy marker, we utilized population PK (popPK) modeling and simulation to evaluate dosing regimens of long-acting recombinant FIX Fc fusion protein (rFIXFc). The PK of rFIXFc, from 135 single-dose and 21 repeat-dose profiles in subjects ≥12 years old (body weight (BW): 45-186.7 kg), was best described by a 3-compartmental model, which showed modest inter-individual variability (IIV) of 17.7% for clearance (CL) and 21.7% for volume of central compartment (V1). The proportional residue error of 10.6% approximates the variability of the one-stage clotting assay for FIX activity. The only covariate that showed a weak association with rFIXFc PK is BW, which accounted for ~3% of IIV for CL and V1, suggesting that BW-independent flat dosing of rFIXFc may be feasible for treating adult hemophilia B subjects.

Aims:

To simulate the BW-based and flat dosing regimens for routine prophylaxis, control of bleeding and perioperative management in the hemophilia B population.

Method:

The validated 3-compartmental popPK model, including inter-occasion variability and BW as the covariate on CL and V1, was used for dosing simulations. For BW-based dosing regimen, PK profiles were simulated for 1000 subjects with BW distribution representative of the phase 3 study. BW distribution was simulated using a power function Z=BW−0.5. The generated BW (1000 values) distribution has a median of 74.9 kg and a range of 38.9 to 172.6 kg, which is similar to our studies (median, 73.3 kg; min and max, 45 and 186.7 kg). For fixed dosing regimen, three populations (n=1000 each) were stratified based on low (≤10th percentile), typical (10th-90th percentile) and high (≥90th percentile) BW. Variability of exposure parameters, percentage of population maintaining target Cmax and trough, and deviations of median exposure parameters in extreme BW groups were compared with BW-based and flat dosing regimens. To simulate steady-state in prophylaxis regimen, six doses were applied for all dosing regimens (once weekly, every 10 days, or every 14 days), with each dosing interval assigned as one occasion. To simulate the PK profile following an episodic treatment, a single dose was applied.

Result:

Consistent with the observations from the phase 3 study, popPK simulation of 50 IU/kg once weekly or 100 IU/kg every 10-14 days predicted peak FIX activity within the physiologic range (Cmax<150%) and trough ≥1% in majority of the population. All simulated regimens predicted that the majority of the population will maintain trough activity at or above 1% (Table 3).

TABLE 3

| Predicted percentage of population with steady-state trough at or above 1% for various prophylaxis dosing regimens | | |
|---|---|---|
| Regimen | Total weekly dose | % of population with trough ≥1% |
| 50 IU/kg weekly | 50 | 95.4 |
| 100 IU/kg weekly | 100 | 99.6 |
| 100 IU/kg every 10 days | 70 | 89.2 |
| 100 IU/kg every 14 days | 50 | 52.8 |

Figure 11:
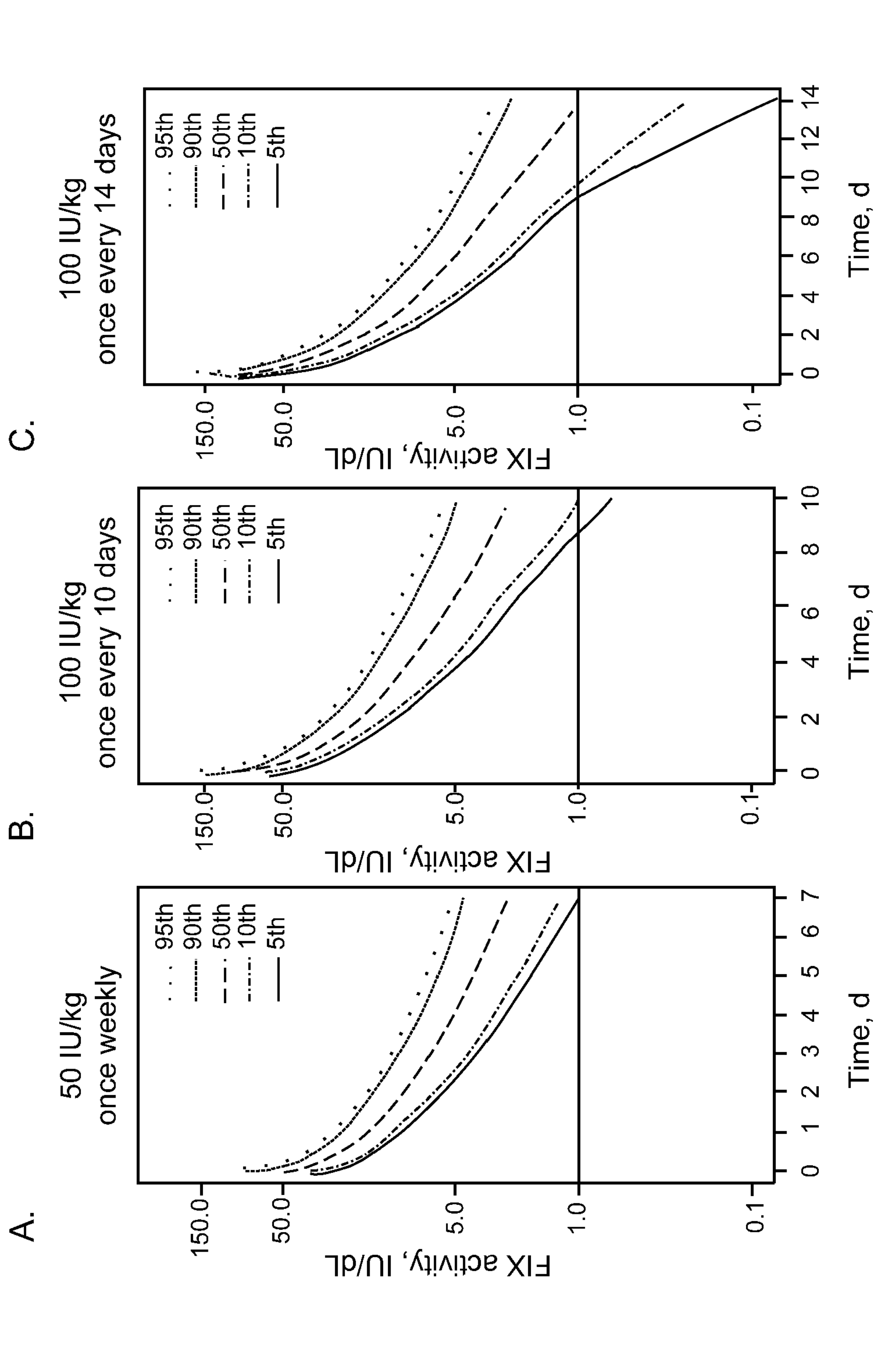
FIG. 11 shows a population simulation of steady-state FIX activity time profile (5th-95th percentile) for a long-acting FIX polypeptide (i.e., rFIXFc).

A plot showing a population simulation of steady-state FIX activity vs. time is shown in FIG. 11. Table 4 shows the predicted steady state FIX activity over the course of 14 days for two dosing regimens: 50 IU/kg weekly and 100 IU/kg every 14 days.

TABLE 4

| Predicted steady state FIX activity | | | | | | | |
|---|---|---|---|---|---|---|---|
| Dose, IU/kg | EOI median [5th, 95th] | Day 1 median [5th, 95th] | Day 3 median [5th, 95th] | Day 5 median [5th, 95th] | Day 7 median [5th, 95th] | Day 10 median [5th, 95th] | Day 14 median [5th, 95th] |
| 50 IU/kg weekly | 52.6 [32.1, 89.3] | 16.9 [11.2, 26.1] | 7.17 [3.85, 12.3] | 4.16 [1.93, 7.83] | 2.67 [1.02, 5.49] | NA | NA |
| 100 100 IU/kg every 14 days | 102 [60.0, 166] | 30.0 [19.6, 46.7] | 12.0 [6.62, 19.9] | 6.78 [3.24, 12.2] | 4.28 [1.82, 8.06] | 2.29 [0.688, 5.33] | 1.07 [0.0758, 3.23] |

Furthermore, BW-based and flat dosing resulted in comparable PK profiles with comparable exposure parameters, e.g., 50 IU/kg and 4000 IU once weekly predicted a median (5th, 95th percentile) Cmax of 52.6 (32.1, 89.3) IU/dL and 56.1 (36.2, 90.9) IU/dL, respectively. Both dosing regimens predicted that >95% of the population maintains Cmax<150% and trough ≥1% (FIG. 12). However, BW-based and flat dosing showed differential effects on the exposure parameters in extreme (≤10th or ≥90th percentile) BW populations. This suggests that BW-independent flat dosing may be feasible for patients 12 years and older.

The popPK model was used to simulate dosing regimens for episodic treatment. The model predicts that for the control of bleeding episodes, a single dose of 50 or 100

IU/kg of rFIXFc is sufficient to maintain the plasma FIX peak activity levels at 40 to 80 IU/dL (Table 5) as recommended by the World Federation of Hemophilia (WFH) guidelines.

TABLE 5

Predicted FIX activity profile after a single dose of rFIXFc in the 5th to 95th percentile of the population

| | rFIXFc dose, median [5th, 95th] | |
|---|---|---|
| | 50 IU/kg | 100 IU/kg |
| End of infusion | 50.8 [30.4, 84.5] | 102 [60.8, 169] |
| 12 hours | 21.1 [13.5, 33.6] | 42.3 [26.8, 67.3] |
| 24 hours (day 1) | 14.8 [9.78, 22.7] | 29.5 [19.6, 45.5] |
| 36 hours | 10.9 [6.79, 17.1] | 21.8 [13.7, 34.1] |
| 48 hours (day 2) | 8.51 [5.14, 13.2] | 17.0 [10.5, 26.6] |
| 72 hours (day 3) | 5.57 [3.05, 9.27] | 11.1 [6.22, 18.5] |
| Day 5 | 3.07 [1.44, 5.62] | 6.14 [3.05, 11.0] |
| Day 7 | 1.93 [0.795, 3.71] | 3.88 [1.82, 7.28] |
| Day 10 | 1.1 [0.277, 2.33] | 2.19 [0.775, 4.56] |
| Day 14 | 0.559 [0, 1.38] | 1.08 [0.125, 2.58] |

Figure 10:
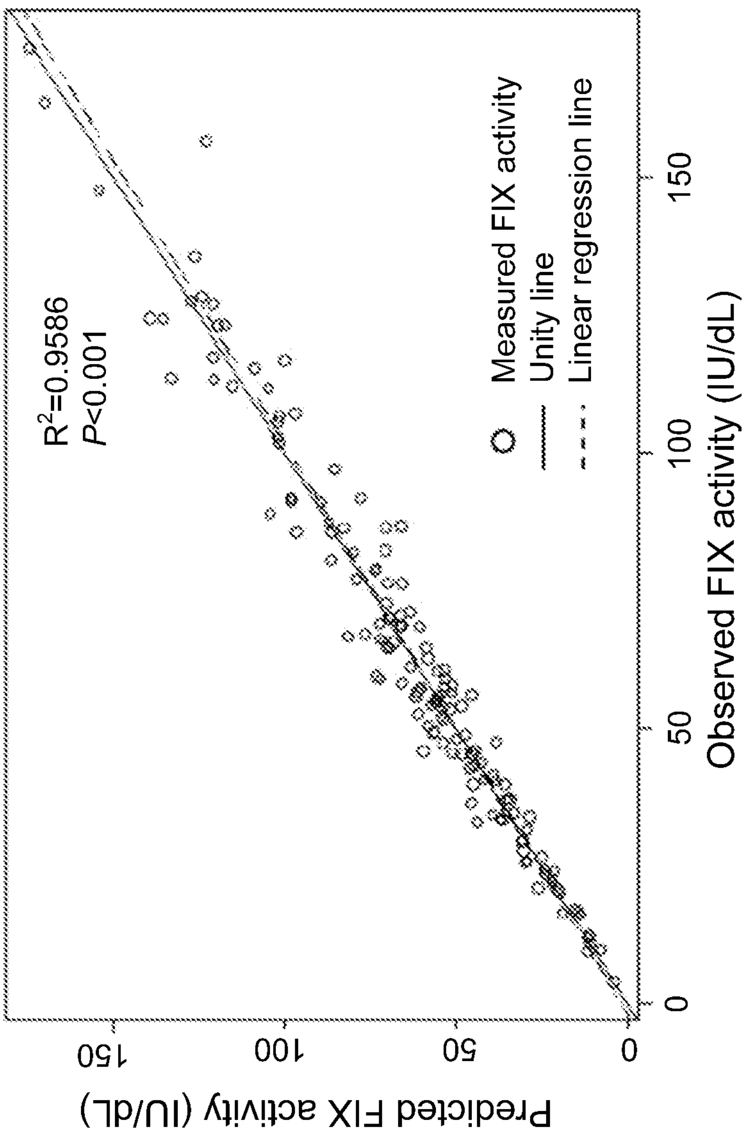
FIG. 10 shows a representative plot of observed and predicted perioperative FIX activity for a long-acting FIX polypeptide (i.e., rFIXFc).

Analysis of 12 major surgeries and 2 minor surgeries found that the FIX activities measured during the perioperative period were largely consistent with the prediction by popPK based on subjects' pre-surgery baseline PK, indicating no substantial factor consumption in these surgeries. A representative plot of observed and predicted perioperative FIX activity is shown in FIG. 10. Simulated and observed FIX activities were compared within the first 21 days after the first rFIXFc surgical dose (n=14: 12 major surgeries, 2 minor surgeries). There was good correlation between the observed FIX activity data and that predicted by the PK model (relative prediction error [95% CI], 0.332% [−2.08%, 1.42%]).

Conclusion:

PopPK provides a robust and effective means to evaluate potential dosing regimens. The predictions by popPK simulation for rFIXFc corroborate the results from the phase 3 study. The simulations of BW-based and flat dosing of rFIXFc achieved similar PK profiles. Considering the wide therapeutic range for factor replacement therapy, flat dosing of rFIXFc and rFIX products may be a potentially viable approach in adult hemophilia B subjects that warrants further clinical investigation. Furthermore, using a population PK model, it is feasible to develop a general dosing guidance to achieve target FIX levels recommended for perioperative management in patients with hemophilia B.

Example 4. Population Pharmacokinetic Analysis of a Long-Acting Recombinant Factor IX-Fc Fusion Protein (rFIXFc) in Subjects with Severe Hemophilia B Background:

Clinical dosing of factor IX (FIX) in treatment of hemophilia B is well established based on empirical practice and clinical outcomes. Since pharmacokinetics (PK) of FIX activity is the surrogate efficacy marker, we utilized population PK (popPK) modeling and simulation to evaluate dosing regimens of long-acting recombinant FIX Fc fusion protein (rFIXFc). The PK of rFIXFc, from 135 single-dose and 21 repeat-dose profiles in subjects ≥12 years old (body weight (BW): 45-186.7 kg), was best described by a 3-compartmental model, which showed modest inter-individual variability (IIV) of 17.7% for clearance (CL) and 21.7% for volume of central compartment (V1). The proportional residue error of 10.6% approximates the variability of the one-stage clotting assay for FIX activity. The only covariate that showed a weak association with rFIXFc PK is BW, which accounted for ~3% of IIV for CL and V1, suggesting that BW-independent flat dosing of rFIXFc may be feasible for treating adult hemophilia B subjects.

Aims:

To simulate the BW-based and flat dosing regimens for routine prophylaxis, control of bleeding and perioperative management in the hemophilia B population.

Method:

The validated 3-compartmental popPK model, including inter-occasion variability and BW as the covariate on CL and V1, was used for dosing simulations. For BW-based dosing regimen, PK profiles were simulated for 1000 subjects with BW distribution representative of the phase 3 study. BW distribution was simulated using a power function Z=BW−0.5. The generated BW (1000 values) distribution has a median of 74.9 kg and a range of 38.9 to 172.6 kg, which is similar to our studies (median, 73.3 kg; min and max, 45 and 186.7 kg). For fixed dosing regimen, three populations (n=1000 each) were stratified based on low (≤10th percentile), typical (10th-90th percentile) and high (≥90th percentile) BW. Variability of exposure parameters, percentage of population maintaining target Cmax and trough, and deviations of median exposure parameters in extreme BW groups were compared with BW-based and flat dosing regimens. To simulate steady-state in prophylaxis regimen, six doses were applied for all dosing regimens (once weekly, every 10 days, or every 14 days), with each dosing interval assigned as one occasion. To simulate the PK profile following an episodic treatment, a single dose was applied.

Result:

Consistent with the observations from the phase 3 study, popPK simulation of 50 IU/kg once weekly or 100 IU/kg every 10-14 days predicted peak FIX activity within the physiologic range (Cmax<150%) and trough ≥1% in majority of the population. All simulated regimens predicted that the majority of the population will maintain trough activity at or above 1% (Table 6).

TABLE 6

Predicted percentage of population with steady-state trough at or above 1% for various prophylaxis dosing regimens

| Regimen | Total weekly dose | % of population with trough ≥1% |
|---|---|---|
| 50 IU/kg weekly | 50 | 95.4 |
| 100 IU/kg weekly | 100 | 99.6 |
| 100 IU/kg every 10 days | 70 | 89.2 |
| 100 IU/kg every 14 days | 50 | 52.8 |

A plot showing a population simulation of steady-state FIX activity vs. time is shown in FIG. 11. Table 7 shows the predicted steady state FIX activity over the course of 14 days for two dosing regimens: 50 IU/kg weekly and 100 IU/kg every 14 days.

TABLE 7

| Dose, IU/kg | EOI median [5th, 95th] | Day 1 median [5th, 95th] | Day 3 median [5th, 95th] | Day 5 median [5th, 95th] | Day 7 median [5th, 95th] | Day 10 median [5th, 95th] | Day 14 median [5th, 95th] |
|---|---|---|---|---|---|---|---|
| | Predicted steady state FIX activity | | | | | | |
| 50 IU/kg weekly | 52.6 [32.1, 89.3] | 16.9 [11.2, 26.1] | 7.17 [3.85, 12.3] | 4.16 [1.93, 7.83] | 2.67 [1.02, 5.49] | NA | NA |
| 100 100 IU/kg every 14 days | 102 [60.0, 166] | 30.0 [19.6, 46.7] | 12.0 [6.62, 19.9] | 6.78 [3.24, 12.2] | 4.28 [1.82 8.06] | 2.29 [0.688, 5.33] | 1.07 [0.0758, 3.23] |

Furthermore, BW-based and flat dosing resulted in comparable PK profiles with comparable exposure parameters, e.g., 50 IU/kg and 4000 IU once weekly predicted a median (5th, 95th percentile) Cmax of 52.6 (32.1, 89.3) IU/dL and 56.1 (36.2, 90.9) IU/dL, respectively. Both dosing regimens predicted that >95% of the population maintains Cmax<150% and trough ≥1% (FIG. 12). However, BW-based and flat dosing showed differential effects on the exposure parameters in extreme (≤10th or ≥90th percentile) BW populations. This suggests that BW-independent flat dosing may be feasible for patients 12 years and older.

The popPK model was used to simulate dosing regimens for episodic treatment. The model predicts that for the control of bleeding episodes, a single dose of 50 or 100 IU/kg of rFIXFc is sufficient to maintain the plasma FIX peak activity levels at 40 to 80 IU/dL (Table 8) as recommended by the World Federation of Hemophilia (WFH) guidelines.

TABLE 8

Predicted FIX activity profile after a single dose of rFIXFc in the 5th to 95th percentile of the population

| | rFIXFc dose, median [5th, 95th] | |
|---|---|---|
| | 50 IU/kg | 100 IU/kg |
| End of infusion | 50.8 [30.4, 84.5] | 102 [60.8, 169] |
| 12 hours | 21.1 [13.5, 33.6] | 42.3 [26.8, 67.3] |
| 24 hours (day 1) | 14.8 [9.78, 22.7] | 29.5 [19.6, 45.5] |
| 36 hours | 10.9 [6.79, 17.1] | 21.8 [13.7, 34.1] |
| 48 hours (day 2) | 8.51 [5.14, 13.2] | 17.0 [10.5, 26.6] |
| 72 hours (day 3) | 5.57 [3.05, 9.27] | 11.1 [6.22, 18.5] |
| Day 5 | 3.07 [1.44, 5.62] | 6.14 [3.05, 11.0] |
| Day 7 | 1.93 [0.795, 3.71] | 3.88 [1.82, 7.28] |
| Day 10 | 1.1 [0.277, 2.33] | 2.19 [0.775, 4.56] |
| Day 14 | 0.559 [0, 1.38] | 1.08 [0.125, 2.58] |

Analysis of 12 major surgeries and 2 minor surgeries found that the FIX activities measured during the perioperative period were largely consistent with the prediction by popPK based on subjects' pre-surgery baseline PK, indicating no substantial factor consumption in these surgeries. A representative plot of observed and predicted perioperative FIX activity is shown in FIG. 10. Simulated and observed FIX activities were compared within the first 21 days after the first rFIXFc surgical dose (n=14; 12 major surgeries, 2 minor surgeries). There was good correlation between the observed FIX activity data and that predicted by the PK model (relative prediction error [95% CI], 0.332% [−2.08%, 1.42%]).

Conclusion:

PopPK provides a robust and effective means to evaluate potential dosing regimens. The predictions by popPK simulation for rFIXFc corroborate the results from the phase 3 study. The simulations of BW-based and flat dosing of rFIXFc achieved similar PK profiles. Considering the wide therapeutic range for factor replacement therapy, flat dosing of rFIXFc and rFIX products may be a potentially viable approach in adult hemophilia B subjects that warrants further clinical investigation. Furthermore, using a population PK model, it is feasible to develop a general dosing guidance to achieve target FIX levels recommended for perioperative management in patients with hemophilia B.

Example 5. Population Pharmacokinetic Analysis of a Long-Acting Recombinant Factor IX-Fc Fusion Protein (rFIXFc) in Subjects with Severe Hemophilia B Background:

Population pharmacokinetic (PK) models are developed to understand the sources of variability in dose requirements (covariates) and to help individualize dosing regimens if necessary. Dosing histories and subject-specific data are used to gain an understanding of drug disposition in order to discern specific demographic and/or clinical factors that may be predictors of PK parameters. By characterizing the population PK (popPK) of long-acting FIX-Fc (rFIXFc) in subjects with severe hemophilia B (≤2 IU/dL plasma FIX activity), a model of estimated population PK parameters of rFIXFc can be established. This model may assist physicians who wish to tailor dosing for individual subjects with sparse PK samples.

Methods:

Male subjects with severe hemophilia B were included from a phase ½a study (n=12) and the phase 3 study (B-LONG, n=123) described above. The subjects ranged in age from 12 to 76 years and in body weight from 45 to 186 kg. The modeling dataset included 135 baseline PK profiles at Week 1, as well as 21 repeat PK profiles at Week 26, with a total of 1400 measured FIX activity records. The final population PK model was validated using 1027 trough/peak FIX activity records from 119 subjects.

In the popPK analysis, plasma FIX activity was measured by the one-stage (activated partial thromboplastin time) clotting assay. Corrected FIX activity was calculated using the formula:

Corrected FIX activity=Measured FIX activity−Baseline−Residual decay. (F)

Baseline FIX activity was defined as the lowest level of activity (LLACT) recorded at screening, predose, postdose, or from historical clinical records. When the baseline is equal to 0, the LLACT is less than 1% (lower limit of quantification). When the baseline FIX activity is equal to LLACT, LLACT is greater than or equal to 1% and less than or equal to 2%.

Prestudy residual decay was performed using terminal half-life obtained from a noncompartmental analysis of the individual data by the following formula:

$$\text{Residual decay}=(\text{predose}-\text{baseline})\times e^{-\text{decay rate}\times\text{time}}. \quad (G)$$

For the popPK model development, NONMEM VII version 1.0 (ICON Development Solutions, Ellicott City, Md.) was used. The modeling and qualification steps are presented below in Table 9.

TABLE 9

Modeling and Qualification Steps

| Steps | Model selection |
|---|---|
| Base model and Inter-individual variability (IIV) evaluation | Base Model, IIV on CL/V1/Q2/V2/Q3 |
| Inter-occasion variability (IOV) evaluation | Base Model with IOV on CL and V1 |
| Covariate Modelling | Final model, body weight as covariate on CL and V1 |
| Internal qualification (bootstrap and VPC) | |
| External qualification using trough/peak records | |

CL, clearance;
V, volume of distribution;
Q, inter-compartmental clearance;
VPC, visual predictive check A first order conditional estimation with interaction method (FOCEI) was used to estimate the popPK parameters. Residual errors were modeled as combined proportional and additive errors. Stepwise forward addition ($p<0.005$) and backward elimination ($p<0.001$) covariate modeling was performed. Potential covariates assessed in this analysis included: body weight (BW), Age, Race, Blood type, Human Immunodeficiency Virus status, Hepatitis C Virus status, haematocrit, $IgG_1$ and albumin concentration, and FIX genotype.

Model qualifications included bootstrap, visual predictive check (VPC) and validation with trough/peak records. The mean relative prediction error (an indicator of accuracy) was calculated as:

$$\frac{1}{N}\sum_{i=1}^{i=N}\frac{[DV-IPRED]}{DV} \quad (H)$$

Figure 1:
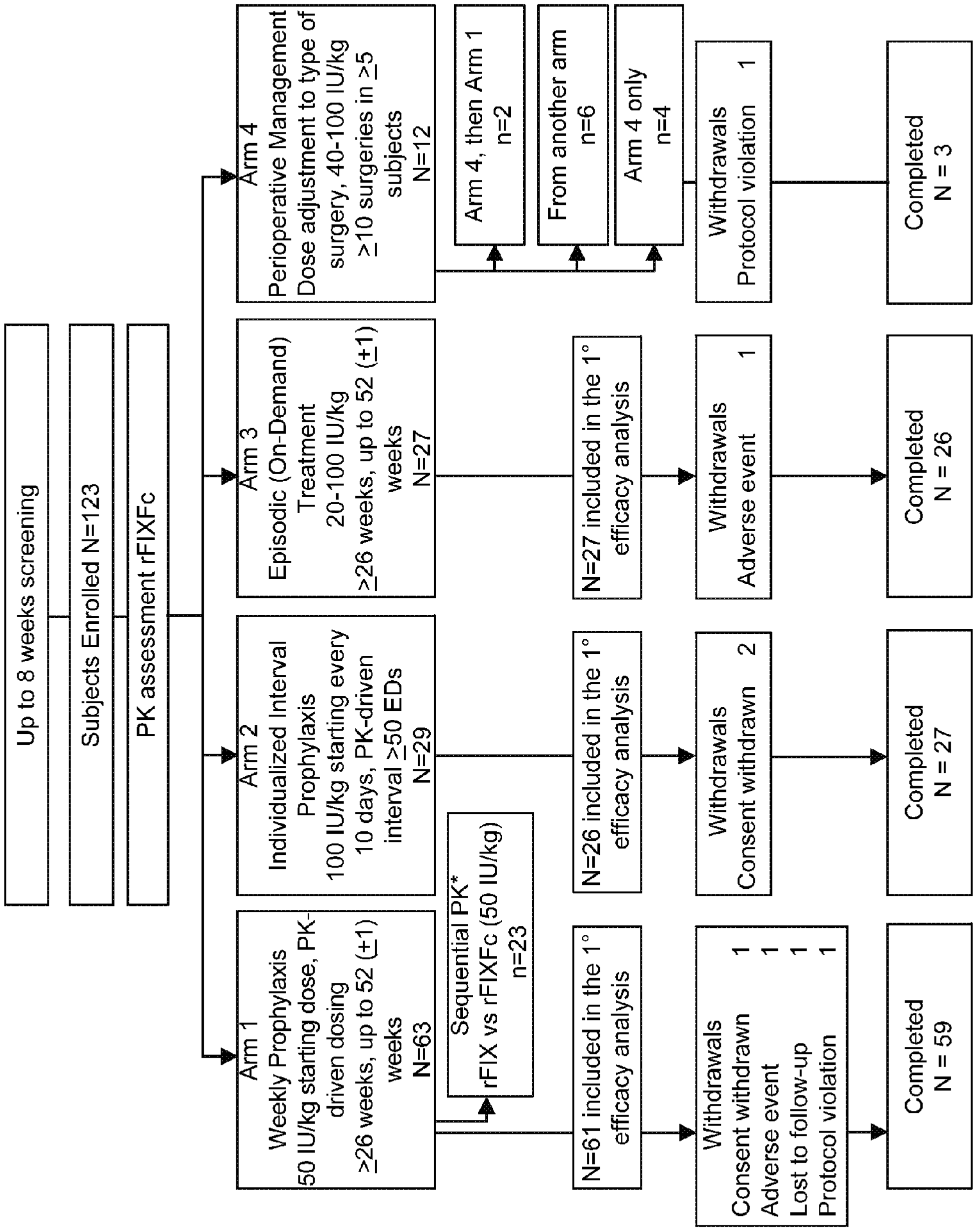
Figure 4:
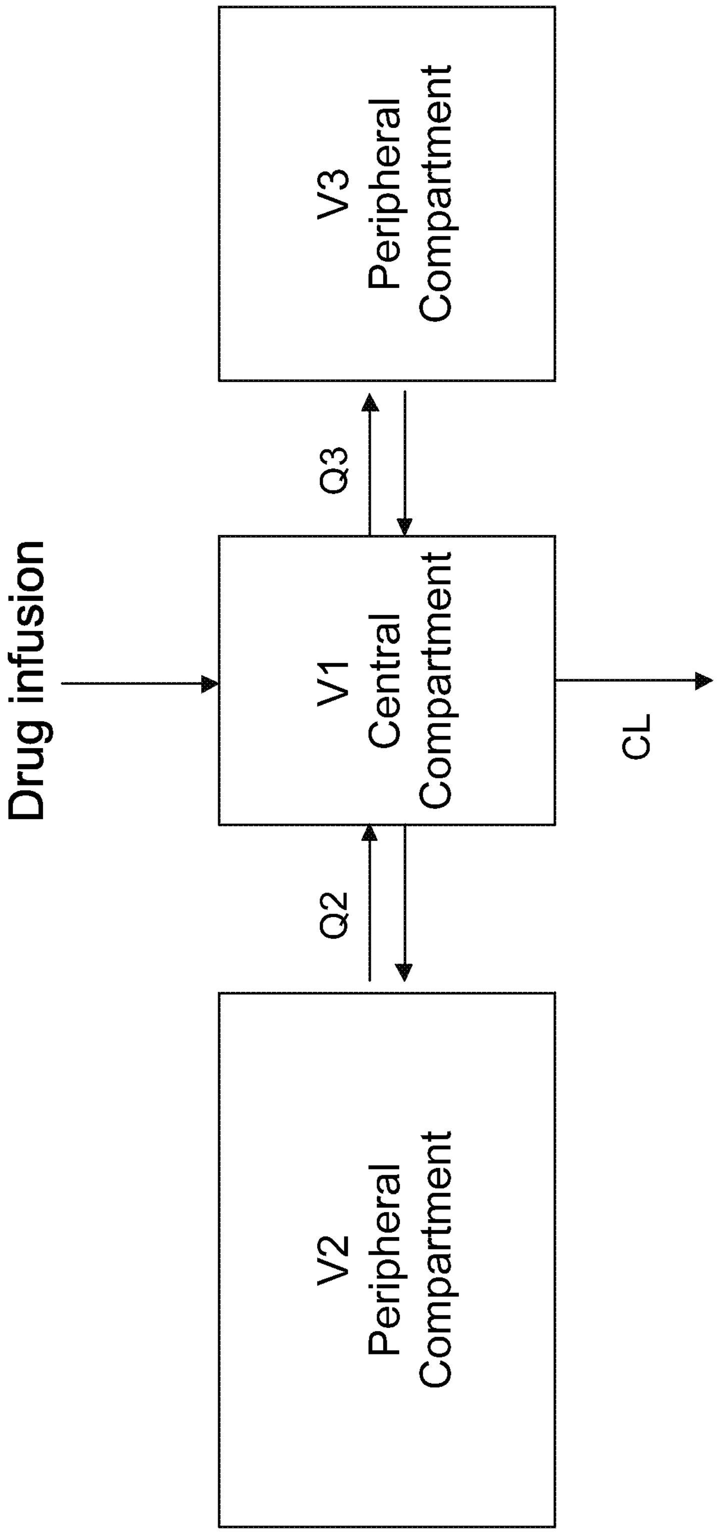
Figure 5:
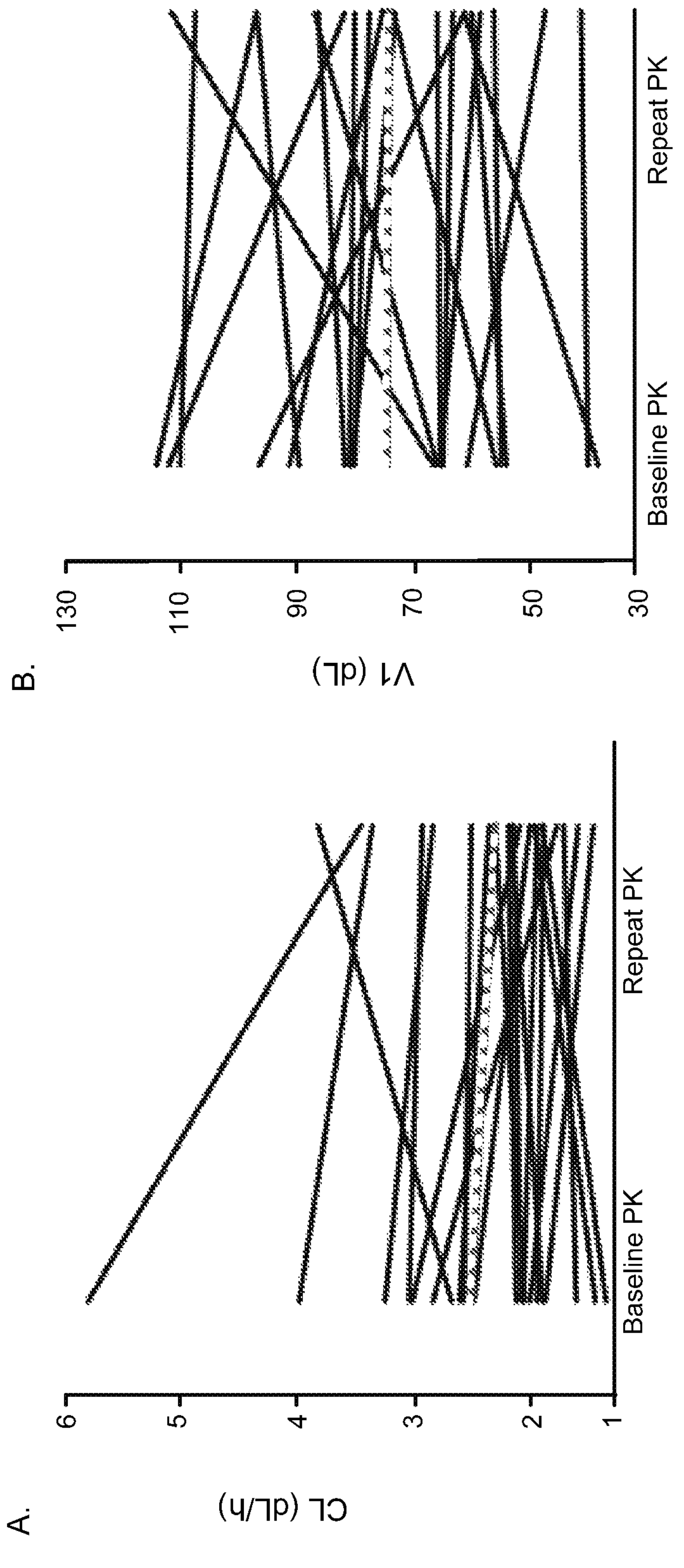

Results:

The rFIXFc disposition was best described by a three-compartment base model (FIG. 4). The model was further improved by including intra-subject random changes at different occasions (i.e., inter-occasion variability, IOV) for CL and V1 (FIG. 5). IOV was smaller than inter-individual variability (IIV), indicating that individual PK was more accurate than the mean popPK for individual PK prediction.

Figure 6:
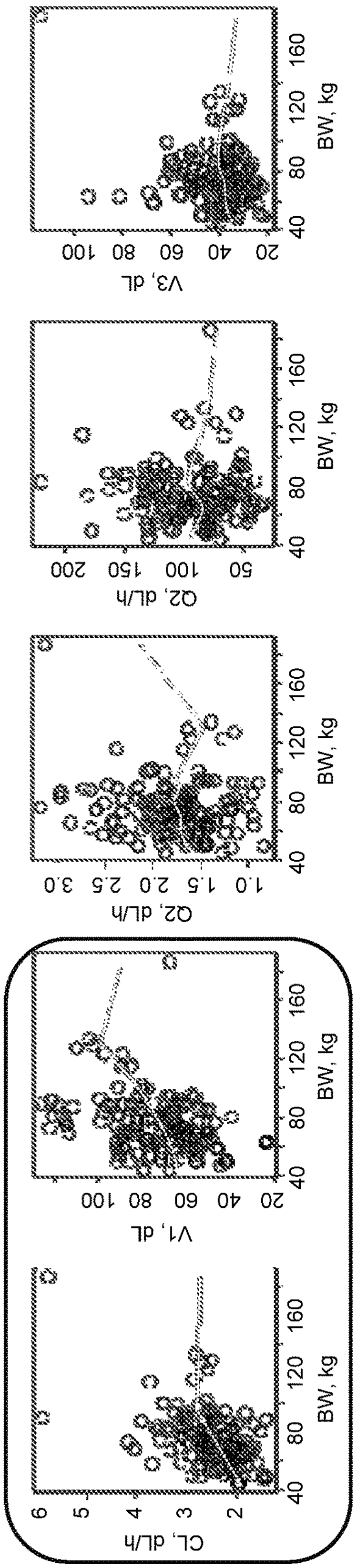

Body weight was found to be a significant covariate for rFIXFc disposition (FIG. 6), although the impact of BW was limited. For example, the BW exponent on CL and V1 was 0.436 and 0.396, respectively, and inclusion of BW reduced inter-individual variability (IIV) for both CL and V1 only by 3.4% and 2.5%, respectively. None of the other covariates assessed, including age, race, blood type or genotype, were significant covariates in this model.

The final popPK model is summarized below in Table 10.

TABLE 10

Summary of the final rFIXFc population pharmacokinetic model.

| Parameter | Population Estimate | 95% non-parametric CI from bootstrap[a] | IIV[b] (%) | IOV (%) |
|---|---|---|---|---|
| $CL = \text{Typical CL}\times\left(\frac{BW}{73}\right)^{0.436}$ | | | | |
| Typical CL for a 73 kg subject (dL/h) | 2.39 | 2.29, 2.49 | 17.7 | 15.1 |
| BW exponent on CL | 0.436 | 0.272, 0.584 | | |
| $V1 = \text{Typical V1}\times\left(\frac{BW}{73}\right)^{0.396}$ | | | | |
| Typical V1 for a 73 kg subject | 71.4 | 58.5, 76.0 | 21.7 | 17.4 |
| BW exponent on V1 | 0.396 | 0.169, 0.580 | | |
| Q2 (dL/h) | 1.67 | 1.35, 1.89 | 35.8 | — |
| V2 (dL) | 87.0 | 79.0, 95.5 | 46.2 | — |
| Q3 (dL/h) | 39.3 | 16.6, 141 | — | — |
| V3 (dL) | 39.9 | 36.6, 52.4 | 37.7 | — |

Figure 7:
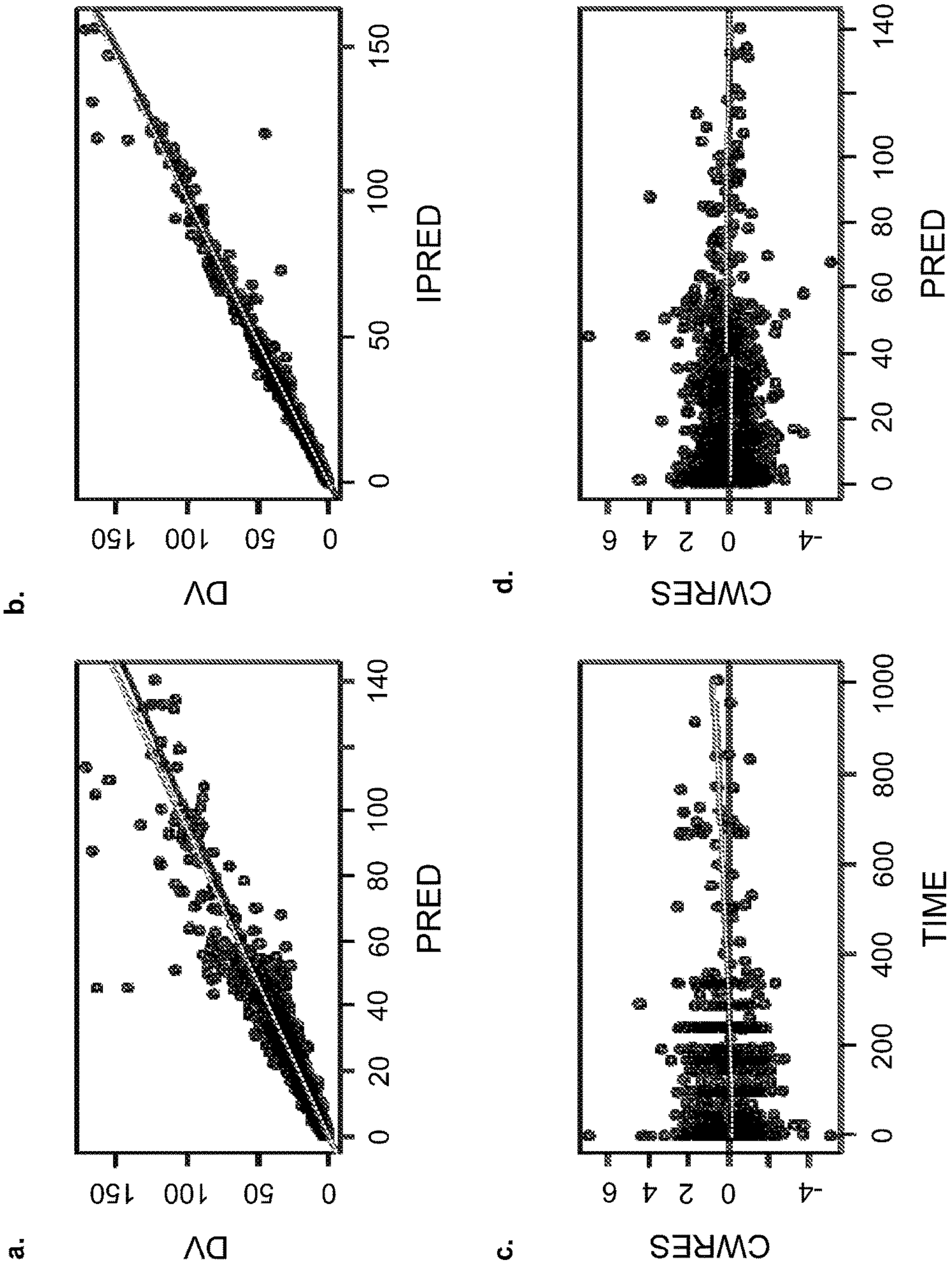

Residual Error:
Proportional 10.6%
Additive 0.24 IU/dL
CI, confidence interval;
IIV, inter-individual variability;
IOV, inter occasion variability;
CL, clearence;
BW, body weight;
V, volume of distribution;
Q, inter-compartmental clearence For a typical 73 kg subject, the predicted popPK values for clearance, volume of central compartment, and volume of distribution at steady state are 2.39 dL/h, 71.4 dL, and 198 dL, respectively. Goodness-of-fit plots show that the predicted popPK data generated by the model closely mimic the observed FIX activity data (FIG. 7).

Figure 8:
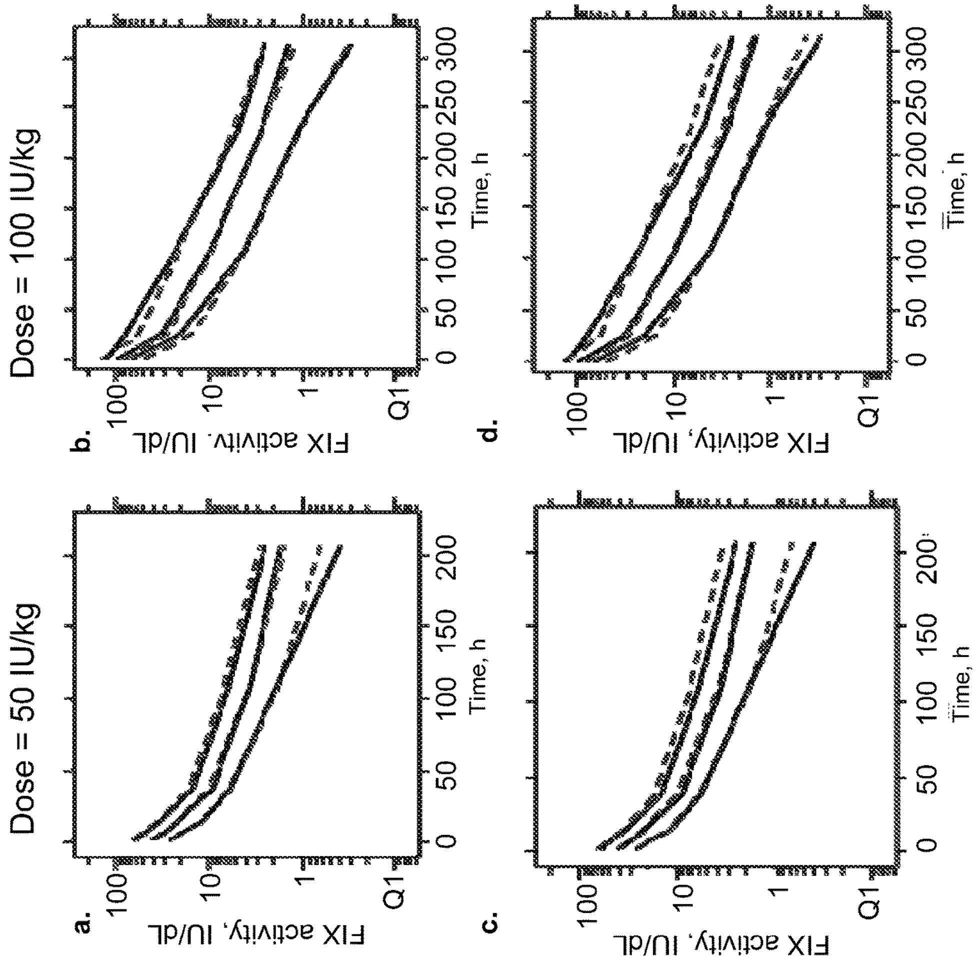
Figure 9:
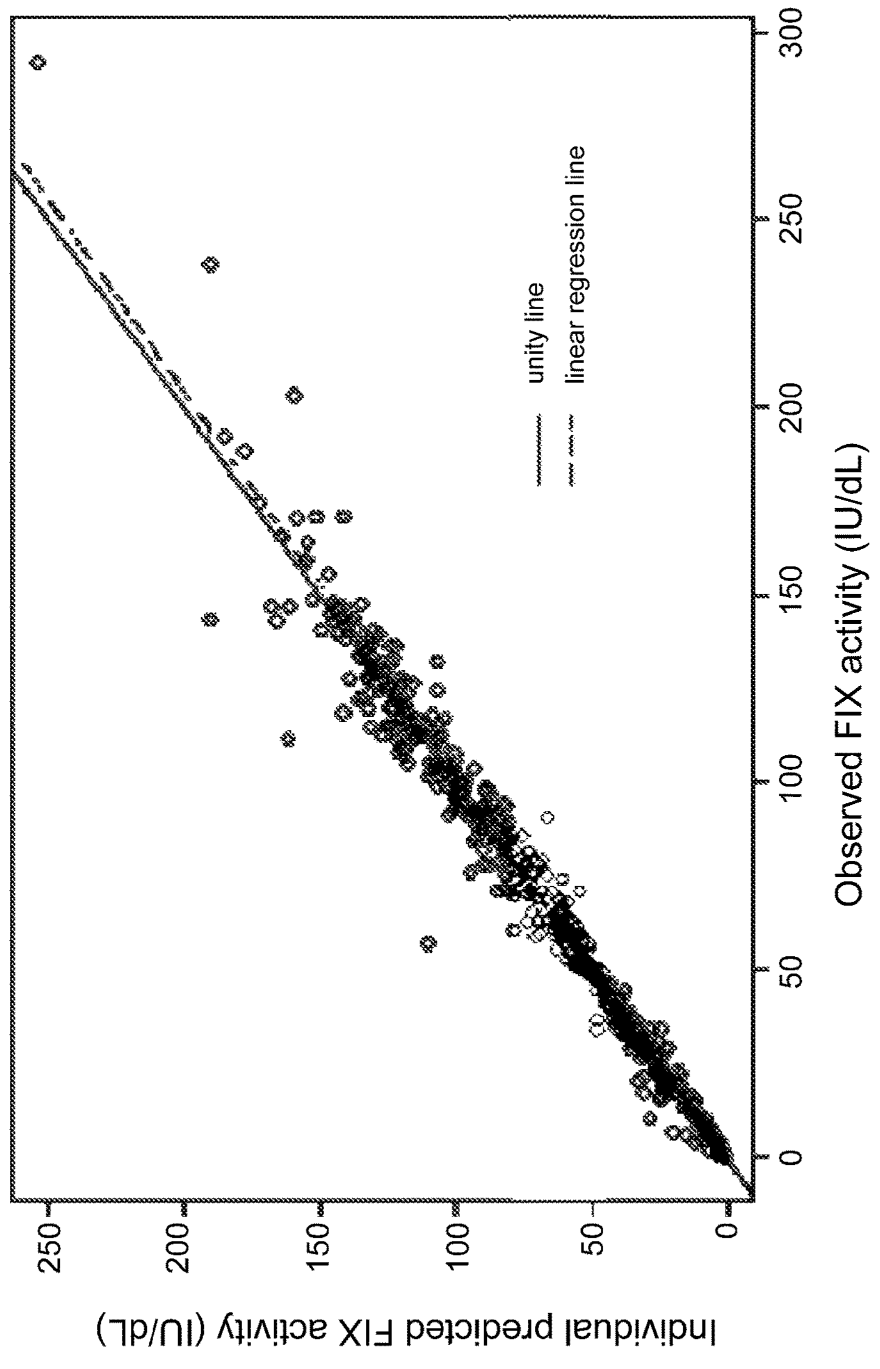
FIG. 9 shows validation of the population PK model with the trough/peak records for a long-acting FIX polypeptide (i.e., rFIXFc). R2=0.9857, P<0.001.

The results of the popPK model were validated using the observed FIX activity data. The median and 80% interval for observed and predicted FIX activity time profiles nearly overlapped, indicating that the final model was able to reproduce both the central tendency and variability of the observed FIX activity data on the time scale (FIG. 8). The strong correlation between observed and predicted FIX activities in the trough/peak dataset suggested that the final popPK model is predictive (FIG. 9).

Finally, the overall relative prediction error was −3.23% with a 95% confidence interval of −5.27% to −1.23%. Post hoc estimates from this popPK analysis were very similar to the results from the conventional PK analysis shown below in Table 11.

TABLE 11

Post hoc empirical Bayesian estimates of key PK parameters.

| Parameter | Phase 3 Mean (SD) | Phase 1/2a Mean (SD) |
|---|---|---|
| Clearance (CL), mL/h/kg | 3.42 (0.89) | 2.82 (0.58) |
| Volume of central compartment (V1), mL | 102 (29.6) | 96.2 (24.7) |
| Incremental in vivo recovery, IU/dL per IU/kg | 1.02 (0.45) | 1.04 (0.19) |
| Volume of distribution at steady-state (Vss), mL/kg | 297 (90.5) | 234 (70.8) |

TABLE 11-continued

Post hoc empirical Bayesian estimates of key PK parameters.

| Parameter | Phase 3 Mean (SD) | Phase 1/2a Mean (SD) |
|---|---|---|
| Terminal Half-life, h | 86.7 (27.9) | 70.9 (13.9) |
| Mean residence time (MRT), h | 89.4 (25.9) | 82.5 (15.5) |

SD, standard deviation

Conclusions:

The three-compartment popPK model predicted disposition of rFIXFc with modest inter-individual variability (IIV). Individual PK parameters derived from the three-compartment popPK model were similar to those derived from the two-compartment conventional PK analysis, indicating a limited 3rd compartment contribution. For a typical 73 kg subject, the popPK model predicted a clearance of 2.39 dL/h; volume of central compartment of 71.4 dL; and volume of distribution at steady state of 198 dL. The only significant covariate assessed in the popPK model was BW, although its impact on rFIXFc PK variability was limited.

The final popPK model can be used to simulate dosing regimens and intervals for routine prophylaxis, control and prevention of bleeding episodes, and peri-operative management. This model may assist physicians who wish to tailor dosing for individual subjects with sparse PK samples.

Example 6. Use of the Population Pharmacokinetic Model of rFIXFc to Simulate or Estimate Individualized and Median Patient Treatment Information As is discussed in Examples 5 and 7, a model of estimated population PK parameters of rFIXFc has been established that can assist physicians and other healthcare practitioners who wish to tailor dosing for individual subjects with, e.g., sparse PK samples. Alternatively, the model can be used to determine dosing based on PK data for the whole population (median PK).

Thus, individualized patient treatment, e.g., pharmacokinetics (PK) and dosing regimens, can be selected using Bayesian estimation (or similar machine learning algorithm) based on the population pharmacokinetic (popPK) model described in Example 5 and 7, above (e.g., Table 10, 13, or 14). In this way, one can determine alternative prophylactic dosing regimens and optimized dosing regimens for peri-operative management that have not previously been studied in the B-LONG trials. Alternatively, the selected dosing regimen is based on population PK (median PK) rather than making an individualized selection.

In some embodiments, the rFIXFc popPK model of Example 5 and 7 (e.g., Table 10, 13, or 14) is used without the Bayesian or similar machine learning algorithm.

In some embodiments of this aspect of the invention, the method is carried out on a computer-based system, e.g., a server, a desk top computer, a lap top computer, a tablet, a hand held device, or a smart phone. In some embodiments, the computer-based system is a computer application. The computer-based system includes a storage medium for the rFIXFc popPK model discussed in Example 5 and 7, e.g., the parameters of Table 10, 13, or 14. In some embodiments, the storage medium can also contain a Bayesian estimating program, e.g., NONMEM or Phoenix NLME. E.g., Example 5 and 7 (e.g., Table 10, 13, or 14); Kiang et al., *Clin. Pharmacokinet* 51:515-525 (2012).

In some embodiments, the system comprises two or more computer-based systems. In some embodiments, the user can input information into a first computer-based system that communicates with a second computer-based system, and the second computer-based system carries out calculations and communicates output information to the first computer-based system. This output information can include recommendations about individualized or non-individualized dosing regimens.

In some embodiments, the user inputs information into the system and the system calculates and outputs one or more PK or dosing regimens. In some embodiments, the system uses the received information to calculate and output individualized or median PK information. In some embodiments, the system calculates individualized dosing or interval information.

Information that can be input by a user and received by the system includes patient information and desired treatment outcome information. Based on the type and value of the received information, the computer-based system calculates output information based on the rFIXFc popPK model and optional machine learning algorithm on the storage medium.

Patient information includes, e.g., age, body weight, diagnostic (baseline) FIX level, PK determinations, time of PK sampling, dosing history if PK samples were taken from multiple doses, actual dose, FIX activity level, etc.

Desired treatment outcome information includes desired PK or desired regimen outcome, e.g., desired rise in plasma FIX activity level following dose, desired dosing interval, and desired dose.

Based on the information that was input and received by the system, the system can output various information, e.g., PK curve, PK parameter such as incremental recovery (Cmax/dose), mean residence time, terminal t½, clearance, Vss, AUC/dose, doses and associated troughs, and intervals and associated troughs.

For example, for assessing individualized patient PK, the system can recommend that the user input 2-3 optimized PK sampling time points. In this case, system output can include PK curve and one or more selected PK parameters, e.g., incremental recovery (Cmax/Dose), mean residence time, terminal t½, clearance, Vss, AUC, and time to 1 or X %, etc. E.g., FIG. 13.

As additional examples, to select an individualized dosing regimen using the output individual PK parameters discussed in the preceding paragraph, (i) the dose selected for acute treatment can be based on user input of the desired rise in plasma FIX activity level following the dose, (ii) the dose selected for prophylaxis can be based on user input of the desired dosing interval, or (iii) the selected interval for prophylaxis can be based on user input for the desired dose. In the first case, the system can output the dose (IU) based in the patient's incremental recovery. E.g., FIG. 14. In the second case, system output can be a table of doses and associated troughs, e.g., x IU/kg, 1% trough, y IU/kg, 2% trough, etc. e.g., FIG. 15, top. In the third case, system output can be a table of intervals and associated troughs, e.g., x days, 1% trough, y IU/kg, 2% trough, etc., E.g., FIG. 15, bottom.

The user may wish to use the system without inputting any individualized PK data. In this case, the dosing output would be based on the population median rather than being individualized for the particular patient. E.g., FIG. 16. In this way, the user inputs, e.g., body weight and age, and (i) the desired rise in plasma FIX activity level following the dose, (ii) the desired dose interval for prophylaxis, or (iii) the desired dose for prophylaxis. In the first case, the system can output the dose. In the second case, the system can output the dose and associated trough, e.g., Table 16. In the third case, the system can output the interval and associated trough, e.g., Table 16.

Age can be input to determine if the system is suitable for the patient because the current version of the popPK model was built for patients 12 years and older.

In some embodiments, the system is compliant with patient privacy laws. In some embodiments, the system is encrypted, e.g., with SSL. In some embodiments, input patient information is made anonymous.

In some embodiments, the system includes a user help function.

The user can be, e.g., a physician, a nurse, or another healthcare practitioner.

In some embodiments, the method further includes selecting a dosing regimen based on the system's output information and administering rFIXFc to the patient according to the selected regimen.

Example 7. Population Pharmacokinetic Modeling of Long-Acting Recombinant Factor IX Fc Fusion Protein (rFIXFc) in Patients with Hemophilia B Background and Objectives:

Recombinant factor IX Fc fusion protein (rFIXFc) is a clotting factor developed using monomeric Fc fusion technology resulting in a longer circulating half-life. The objective of this analysis is to elucidate the pharmacokinetic characteristics of recombinant factor IX Fc fusion protein (rFIXFc) in patients with hemophilia B and identify covariates that affect rFIXFc disposition.

Methods:

Population pharmacokinetic analysis using NONMEM® was performed with clinical data from two completed trials in previously treated patients with severe to moderate hemophilia B. Twelve patients from a phase ½a study and 123 patients from a registrational phase 3 study were included in this population pharmacokinetic analysis.

Results:

A three-compartmental model was found to best describe the pharmacokinetics of rFIXFc. For a typical 73-kg patient, population predicted clearance (CL), volume of central compartment ($V_1$), and volume of distribution at steady state ($V_{ss}$) were 2.39 dL/h, 71.4 dL and 198 dL, respectively. Because of repeat pharmacokinetic profiles at week 26 for patients in a subgroup, inclusion of inter-occasion variability (IOV) on CL and $V_1$ were evaluated and significantly improved the model. The magnitude of IOV on CL and $V_1$ were both low to moderate (<20%) and less than the corresponding inter-individual variability. Body weight (BW) was found to be the only significant covariate for rFIXFc disposition. However, the impact of BW was limited, as the BW power exponents on CL and $V_1$ were 0.436 and 0.396, respectively.

Conclusions:

This is the first population pharmacokinetic analysis that systematically characterized the pharmacokinetics of long-acting rFIXFc in patients with hemophilia B. The population pharmacokinetic model for rFIXFc can be utilized to evaluate and optimize dosing regimens for the treatment of patients with hemophilia B.

1. Background

Hemophilia B is a rare bleeding disorder caused by a deficiency of coagulation factor IX (FIX). The disease is caused by a mutation on the X chromosome and affects approximately 1 in 30,000 males. Hemophilia B results in abnormal clot formation, causing prolonged and abnormal bleeding, including bleeding into joints, soft tissue, muscle and body cavities. Bleeding episodes may be associated with trauma or occur in the absence of trauma (spontaneous bleeding). If not treated appropriately, bleeding can be life-threatening or result in significant morbidity. The current mainstay of treatment is FIX replacement therapy.

Recombinant factor IX Fc fusion protein (rFIXFc) is a recombinant protein consisting of a single molecule of FIX covalently fused to the Fe domain of human immunoglobulin G1 (IgG1) with no intervening sequence. The Fc domain is responsible for the long circulating half-life of IgG1 through interaction with the neonatal Fc receptor (FcRn) that is expressed in many different cell types. rFIXFc was therefore designed as a long-acting version of recombinant FIX. rFIXFc has the potential to fulfill an unmet medical need by providing a long-acting therapy for control and prevention of bleeding episodes, routine prophylaxis and perioperative management in patients with hemophilia B. Two clinical trials with rFIXFc have been completed in previously treated patients with severe to moderate hemophilia B (with ≤2 IU/dL [%] endogenous FIX): one single dose phase ½a study in 14 patients (12 of them who received doses ≥12.5 IU/kg had pharmacokinetic assessment) [6], and one registrational phase 3 study in 123 patients [8]. rFIXFc was shown to be well tolerated and efficacious in the treatment of bleeding, routine prophylaxis and perioperative management.

The purpose of this analysis is to characterize the population pharmacokinetics of rFIXFc in patients with hemophilia B and to identify demographic and clinical factors that are potential determinants of rFIXFc pharmacokinetic variability. The population pharmacokinetic model of rFIXFc can be used to evaluate and guide dosing regimens of rFIXFc in the treatment of patients with hemophilia B.

2 Methods 2.1 Clinical Studies

FIX activity data were obtained from two completed clinical trials in previously treated patients with severe to moderate hemophilia B. Twelve evaluable patients from the phase ½a study and 123 patients from the phase 3 study (B-LONG) who had measurable FIX activities were included in this population pharmacokinetic analysis. The clinical studies are summarized in FIGS. 2A and 2B. All subjects were patients with severe to moderate hemophilia B previously treated with FIX products, from 12.1 to 76.8 years of age. All patients, or patient guardians, gave informed written consent. The studies were approved by the Ethics committee and conducted in accordance with the International Conference on Harmonisation guidelines for Good Clinical Practice.

2.2 Pharmacokinetic Sampling and Bioanalytical Methods

In the phase ½a study, 12 patients underwent rFIXFc pharmacokinetic sampling up to 14 days. In the phase 3 study, pharmacokinetic samples were collected for rFIXFc in all patients according to the schedule in FIG. 2C. Pharmacokinetic profiles of rFIXFc were assessed at week 1 (baseline) for all patients and at week 26 for the Arm 1 sequential pharmacokinetic subgroup. For patients on prophylaxis in Arms 1 and 2, additional trough and peak samples were collected at clinical visits throughout the study.

The population pharmacokinetic modeling was performed using plasma FIX activity data as measured by the one-stage activated partial thromboplastin time (aPTT) clotting assay using commercially available aPTT reagents (Trinity Biotech) and normal reference plasma (Precision BioLogic). Lower limit of quantitation (LLOQ) was 1 IU/dL (%). The accuracy of the assay was within 95-104%, and the intra- and inter-assay precision was approximately 10%.

2.3 Data Handling

A total of 11 data post-infusion were below the limit of quantification (BLQ, below LLOQ of 1%). Since those post-infusion BLQ values represent <0.5% of the observations, they were excluded from the analysis as the first step of data handling.

The one-stage clotting assay does not distinguish between FIX activities resulting from endogenous baseline residual activity and incomplete washout of the pre-study FIX product or the input study drug, rFIXFc. Therefore, the baseline and residual activity corrections were applied to the observed FIX activity data (formulas (I) and (J)). The corrected FIX activities were recorded as the dependent variable (DV) in the population pharmacokinetic dataset. Similar baseline and residual activity corrections were reported previously for the pharmacokinetic analyses of other FIX products [12-15]. See Bjorkman et al., Eur J Clin Pharmacol. 2012; 68(6):969-77; Bjorkman et al., Eur J Clin Pharmacol. 1994; 46(4):325-32; Bjorkman et al., Haemophilia. 2001; 7(2):133-9; and Carlsson et al., Haemophilia. 1998; 4(2):83-8.

$$\text{Residual decay correction}=(\text{Predose}-\text{baseline})\times e^{-decay\ rate\times time} \quad (I)$$

$$\text{Corrected FIX activity}=\text{Measured FIX activity}-\text{baseline}-\text{residual decay correction} \quad (J)$$

The endogenous baseline FIX activity level is dictated by the defective FIX genotype and thus is stable in each individual subject, yet could be overestimated in patients receiving FIX replacement therapy who underwent incomplete washout. Therefore the baseline FIX activity was defined as the lowest FIX activity observed throughout the study, including all the screening, pre-dose, and post-dose records. For patients whose lowest observed FIX activity was <1% (LLOQ), the baseline FIX activity was set at 0; for patients whose lowest observed FIX activity was between 1-2%, the baseline FIX activity was set at the lowest observed FIX activity. The study enrollment was limited to subjects with baseline FIX activity≤2%.

For each individual subject, baseline activity was first subtracted from observed FIX activity and then residual activity, if any, was decayed from baseline-corrected FIX activity to obtain the corrected FIX activity. Residual activity was defined as pre-dose activity minus baseline FIX activity. For subjects in the Arm 1 sequential pharmacokinetic subgroup who underwent pharmacokinetic assessment with the comparator FIX product (BENEFIX®, Pfizer Inc, New York, N.Y.) prior to rFIXFc pharmacokinetic assessment, the residual activity was decayed using the individual subject's BENEFIX® terminal first-order decay rate estimated by the non-compartmental analysis in PHOENIX™ WinNonlin 6.2 (Pharsight, Sunnyvale, Calif.). For any subjects who did not have a BENEFIX® pharmacokinetic assessment, the residual activity was decayed from the rFIXFc pharmacokinetic profiles using the average BENEFIX® terminal first-order decay rate from the Arm 1 sequential pharmacokinetic subgroup.

2.4 Modeling Strategy and Datasets

Demographic and clinical factors collected and examined in the analysis included age, body weight (BW), race, height, human immunodeficiency virus (HIV) and hepatitis C virus (HCV) status, IgG1 and albumin concentration, hematocrit (HCT) level, FIX genotype and blood type.

The pharmacokinetic dataset was split into the modeling dataset, which was used to build the population pharmacokinetic model and validation dataset, which was used to qualify the final model. The modeling dataset for rFIXFc included 1400 FIX activity records from 135 baseline pharmacokinetic profiles in both phase ½a and 3 studies, as well as 21 repeat pharmacokinetic profiles that were collected at week 26 from the Arm 1 sequential pharmacokinetic subgroup in the phase 3 study. The validation dataset included 1027 trough/peak FIX activity records from the phase 3 study, excluding the records during and after surgeries. Peak/trough collection times were recorded by patients retrospectively into their electronic diary following the clinic visit. A summary of the modeling and validation datasets is listed in Table 12.

TABLE 12

Summary of modeling and validation datasets

| Dataset | No. of patients | No. of FIX activity records | Median age (year [range]) | Median body weight (kg [range]) |
|---|---|---|---|---|
| Modeling dataset | 12 (Phase 1/2a)<br>123 (Phase 3) | 1,400 | 31.3<br>(12.1-76.8) | 73.3<br>(45.0-186.7) |
| Validation dataset | 100 (Phase 3) | 1,027 | 30.7<br>(12.1-71.6) | 72.5<br>(45.2-186.7) |

FIX Factor IX

The modeling strategy was a two-step approach. The first step was to build the population pharmacokinetic model using the modeling dataset and the second step was to validate the model with goodness-of-fit plots, bootstrapping, visual prediction check (VPC) and the trough/peak validation dataset. As a comparison, the rFIXFc model using the full dataset, which combined the modeling and validation dataset, was also developed.

2.5 Population Pharmacokinetic Modeling

NONMEM® 7 version 1.0 (ICON Development Solutions, Ellicott City, Md., USA) with an Intel Fortran compiler (version 12) was used for the population pharmacokinetic model development. Statistical program R (version 2.15.0, R Foundation for Statistical Computing, Vienna, Austria) was used to compile NONMEM datasets and generate graphics. Perl Speaks NONMEM (PsN, version 3.5.3) (Lindbom et al., Comput Methods Programs Biomed. 2004; 75(2): 85-94) was used to conduct bootstrapping. PsN and Xpose 4 (Jonsson et al., Comput Methods Programs Biomed. 1999; 58(1): 51-64) were used to perform VPC.

A first-order conditional estimation with interaction method (FOCEI) was used to estimate population pharmacokinetic parameters. Inter-individual variability (IIV) was modeled using exponential function. The inclusion of IIV terms on pharmacokinetic parameters was tested sequentially, with the most significant objective function value (OFV) reduction (P<0.005) entering the model first. Inter-occasion variability (IOV) (Karlsson et al., J. Pharmacokinet-Biopharm. 1993: 21(6): 735-50) was also evaluated. For the modeling dataset, two occasions were defined including baseline pharmacokinetic profiling at week 1 and repeat pharmacokinetic profiling at week 26. For the full dataset, six occasions were defined according to the data density. Residual errors were modeled as combined proportional and additive errors.

Plots of IIV versus covariates were used to screen for potential demographic and clinical factors that affect rFIXFc pharmacokinetics. For continuous covariates, scatter plots of ETA (IIV code used in NONMEM) versus covariates were overlaid with a non-parametric locally weighted smoother LOESS line to determine functional relationships; for categorical covariates, box and whisker plots were used to identify potential differences between groups (data not shown). A clear trend of positive or negative slopes and noteworthy correlation coefficients (data not shown) would suggest a possible influence by the continuous covariates; pronounced differences among the groups would suggest a possible influence by the categorical covariates. After identifying potential covariates, a full stepwise forward addition ($P<0.005$) and backward elimination ($P<0.001$) procedure was conducted for covariate modeling.

Besides statistical considerations, model selection was also aided by goodness-of-fit plots, including DV (observed FIX activity adjusted for baseline activity and residual decay) versus population prediction (PRED), DV versus individual prediction (IPRED), conditional weighted residual (CWRES) versus TIME and PRED plots. See Wade et al., AAPS J. 2005; 7(2): 45; and Ette et al., Pharm Res. 1995; 12(12); 1845-55. Other diagnostics also helped to select the proper model, including parameter precision, ETA, and CWRES distribution and shrinkage. See Savic et al., AAPS J. 2009; 11(3): 558-69; and Xu et al., AAPS J. 2012; 14(4); 927-36.

2.6 Model Qualification

Bootstrapping was conducted with 1,000 datasets generated by random sampling through replacement. Non-parametric median and 95% ($2.5^{th}$ and $97.5^{th}$ percentiles) confidence intervals (CIs) of pharmacokinetic parameters were obtained and compared with final model estimates.

To check the predictive performance of the model, VPC was performed to obtain 1,000 simulated pharmacokinetic profiles. Median, $10^{th}$, and $90^{th}$ percentile of simulated and observed FIX activities, stratified by dose (50 and 100 IU/kg), were plotted.

The trough/peak validation dataset was used to check the predictability of the model. Specifically, the model was used to derive Bayesian feedback predictions of FIX activities at trough/peak time points by setting MAXEVAL=0 in NONMEM control stream. The mean relative prediction error (an indicator of accuracy) was calculated using formula:

$$\frac{1}{N}\sum_{i=1}^{i=N}\frac{DV - IPRED}{DV} \quad (K)$$

3 Results 3.1 Structural Model and Evaluation of IIV

Based on previous conventional pharmacokinetic analyses of rFIXFc, a two-compartment model appropriately described individual pharmacokinetics, hence a two-compartment model was evaluated first followed by a three-compartment model. IIV (ETA, $\eta$ values) was assumed for clearance (CL) and volume of compartment 1 ($V_1$). A covariance between CL and $V_1$ was also included. The three-compartment model resulted in a reduction of OFV by over 400 units (for additional four parameters) compared with the two-compartment model, thus was selected as the base model (FIG. 4). Primary pharmacokinetic parameters included CL, $V_1$, volume of compartment 2 ($V_2$) and 3 ($V_3$), inter-compartmental clearance between compartments 1 and 2 ($Q_2$), as well as between 1 and 3 ($Q_3$). The inclusion of IIV for the rest of the pharmacokinetic parameters ($V_2$, $V_3$, $Q_2$ and $Q_3$) led to further improvement in the model fitting. However, IIV on $Q_3$ was associated with a high standard error (87%), indicating that the data cannot support a precise estimation of IIV on $Q_3$, which was thus not included in the model. No additional covariance between IIV of pharmacokinetic parameters could be estimated with precision, thus the only covariance between IIV retained in the model was the covariance between IIV on CL and $V_1$.

3.2 Evaluation of IOV

Since the Arm 1 sequential pharmacokinetic subgroup had repeat pharmacokinetic profiles at week 26 in addition to baseline pharmacokinetic profiles at week 1, IOV was evaluated with baseline pharmacokinetics as occasion 1 and repeat pharmacokinetics as occasion 2. The inclusion of IOV on CL significantly improved the model with a reduction of OFV by 171.6 units. The inclusion of IOV on both CL and V1 achieved an additional OFV drop of 41.6 units, whereas IOV on $V_2$ or $Q_2$ did not improve the model fit ($P>0.05$). The IOV on $V_3$ improved the model fit at $P<0.005$ but with a large percentage of relative standard error (78.4%); Therefore, IOV was only included for CL and $V_1$.

Pairwise comparisons of CL and $V_1$ estimates for baseline and repeat pharmacokinetics, derived from the base model with IOV, were plotted in FIG. 5. The changes of either CL or $V_1$ between the two occasions were random and small with only one exception, and the mean CL or $V_1$ for the two occasions were similar.

Overall, the inclusion of IOV reduced the corresponding IIV on CL and $V_1$ from 24.0% and 29.6% to 21.1% and 24.2%, respectively. The inclusion of IOV also reduced proportional and additive residual errors from 12.1% and 0.30 IU/dL, to 10.5% and 0.24 IU/dL, respectively. The base model with IOV provided a reasonable fit to the data, and explained the random as well as small pharmacokinetic changes between occasions studied in the trial, therefore was chosen for further covariate modeling.

3.3 Covariate Modeling

Based on ETA versus covariate plots, BW, albumin and race on CL, and "study" on $V_2$ were speculated to be potential covariates. Covariate modeling included BW on all pharmacokinetic parameters, albumin on CL, and "study" on $V_2$ and CL. BW was assessed for all pharmacokinetic parameters because it is an important physiology factor. "Study" was assessed on CL because of the importance of CL.

A full stepwise forward addition and backward elimination procedure was performed. Following the forward covariate inclusion, the full covariate model was identified with BW on CL and $V_1$, and "study" on $V_2$. However, "study" on $V_2$ was removed following the backward elimination procedure ($P>0.001$).

Further, the potential residual variability difference between the phase ½a and 3 studies was tested by including two sets of proportional and additive errors for two studies in the residual error model. No significant reduction in OFV was observed (13.7 units, df=2).

Therefore, although the phase ½a and phase 3 studies have different dosing and sampling schemes, the population pharmacokinetic modeling did not suggest a PK difference between the two studies.

3.4 Final Model

The final model of rFIXFc had IIV on $CL/V_1/Q_2/V_2/V_3$ but not $Q_3$, IOV on CL and $V_1$ and BW as a covariate on CL and $V_1$. The model described the data well (FIG. 4). There were no outstanding trends observed in the CWRES plots and most CWRES were randomly distributed between −2 and 2, indicating overall small discrepancies between measured FIX activities and population predictions (FIGS. 7C and 7D). Population pharmacokinetic parameter estimates, IIV and IOV, as well as residual errors were estimated with precision, evidenced by narrow 95% CIs for each pharmacokinetic parameter (Table 3). The IIV for CL and $V_1$ were 17.7 and 21.7%, respectively, which are low to moderate, and IOV for CL and $V_1$ were low at 15.1 and 17.4%, respectively.

The magnitude of ETA shrinkage on the IIVs was moderate (<30% for all pharmacokinetic parameters with IIV terms), while the magnitude of ETA shrinkage on the IOV was occasion-specific, moderate at first occasion (around 30% on CL and $V_1$) and higher at occasion 2 (around 70%) because there were fewer pharmacokinetic profiles for the second occasion (21 for occasion 2 repeat pharmacokinetics vs. 135 for occasion 1 baseline pharmacokinetics). The distributions of ETAs and CWRES showed approximate normal distribution centered around zero without apparent skewness (data not shown). This was consistent with the ETABAR P values, all of which were non-significant (P>0.05).

3.5 Model Qualification

Non-parametric bootstrapping was applied to the final model to assess the model stability. Bootstrapping generated medians and CIs for the pharmacokinetic parameters, IIV and IOV estimates (Table 13). The median values from the bootstrapping were very similar to the model estimates for all the pharmacokinetic parameters.

TABLE 13

Summary of rFIXFc population pharmacokinetic final model

| Parameter | Model estimate | Bootstrap median (95% CI[a]) |
|---|---|---|
| $CL = \text{Typical } CL \times \left(\frac{BW}{78}\right)^{0.436}$ | | |
| Typical CL for a 73-kg patient (dL/h) | 2.39 | 2.39 (2.29, 2.49) |
| BW exponent on CL | 0.436 | 0.437 (0.272, 0.584) |
| $V_1 = \text{Typical } V1 \times \left(\frac{BW}{78}\right)^{0.396}$ | | |
| Typical $V_1$ for a 73-kg patient (dL) | 71.4 | 71.2 (58.5, 76.0) |
| BW exponent on $V_1$ | 0.396 | 0.390 (0.169, 0.580) |
| $Q_2$ (dL/h) | 1.67 | 1.66 (1.35, 1.89) |
| $V_2$ (dL) | 87.0 | 87.0 (79.0, 95.5) |
| $Q_3$ (dL/h) | 39.3 | 39.0 (16.6, 141) |
| $V_3$ (dL) | 39.9 | 41.2 (36.6, 52.4) |
| IIV[b] on CL, % | 17.7 | 17.5 (11.8, 22.4) |
| IOV[c] on CL, % | 15.1 | 15.0 (10.7, 19.1) |
| IIV on $V_1$, % | 21.7 | 22.4 (15.5, 32.1) |
| IOV on $V_1$, % | 17.4 | 16.5 (8.7, 22.8) |
| IIV on $Q_2$, % | 35.8 | 35.0 (22.6, 45.8) |
| IIV on $V_2$, % | 46.2 | 45.9 (38.0, 55.3) |
| IIV on $V_3$, % | 37.7 | 37.9 (30.2, 54.3) |
| Correlation between IIV on CL and $V_1$, % | 75.6 | 74.8 |
| Proportional residual error, % | 10.6 | 10.4 (8.64, 12.0) |
| Additive residual error, IU/dL | 0.24 | 0.24 (0.17, 0.31) |

[a]95% CI: Non-parametric 95% CI from bootstrap results with 1,000 datasets
[b]IIV calculated as $\sqrt{\text{variance}} \times 100$
[c]IOV calculated as $\sqrt{\text{variance}} \times 100$
BW body weight, CI confidence interval, CL clearance, IIV inter-individual variability, IOV inter-occasion variability, $Q_2$ inter-compartmental clearance of compartment 2, $Q_3$ inter-compartmental clearance of compartment 3, rFIXFc recombinant factor IX Fc, $V_1$ volume of compartment 1, $V_2$ volume of compartment 2, $V_3$ volume of compartment 3

The graphic results of the VPC of the final model stratified by the dose are presented in FIG. 8. The median and 80% interval ($10^{th}$ to $90^{th}$ percentile) time-activity observed and predicted profiles nearly overlapped, indicating that the final model was able to reproduce both the central tendency and variability of the observed FIX activity time profiles.

The predictive capability of the final model was further evaluated using a validation dataset, which contains the trough/peak FIX activity records that were not included in the modeling dataset. The final model was used to derive the individual predictions for the trough and peak observations. Individual predictions showed good correlation ($R^2$=0.9857, P<0.001) with the observations (FIG. 9). The mean relative prediction error was low at −3.23%, indicating that the final model was qualified to predict rFIXFc pharmacokinetics in the hemophilia B patient population.

3.6 Full Dataset Model

Further, a population pharmacokinetic model of rFIXFc was also built based on the full dataset, including both pharmacokinetic profile and trough/peak data. The population parameter estimates of the resulting model, as well as IIV and IOV (Table 14 below), were comparable with those of the final model derived from the modeling dataset (Table 13 above). The goodness-of-fit plots indicated that the model also described the data adequately (FIG. 20). A slightly greater over-prediction of FIX activity in the lower range (<10 IU/dL) was observed for the VPC of the full dataset model. (FIGS. 8C and 8D).

TABLE 14

Summary of rFIXFc population pharmacokinetic model derived from the full dataset

| Parameter | Population estimate (95% CI)[a] |
|---|---|
| $CL = \text{Typical } CL \times \left(\frac{BW}{73}\right)^{0.432}$ | |
| Typical CL for a 73-kg patient (dL/h) | 2.21 (2.10, 2.32) |
| BW exponent on CL | 0.432 (0.251, 0.613) |
| $V_1 = \text{Typical } V_1 \times \left(\frac{BW}{73}\right)^{0.517}$ | |
| Typical $V_1$ for a 73-kg patient (dL) | 70.6 (66.3, 74.9) |
| BW exponent on $V_1$ | 0.517 (0.282, 0.752) |
| $Q_2$ (dL/h) | 1.63 (1.39, 1.87) |
| $V_2$ (dL) | 99.1 (84.6, 114) |
| $Q_3$ (dL/h) | 45.6 (35.6, 55.6) |
| $V_3$ (dL) | 40.7 (38.3, 43.1) |
| IIV[b] on CL, % | 19.7 (16.6, 22.8) |
| IOV[c] on CL, % | 17.8 (17.0, 18.7) |
| IIV on $V_1$, % | 21.7 (17.9, 25.6) |
| IOV on $V_1$, % | 13.8 (12.3, 15.3) |
| IIV on $Q_2$, % | 48.1 (38.5, 57.6) |
| IIV on $V_2$, % | 51.0 (40.6, 61.3) |
| Correlation between IIV on CL and $V_1$, % | 60.7 |
| Proportional residual error, % | 14.8 (9.56, 20.1) |
| Additive residual error, IU/dL | 0.279 (0.112, 0.445) |

[a]95% CI: The lower and upper limits for 95% CI were calculated asymptotically using the standard errors estimated by the covariance step in NONMEM
[b]IIV calculated as $\sqrt{\text{variance}} \times 100$
[c]IOV calculated as $\sqrt{\text{variance}} \times 100$
BW body weight, CI confidence interval, CL clearance, IIV inter-individual variability, IOV inter-occasion variability, rFIXFc recombinant factor IX Fc, RSE relative standard error, $Q_2$ inter-compartmental clearance of compartment 2, $Q_3$ inter-compartmental clearance of compartment 3, $V_1$ volume of compartment 1, $V_2$ volume of compartment 2, $V_3$ volume of compartment 3.

4 Discussion

This is the first systematic population pharmacokinetic modeling of rFIXFc in patients with hemophilia B. A three-compartment model described the pharmacokinetics of rFIXFc well. For a typical 73-kg patient, $V_1$ for rFIXFc at 71.4 dL is larger than the plasma volume, which is around 30 dL for a typical adult, indicating that rFIXFc is not limited in the plasma for the initial distribution phase after intravenous administration, similar to that of FIX which is known to bind to collagen IV in the subendothelium. The IIV for CL and $V_1$ were low to moderate at 17.7% and 21.7%, respectively, which are consistent with those reported for plasma-derived FIX (23% for CL and 19% for V1). Residual errors were small with a proportional error of 10.6% and additive error of 0.24 IU/dL. The proportional residual error is similar to the inter-assay variability of the one-stage aPTT clotting assay. The small IIV and residual errors indicate that the model described the data adequately and rFIXFc pharmacokinetics do not vary substantially among patients. The estimated IOVs for CL and $V_1$ were 15.1% and 17.4%, respectively, similar to those reported for plasma-derived FIX (15% for CL and 12% for $V_1$). The small and randomly distributed IOV on CL and $V_1$ indicate that rFIXFc pharmacokinetics is relatively stable at different occasions.

The approach of using the model to estimate baseline and differentiate baseline from pre-dose residual activity for each individual was investigated. However, population modeling cannot reliably separate baseline from residual activity because not every FIX activity profile returned to baseline at the last sampling time point (i.e., the baseline [endogenous] and exogenous signals were confounded). We also investigated setting baseline activity at 0, 0.5, or an individualized baseline. The individualized baseline resulted in relatively conservative pharmacokinetic estimates and more accurate prediction of the trough levels in individual subjects. Therefore, an individualized baseline was chosen to handle the activity data in the population pharmacokinetic modeling, which was also utilized in the conventional pharmacokinetic analysis.

BW on CL and $V_1$ was the only covariate that showed a statistically significant impact on rFIXFc pharmacokinetics. It was suggested that the exponent of a physiological or pharmacokinetic parameter shall not revolve around a fixed number. Hence, the exponents of BW on CL and $V_1$ were estimated during the modeling instead of fixed at presumed values, e.g., 0.75 for CL and 1 for $V_1$. The estimated BW exponents for CL and $V_1$ in the final model were markedly lower at 0.436 and 0.396, respectively. Furthermore, inclusion of BW as a covariate decreased IIV for CL by only 3.4% and for $V_1$ by only 2.5%, suggesting that a considerable portion of the variability was not explained by BW.

The limited impact of BW was not unique to rFIXFc pharmacokinetics, which was also observed for BENEFIX® in the phase 3 study (data not shown). The weak correlation between BW and pharmacokinetics in our studies differs from a previous report, which showed that BW, with an exponent of 0.7 on CL, accounted for a significant portion of the variability in BENEFIX® pharmacokinetics in a two-compartment population pharmacokinetic model. The discrepancy probably can be explained by the different populations studied, i.e., the adult patients (>19 years) in our study versus pooled data from 111 children (≤15 years), including 53 infants (<2 years) and 80 adults (>15 years). This previous report represents a wider range for age and BW than in our study. See Bjorkman et al., Haemophilia. 2013; 19(5): 753-7. A recently published paper reported that BeneFIX pharmacokinetics in 56 patients aged 4-56 years and weighing 18-133 kg, described also by a three-compartment model, had allometric exponent of CL terms of 0.66 and volume terms of 0.64. See Id. The slightly reduced allometric exponent of CL compared with the previous report might also be explained by the difference of age and BW range studied. See Udata et al., Blood. 2008; 112(11): 443-4.

Data splitting is a useful internal model validation approach in population pharmacokinetic modeling. See Sherwin et al., Clin. Pharmacokinet. 2012; 51(9); 573-90. Because in the clinic intensive pharmacokinetic profile data are used to predict subsequent trough/peak sparse data, the data were split into a modeling dataset including the intensive pharmacokinetic profile data from all subjects at week 1 and week 26 and a validation dataset including the sparse peak and trough data throughout the phase 3 study. To verify that our modeling strategy was robust, i.e., building the model with the baseline/repeat pharmacokinetic profiles without additional trough/peak FIX activity records, we also built the model using the full dataset consisting of all the FIX activity records from both the modeling and validation datasets. The two models were highly comparable with <10% difference in the pharmacokinetic parameters, IV and IOV estimates (Table 13 and Table 14). The comparability between the two models was also demonstrated by the similar VPC plots for the two models (FIG. 8). FIX activities in the lower range (<10 IU/dL) were slightly more over-predicted by the full dataset model. This difference might be attributed to the imprecise recordings of the peak/trough collection time in the full dataset, which was recorded by patients retrospectively into their electronic diary following the clinic visit. The final model derived from the modeling dataset is slightly more accurate in predicting trough levels, which is essential for maintenance of the therapeutic efficacy. Therefore, the final model derived from the modeling dataset is robust and predictive to be used for simulation of the dosing regimens for rFIXFc.

Finally, the population pharmacokinetic predictions were largely consistent with the results derived from the conventional two-stage pharmacokinetic analysis, which used a two-compartment model, despite a minority (~14%) of the pharmacokinetic profiles could also be described by a three-compartmental model. The ambiguity in the model selection in the conventional pharmacokinetic analysis was at least partially due to the different sampling schemes in different study arms. Such ambiguity was avoided using population pharmacokinetic modeling. The post-hoc estimates from this population pharmacokinetic analysis were very similar to the results from the conventional pharmacokinetic analysis (Table 15).

TABLE 15

Comparison of pharmacokinetic parameters derived from population pharmacokinetic post hoc analysis and conventional pharmacokinetic analysis for phase III study

| Parameter (units) | Population pharmacokinetics post hoc (n = 123) Geometric mean (95% CI) | Conventional pharmacokinetics analysis (n = 22)[a] Geometric mean (95% CI) |
|---|---|---|
| CL (mL/h/kg) | 3.3 (3.2, 3.5) | 3.2 (2.8, 3.6) |
| $V_{ss}$ (mL/kg) | 280.8 (266.4, 296) | 314.8 (277.8, 356.8) |
| Terminal half-life (h) | 81.1 (76.5, 86.1) | 82.1 (71.4, 94.5) |
| MRT (h) | 84.1 (79.8, 88.6) | 98.6 (88.2, 110.3) |

[a]Pharmacokinetic parameters derived from 22 patients with intensive sampling schedule in Arm 1 sequential pharmacokinetic subgroup CI confidence interval, CL clearance, MRT mean residual time, $V_{ss}$ volume of distribution at steady state For example, the geometric mean t % estimated in population pharmacokinetic and conventional pharmacokinetic are 81.1 h and 82.1 h, respectively. The highly comparable pharmacokinetic parameters derived from a two-compartment conventional pharmacokinetic analysis and a three-compartment population pharmacokinetic analysis suggests that the contribution of the third compartment to rFIXFc PK was probably limited, but nevertheless provided better profile definition for the more complex population modeling. The advantage of developing a population pharmacokinetic model for rFIXFc is that the model can be utilized for dosing regimen simulation taking into account IIV and IOV, because FIX activity is considered as a surrogate for efficacy; Further, the population pharmacokinetic model combined with individual sparse pharmacokinetic data can be used to derive an individualized dosing regimen through Bayesian estimation, which can alleviate the requirement for extensive sampling. Since hemophilia is a lifelong disease impacting children as well as adults, the benefit of pharmacokinetics-tailored dosing regimens based on data from limited blood sampling is of great interest to the hemophilia community.

5 Conclusion

This is the first population pharmacokinetic analysis that systematically characterized the pharmacokinetics of the long-acting rFIXFc in patients with hemophilia B. The disposition of rFIXFc was well described by a three-compartment model with low to moderate IIV and IOV. Body weight was found to be the only statistically significant but weak covariate on CL and $V_1$ with limited impact. The qualified population pharmacokinetic model for rFIXFc is appropriate and predictive, providing a valuable tool to evaluate and optimize dosing regimens of rFIXFc for the treatment of patients with hemophilia B.

Example 8. Dosage and Method of Administration/Method of Calculating Initial Estimated Dose rFVIIIFc is long-acting anti-hemophilic factor (recombinant) indicated in adults and children (≥12 years) with hemophilia A (congenital Factor FVIII deficiency) for, e.g., control and prevention of bleeding episodes, routine prophylaxis to prevent or reduce the frequency of bleeding episodes, and perioperative management (surgical prophylaxis).

Dosing of rFVIIIFc can be estimated as described in this example, but can also be determined by standard tests such as FVIII activity assays described elsewhere herein.

1 IU of rFVIIIFc per kg body weight is expected to increase the circulating level of Factor VIII by 2 [IU/dL]. rFVIIIFc has been shown to have a prolonged circulating half-life.

Since patients can vary in their pharmacokinetic (e.g., half-life, in vivo recovery) and clinical responses to rFVIIIFc, the expected in vivo peak increase in Factor VIII level expressed as IU/dL (or % of normal) or the required dose can be estimated using the following formulas:

IU/dL (or % of normal)=[Total Dose (IU)/body weight (kg)]×2 (IU/dL per IU/kg)  (L)

OR

Dose (IU)=body weight (kg)×Desired Factor VIII Rise (IU/dL or % of normal)×0.5 (IU/kg per IU/dL)  (M)

The following table (Table 16) can be used to guide dosing in bleeding episodes:

TABLE 16

Guide to rFVIIIFc Dosing for Treatment of Bleeding

| Severity of Bleed | Desired Factor VIII Level (IU/dL or % of normal) | Dose (IU/kg)/ Frequency of Doses (hrs) |
|---|---|---|
| Minor and Moderate For example: joint, superficial muscle/no neurovascular compromise (except iliopsoas), deep laceration and renal, superficial soft tissue, mucous membranes | 40-60 | 20-30 IU/kg Repeat every 24-48 hours until bleeding is resolved |
| Major For example: iliopsoas and deep muscle with neurovascular injury, or substantial blood loss, retroperitoneum, CNS, throat and neck, gastrointestinal. | 80-100 | 40-50 IU/kg Repeat every 12-24 hours until bleeding is resolved |

Adapted from WFH 2012

Subsequent dosage and duration of treatment depends on the individual clinical response, the severity of the Factor VIII deficiency, and the location and extent of bleeding.

The following table (Table 17) can be used to guide dosing for perioperative management (surgical prophylaxis):

TABLE 17

Guide to rFVIIIFc Dosing for Perioperative Management (Surgical Prophylaxis)

| Type of Surgery | Target Factor VIII Level (IU/dL or % of normal) | Dose (IU/kg)/ Frequency of Doses (hrs) |
|---|---|---|
| Minor Minor operations including uncomplicated dental extraction | 50 to 80 | 25-40 IU/kg A single infusion can be sufficient. Repeat every 24 hours as needed to control bleeding. |
| Major Major operations including intra-abdominal, joint replacement surgery | 80 to 120 | An initial preoperative dose of 40-60 IU/kg followed by a repeat dose of 40-50 IU/kg after 8-24 hours and then every 24 hours to maintain FVIII activity within the target range. rFVIIIFc has a longer half-life than plasma and recombinant FVIII products |

For routine prophylaxis, the recommended regimen is 50 IU/kg every 3-5 days. The dose can be adjusted based on patient response in the range of 25-65 IU/kg.

For weekly prophylaxis, the recommended dose is 65 IU/kg.

rFVIIIFc is contraindicated in patients who have manifested severe hypersensitivity reactions, including anaphylaxis, to the product or its components. Severe hypersensitivity reactions were not observed in clinical trials; however, these have been known to occur with use of other factor VIII replacement factors.

The clinical response to rFVIIIFc can vary. If bleeding is not controlled with the recommended dose, the plasma level of Factor VIII can be determined, and a sufficient dose of rFVIIIFc can be administered to achieve a satisfactory clinical response. If the patient's plasma Factor VIII level fails to increase as expected or if bleeding is not controlled after rFVIIIFc administration, the presence of an inhibitor (neutralizing antibodies) should be suspected, and appropriate testing performed. Patients using rFVIIIFc can be monitored for the development of Factor VIII inhibitors by appropriate clinical observations and laboratory tests known to those of ordinary skill in the art.

Patient's plasma can be monitored for Factor VIII activity levels, e.g., the one-stage clotting assay to confirm adequate Factor VIII levels have been achieved and maintained, when clinically indicated. Patient's plasma can further be monitored for the development of Factor VIII inhibitors.

Example 9. Population Pharmacokinetic Analysis of Long-Acting Recombinant Factor VIII-Fc Fusion Protein (rFVIIIFc) in Patients with Severe Haemophilia A Introduction:

In a recently completed Phase 3 clinical study (A-LONG), rFVIIIFc, a recombinant fusion protein composed of a single molecule of B domain deleted human coagulation factor VIII (FVIII) attached to the Fc domain of human immunoglobulin G1 (IgG1), was well-tolerated and effective in the treatment of bleeding, routine prophylaxis, and perioperative management. The duration of activity of rFVIIIFc was prolonged, compared to another recombinant FVIII product (ADVATE).

Objectives:

To characterize the activity-time profiles of rFVIIIFc in hemophilia A patients as measured by the one-stage clotting assay by population PK analysis; to identify intrinsic and extrinsic covariates that can affect the variability of rFVIIIFc PK; and to simulate the rFVIIIFc dosing scenarios of interest using the model developed.

Methods:

The modeling dataset included activity-time profiles in a total of 180 subjects (16 from a Phase ½a study and 164 from A-LONG) taken over up to 52 weeks of treatment.

The Phase ½a study was an open-label, multicenter, dose-escalation study that included 2 dose levels. A total of 16 subjects received either 25 IU/kg (n=6) or 65 IU/kg (n=10) of ADVATE® followed 3 or 4 days later, respectively, by an equal dose of rFVIIIFc with an extensive PK sampling scheme following each dose administration.

A-LONG was an open-label, multinational, multicenter study that included 3 treatment arms.

Subjects were 12 to 65 years old and weighing between 41 kg and 132 kg. The analysis was done with NONMEM 7 software, and included model building, covariate search, and model qualification steps. The data were analyzed using mixed-effects modeling with maximal likelihood parameter estimation methods. Covariate-parameter relationships were explored for parameters with inter-individual variability (IIV) terms, and model diagnostics were performed to guide model selection. rFVIIIFc dosing regimens of therapeutic interest were simulated using the current model.

Results:

A 2-compartmental model was found to describe adequately the activity of rFVIIIFc, described by the formulas (M), (N), and (O) below:

$$CL = TVCL \cdot \left[\frac{VWF}{118}\right]^{\Theta_{10}}$$

$$V_1 = TVV_1 \cdot \left[\frac{WT}{73}\right]^{\Theta_8} \cdot \left[\frac{HCT}{45}\right]^{\Theta_9}$$

$$\varepsilon_{add} = STUD \cdot \Theta_5 + (1 - STUD) \cdot \Theta_6$$

$$STUD = \begin{cases} 1 & \text{for Phase1} \\ 0 & \text{for Phase3} \end{cases}$$

The tight confidence intervals (Cis) indicate that the parameters are estimated with very good precision (Table 18).

TABLE 18 rFVIIIFc Population PK parameters and bootstrap-derived 95% Confidence Intervals

| Parameter | Symbol | Population Estimate | Nonparametric 95% CI |
|---|---|---|---|
| Clearance, CL, [dL/h] | Θ1 | 1.65 | 1.57-1.74 |
| Exponent on VWF | Θ10 | −0.343 | −0.439-−0.247 |
| Central Volume, V1, [dL] | Θ2 | 37.5 | 36.5-38.4 |
| Allometric exponent on V1 | Θ8 | 0.382 | 0.271-0.499 |
| Exponent on HCT | Θ9 | −0.419 | −0.656-−0.208 |
| Intercompartmental Clearance, Q, [dL/h] | Θ3 | 0.0746 | 0.0594-0.184 |
| Peripheral Volume, V2, [dL] | Θ4 | 6.92 | 3.80-13.8 |
| IIV on CL, [%] | η1 | 24.3 | 20.5-27.7 |
| IIV on V1, [%] | η2 | 13.4 | 11.0-15.5 |
| Correlation between IIV on CL and V1 | η12 | 0.548 | Not calculated |
| IOV on CL, [%] | η3 | 20.6 | 16.7-25.1 |
| IOV on V1, [%] | η4 | 12.0 | 7.46-16.3 |
| Correlation between IOV on CL and V1 | η34 | 0.639 | Not calculated |
| Additive error, Phase 1/2A study, [IU/dL] | Θ5 | 0.421 | 0.172-0.612 |
| Additive error, Phase 3 study, [IU/dL] | Θ6 | 0.208 | 0.126-0.275 |
| Proportional error, [%] | Θ7 | 13.6 | 12.0-15.3 |

The IIV and the residual errors are very low. The goodness of fit diagnostics (FIG. 24) indicate that the model adequately describes the data.

The population estimate for the clearance (CL) is 1.65 dL/h, and Vss is 44.4 dL. The inter-individual variability (IIV) of CL is moderate (CV=24.3%) and of central volume of distribution (V1) is low (CV=13.4%). The inter-occasional variability (IOV) of both CL and V1 is low (20.6 and 12.0% respectively). The additive residual error is very low (0.208 IU/dL), and so is the proportional residual error (13.6%), approximating the precision of the one-stage clotting assay for FVIII activity. Von Willebrand Factor (VWF) level was identified as the major covariate for CL. Consistent with mechanistic knowledge (Lillicrap 2008), higher levels of VWF yielded lower clearance values, reflecting the protective role that VWF has on FVIII activity. This is reflected in the negative exponent on VWF. Body Weight (BW) and Hematocrit (HCT) were identified as weak covariates on V1. This is the first population PK analysis that systematically describes and characterizes the prolonged activity profile of the long-acting rFVIIIFc.

Conclusion:

The population PK model of rFVIII activity adequately describes the observed activity-time profiles after long term administration. The clearance of rFVIIIFc activity is lower than the clearance reported for ADVATE®, resulting in longer duration of activity. The low IIV underlines the consistency and homogeneity of the activity profiles. The low IOV indicates that rFVIIIFc maintains stable and predictable activity with long term administration over time. The set of covariates identified is physiologically relevant. Therefore, the population model developed can be used to simulate various dosing scenarios in support of dosing regimen selection and other decision making related to rFVIIIFc therapy.

The model was used to predict the activity time profile following a single dose of rFVIIIFc in patients with severe hemophilia A. In addition the model was used to predict trough activity for three different prophylaxis regimens.

Table 19 presents the model-predicted steady state peaks and troughs of the rFVIIIFc activity-time profiles with 50 IU/kg dose administered every 3, 4, or 5 days. The simulated steady-state activity profiles are presented in FIG. 25.

TABLE 19

Predicted Steady-State Peaks and Troughs of rFVIIIFc Activity-Time Profiles with 50 IU/kg Dose Administered Every 3, 4, or 5 Days

| Percentile of | Dosing Frequency | | | | | |
|---|---|---|---|---|---|---|
| | Every 3 Days | | Every 4 Days | | Every 5 Days | |
| Subjects | Peak | Trough | Peak | Trough | Peak | Trough |
| Median ($5^{th}$, $95^{th}$ prediction interval) | 102 (70.4, 149) | 5.27 (0.774, 20.4) | 100 (69.9, 141) | 2.32 (<0.5a, 11.4) | 98.5 (69.1, 139) | 1.10 (<0.5, 6.17) |

A dosing regimen of 50 IU/kg every 5 days is predicted to yield troughs above 1 IU/dL in 53.4% of individuals and a dosing regimen of 65 IU/kg administered weekly is predicted to yield troughs above 1 IU/dL in 26.6% of the individuals treated.

The population PK models for rFVIIIFc and ADVATE® adequately described the combined activity data from the two clinical studies. The major covariate for rFVIIIFc activity identified by the population PK analysis was VWF level on CL. Weight and hematocrit were identified as minor covariates on the central volume of distribution. The results from the simulations support the dosing recommendations derived from the Phase 3 study results and can be used to aid dosing regimen selection and adjustment.

Simulation of Regimens for Perioperative Management

According to the WFH Guidelines, minor surgical procedures may require the attainment of target factor levels of 50 to 80 IU/dL, which can be achieved with a single rFVIIIFc infusion of 25 to 40 IU/kg. If a finer adjustment of the target is desirable, the required rFVIIIFc dose can be determined based on the predicted activity profiles in Table 20, below:

TABLE 20

Predicted rFVIIIFc Activity-Time Profiles (in IU/dL) After a Single Administration

| Dose (IU/kg) | Time (h) EOI | 12 | 24 | 36 | 48 | 72 | 96 |
|---|---|---|---|---|---|---|---|
| | Median ($5^{th}$, $95^{th}$ Prediction Interval) | | | | | | |
| 20 | 38.7 (27.3, 54.5) | 22.7 (13.5, 35.0) | 13.4 (5.79, 23.8) | 7.92 (2.44, 16.7) | 4.72 (1.06, 12.0) | 1.79 (<0.5*-6.52) | 0.763 (<0.5*-3.63) |
| 25 | 48.4 (34.2, 68.1) | 28.3 (16.9, 43,7) | 16.8 (7.24, 29.8) | 9.90 (3.05, 20.8) | 5.90 (1.32, 15.0) | 2.24 (<0.5*-8.15) | 0.953 (<0.5*-4.54) |
| 30 | 58.1 (41.0, 81.7) | 34.0 (20.2, 52.5) | 20.2 (8.69, 35.8) | 11.9 (3.66, 25.0) | 7.07 (1.59, 18.0) | 2.69 (<0.5*-9.78) | 1.14 (<0.5*-5.44) |
| 40 | 77.5 (54.7, 109) | 45.3 (27.0, 70.0) | 26.9 (11.6, 47.7) | 15.8 (4.88, 33.3) | 9.43 (2.11, 24.0) | 3.58 (<0.5*-13.0) | 1.53 (<0.5*-7.26) |
| 50 | 96.8 (68.3, 136) | 56.6 (33.7, 87.5) | 33.6 (14.5, 59.6) | 19.8 (6.10, 41.7) | 11.8 (2.64, 30.0) | 4.48 (0.615-16.3) | 1.91 (<0.5*-9.07) |
| 65 | 126 (88.9, 177) | 73.6 (43.8, 114) | 43.7 (18.8, 77.5) | 25.7 (7.94, 54.2) | 15.3 (3.44, 38.9) | 5.82 (0.800-21.2) | 2.48 (<0.5*-11.8) |

EOI = end of infusion.

*BLQ values were set at <0.5.

For major surgery, WFH recommends a stricter control of Factor VIII dosing, with high activity levels attained in the pre-operative period and during surgery, followed by step-wise decrease of the activity levels during the post-operative period, e.g., within 1 to 3 days, 4 to 6 days, and as long as needed. The population PK model developed can be used as a tool to design such complicated activity profiles.

An evaluation of the population PK model, similar to external model validation, indicated that the population PK model is in good concordance with the activity observed during the surgical period. The correlation coefficient between the observed and individual predicted activity during surgery is high (R=0.742). The minimal discrepancies between observed and model-predicted activities during surgery are not more than 10% and point to a modest over-prediction associated with peak activity. This may be due to minimal loss of rFVIIIFc during surgery, associated with blood loss. For the surgeries performed in this study, the average blood loss was less than 200 mL.

Table 21 presents the dosing times, doses, and predicted FVIII activity for a hypothetical perioperative dosing regimen, to achieve levels recommended by WFH Guidelines. The doses, times, and administration as well as the predicted activities are listed for each subsequent dose. All doses after the second one are administered at 24-hour intervals. The resulting activity time profile is presented in FIG. 26.

TABLE 21

Dosing Times, Doses and Predicted FVIII Activity for a Hypothetical Perioperative Dosing Regimen for rFVIIIFc

| Dosing Day | Dosing Time (h) | Dose (IU/kg) | Trough (IU/dL) Median ($5^{th}$, $95^{th}$ Prediction Interval) |
|---|---|---|---|
| 0 | 0 | 60 | |
| 0 | 12 | 50 | 67.3 (39.6, 105) |
| 1 | 24 | 50 | 95.4 (50.7, 159) |
| 2 | 48 | 50 | 67.0 (23.6, 140) |
| 3 | 72 | 40 | 57.9 (19.0, 132) |
| 4 | 96 | 40 | 48.1 (15.4, 119) |
| 5 | 120 | 40 | 45.0 (14.8, 112) |
| 6 | 144 | 40 | 44.0 (14.7, 109) |
| 7 | 168 | 30 | 43.6 (14.7, 108) |
| 8 | 192 | 30 | 36.9 (11.9, 95.6) |
| 9 | 216 | 30 | 34.5 (11.3, 88.9) |
| 10 | 240 | 30 | 33.6 (11.2, 85.6) |
| 11 | 264 | 30 | 33.2 (11.2, 83.6) |
| 12 | 288 | 30 | 33.0 (11.2, 82.4) |
| 13 | 312 | 30 | 32.9 (11.1, 81.7) |

Table 21 presents the dosing times, doses and predicted FVIII activity for a simpler hypothetical perioperative dosing regimen. All doses after the fourth dose are administered at 48 h intervals. FIG. 27 shows the predicted FVIII activity for the hypothetical perioperative dosing regimen in Table 22.

TABLE 22

Dosing times, Doses and Predicted FVIII Activity for a Sample Perioperative Dosing Regimen II

| Dosing Day | Dosing Time (hr) | Dose (IU/kg) | Trough (IU/dL) Median [$5^{th}$, $95^{th}$ PI] |
|---|---|---|---|
| 0 | 0 | 60 | |
| 0 | 12 | 50 | 68.2 [39.8, 105] |
| 1 | 24 | 50 | 97.7 [50.8, 160] |
| 2 | 48 | 50 | 68.6 [23.7, 144] |
| 4 | 96 | 50 | 22.0 [3.96, 75.1] |
| 6 | 144 | 50 | 16.4 [3.32, 57.6] |

TABLE 22-continued

Dosing times, Doses and Predicted FVIII Activity for a Sample Perioperative Dosing Regimen II

| Dosing Day | Dosing Time (hr) | Dose (IU/kg) | Trough (IU/dL) Median [$5^{th}$, $95^{th}$ PI] |
|---|---|---|---|
| 8 | 192 | 50 | 15.6 [3.25, 52.7] |
| 10 | 240 | 50 | 15.4 [3.23, 51.0] |
| 12 | 288 | 50 | 15.3 [3.22, 50.4] |

The model was used to predict FVIII activity in patients during the post-operative period based on subjects' presurgery baseline PK. In the Phase 3 study, there were 13 subjects who underwent major and minor surgeries and also had their rFVIIIFc activity measured during the perioperative period. These subjects had variable dosing regimens and time intervals in perioperative management. To check whether the observed FVIII activity during this period (coded as OCC=0 in the database) are in agreement with the population PK model, an evaluation, similar to external model validation, was performed.

Predicted FVIII activity was largely consistent with observed FVIII activity. FIG. 28 is a representative plot comparing the predicted and observed FVIII activities within the first 21 days after the first rFVIIIFc surgical dose (n=13; 9 major surgeries, 4 minor surgeries). There was good correlation between the observed FVIII activity data and that predicted by the PK model (relative prediction error 95% CI). The resulting Goodness of Fit (observed DV, versus individual predicted, IPRED) diagnostics, shown in FIG. 28, indicates that the population PK model is in concordance with the activity observed during the surgical period. The correlation coefficient between the observed and individual predicted activity is high (R=0.742).

The nonparametric fit of the data, represented by the lower line in FIG. 28, diverges only slightly from the identity line (upper line). This divergence is not more than 10% and points to a modest over-prediction in the region of high activity. This may be due to minimal loss of rFVIIIFc during surgery, associated with blood loss. For the surgeries performed in this study, the average blood loss was less than 200 mL. These results indicate that the surgical procedures that have been studied in the Phase 3 study had no significant impact on the PK properties of rFVIIIFc.

In conclusion, it is feasible to develop a general dosing guidance to achieve target FVIII levels recommended for perioperative management in patients with haemophilia A using a population PK model.

Example 10. Use of the Population Pharmacokinetic Model of rFVIIIFc to Simulate or Estimate Individualized and Median Patient Treatment As is discussed in Example 9 or 11 or 16, the rFVIIIFc population model that has now been developed can be used to simulate (estimate) various dosing scenarios in support of dosing regimen selection and other decision making related to rFVIIIFc therapy.

For example, individualized patient treatment, e.g., pharmacokinetics (PK) and dosing regimens, can be selected using Bayesian estimation (or similar machine learning algorithm) based on the population pharmacokinetic (popPK) model described in Example 9 or 11 or 16, (e.g., Table 18, 24, 25, or 33). In this way, one can determine alternative prophylactic dosing regimens and optimized dosing regimens for peri-operative management that have not previously been studied in the A-LONG trials. Alternatively, the selected dosing regimen is based on population PK (median PK) rather than making an individualized selection.

In some embodiments, the rFVIIIFc popPK model of Example 9 or 11 or 16 (e.g., Table 18, 24, 25, or 33) is used without the Bayesian or similar machine learning algorithm.

In some embodiments of this aspect of the invention, the method is carried out on a computer-based system, e.g., a server, a desk top computer, a lap top computer, a tablet, a hand held device, or a smart phone. In some embodiments, the computer-based system is a computer application. The computer-based system includes a storage medium for the rFVIIIFc popPK model discussed in Example 9 or 11 or 16, e.g., the parameters of Table 18, 24, 25, or 33. In some embodiments, the storage medium can also contain a Bayesian estimating program, e.g., NONMEM or Phoenix NLME. E.g., Example 9 or 11 or 16; Kiang et al., *Clin. Pharmacokinet* 51:515-525 (2012).

In some embodiments, the system comprises two or more computer-based systems. In some embodiments, the user can input information into a first computer-based system that communicates with a second computer-based system, and the second computer-based system carries out calculations and communicates output information to the first computer-based system. This output information can include recommendations about individualized or non-individualized dosing regimens.

In some embodiments, the user inputs information into the system and the system calculates and outputs one or more PK or dosing regimens. In some embodiments, the system uses the received information to calculate and output individualized or median PK information. In some embodiments, the system calculates individualized dosing or interval information.

Information that can be input by a user and received by the system includes patient information and desired treatment outcome information. Based on the type and value of the received information, the computer-based system calculates output information based on the rFVIIIFc popPK model and optional machine learning algorithm on the storage medium.

Patient information includes, e.g., age, Von Willebrand Factor (VWF) level, hematocrit (HCT), body weight (BW), diagnostic (baseline) FVIII level, PK determinations, time of PK sampling, dosing history if PK samples were taken from multiple doses, actual dose, FVIII activity level, etc.

Desired treatment outcome information includes desired PK or desired regimen outcome, e.g., desired rise in plasma FVIII activity level following dose, desired dosing interval, and desired dose.

Based on the information that was input and received by the system, the system can output various information, e.g., PK curve, PK parameter such as incremental recovery (Cmax/dose), mean residence time, terminal t½, clearance, Vss, AUC/dose, doses and associated troughs, and intervals and associated troughs.

For example, for assessing individualized patient PK, the system can recommend that the user input 2-3 optimized PK sampling time points. In this case, system output can include PK curve and one or more selected PK parameters, e.g., incremental recovery (Cmax/Dose), mean residence time, terminal t½, clearance, Vss, AUC, and time to 1 or X %, etc. E.g., FIG. 13.

As additional examples, to select an individualized dosing regimen using the output individual PK parameters discussed in the preceding paragraph, (i) the dose selected for acute treatment can be based on user input of the desired rise in plasma FVIII activity level following the dose, (ii) the dose selected for prophylaxis can be based on user input of the desired dosing interval, or (iii) the selected interval for prophylaxis can be based on user input for the desired dose. In the first case, the system can output the dose (IU) based in the patient's incremental recovery. E.g., FIG. 14. In the second case, system output can be a table of doses and associated troughs, e.g., x IU/kg, 1% trough, y IU/kg, 2% trough, etc. E.g., FIG. 15, top. In the third case, system output can be a table of intervals and associated troughs, e.g., x days, 1% trough, y IU/kg, 2% trough, etc., E.g., FIG. 15, bottom.

The user may wish to use the system without inputting any individualized PK data. In this case, the dosing output would be based on the population median rather than being individualized for the particular patient. E.g., FIG. 29. In this way, the user inputs, e.g., body weight and age, and (i) the desired rise in plasma FVIII activity level following the dose, (ii) the desired dose interval for prophylaxis, or (iii) the desired dose for prophylaxis. In the first case, the system can output the dose. In the second case, the system can output the dose and associated trough. E.g., Table 20 In the third case, the system can output the interval and associated trough. E.g., Table 19.

Age can be input to determine if the system is suitable for the patient because the current version of the popPK model was built for patients 12 years and older.

In some embodiments, the system is compliant with patient privacy laws. In some embodiments, the system is encrypted, e.g., with SSL. In some embodiments, input patient information is made anonymous.

In some embodiments, the system includes a user help function.

The user can be, e.g., a physician, a nurse, or another healthcare practitioner.

In some embodiments, the method further includes selecting a dosing regimen based on the system's output information and administering rFVIIIFc to the patient according to the selected regimen.

Example 11. Population Pharmacokinetics of Recombinant Factor VIII:Fc

Abstract

Population pharmacokinetics (PK) of FVIII activity-time profiles following recombinant factor VIII Fc fusion protein (rFVIIIFc) and recombinant factor VIII (rFVIII) dosing were evaluated in treated patients with severe hemophilia A (from two clinical trials). Potential covariates were determined. A 2-compartment model adequately described the PK of both compounds. Von Willebrand Factor (vWF) concentration was the major covariate for rFVIIIFc clearance, reflecting its protective role in FVIII activity clearance. The effect of body weight and hematocrit on the central volume of distribution (V1) of rFVIIIFc was minor. The population PK for rFVIII demonstrated similar behavior to that in the published literature. The results of these analyses confirmed that rFVIIIFc clearance (1.65 dL/h) is much lower than that of rFVIII (2.53 dL/h), while $V_1$ at steady state was similar. The strong positive correlations between the PK parameters of rFVIIIFc and rFVIII suggest that individuals who have high time-related PK characteristics with rFVIII are likely to have comparable characteristics with rFVIIIFc. Steady-state activity-time profiles for selected rFVIIIFc dosing regimens were simulated accounting for model prediction uncertainty. These population PK analyses and simulations provide a comprehensive characterization of the PK of rFVIIIFc and rFVIII and may be useful for designing dosing regimens.

Introduction

Hemophilia A is an X-chromosome-linked coagulation disorder that primarily affects males, and occurs in approximately 1-2 per 10,000 live births. It is caused by mutations and/or deletions in the F8 gene, resulting in a deficiency of factor VIII (FVIII) activity. Severe hemophilia A is defined as a coagulation activity of FVIII in plasma (FVIII:C) level<1% (<1 IU/dL), and individuals with this severe form of the disease experience recurrent spontaneous bleeding, primarily into the muscles and joints, leading to joint damage and severe disability. This is associated with a negative impact on psychosocial well-being and quality of life.

Modern FVIII replacement therapy for hemophilia A relies on the infusion of specific concentrates to substitute the deficient or inactive endogenous FVIII. Such infusions are performed either episodically (e.g., for on-demand treatment of bleeding or before/during and after surgery) or prophylactically. Target factor activity levels may vary depending on the dosing paradigm; for acute bleeding such as during major surgeries, this may be as high as 80 to 100 IU/dL, while the goal for prophylaxis is to maintain trough activity levels >1 IU/dL.

Recombinant factor VIII Fc fusion protein (rFVIIIFc) is a novel protein composed of a single B-domain-deleted human coagulation FVIII molecule attached to the Fc domain of human immunoglobulin G1 (IgG1), designed to offer a longer circulating half-life ($t_{1/2}$) than currently available FVIII products. Clinical studies have confirmed this increase in $t_{1/2}$ relative to recombinant FVIII (rFVIII) and demonstrated the safety and efficacy of rFVIIIFc for the prevention and treatment of bleeding episodes in patients with hemophilia A.

The quantitative characterization of FVIII activity-time profiles (referred to as pharmacokinetics [PK]) provides critical information for determining dose levels and dosing frequencies to achieve target therapeutic levels. Traditionally, the PK of most marketed agents have been characterized by non-compartmental or compartmental 2-stage methods. More recently, a number of population PK models and model implementations for several FVIII products have been published.

The objective of this example is to present the development of a population PK model based on rFVIIIFc activity data in individuals with severe hemophilia. The PK parameters of the model were estimated and significant determinants (covariates) of variability in rFVIIIFc PK in subjects with hemophilia A were identified. The population PK model was then used to simulate rFVIIIFc dosing regimens of interest. A population PK model for antihemophilic factor ([recombinant], plasma albumin-free method), a rFVIII product used as comparator in the clinical studies performed, was also developed.

Methods: Clinical Studies

The clinical data that served as a basis for the population PK model development originated from two studies—a phase ½a (n=16) and a phase 3 study (n=164). These protocols were approved by local institutional review boards/ethics committees, and the studies were conducted in accordance with the International Conference on Harmonization guidelines for Good Clinical Practice.

The Phase ½a study was an open-label, crossover, dose-escalation, multicenter study to determine the safety, tolerability, and PK of a single intravenous (IV) injection of rFVIIIFc in previously treated patients with severe hemophilia A. (Powell J S, Josephson N. c, Quon D, et al, *Safety and prolonged activity of recombinant factor VIII Fc fusion protein in hemophilia A patients*. Blood, 2012, 119 (13), 3031-7). The study included two cohorts dosed at the 25 IU/kg (Cohort A) and 65 IU/kg (Cohort B) level. After screening and a minimum of 4 days initial washout period, subjects from both cohorts received a single 25 IU/kg (Cohort A) or 65 IU/kg (Cohort B) dose of rFVIII followed by a 3-day (Cohort A) or 4-day (Cohort B) blood sampling regimen for PK assessment (see upper panel of Table 23 for the Phase ½a sampling schedule). These patients then received a 25 IU/kg (Cohort A) or 65 IU/kg (Cohort B) single dose of rFVIIIFc followed by a 7-day (Cohort A) or 10-day (Cohort B) blood sampling regimen for PK assessment.

TABLE 23

Intensive sampling schedules in the Phase 1/2a and Phase 3 studies

| Study | Arm/Cohort | Agent | Dose | Sampling Schedule |
|---|---|---|---|---|
| Phase 1/2a | Cohort A | rFVIII | 25 IU/kg | 0, 0.167, 0.5, 1, 3, 6, 9, 24, 48, 72 h |
| | | rFVIIIFc | 25 IU/kg | 0, 0.167, 0.5, 1, 3, 6, 9, 24, 48, 72, 96, 120, 168 h |
| | Cohort B | rFVIII | 65 IU/kg | 0, 0.167, 0.5, 1, 3, 6, 9, 24, 48, 72, 96 h |
| | | rFVIIIFc | 65 IU/kg | 0, 0.167, 0.5, 1, 3, 6, 9, 24, 48, 72, 96, 120, 168, 192, 216, 240 h |
| Phase 3 | Arm 1 PK | rFVIII | 50 IU/kg | 0, 0.5, 1, 6, 24, 48, 72 h |
| | Arm 1 PK | rFVIIIFc | 50 IU/kg | 0, 0.5, 1, 6, 24, 72, 96 and 120 h |
| | Arm 1 Non-PK | rFVIIIFc | 50 IU/kg | 0, 0.5, 3, 72, 96 h |
| | Arm 2 | rFVIIIFc | 65 IU/kg | 0, 0.5, 3, 72, 96 h |
| | Arm 3 | rFVIIIFc | 50 IU/kg | 0, 0.5, 3, 72, 96 h |

The Phase 3 study was an open-label, multinational, multicenter study to evaluate the safety, PK, and efficacy of rFVIIIFc administered as an IV injection to subjects with severe hemophilia A, at least 12 years of age (Mahlangu J. et al. *Phase* 3 *study of recombinant factor VIII Fc fusion protein in haemophilia A*, Lancet, submitted 2013). At study start, all subjects underwent a washout of FVIII products for 72-96 hours followed by an initial PK sampling. The study comprises 3 treatment arms:

In Arm 1 (n=118) patients received individualized prophylaxis regimen, consisting of two subgroups—a Sequential PK Subgroup and a Non-sequential PK Subgroup. Subjects assigned to the Arm 1 Sequential PK subgroup received a single dose of rFVIII 50 IU/kg on Day 0 followed by semi-sparse blood sampling for PK assessment over a 72-hour period (7 timepoints) according to the schedules shown in Table 23 (lower panel). Following a washout period, these subjects then received a single dose of rFVIIIFc 50 IU/kg followed by a semi-sparse PK sampling at 8 timepoints over a 120-hour period. PK profiling of rFVIIIFc 50 IU/kg was reassessed 12-24 weeks later. Subjects in Arm 1 non-sequential PK subgroup received a single rFVIIIFc dose of 50 IU/kg of rFVIIIFc, on Day 0 followed by a semi-sparse PK blood sampling performed at 5 timepoints. Upon completion of the rFVIIIFc PK assessment, an individualized prophylaxis regimen was established for each individual in Arm 1 (both subgroups) based on their PK, in which the dose (25-65 IU/kg) and dosing interval (3-5 days) were determined to maintain a trough level of 1% to 3% rFVIIIFc activity.

In Arm 2 (n=24) patients received a weekly prophylaxis regimen. Subjects received a single rFVIIIFc dose of 65 IU/kg of rFVIIIFc on Day 0 followed by a semi-sparse PK blood sampling performed at 5 timepoints. After the PK assessment, subjects in Arm 2 were administered a fixed weekly prophylaxis rFVIIIFc dose of 65 IU/kg.

In Arm 3 (N=23) patients received episodic dosing regimen with a single rFVIIIFc dose of 50 IU/kg of rFVIIIFc on Day 0 followed by a semi-sparse PK blood sampling performed at 5 timepoints. During the study, subjects in Arm 3 were treated episodically at rFVIIIFc doses of 10-50 IU/kg depending on the severity of the bleed.

In addition to the PK profiling, peak and trough measurements were carried out periodically, at nominal times spread over the whole course of study participation (e.g., peak/trough collections at week 7, 14, 28, 38, 52, etc.) for subjects in Arms 1 and 2.

Assay Methodology

For the Phase ½a study, the FVIII activity was measured by one-stage clotting (activated partial thromboplastin time [aPTT]) assay with a Siemens BCS-XP analyzer (Siemens AG, Erlangen, Germany) with the use of commercial reagents (Dade Actin FSL; Siemens Healthcare Diagnostics, Inc., Newark, Del., USA) and calibration against a normal reference plasma (CRYOCHECK™; Precision Biologics, Dartmouth, Nova Scotia, Canada) traceable to the World Health Organization (WHO) Fifth International Standard for human plasma. In addition, FVIII activity was also measured by a chromogenic substrate assay with the use of a commercially available kit (Aniara BIOPHEN™ FVIII:C; Aniara, West Chester, Ohio, USA) that complies with European Pharmacopoeia recommendations. This assay was calibrated against normal human reference plasma (ORKE45; Instrumentation Laboratory, Bedford, Mass., USA), which also had a potency assigned against the human plasma standard from the WHO Fifth International Standard. The lower limits of quantification (LLOQ) for the aPTT and chromogenic assays were 0.5 IU/dL and 0.4 IU/dL, respectively. In the phase 3 study, FVIII activity was measured using the one-stage aPTT assay as outlined above.

Data Assembly and Manipulation

Datasets generated from both studies were merged together to form the population PK analysis dataset. An occasion (OCC) variable was added to the rFVIIIFc dataset to enable the inclusion of inter-occasional variability (IOV) in the models. Occasions are defined within each individual, as clusters of observations, separated from previous observations by at least 1 week of dosing. Occasions 1 and 2 are reserved for the Baseline (first) and Repeat (second) intensive PK sampling period. The rest of the occasions are allocated to trough and peak measurements, and as such, represent sparse observation periods.

Some missing covariate values were imputed by substituting with a typical (median) value. Where missing covariate values could not be imputed, these were replaced by negative values and ignored. Where only a fraction of the covariate values for a given individual were missing, they were imputed from the remaining values by a LOCF (Last Observation Carried Forward) technique—this was the case for von Willebrand Factor (VWF) antigen levels, IgG1 levels (IGG1), and hematocrit (HCT).

Baseline Correction and Residual Decay

Activity levels observed before administration of a rFVIII product represent a combination of endogenous activity (baseline) and residual activity from pre-study drug. To account for that, baseline and residual drug corrections were performed on the observed FVIII activity results for both rFVIIIFc and rFVIII. Similar corrections are typical for PK analyses of other FVIII and factor IX products (Björkman S, C. M., Berntop E, *Pharmacokinetics of Factor IX in patients with hemophilia B*. Eur J Clin Pharmacol, 1994. 46: p. 325-332; Carlsson M, B.S., Berntop E, *Multidose pharmacokinetics of factor IX: Implications for dosing in prophylaxis. Hemophilia,* 1998. 4: p. 83-88; Björkman S, S.A., Berntop E, *Pharmacokinetics of recombinant factor IX in relation to age of the patients: Implications for dosing in prophylaxis*. Hemophilia, 2001. 7: p. 133-139; Björkman S, O.M., Spotts G, et al., *Population pharmacokinetics of recombinant factor VIII—the relationships of pharmacokinetics to age and body weight.* Blood, 2012. 119: p. 612-618 ("Björkman 2012 A"); Björkman S, A.V., *Population pharmacokinetics of plasma-derived factor IX in adult patients with hemophilia B: Implications for dosing in prophylaxis*. Eur J Clin Pharmacol, 2012. 68(6): p. 969-77). These corrected activity-time profiles were included in the population PK datasets. It should be noted that only the first (baseline) rFVIII and rFVIIIFc activity-time profiles were corrected for residual decay.

Residual decay was performed using the terminal half-life ($t_{1/2}$) obtained from noncompartmental analysis (NCA) of the raw, observed activity data. For the Arm 1 PK subgroup, rFVIII and Baseline rFVIIIFc PK profiles were decayed using the respective subject's rFVIII $t_{1/2}$. For the Arm 1 non PK subgroup, Arm 2, and Arm 3, rFVIIIFc PK profiles were decayed using the average rFVIII $t_{1/2}$ obtained from the Arm 1 PK subgroup.

The pre-dose FVIII activity levels are a combination of endogenous activity (baseline) and the residual activity from previous pre-study drug administration(s). Therefore, the baseline and residual drug corrections were performed on the observed FVIII activity results prior to data analysis.

The baseline- and residual-corrected activity (FVIII:C-corr) is calculated from the actual observed activity (FVIII:Cobs) based on the formula given below:

$$\text{FVII:Ccorr} - \text{FVIII:Cobs} - \text{Baseline Activity} - \text{Residual decay} \quad \text{(Eq. X)}$$

where the Residual decay=(Pre-dose Activity−Baseline Activity)*$e^{-\lambda * time}$ Residual decay, to account for activity as a result of previous administration of a FVIII product, was performed using the terminal first-order decay rate (λ) obtained from noncompartmental analysis (NCA) of the raw, observed activity data. The endogenous or baseline activity was set to zero for all subjects in the above equation.

For the Arm 1 sequential PK subgroup, the FVIII activities following Advate and Baseline rFVIIIFc PK administrations were decayed using the respective subject's Advate λ The FVIII activity-time profiles resulting from rFVIIIFc infusions for the subjects in Arm 1 non-sequential PK subgroup, Arm 2, and Arm 3 were decayed using the average Advate λ obtained from the Arm 1 sequential PK subgroup.

Population Analysis Methodology

Two population PK models were developed independently of each other—one for rFVIIIFc, based on the rFVIIIFc data, and one for rFVIII, based on the rFVIII data alone.

Mixed-effects modeling with maximum likelihood parameter estimation methods were used to evaluate the population characteristics of rFVIIIFc and rFVIII in hemophilia A patients. For the description of random inter-individual variability (IIV), a log-normal distribution of the random effects, with a block covariance matrix was used. Various random residual error configurations were tested by combinations of additive and proportional variance terms. Inclusion of IOV to account for the change in the system properties with time was evaluated. First order conditional estimation with interaction (FOCEI) method was implemented for parameter estimation.

Diagnostic plots, minimum value of the objective function (OFV), and the evaluation of shrinkage were used to guide model building and assess goodness-of-fit. The Likelihood Ratio Test was used to compare hierarchical models.

The base pharmacokinetic model was developed by exploring typical structural models, including one- and two-compartment linear models. Models were compared by goodness-of-fit diagnostics including the Likelihood Ratio Test (significance level of 0.01, change in objective function value (OFV)=6.64 for 1 degree of freedom [df]), diagnostic plots, and estimates and standard errors of model parameters. The statistical model was built by testing and discriminating between various IIV and IOV structures and between different combinations of additive and proportional residual error terms. Candidate models were run from a number (usually 25-50) of different randomly generated initial estimates to assess the model stability and convergence.

Weight (WT) and Study (STUD), although technically assumed covariates, are sometimes considered as intrinsic to the basic model as their inclusion can be postulated a priori. For this reason the base models developed included these covariates.

The following factors were considered as potential covariates: height, age, race, blood type, hematocrit, von Willebrand factor antigen levels, IgG1 levels, albumin levels, non-neutralizing antibody (ADA) presence, HCV status, HIV status.

The continuous covariates were centered around a standard value—usually the median of the study population. For the forward covariate inclusion procedure, the Likelihood Ratio Test was used to compare hierarchical models with a significance level of 0.01. Decrease in the respective IIV term and other Goodness of Fit measures were also considered for inclusion. Once the full population covariate model was constructed a stepwise backwards deletion method with a significance level of 0.001 (change in objective function value=10.8 for 1 degree of freedom) was used to determine the final model. In all cases, physiological relevance of the covariates was considered before accepting a covariate.

A bootstrap procedure (nominally 1000 bootstraps), implemented by the bootstrap function of the Perl speaks NONMEN software package (PsN) was used to characterize the uncertainty in the model parameter estimates. Nonparametric 95% confidence intervals (CI) of all parameters were constructed based on the bootstrap results.

The predictive ability of the final model(s) was evaluated using simulation in a visual predictive check (vpc) using the vpc function of PsN. Outliers with |CWRES (Conditional Weighted RESiduals)|>5 were evaluated for impact on the qualified models by sensitivity analysis. Atypical drug activity data (such as very low or very high activity levels, or data not compliant with the trough-dose-peak sequence) were excluded from the analysis if no apparent explanation for these observations was provided. Activity data were excluded from the analysis if corresponding dosing or sampling times were missing or could not be reconstructed.

In order to evaluate the impact of values below the level of quantitation (BLQ), the analysis was performed using various approaches, either (i) excluding the BLQ values or (ii) using method(s) outlined in the literature to handle BLQ values (Beal, S., *Ways to fit a PK model with some data below the quantification limit*. J Pharmacokin Pharmacodyn, 2001. 28: p. 481-504; Jae Eun Ahn, M.O.K., Adrian Dunne and Thomas M. Ludden, *Likelihood based approaches to handling data below the quantification limit using NONMEM VI* J Pharmacokin Pharmacodyn, 2008. 35(4): p. 401-21).

Simulations

A number of rFVIIIFc dosing regimens were simulated. During the simulations, the activity-time profiles at Steady State (SS) for 2000 individuals were generated. Weight characteristics of the population simulated were derived from the Phase 3 study data. Where IOV was part of the model, the SS dosing interval or period simulated was set up as a single occasion. All dosing regimens were simulated using the same value of the random seed(s) to ensure comparability of the results. Simulation results are represented as the median as well as the 5th, 25th, 75th, and 95th percentiles activity-time curves.

Two types of simulation exercises were performed. In the first type, simulations were performed with models without including uncertainty in the model parameters. These simulations were used to illustrate the dosing regimen of interest and to derive parameters of therapeutic relevance (such as the percentage of individuals with FVIII activity levels >1 IU/dL). In the second type of simulation, univariate uncertainty distributions were reconstructed from the bootstrap results and used to explore the impact of modeling uncertainties on model predictions. The uncertainty distributions were sampled 1,000 times and 2,000 individuals were simulated with each set of parameter values. The 90% CIs of the activity percentile profiles were calculated from the simulated curves.

Software and Hardware

NONMEM (ICON plc, Dublin, Ireland, versions 7.1.2, and 7.2) was used for population PK analysis with Intel Fortran compiler (Intel Corporation, Santa Clara, Calif., version 11.1.048 and version 12.1).

Most of the model development was done on a workstation with a Quad Xeon Intel Processor and 8 GB of RAM. The computer intensive procedures such as bootstraps, visual predictive checks, etc. were run with up to 24 parallel cores on an HP 20-node cluster, each node with 2 quad-core Intel Xeon E5630 (160 cores in total) at 2.53 GHz and 24 to 60 GB of RAM.

Results: Base Model for rFVIIIFc

The base model for rFVIIIFc is a two compartment model with covariate WT on the central volume of distribution ($V_1$); IOV, and BLOCK(2) IIV on clearance (CL) and $V_1$; common proportional error, and separate additive residual error for the Phase ½a and Phase 3 data ($TVV_1$: typical apparent value for central volume of distribution):

$$V_1 = TVV_1 \cdot \left[\frac{WT}{73}\right]^{\Theta_8} \quad \text{(P)}$$

$$\varepsilon_{add} = STUD \cdot \Theta_5 + (1 - STUD) \cdot \Theta_6, \quad \text{(Q)}$$

where $$STUD = \begin{cases} 1 & \text{for Phase1} \\ 0 & \text{for Phase3} \end{cases}$$

The population parameters and the bootstrap-derived nonparametric 95% CIs are given in Table 24:

TABLE 24

Population parameters of the base model for rFVIIIFc

| | | Method | | |
|---|---|---|---|---|
| | | BLQ values commented out | | M3 Method |
| Parameter | Symbol | Population Estimate | Nonparametric 95% CI | Population Estimate |
| Clearance, CL, [dL/h] | $\Theta_1$ | 1.63 | 1.54-1.73 | 1.72 |
| Central Volume, $V_1$, [dL] | $\Theta_2$ | 37.9 | 36.9-38.8 | 36.4 |
| Allometric exponent on $V_1$ | $\Theta_8$ | 0.448 | 0.341-0.552 | 0.498 |
| Intercompartmental Clearance, Q, [dL/h] | $\Theta_3$ | 0.0742 | 0.0581-0.187 | 1.15 |
| Peripheral Volume, $V_2$, [dL] | $\Theta_4$ | 6.77 | 3.83-12.7 | 5.79 |
| IIV on CL, [%] | $\eta_1$ | 29.3 | 24.9-33.5 | 31.1 |
| IIV on V1, [%] | $\eta_2$ | 13.5 | 11.3-15.5 | 13.8 |
| Correlation between IIV on CL and $V_1$ | $\eta_{12}$ | 0.464 | N.C. [a] | 0.461 |
| IOV on CL, [%] | $\eta_3$ | 20.7 | 16.5-25.1 | 21.9 |
| IOV on $V_1$, [%] | $\eta_4$ | 12.2 | 7.81-16.2 | 10.5 |
| Correlation between IOV on CL and $V_1$ | $\eta_{34}$ | 0.643 | N.C. [b] | 0.558 |
| Additive error, Phase 1/2a study, [IU/dL] | $\Theta_5$ | 0.419 | 0.150-0.634 | 0.469 |
| Additive error, Phase 3 study, [IU/dL] | $\Theta_6$ | 0.207 | 0.112-0.270 | 0.264 |
| Proportional error, [%] | $\Theta_7$ | 13.7 | 12.1-15.5 | 14.6 |

[a] Nonparametric 95% CI of 0.00972-0.0281 for a population mean of the covariance ω 12 of 0.0184

[b] Nonparametric 95% CI of 0.00637 0.0310 for a population mean of the covariance ω34 of 0.0163

The observation records containing BLQ activity values were excluded while developing the base model. In order to assess the influence of the BLQ values on the population estimates, these data records were re-introduced and the estimation was re-run using the M3 and M4 methods. Those runs experienced some instability in both the estimation and covariance steps; M4 was more unstable than M3. When an Importance Sampling estimation step (METHOD=IMP) was implemented following the FOCEI estimation, both the minimization and covariance step converged with the M3 method. Despite the inherent estimation instability with the inclusion of the BLQ values, whenever the estimation converged, the parameter estimates were very close to the estimates obtained in the same model that excluded BLQ values (see Table 24, last column).

Covariate Model Building and Final Model for rFVIIIFc

As a result of the forward covariate inclusion, the full covariate model was identified, with VWF, AGE, and Hepatitis C virus (HCV, binary) as covariates on CL, and hematocrit (HCT), in addition to the base model WT and STUD as covariates on the central volume of distribution ($V_1$).

According to the accepted mechanistic hypothesis about the influence of antibodies on protein kinetics, the presence of antibodies usually increases the clearance of the target proteins by speeding up their rate of elimination. The incidence of antibodies in the dataset was low—5 individuals had antibodies at baseline, while 6 individuals acquired antibodies during the course of the clinical trial. It should be noted also that the antibody detection was transient within the same individual.

Testing the antibody presence (ADA) as a binary covariate on $V_1$ unexpectedly led to a statistically significant drop in the OFV, while the influence on ADA on clearance was negligible. A closer inspection of the model revealed that although the drop in the OFV was statistically significant, the IIV term on $V_1$ decreased only marginally (from 0.018 in to 0.0173) following the covariate inclusion. The $V_1$ in the presence of antibodies increased by 18%, which is unlikely to be clinically meaningful. A possible explanation for the assignment of the ADA covariate to the $V_1$, rather than to the clearance, is the dominant influence of those individuals who are antibody-positive at baseline over the individuals who acquire antibodies during therapy.

Due to the small number of those individuals as well as the transient character of the antibody response, the antibody covariate (ADA) on $V_1$ was rejected. Thus, no definitive effect of the presence of non-neutralizing antibodies on the PK of rFVIIIFc activity could be detected by this analysis.

As a result of the backward elimination procedure, STUD covariate on $V_1$ as well as HCV and AGE covariates on clearance were removed from the full covariate model without a significant impact on the OFV. The removal of the HCT on $V_1$, however, led to a significant increase in the OFV, therefore HCT was retained.

The final population PK model for rFVIIIFc was a two compartment model with covariates VWF on CL, WT and HCT on $V_1$, IOV (7 occasions), BLOCK(2) variance-covariance matrix on CL and $V_1$, and separate additive residual error for the Phase ½a and Phase 3 with a common proportional error term, as follows (TVCL: typical apparent value for clearance):

$$CL = TVCL \cdot \left[\frac{VWF}{118}\right]^{\Theta_{10}}. \quad \text{(R)}$$

$$V_1 = TVV_1 \cdot \left[\frac{WT}{73}\right]^{\Theta_8} \cdot \left[\frac{HCT}{45}\right]^{\Theta_9} \quad \text{(S)}$$

$$\varepsilon_{add} = STUD \cdot \Theta_5 + (1 - STUD) \cdot \Theta_6, \quad \text{(T)}$$

where $$STUD = \begin{cases} 1 & \text{for Phase1} \\ 0 & \text{for Phase3} \end{cases}$$

The population parameters of the final model and the bootstrap-derived nonparametric 95% CIs are given in Table 25:

TABLE 25

Population parameters of the final model for rFVIIIFc

| | | Method | | |
|---|---|---|---|---|
| | | BLQ values commented out | | M3 Method |
| Parameter | Symbol | Population Estimate | Nonparametric 95% CI | Population Estimate |
| Clearance, CL, [dL/h] | $\Theta_1$ | 1.65 | 1.57 to 1.74 | 1.73 |
| Exponent on VWF | $\Theta_{10}$ | −0.343 | −0.439 to −0.247 | −0.391 |
| Central Volume, $V_1$, [dL] | $\Theta_2$ | 37.5 | 36.5 to 38.4 | 36.8 |
| Allometric exponent on $V_1$ | $\Theta_8$ | 0.382 | 0.271 to 0.499 | 0.423 |
| Exponent on HCT | $\Theta_9$ | −0.419 | −0.656 to −0.208 | −0.412 |

TABLE 25-continued

| Population parameters of the final model for rFVIIIFc | | | | |
|---|---|---|---|---|
| | | Method | | |
| | | BLQ values commented out | | M3 Method |
| Parameter | Symbol | Population Estimate | Nonparametric 95% CI | Population Estimate |
| Intercompartmental Clearance, Q, [dL/h] | $\Theta_3$ | 0.0746 | 0.0594 to 0.184 | 0.279 |
| Peripheral Volume, $V_2$, [dL] | $\Theta_4$ | 6.92 | 3.80 to 13.8 | 4.09 |
| IIV on CL, [%] | $\eta_1$ | 24.3 | 20.5 to 27.7 | 25.1 |
| IIV on $V_1$, [%] | $\eta_2$ | 13.4 | 11.0 to 15.5 | 13.6 |
| Correlation between IIV on CL and $V_1$ | $\eta_{12}$ | 0.548 | N.C. [a] | 0.563 |
| IOV on CL, [%] | $\eta_3$ | 20.6 | 16.7 to 25.1 | 22.0 |
| IOV on $V_1$, [%] | $\eta_4$ | 12.0 | 7.46 to 16.3 | 9.27 |
| Correlation between IOV on CL and $V_1$ | $\eta_{34}$ | 0.639 | N.C. [b] | 0.526 |
| Additive error, Phase 1/2a study, [IU/dL] | $\Theta_5$ | 0.421 | 0.172 to 0.612 | 0.416 |
| Additive error, Phase 3 study, [IU/dL] | $\Theta_6$ | 0.208 | 0.126 to 0.275 | 0.240 |
| Proportional error, [%] | $\Theta_7$ | 13.6 | 12.0 to 15.3 | 15.4 |

[b] Nonparametric 95% CI of 0.00956-0.0264 for a population mean of the covariance ω 12 of 0.0179

[c] Nonparametric 95% CI of 0.00579-0.0312 for a population mean of the covariance ω 34 of 0.0158

As with the base model case, the influence of the BLQ values on the population estimates was assessed by running the M3 method on the final model with the BLQ values re-included in the dataset. The run completed with a successful minimization, but the covariance step was aborted, confirming the inherent instability introduced by the inclusion of BLQ values. There are minimal differences between the two sets of parameter estimates (Table 25); all M3 method parameters, except the intercompartmental clearance and the proportional error terms, lie within the non-parametric 95% CI identified for the final model.

The Goodness of Fit (GoF) diagnostics of the final model are shown in FIG. 30A-D; the results of a Visual Predictive Check are presented in FIG. 31A-F.

The IIV of the activity was low to moderate. Typically, as with other FVIII products (Bjorkman S, Blanchette V S, Fischer K, et al., *J Thromb Haemost.,* 8(4):730-736 (2010); Bjorkman S, Oh M, Spotts G, et al., *Blood,* 119(2):612-618 (2010)) the CL had higher IIV while the IIV of the volume of distribution, characterized by a coefficient of variation (CV) of 13.4%, was very low. Similarly, the IOV was low, which was in line with observations from other FVIII products (Bjorkman S, Blanchette V S, Fischer K, et al., *J Thromb Haemost.,* 8(4):730-736 (2010); Bjorkman S, Oh M, Spotts G, et al., *Blood,* 119(2):612-618 (2010)). As with the IIV, the IOV of the clearance was higher than the IOV of the volume of distribution.

The GoF plots indicate that the model fitted the experimental data very well, specifically at the lower end of the activities (which is the range of interest with respect to therapeutic effects). There were no systematic deviations or shapes detectable in the residual plots and no notable deviations from the symmetry distribution assumption for most of the exponential inter-individual variability (ETA) terms.

The residual error values for both the base and the final models were very low. The additive error was less than the LLOQ. The proportional error was of the same magnitude as the precision of the assay (CV <10%). This showed that the final model had almost completely extracted the information contained in the data: the unexplained variance was almost exclusively due to the inherent activity assay variability.

The ETA shrinkage of the IIV terms was moderate, whereas the ETA shrinkage on the IOV terms was higher (>25%) and was especially high for occasions containing sparse data.

The results from both the base and the final models indicate that the activity of rFVIIIFc does not display strong dependence on weight. CL did not accept a WT covariate, while the retained WT covariate on the $V_1$ had a low value exponent (0.382 with 95% CI of 0.271-0.499). This opens the opportunity of exploring fixed (weight-independent) dosing regimens for rFVIIIFc if such are of benefit to the patients.

AGE was included in the full covariate model as a very weak covariate, which was cancelled during the backward elimination of covariates. The dataset did not include individuals <12 years of age. Therefore, the activity of rFVIIIFc is not impacted by age for individuals aged >12 years.

External Validation of the rFVIIIFc Model

In order to further qualify the predictive performance of the PK model, an external validation procedure was performed. A model development (training) dataset was constructed, containing the intensive sampled profiles from the two studies (a total of 1162 observation records in the training set). In addition, a model validation set included all of the remaining observed data (predominantly peak and trough observations, a total of 888 observation records in the validation set). As the first step of the external validation, a model development procedure, similar to the base model development, was carried out with the training dataset. The parameters estimated from the whole dataset and from the training dataset only were very similar (results not shown).

At the validation step, the validation data (peak and trough data for occasions 3 through 7) were re-introduced. The model was run with parameter estimates set to the population means from the training set model with the NONMEM option MAXEVAL=0. The GoF diagnostics for the validation set only (troughs and peaks) are shown in FIG. 32. There was a very good agreement between the observed data in the validation dataset and the predicted data by the model developed on the training set.

Base Model for rFVII

The base model for rFVIII (model Adv0D) is a two compartment model with covariates WT on $V_1$ and study (STUD) on the peripheral volume (V2), BLOCK(2) IIV on CL, $V_1$, common additive error and separated proportional residual error by study:

$$V_1 = TVV_1 \cdot \left[\frac{WT}{73}\right]^{\Theta_8} \quad \text{(U)}$$

$$V_2 = TVV_2 \cdot [\Theta_9]^{STUD} \quad \text{(V)}$$

$$\varepsilon_{prop} = STUD \cdot \Theta_6 + (1 - STUD) \cdot \Theta_7, \quad \text{(W)}$$

where $$STUD = \begin{cases} 1 & \text{for Phase1} \\ 0 & \text{for Phase3} \end{cases}$$

The population parameters of model Adv0D and the bootstrap-derived nonparametric 95% Cis are given in Table 26. No IOV was included in Adv0D as only single dose data were available for this agent. No covariate model was built in this case as developing a full rFVIII model was outside the scope of this modeling exercise.

Figure 33:
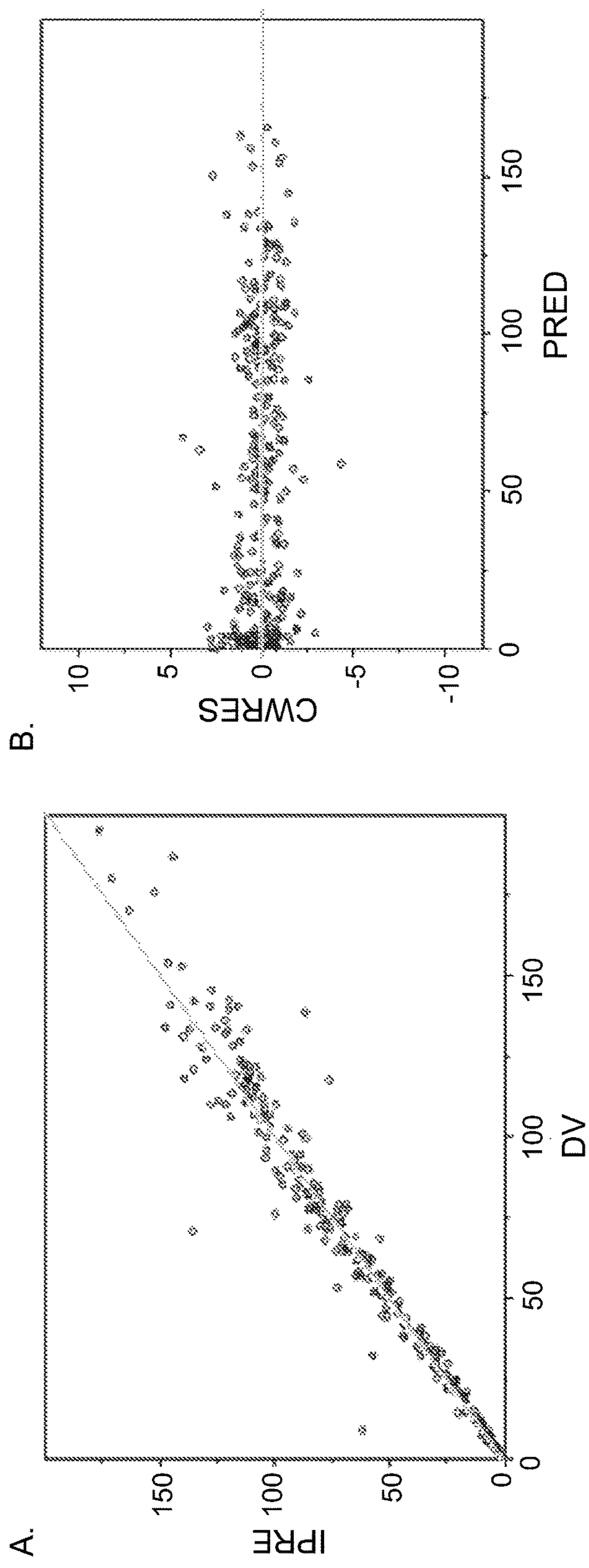

The GoF diagnostics of model Adv0D are shown in FIG. 33.

TABLE 26

Population parameters and bootstrap-derived nonparametric 95% CI's for the base ADVATE ® model

| Parameter | Symbol | Population Estimate | Nonparametric 95% CI[a] |
|---|---|---|---|
| Clearance, CL, [dL/h] | $\Theta_1$ | 2.53 | 2.32-2.78 |
| Central Volume, $V_1$, [dL] | $\Theta_2$ | 34.6 | 32.5-36.2 |
| Allometric exponent on $V_1$ | $\Theta_8$ | 0.508 | 0.277-0.762 |
| Intercompartmental Clearance, Q, [dL/h] | $\Theta_3$ | 0.548 | 0.401-0.929 |
| Peripheral Volume for Phase 3, $V_2$, [dL] | $\Theta_4$ | 4.94 | 3.82-6.51 |
| $V_2$ Correcting Coefficient for Phase 1/2a | $\Theta_9$ | 2.17 | 1.64-3.00 |
| IIV on CL, [%] | $\eta_1$ | 30.4 | 24.4-35.8 |
| IIV on $V_1$, [%] | $\eta_2$ | 16.2 | 11.4-19.3 |
| Correlation between IIV on CL and $V_1$ | $\eta_{12}$ | 0.532 | N.C. [b] |
| IIV on $V_2$, [%] | $\eta_4$ | 30.6 | 0.31-42.4 |
| Additive error, [IU/dL] | $\Theta_5$ | 0.110 | 0.00110-0.256 |
| Proportional error, Phase 1/2a study, [%] | $\Theta_6$ | 10.9 | 8.42-12.6 |
| Proportional error, Phase 3 study [%] | $\Theta_7$ | 16.8 | 10.0-22.4 |

[a]Out of 1000 bootstraps, 23 runs with minimization terminated were skipped when calculating the bootstrap results.
[b] Nonparametric 95% CI of 0.00773-0.0442 for a population mean of the covariance □$_{12}$ of 0.0263

The narrow CIs of the rFVIII model parameter estimates indicate that they were estimated with very good precision. $V_1$ approximates the plasma volume, and the IIV of the activity was low to moderate. The residual errors of Adv0D were very low, and the additive error was less than one-quarter of the LLOQ. The proportional errors for both studies were of the same magnitude as the precision of the aPTT assay (CV <10%). This shows that Adv0D almost completely captured the information contained in the data; the unexplained variance was almost exclusively due to the measurement errors. The model diagnostics suggest that the model described the data adequately. There were no systematic deviations or shapes detectable in the residual plots. The lower end of the activities (which is the range of interest with respect to therapeutic effects) was approximated very well.

Model Implementation: Simulations of Prospective Dosing Regimens

The population PK models adequately describe the time course of both rFVIII and rFVIIIFc activity. Therefore, they can be used to simulate various dosing scenarios in the target population with the aim to explore and compare the resulting activity profiles. Such model based simulations have been widely used, especially in recent years, and have become a valuable tool in support of operational, regulatory, and therapeutic decision making.

In patients with hemophilia, it is widely accepted that 1 IU/dL (or 1% activity) is a threshold value under which the risk of bleeding increases (Collins P W, B.V., Fischer K, et al., Break-through bleeding in relation to predicted factor VIII levels in patients receiving prophylactic treatment for severe hemophilia A. J Thromb Haemost., 2009. 7(3): p. 413-20; MASAC, Recommendation #190 Concerning Products Licensed for the Treatment of Hemophilia and Other Bleeding Disorders. March 2009 (Replaced by Recommendation #215, November 2012). New York, N.Y.: National Hemophilia Foundation). It should be noted, however, that the threshold cannot be considered an "absolute criterion" by itself; other factors, such as duration of time with low activity levels, patient characteristics, etc. are likely also involved.

For the simulation of rFVIIIFc activity, the base model (Eq. Q) was used. This was preferred to the final model as: (i) the base model and the final model provided the same approximation of the data; the final model only assigned part of the IIV to the covariates selected, and (ii) no covariate model was developed for rFVIII, so it is meaningful to compare simulations from base models when FVIIIFc is referenced to rFVIII. In addition to that, at this moment, the course of the time-variant covariates, VWF and HCT, has not qualitatively characterized. In any case, the parameter values of the base and final models from Tables 24 and 25 indicate that the base model is adequate and can be used for simulations.

The simulations without uncertainty were performed with both the base model without BLQ data (considered to be mildly optimistic, see the Discussion section) and with the base model with BLQ data included (considered to be conservative, see the Discussion section). The simulations with uncertainty were based upon the base model without BLQ values.

Several rFVIIIFc prophylaxis dosing regimens that are of therapeutic interest have been simulated. Table 28 presents the predicted SS peaks and troughs of the rFVIIIFc activity-time profiles ($5^{th}$, $25^{th}$, $50^{th}$ [median], $75^{th}$, and $95^{th}$ percentiles) at various dose levels administered every 3, 4, or 5 days (E3D, E4D, and E5D administration, respectively). The top section of Table 28 displays the simulation results with the base model with no BLQ data included and no uncertainty. The bottom section of Table 28 displays the simulation results with the base model with BLQ included and no uncertainty. The middle section of Table 28 displays the simulation results with uncertainty in the model parameters. The simulated SS activity profiles of selected rFVIIIFc prophylaxis dosing regimens are given in FIG. 35 for illustrative purposes. Panels A, C, E, and G display the simulations without uncertainty; panels B, D, F, and H display the 90% confidence regions around the 5%, 50%, and 95% percentile curves calculated from the uncertainty simulations.

These simulation results can be considered when determining long-term prophylaxis dosing regimens. It should be noted also that a dosing regimen of 65 IU/kg administered weekly (QW) is predicted to yield troughs >1 IU/dL in 26.6% of the individuals treated (also shown in FIG. 35, using the base model with no BLQ data), or 16.8% of the individuals treated (using the base model with BLQ data). The 90% confidence region of these predictions is 14.6% to 35.8%. The dosing regimens simulated include dose levels and dosing intervals that have been tested in the phase ½a and phase 3 studies. Therefore, the simulations can be considered to interpolate within the existing clinical experience, increasing the credibility of the predictions.

TABLE 27

Comparison of ADVATE ® population PK parameters from the current analysis and the analysis published in Björkman 2012 A

| Parameter | This Analysis Estimates | Estimates from [Björkman 2012a] |
|---|---|---|
| Clearance, CL, [dL/h] | 2.53 | 2.30* |
| Allometric exponent on CL | Not estimated | 0.8 |
| Central Volume, $V_1$, [dL] | 34.6 | 28.6* |
| Allometric exponent on $V_1$ | 0.508 | 0.95 |
| Intercompartmental Clearance, Q, [dL/h] | 0.548 | 1.47 |
| Peripheral Volume, $V_2$, [dL] | 4.94 | 8.92* |
| Allometric exponent on $V_2$ | Not estimated | 0.76 |
| $V_2$ Correcting Coefficient for Phase 1/2a | 2.17 | Not estimated |
| IIV on CL, [%] | 30.4 | 30.0 |
| IIV on $V_1$, [%] | 16.2 | 21.0 |
| Correlation between IIV on CL and $V_1$ | 0.532 | 0.45 |
| IIV on $V_2$, [%] | 30.6 | Not estimated |
| Additive error, [IU/dL] | 0.110 | 8.90 |
| Proportional error, Phase 1/2a study, [%] | 10.9 | Not estimated |
| Proportional error, Phase 3 study [%] | 16.8 | Not estimated |

*CL, V1 and V2 calculated for an average 73 kg, 30 yr old subject from equations 4-7 (Bj örkman 2012 A)

The dosing regimens simulated include dose levels (20-65 IU/kg) and dosing intervals that have been tested in the Phase ½a and Phase 3 studies. Therefore, the simulations can be considered to interpolate within the existing clinical experience, increasing the credibility of the predictions.

TABLE 28

Predicted SS peak and troughs of the rFVIIIFc activity-time profiles with various dose regimens

| Unit Dose Level | Percentile of Subjects | Dosing Frequency Every 3 days Peak | Every 3 days Trough | Every 4 days Peak | Every 4 days Trough |
|---|---|---|---|---|---|
| 25 IU/kg | 5% | 35.2 | <0.5[a] | 34.9 | <0.5[a] |
| | 50% | 51.2 | 2.64 | 50.0 | 1.16 |
| | 95% | 74.5 | 10.2 | 70.7 | 5.69 |
| 40 IU/kg | 0.05 | 56.3 | 0.619 | 55.9 | <0.5[a] |
| | 50% | 82.0 | 4.22 | 80.0 | 1.85 |
| | 95% | 119 | 16.3 | 113 | 9.11 |
| 50 IU/kg | 0.05 | 70.4 | 0.774 | 69.9 | <0.5[a] |
| | 50% | 102 | 5.27 | 100 | 2.32 |
| | 95% | 149 | 20.4 | 141 | 11.4 |
| 25 IU/kg | 5% | 35.2 (33.8, 36.7) | <0.5[a] (<0.5[a], 0.545) | 34.9 (33.7, 36.3) | <0.5[a] (<0.5[a], <0.5[a]) |
| | 50% | 51.5 (50.5, 52.5) | 2.63 (2.23, 3.05) | 50.0 (49.0, 51.0) | 1.16 (0.89, 1.45) |
| | 95% | 74.5 (72.0, 77.0) | 10.3 (8.60, 12.2) | 71.0 (68.5, 73.5) | 5.80 (4.60, 7.05) |
| 40 IU/kg | 0.05 | 56.3 (54.1, 58.6) | 0.59 (<0.5[a], 0.872) | 55.8 (53.8, 58.0) | <0.5[a] (<0.5[a], <0.5[a]) |
| | 50% | 82.4 (80.8, 84.0) | 4.21 (3.57, 4.88) | 80.0 (78.4, 81.6) | 1.85 (1.43, 2.31) |
| | 95% | 119 (115, 123) | 16.5 (13.8, 19.4) | 114 (110, 118) | 9.28 (7.35, 11.3) |
| 50 IU/kg | 0.05 | 70.4 (67.6, 73.3) | 0.739 (<0.5[a], 1.09) | 69.8 (67.3, 72.5) | <0.5[a] (<0.5[a], 0.521) |
| | 50% | 103 (101, 105) | 5.26 (4.46, 6.10) | 100 (98.0, 102) | 2.31 (1.79, 2.89) |
| | 95% | 149 (144, 154) | 20.6 (17.2, 24.3) | 142 (137, 147) | 11.6 (9.19, 14.1) |
| 25 IU/kg | 5% | 37.2 | <0.5[a] | 37.0 | <0.5[a] |
| | 50% | 52.9 | 2.54 | 51.6 | 1.01 |
| | 95% | 75.6 | 10.8 | 71.8 | 5.92 |
| 40 IU/kg | 0.05 | 59.5 | <0.5[a] | 59.2 | <0.5[a] |
| | 50% | 84.7 | 4.06 | 82.5 | 1.61 |
| | 95% | 121 | 17.2 | 115 | 9.47 |
| 50 IU/kg | 0.05 | 74.3 | 0.509 | 74.1 | <0.5[a] |
| | 50% | 106 | 5.07 | 103 | 2.01 |
| | 95% | 151 | 21.5 | 144 | 11.8 |

| Unit Dose Level | Percentile of Subjects | Dosing Frequency Every 5 days Peak | Every 5 days Trough | Model |
|---|---|---|---|---|
| 25 IU/kg | 5% | 34.6 | <0.5[a] | Base model with BLQ values commented out |
| | 50% | 49.2 | 0.549 | |
| | 95% | 69.6 | 3.08 | |
| 40 IU/kg | 0.05 | 55.3 | <0.5[a] | |
| | 50% | 78.8 | 0.878 | |
| | 95% | 111 | 4.94 | |
| 50 IU/kg | 0.05 | 69.1 | <0.5[a] | |
| | 50% | 98.5 | 1.10 | |
| | 95% | 139 | 6.17 | |
| 25 IU/kg | 5% | 34.3 (33.0, 35.9) | <0.5[a] (<0.5[a], <0.5[a]) | Base model with BLQ values |
| | 50% | 49.3 (48.2, 50.5) | 0.535 (0.5[a], 0.69) | |
| | 95% | 69.5 (66.5, 72.5) | 3.1 (2.27, 3.96) | |

TABLE 28-continued

Predicted SS peak and troughs of the rFVIIIFc activity-time profiles with various dose regimens

| | | | | |
|---|---|---|---|---|
| 40 IU/kg | 0.05 | 54.8 (52.7, 57.4) | <0.5[a] (<0.5[a], <0.5[a]) | commented out (with uncertainty)* |
| | 50% | 78.8 (77.1, 80.8) | 0.856 (0.560, 1.10) | |
| | 95% | 111 (106, 116) | 4.96 (3.63, 6.34) | |
| 50 IU/kg | 0.05 | 68.5 (65.9, 71.7) | <0.5[a] (<0.5[a], <0.5[a]) | |
| | 50% | 98.5 (96.4, 101) | 1.07 (0.700, 1.38) | |
| | 95% | 139 (133, 145) | 6.20 (4.54, 7.92) | |
| 25 IU/kg | 5% | 35.8 | <0.5[a] | Base model with BLQ (M3 method) |
| | 50% | 51.0 | <0.5[a] | |
| | 95% | 70.9 | 3.27 | |
| 40 IU/kg | 0.05 | 57.2 | <0.5[a] | |
| | 50% | 81.5 | 0.619 | |
| | 95% | 113 | 5.23 | |
| 50 IU/kg | 0.05 | 71.5 | <0.5[a] | |
| | 50% | 102 | 0.774 | |
| | 95% | 142 | 6.54 | |

[a]Below the level of quantification.

*Simulation results shown as median and 90% CI

Other Implementations

Although the rFVIIIFc and rFVIII population PK models were developed separately, a comparative evaluation of the individual Bayesian PK parameter estimates of the subjects (from the Phase 1 study and the Arm 1 PK Subgroup of the Phase 3 study) who received both rFVIII and rFVIIIFc indicates that they are highly correlated. FIG. 36A-C presents the individual Bayesian CL, $V_1$, and Time to 1 IU/dL (Time 1%) estimates for rFVIII and rFVIIIFc, where each point represents one individual. The correlation coefficients are uniformly high: R=0.839 (R2=0.7043) for CL, R=0.862 (R2=0.7437) for $V_1$, and R=0.865 (R2=0.7481) for Time 1%.

Discussion

The generally narrow CIs of the parameter value estimates of both the base and final rFVIIIFc models indicate that the population PK parameters were estimated with good precision. The PK behavior of the activity profiles as assessed by population analysis is typical for a FVIII product (Bjorkman S, Oh M, Spotts G, et al., *Blood.,* 119(2): 612-618 (2012)) with a peripheral compartment much smaller than the central volume ($V_2$ is >5 times lower than $V_1$). The $V_1$ approximates the plasma volume.

By far the strongest covariate for rFVIIIFc identified in this analysis was vWF on CL. As a result of the inclusion of the vWF covariate on CL, the CV of the IIV on this parameter decreased by approximately 20%. These results are expected, as the vast majority of circulating FVIII (>95%) is in complex with vWF and is protected from proteolytic degradation, premature binding to its receptors, and rapid CL from the blood. The negative exponent on vWF indicates that the higher the measured level of vWF, the lower the rFVIII CL, which is in line with the above mechanistic hypothesis.

The (across and within) individual range of vWF in the model development dataset was in the range of 10 495%. The 10% value was repeated and found to be erroneous (after database lock). This would result in a variation of the rFVIIIFc CL from 3.85-1.10 dL/hr, the population mean being 1.65 dL/hr. It should be noted that VWF is a time-varying parameter within the same individual. The exact mechanisms and relationships governing this within-individual variation are not well elucidated or quantitatively characterized. A quantitative framework for the vWF level IIVs needs to be combined with the current population PK model to permit further investigation of the possible dosing implications of the VWF covariate. Another time-varying covariate that was identified was HCT on $V_1$; however, the influence of HCT was rather weak. Such a relationship has not been reported for FVIII products previously and a mechanistic hypothesis linking HCT with FVIII activity has not been proposed.

Although no definitive effect of non-neutralizing antibodies on the observed activity was detected as a result of the population PK analysis, due to the small number of subjects with antibodies and the transient character of the antibody response, such an effect cannot be totally excluded.

The results from the VPC and the simulations indicate that both the full and the base model without the BLQ values (not shown) in the dataset mildly overestimate the trough activity. For example, with 65 IU QW dosing, the base model predicts that more than one-quarter of the individuals will have trough values above the 1 IU/dL threshold. This prediction can be compared with the results from Arm 2 (weekly dosing with 65 IU/kg) of the phase 3 study, where 9 of 21 (42.9%) had troughs above 1 IU/dL at Week 7; 6 of 19 (31.6%) had troughs above 1 IU/dL at Week 14, and 1 of 6 (16.7%) had troughs above 1 IU/dL at Week 18. On the other hand, both the full and base model with the BLQ values included seem to underestimate the trough activity—using the base version of this model predicts that 16.8% of the Arm 2 individuals will have troughs >1 IU/dL. This apparent discrepancy is reconciled in the simulations with uncertainty, where the predicted 90% CI include any of the respective predicted troughs and peaks using either the base model with or without BLQ values in the dataset (compare the middle section with the top and bottom sections of Table 28). These simulation results confirm the power of population PK model-based simulations with uncertainty, which can be seen as a generalization of the two alternative base models.

Evidence from the published literature (Bjorkman S, Folkesson A, Jonsson S., A. *Eur J Clin Pharmacol;* 65(10): 989-998 2009), Bjorkman S, Oh M, Spotts G, et al., *Blood.,* 119(2):612-618 (2012)), as well as from the current research, indicates that FVIII displays a 2-compartment disposition; however, the peripheral compartment has a small $V_1$ and its impact on the activity profiles is very subtle. The weak influence of the second compartment on the observed activity profiles has led to the inability to fit a 2-compartment model to clinical data in at least one instance (Karafoulidou A, Suarez E, Anastasopoulou I, et al., *Eur J Clin Pharmacol.;* 65(11):1121-1130 (2009)).

The mechanisms determining the observed shapes are not well elucidated—as stated in Bjorkman S, Folkesson A, Jonsson S. A., *Eur J Clin Pharmacol.;* 65(10):989-998 (2009): " . . . It is still not clear whether the 2-compartment characteristic reflects distribution of FVIII from the circulation or rapid initial elimination of some of the injected protein." In the absence of well-defined mechanistic understanding, the information contained in the clinical data available remains critical for model selection.

The observed variation in the intercompartmental clearance (Tables 24 and 25) leads to the effect that for the models (either base or final) developed without BLQ data, the estimator captures a curvature in the profiles due to the second compartment close to the limit of detection. This behavior of the estimator is the source of the apparent terminal tin value. It should be pointed out that: (i) such an overestimation occurs at very low activities, close to the LLOQ; (ii) such an overestimation is not likely to affect meaningfully the predictive performance of the model within the time window of interest (up to 5-7 days); and (iii) such an overestimation affects only a very small portion (less than 2-3%) of the overall area under the curve associated with the activities close to the LLOQ, where the divergence between the models begins.

When the BLQ values were reintroduced into the dataset and the M3 method was applied in NONMEM, the estimator seemed to move the curvature due to the second compartment toward the initial portion of the profile. It should be kept in mind that the M3 method treats the BLQ values as categorical variables and what happens under the LLOQ is quantitatively unknown.

A similar effect was observed for the 2 variants of the rFVIII base model (Table 26), where the model derived from phase ½a data overestimated terminal $t_{1/2}$, whereas the model from the phase 3 data provided a terminal tin value in line with the conventional analyses results. Similar to the rFVIIIFc models, the mean residence time (MRT) and the Time to 1% were largely unaffected. Based on this discussion, the rFVIIIFc models developed from data without the BLQ values as well as the rFVIII model reflective of the phase ½a data have the potential to over-predict the activity during simulation. Such an over-prediction within the time window of interest (up to 5-7 days) is expected to be low. On the other hand, the models developed from data with the BLQ values as well as the rFVIII model reflective of the phase 3 data have the potential to under-predict the activity during simulation. The impact of the model variation on the model predictions were quantified by the simulations performed.

The results from the uncertainty simulations demonstrate that any of the developed pivotal models (with and without BLQ values, base and final, etc.) can be used for simulations without an impact on the overall PK conclusions, provided that the random nature of the predictions is acknowledged. The selection of the simulation model should be determined by the objectives and/or the context (eg, risk tolerance) of the simulation exercise. When risk tolerance is low, the more conservative models (with the BLQ data included) may be the best simulation option. For population-oriented simulations (such as those shown in Table 28) the base model simulation is adequate, whereas for individual-oriented simulations, when the individual covariate values are of interest, the final covariate model may be more appropriate. It is suggested that simulations with uncertainty should be the preferred option, accounting for the inherent randomness of the simulations. It is also important to note that when referencing between rFVIII and rFVIIIFc dosing regimens, it is meaningful to use either the optimistic models for both agents, or the conservative models for both agents to avoid the potential of bias.

Although the external validation exercise was not conducted in a random manner, the results emphasize the strong predictive potential of the current population PK model and indicate that the peak and troughs in the long term can be predicted by a model developed on a semi-sparse sampling schedule. This represents one possible treatment scenario, when the physician adjusts the dosing regimen (initially or during the course of therapy) based on PK information derived from more or less intensive sampling scheme. Due to the low IOV, this adjustment is likely to be valid for extended periods in the absence of abrupt changes in the system state (such as illness, trauma, etc.).

There is a subtle difference between the rFVIII models derived from the phase 3 data and the one identified from the phase ½a data—the peripheral volume of distribution $V_2$ is 4.94 dL from phase 3 and 2.17 times higher, when identified from phase ½a data. This difference may originate from the difference in the sampling schemes between the two studies (10-11 sampling points in phase ½a and fewer sampling points in phase 3) and makes the rFVIII phase 3 model more conservative with respect to predicting trough values (predicts lower trough values) than the rFVIII phase ½a model. This subtle difference is built into the STUD covariate (Table 26) and may account for any differences in design, assays, execution, and other conditions across the 2 studies. No BLQ model has been developed for rFVIII due to the very low number of BLQ values in the rFVIII dataset as a result of the shorter sampling window for this agent (see Table 23).

Table 27 shows that the FVIII population PK parameters from the current analysis and the analysis published by Bjorkman S, Oh M, Spotts G, et al., *Blood,* 119(2):612-618 (2010) are comparable, although there are differences in the analysis methodology. Björkman's model identified a weight dependence of CL and $V_2$, which was not substantiated by our data. Additionally, age was not identified by our modeling as a covariate of rFVIIIFc clearance. It is worth mentioning that the data used by Bjorkman S, Oh M, Spotts G, et al., *Blood,* 119(2):612-618 (2010) include PK profiles from subjects as young as 1 year; hence the, age and weight range in this dataset may be considerably wider. The latter would facilitate the identification of WT/AGE covariates from such data.

The high positive correlations between the PK parameters of rFVIII and rFVIIIFc, illustrated in FIG. 36A-C, suggest that individuals who had high CL values for rFVIII are very likely to have had high CL values for rFVIIIFc as well, and vice-versa. The population PK models predicted that the average population CL for rFVIIIFc (1.65 dL/hr) is about 35% lower than that of rFVIII (2.53 dL/hr). This is consistent with the geometric mean (95% CI) for the intraindividual CL ratio of rFVIIIFc to rFVIII (0.64 [0.60-0.69]) derived from the conventional 2-stage compartmental analysis. At the same time, the $V_1$ panel of FIG. 36A-C indicates that individuals had similar $V_1$ values for rFVIII and for rFVIIIFc. These two relationships rise the hypothesis that individuals who had high time-related characteristics (such as $t_{1/2}$, MRT, Time to 1%, and Time to 3%) for rFVIII are very likely to have had high characteristics for rFVIIIFc, and vice-versa. This hypothesis was confirmed in the Time 1% panel of FIG. 36A-C, where the individual Times to 1%, calculated based on the Bayesian estimates from the rFVIII and rFVIIIFc model, are plotted.

Time to 1% activity is a PK outcome parameter that is directly related to frequency of dosing under the paradigm of maintaining target activity above this threshold. Therefore, based on the relationship identified, a conclusion can be made, that individuals who were on less frequent rFVIII dosing would require less frequent rFVIIIFc dosing, and vice-versa. Such a relationship could be useful when transition between the two products is considered.

Conclusions

The population PK analysis and simulations presented provide a comprehensive quantitative characterization of the activity-time profiles for rFVIIIFc and rFVIII. These confirm that the CL of rFVIIIFc is much lower than the CL of rFVIII, while the volumes of distribution at steady state are similar. This was first observed following noncompartmental analysis and conventional 2-stage analysis of the same data and explain the extended duration of activity achieved by rFVIIIFc relative to rFVIII.

The population PK model for rFVIIIFc was used for simulation of various dosing scenarios to aid dosing regimen selection and adjustment. Based on this, it was concluded that individuals on a less frequent rFVIII dosing regimen would require less frequent rFVIIIFc dosing, and vice-versa. Such a relationship could be useful when transitioning from one agent to the other.

The population PK models are useful tools for predicting peak, trough, and average activity of various dosing scenarios, and can be further extended to develop aids and methods for individualizing treatment. Many efforts have been made to correlate activity levels with bleeding risk, although a definitive quantitative relationship to calculate bleeding probability based on activity has not yet been identified. These population PK models may serve as a basis for the development of a population PK/pharmacodynamics model to better understand the relationship between FVIII activity and bleeding.

Example 12. Association of Bleeding Tendency with Time Under Target FIX Activity Levels in Severe Hemophilia B Patients Treated with Recombinant Factor IX-Fc Fusion Protein (rFIXFc)

The objective of this post hoc analysis was to evaluate the relationship between the annualized time spent under target 1, 3, and 5 IU/dL FIX activity levels and clinical outcomes (overall, spontaneous, traumatic, and joint bleeds), as well as the probability of experiencing bleeding episodes given time spent under the target trough.

Subjects

Subjects enrolled in the B-LONG study with available efficacy data were used for this analysis. This study included male subjects (≥12 years of age) with hemophilia B (FIX levels ≤2 IU/dL), no history of FIX inhibitors, and ≥100 exposure days to FIX.

Design

B-LONG was a phase 3 interventional, nonrandomized, open-label, multicenter study of rFIXFc in subjects with hemophilia B.

Subjects were assigned by the investigator based on the clinical site's standard of care to 1 of 4 treatment arms: Arm 1, weekly prophylaxis (50 IU/kg every 7 days; dose adjusted to maintain factor levels); Arm 2, individualized interval prophylaxis (100 IU/kg dose, every 10 days; interval adjusted to maintain factor levels); Arm 3, episodic (on-demand) treatment as needed for bleeding episodes (20-100 IU/kg, depending on bleeding severity); Arm 4, perioperative management.

The dose (in Arm 1) and the interval (in Arm 2) were adjusted during the study to maintain a trough level of 1 to 3 IU/dL above baseline, or higher if clinically necessary. The end of the study was defined as the point in time when pre-specified criteria were reached (e.g., 53 subjects completed ≥50 rFIXFc exposure days, in conjunction with additional criteria).

Statistical Analysis

Data from the B-LONG study were used to evaluate the relationship between bleeding tendency and FIX activity in individuals with severe hemophilia B. A 3-compartment population pharmacokinetics model of rFIXFc was developed based on the activity-time profiles of 12 subjects from a phase ½a study 7 of rFIXFc and 123 subjects from the B-LONG study.

Individual post hoc pharmacokinetic parameters were used to construct continuous FIX activity-time profiles for each dose of rFIXFc administered over the course of the study for all individual subjects in the B-LONG study.

The cumulative time spent under the target trough FIX levels of 1, 3, and 5 IU/dL for each individual on-study was calculated and normalized to obtain an annualized time under the respective target trough level, expressed in days. The time spent under the target trough level (1, 3, or 5 IU/dL) is summarized by treatment arm (individualized weekly prophylaxis, individualized interval prophylaxis, and episodic treatment).

Negative binomial regression models, unadjusted and adjusted for the number of pre-study bleeding episodes and pre-treatment switch (i.e., switching from on-demand to prophylaxis), were used to evaluate the association between the annualized time spent under the target trough FIX activity levels of 1, 3, or 5 IU/dL and the number of bleeding episodes experienced on-study Subjects.

Results

Of the 123 subjects in the study, 117 subjects in the prophylactic and episodic arms had available information for calculating time spent under target trough levels; 106 subjects had available efficacy data for inclusion in multivariable models. Of the 117 subjects evaluated for time under the target trough, 2 declined to switch to study drug, 1 did not participate in the efficacy period, 7 were missing information regarding pre-study bleeding episodes, and 1 was missing information regarding pre-study treatment. Demographic and baseline characteristics for these 106 subjects were consistent with that expected in the severe hemophilia B population.

The median time under the target trough level is summarized by treatment arm in Table 29. The annualized median time spent under the 1 IU/dL target trough level in both prophylaxis arms was 0 days, while the annualized median time spent under the 1 IU/dL target trough level in the episodic arm was 146.28 days.

TABLE 29

Annualized Time (Days) Under Target FIX Trough Levels by Treatment Arm in the B-LONG Study[a]

| Target trough level | Weekly prophylaxis (N = 62) | Individualized interval prophylaxis (n = 28) | Episodic treatment (n = 27) |
|---|---|---|---|
| 1 IU/dL | | | |
| Mean (SD) | 0.1 (0.81) | 0.00 (0.00) | 140.12 (95.79) |
| Median | 0.00 | 0.00 | 146.28 |
| IQR | 0.00, 0.00 | 0.00, 0.00 | 65.5, 214.2 |

TABLE 29-continued

Annualized Time (Days) Under Target FIX Trough Levels by Treatment Arm in the B-LONG Study[a]

| Target trough level | Weekly prophylaxis (N = 62) | Individualized interval prophylaxis (n = 28) | Episodic treatment (n = 27) |
|---|---|---|---|
| 3 IU/dL | | | |
| Mean (SD) | 37.67 (43.47) | 35.01 (32.39) | 248.70 (76.33) |
| Median | 19.86 | 34.12 | 270.47 |
| IQR | 3.61, 64.92 | 8.87, 50.75 | 207.9, 298.6 |
| 5 IU/dL | | | |
| Mean (SD) | 121.22 (73.28) | 118.46 (52.84) | 293.19 (43.06) |
| Median | 140.48 | 129.32 | 308.54 |
| IQR | 51.49, 178.5 | 78.74, 162.4 | 257.1, 302.6 |

FIX, factor IX; SD, standard deviation, IQR, interquartile range.

[a]The median (IQR) on-study weekly dose among subjects with time under target trough information in Arm 1 was 45.2 IU/kg (38.1, 53.7 IU/kg; n = 61) and in Arm 2 was 57.1 IU/kg (53.5, 68.9 IU/kg; n = 26).

The predicted ABRs by annualized time (in days) under the targeting trough FIX levels of 1, 3, and 5 IU/dL based on the adjusted negative binomial regression model are shown in FIG. 37.

Based on the unadjusted negative binomial regression model, for every additional day spent under the target troughs of 1, 3, and 5 IU/dL, there was an estimated increase in the overall ABR of 0.8%, 0.5%, and 0.5%, respectively (P<0.0001 for all comparisons). Based on the adjusted negative binomial regression model, for every additional day spent under the target troughs of 1, 3, and 5 IU/dL, there was an estimated increase in the overall ABR of 0.5%, 0.3%, and 0.2%, respectively (P<0.05 for all comparisons).

This is the first report to demonstrate a relationship between bleeding tendency and time spent under 1, 3, and 5 IU/dL FIX activity in hemophilia B subjects. The majority of subjects in the prophylaxis arms (60%) did not spend any time under 1 IU/dL FIX activity during the trial. Results of this study demonstrated a significant association between increased duration of time spent under a target therapeutic FIX activity level (1, 3, or 5 IU/dL) and an increased bleeding tendency, after adjusting for baseline bleeding tendency in the past 12 months and switching from an on-demand therapy at baseline to a prophylaxis regimen on-study. Although all trough levels were associated with changes in ABR, a steeper slope was seen with a target trough of 1 IU/dL; hence, that trough is more sensitive to change and potentially more meaningful to subjects compared with troughs of 3 and 5 IU/dL. The statistical power to determine a change in bleeding probability under a target trough of 1 IU/dL was limited due to the relatively small number of subjects spending time under this activity level. These results confirm the importance of a minimum therapeutic threshold of 1 IU/dL for prophylactic FIX replacement therapy and provide additional support for the use of 1% as the minimal trough level in the population pharmacokinetic simulations for establishing effective rFIXFc prophylaxis regimens.

Example 13. Dosing Long-Lasting Recombinant Factor VIII-Fc Fusion Protein (rFVIIIFc) Clotting Factors A-LONG Study Design A-LONG is a phase 3, open-label, multicenter, partially randomized study of the PK, efficacy, and safety of rFVIIIFc in patients with severe hemophilia A.

Methods:

The study enrolled 165 subjects into 1 of 3 treatment arms (FIG. 38). In Arm 1, dosing recommendations were based on individual subject PK evaluations to target a steady-state FVIII activity trough of 1% to 3% (1-3 IU/dL) or higher, with additional regimen adjustments made if the subject experienced ≥2 spontaneous bleeding episodes over a rolling 8-week period.

Study Population:

Previously treated males aged ≥12 years with severe hemophilia A (<1 IU/dL [1%] endogenous FVIII activity or severe genotype) and treated prophylactically, or treated episodically and with a history of ≥12 bleeding events in the 12 months prior to the study. Exclusion criteria: history of inhibitors (neutralizing antibodies), history of hypersensitivity associated with any FVIII concentrate or intravenous immunoglobulin, or other coagulation disorders.

Prophylactic Dosing Subgroup Analysis:

The subgroup of subjects with ≥6 months on-study who were (1) previously on prophylactic therapy (≥2 injections/week) and assigned to the individualized prophylaxis arm (Arm 1), or (2) previously treated episodically and assigned to the weekly prophylaxis arm (Arm 2; FIG. 38) was analyzed. Self-reported information collected at the time of study enrollment from patient logs and/or hospital records included prestudy prophylactic dose and dosing frequency (infusions per week), and the number of bleeding episodes in the prior 12 months. On-study parameters recorded included rFVIIIFc dose and dosing interval (number of days), and the median ABR for the last 3 months on-study, once subjects' treatment regimens had stabilized. Subjects were stratified according to their final on-study rFVIIIFc dose and dosing interval, and the corresponding self-reported prestudy FVIII dose and infusion frequency were analyzed. Subjects were also stratified according to their prestudy FVIII infusion frequency, and their final on-study dosing interval was examined. Population PK models for rFVIIIFc and ADVATE® were developed based on A-LONG PK data (collected in 164 subjects over ≤52 weeks of treatment, and in 30 subjects participating in the sequential PK analysis, respectively), and factors that may be determinants of variability in FVIII activity were identified. Subjects were monitored for the development of inhibitors and adverse events. The presence of inhibitors was assessed by the Nijmegen-modified Bethesda assay. Descriptive statistics included the median and interquartile range (IQR) values for demographic characteristics, estimated number of prestudy bleeding events, and on-study ABR for the prophylactic dosing subgroups of Arms 1 and 2.

Results: Study Participants—

Baseline characteristics of the subjects in the prophylactic dosing subgroups were consistent with the overall A-LONG study population and were representative of a population with severe hemophilia A (FIG. 38). Among Arm 1 subjects previously treated prophylactically, >80% were on their prestudy regimen for 12 months; the most common products used for prophylaxis prior to study entry were Kogenate/Helixate (25/80 subjects; 31.3%) and rFVIII (22/80 subjects; 27.5%).

Dosing Interval Analysis:

Nearly all subjects (79/80; 98.8%) had a decrease in the number of prophylactic infusions administered per week on-study compared with their self-reported prestudy infusion frequency, as shown in FIG. 39. Prior to entering the study, most subjects (65/80; 81.3%) reported a FVIII prophylactic regimen of 3 times per week. On-study, the most common rFVIIIFc prophylactic dosing intervals were every 3 days (29/80 subjects; 36.3%), twice weekly (23/80 subjects; 28.8%), and every 5 days (24/80 subjects; 30.0%).

On-Study rFVIIIFc Dosing:

The median on-study rFVIIIFc dose was 50 IU/kg, most commonly administered every 5 days (19/37 subjects; 51.4%), or every 3 days (16/37 subjects; 43.2% [Table 30, solid box]). At study end, 22/80 subjects (27.5%) were taking the twice-weekly starting regimen of 25 IU/kg on Day 1 and 50 IU/kg on Day 4 (Table 30, dashed box). Comparison of individual subject half-lives for rFVIII and rFVIIIFc in subjects from the A-LONG sequential PK subgroup indicates a longer half-life for rFVIIIFc compared with rFVIII (1.53-fold longer; P<0.0001), 5 which supports the increased dosing intervals for rFVIIIFc observed in the trial.

TABLE 30

Prescribed Prophylactic
Dose and Dosing Interval (End of Study) in Arm 1 Subjects

| Dose per injection (IU/kg)[a] | Last on-study dosing frequency: Every 3 days | Twice weekly | Every 4 days | Every 5 days | Total, n |
|---|---|---|---|---|---|
| 25-35 | 4 | — | — | — | 4 |
| 25/50[b] | — | 22 | — | — | 22 |
| 40-45 | 2 | 1 | — | — | 3 |
| 50 | 16 | — | 2 | 19 | 37 |
| 60-65 | 7 | — | 2 | 5 | 14 |
| Total | 29 | 23 | 4 | 24 | 80 |

[a]Black boxes indicate most common dose at study end (50 IU/kg); dashed box indicates second most common regimen at study end (25 IU/kg (Day 1); 50 IU/kg (Day 4)).
[b]Initial dosing regimen of 25 IU/kg on Day 1, followed by 50 IU/kg on Day 4.

Factor Consumption:

Overall, weekly factor consumption for prophylaxis remained consistent for the majority of patients; the median difference in weekly dose (last on-study minus prestudy) was 4.4 (data not shown) Prestudy median (IQR) weekly dose: 78.0 IU/kg (60.0, 102.5). On-study (last 3 months) median (IQR) weekly dose: 79.2 IU/kg (72.1, 111.5).

Prior Episodic/Weekly Prophylaxis Subgroup (Arm 2):

Per protocol, dose and dosing interval were unchanged in Arm 2 during the course of the study. The median (min, max) dose of rFVIIIFc was 65.9 (51.2, 76.5) IU/kg per week.

Efficacy Outcome: ABR:

Median ABR in the last 3 months on-study was lower than the self-reported prestudy median number of bleeding episodes across all rFVIIIFc dosing interval subgroups, as shown in FIG. 40. Overall, subjects in the prior prophylaxis/individualized prophylaxis subgroup (Arm 1) reported a median of 6.0 bleeding episodes in the 12 months prior to study; in the last 3 months on-study they had a median ABR of 0.0. Subjects in the prior episodic/weekly prophylaxis subgroup (Arm 2) reported a median of 29.0 bleeding episodes in the 12 months prior to study; in the last 3 months on-study they had a median ABR of 4.0.

Simulation of FVIII Activity (Population PK Modeling):

Dosing regimen simulations using population PK models of ADVATE® and rFVIIIFc predicted the proportion of subjects who would maintain a trough FVIII activity level at steady-state above 1 IU/dL (1%; FIG. 41). The values reported are the lowest and highest predicted proportions of subjects, respectively, who would remain protected (e.g., >1%) during the shortest and longest portions of the dosing period, respectively.

Example 14. The Bleeding Tendency in Relation to Predicted FVIII Activity Levels in Severe Hemophilia A Patients Treated with Recombinant Factor VIII Fc Fusion Protein (rFVIIIFc)

The objective of this post hoc analysis was to evaluate the relationship between the annualized time spent under target 1 IU/dL, 3 IU/dL, and 5 IU/dL FVIII activity levels and clinical outcomes (e.g., overall, spontaneous, traumatic, and joint bleeds), as well as the probability of experiencing ≥1 bleed given time spent under the target trough level.

Methods:

Subjects enrolled in the A-LONG study who had available efficacy data were used in this analysis. The study included previously-treated male subjects (≥12 years of age) with severe hemophilia A and no history of FVIII inhibitors. Subjects on prophylaxis prior to study entry were assigned to treatment in Arm 1, individualized prophylaxis (twice-weekly dosing; 25 IU/kg on Day 1 and 50 IU/kg on Day 4 during the first week, followed by 25-65 IU/kg every 3-5 days; dose and interval adjusted to maintain factor trough levels of 1 to 3 IU/dL above baseline, or higher if clinically necessary). Subjects on prior episodic treatment were randomized to Arm 2, weekly prophylaxis (65 IU/kg), or Arm 3, episodic (on-demand) treatment as needed for bleeding episodes (10-50 IU/kg, depending on bleeding severity). The end of the study was defined as the point in time when prespecified criteria were reached (e.g., 104 subjects completed ≥50 rFVIIIFc exposure days, in conjunction with additional criteria).

Data from the A-LONG study were used to evaluate the relationship between bleeding tendency and FVIII activity in individuals with severe hemophilia A. A two-compartment population pharmacokinetics (PK) model of rFVIIIFc was developed based on FVIII activity data collected from a total of 180 subjects (16 subjects from a phase 1 study and 164 subjects from the phase 3 A-LONG study). Individual post hoc PK parameters were used to construct continuous FVIII activity-over-time profiles for each dose of rFVIIIFc administered over the course of the study for all individual subjects in the A-LONG study.

The cumulative annualized time spent under the target trough FVIII levels of 1 IU/dL, 3 IU/dL, and 5 IU/dL, for each individual on-study, was calculated and normalized to obtain an annualized time under the respective target trough level, expressed in days. The time spent under the target trough level (1 IU/dL, 3 IU/dL, and 5 IU/dL) is summarized by treatment arm (i.e., individualized prophylaxis, weekly prophylaxis, and episodic treatment). Negative binomial regression models, unadjusted and adjusted for the annualized number of pre-study bleeding episodes and pre-treatment switch (i.e., switching from on-demand to prophylaxis), were used to evaluate the association between the annualized time under the target trough FVIII levels of 1 IU/dL, 3 IU/dL, and 5 IU/dL and the numbers of spontaneous, traumatic, and joint bleeds, and bleeds overall. Logistic regression models, unadjusted and adjusted for the number of pre-study bleeding episodes and pre-treatment switch, were used to evaluate the association between the time spent under the target trough level of 1 IU/kg, 3 IU/kg, and 5 IU/kg and the probability of experiencing bleeding. Data were also stratified by the type of bleed (e.g., spontaneous, traumatic, or joint bleeds).

Results:

Of the 165 subjects who enrolled in the A-LONG study, the time spent under the target troughs was calculated for 163 subjects; 162 subjects had available data for inclusion in multivariable models. Demographic and baseline characteristics of subjects enrolled in A-LONG were consistent with that expected in a severe hemophilia A population (Table 31).

TABLE 31

Baseline Demographic and Clinical Characteristics

| Characteristic | Total A-LONG population (n = 165) |
|---|---|
| Median (min, max) age, y | 30.0 (12, 65) |
| Median (min, max) weight, kg | 71.60 (42.0, 127.4) |
| Median (min, max) BMI, kg/$m^2$ | 23.90 (15.3, 37.4) |
| Race, n (%) | |
| White | 107 (64.8) |
| Asian | 43 (26.1) |
| Black | 10 (6.1) |
| Other | 5 (3.0) |
| Geographic location, n (%) | |
| North America | 56 (33.9) |
| Europe | 41 (24.8) |
| Other | 68 (41.2) |
| Received pre-study episodic treatment, n/N (%) | 78/165 (47.3) |
| Estimated median (min, max) number of bleeding episodes during the 12 months prior to the start of the study | 16 (0, 120) |

BMI, body mass index.

The annualized median time under the target trough level is summarized by treatment group in Table 32 and FIG. 42. The annualized median time spent under the 1 IU/dL target trough level was 2.17 days in the individualized prophylaxis arm, 51.55 days in the weekly prophylaxis arm, and 224.8 days in the episodic treatment arm.

TABLE 32

Annualized Time (Days) Under Target FVIII Trough Levels by Treatment Arm in the A-LONG Study[a]

| Target trough level | Individualized prophylaxis (n = 117) | Weekly prophylaxis (n = 23) | Episodic treatment (n = 23) |
|---|---|---|---|
| 1 IU/dL | | | |
| Mean (SD) | 9.5 (20.2) | 54.81 (55.9) | 200.7 (77.0) |
| Median | 2.17 | 51.55 | 244.8 |
| IQR | 0.00, 8.49 | 0.84, 98.81 | 140.3, 260.6 |
| 3 IU/dL | | | |
| Mean (SD) | 50.19 (40.8) | 126.2 (61.5) | 246.3 (60.5) |
| Median | 43.72 | 130.3 | 266.6 |
| IQR | 21.75, 66.57 | 74.58, 176.7 | 195.2, 292.5 |
| 5 IU/dL | | | |
| Mean (SD) | 91.36 (46.9) | 159.6 (59.5) | 267.1 (51.4) |
| Median | 92.39 | 167.3 | 284.0 |
| IQR | 66.44, 117.0 | 123.0, 205.8 | 225.8, 305.2 |

FVIII, factor VIII; SD, standard deviation, IQR, interquartile range.

[a]The median (IQR) on-study weekly dose among subjects with time under target trough information in Arm 1 was 77.9 IU/kg (72.3, 91.2 IU/kg; n = 117) and in Arm 2 was 65.6 IU/kg (64.2, 68.2 IU/kg; n = 23).

The predicted ABRs by annualized time (in days) under the target trough FVIII levels of 1 IU/dL, 3 IU/dL, and 5 IU/dL based on the unadjusted and adjusted negative binomial regression models are shown in FIGS. 43A and B, respectively. Based on both the unadjusted and adjusted negative binomial regression models, a significant increase was observed in the predicted overall ABR for each additional annualized day under the target troughs of 1 IU/dL, 3 IU/dL, and 5 IU/dL (FIG. 43). Based on the unadjusted negative binomial regression model, for every additional day spent under the target troughs of 1 IU/dL, 3 IU/dL, and 5 IU/dL, there was an estimated increase in the overall ABR of 1%, 0.9%, and 0.9%, respectively ($P<0.0001$ for all comparisons). Based on the adjusted negative binomial regression model, for every additional day spent under the target troughs of 1 IU/dL, 3 IU/dL, and 5 IU/dL, there was an estimated increase in the overall ABR of 0.9%, 0.8%, and 0.8%, respectively ($P<0.0001$ for all comparisons). For spontaneous bleeds, traumatic bleeds, and joint bleeds, a significant increase was also observed in the predicted ABR for each additional day under the target trough (1 IU/dL, 3 IU/dL, and 5 IU/dL), based on both the unadjusted and adjusted negative binomial regression models ($P\leq0.0003$).

The adjusted probability of experiencing any bleed according to the time (in days) under target trough FVIII levels of 1 IU/dL, 3 IU/dL, and 5 IU/dL is shown in FIG. 44. Results for the adjusted probability of experiencing spontaneous, traumatic, or joint bleeds according to time (in days) under target trough FVIII levels of 1 IU/dL, 3 IU/dL, and 5 IU/dL are also shown in FIG. 44. As the time spent under the target trough FVIII levels of 1 IU/dL, 3 IU/dL, and 5 IU/dL increased, the adjusted probability of experiencing all types of bleeding episodes increased.

Example 15. Pharmacokinetics of Recombinant Factor VIII Fc Fusion Protein (rFVIIIFc) in Previously-Treated Children with Severe Hemophilia A (Kids-ALONG)

Kids A-LONG was a phase 3 open-label study evaluating the safety, efficacy, and pharmacokinetics of recombinant factor VIII Fc fusion protein (rFVIIIFc), in previously treated children with severe hemophilia A (endogenous FVIII level <1 IU/dL [<1%]).

Methods:

The study enrolled 71 subjects. The starting rFVIIIFc regimen was twice-weekly prophylaxis (Day 1, 25 IU/kg; Day 4, 50 IU/kg); dose (≤80 IU/kg) and dosing interval (≥2 days) were adjusted as needed. A subset of subjects had sequential pharmacokinetic evaluations of FVIII and rFVIIIFc. The primary endpoint was development of inhibitors (neutralizing antibodies). Secondary endpoints included pharmacokinetics, annualized bleeding rate (ABR) and number of infusions required to control a bleed.

Results:

No subject developed an inhibitor to rFVIIIFc. Adverse events were typical of a pediatric hemophilia population. rFVIIIFc half-life was prolonged relative to FVIII, consistent with observations in adults and adolescents. The median ABR was 1.96 overall, and 0.00 for spontaneous bleeds; 46.4% of subjects reported no bleeding episodes on study. 93.0% of bleeding episodes were controlled with 1-2 infusions. The median average weekly rFVIIIFc prophylactic dose was 88.1 IU/kg. At study end, 62/69 of subjects (90%) were infusing twice-weekly. Among subjects previously on FVIII prophylaxis, 74% reduced their dosing frequency with rFVIIIFc.

Pharmacokinetics:

Of the 60 subjects dosed with rFVIIIFc in the pharmacokinetics subgroup, 54 (<6 years of age, n=23; 6 to <12 years of age, n=31) had evaluable pharmacokinetic data by the one-stage clotting assay. The activity-time profiles in both age cohorts, adjusted for baseline and residual prestudy FVIII activity, were adequately characterized by noncompartmental analysis with moderate inter-subject variability. All numbers are given in arithmetic mean (95% confidence interval). The terminal half-life of rFVIIIFc in subjects aged <6 years of age and 6 to <12 years of age was 12.67 (11.23, 14.11) hours and 14.88 (11.98, 17.77) hours, respectively. An age-dependent effect on clearance was observed, with mean clearance higher in the younger cohort of 3.60 (3.13, 4.07) mL/h/kg than in the older cohort of 2.78 (2.44, 3.13) mL/h/kg. Incremental recovery of rFVIIIFc was consistent between the age cohorts (mean of approximately 2 IU/dL per IU/kg) (with the younger cohort having 1.92 (1.80, 2.04) IU/dL per IU/kg and the older cohort having 2.44 (2.07, 2.80) IU/dL per IU/kg. The mean recovery time was 17.24 (15.40, 19.07) hours in the younger cohort and 20.90 (17.06, 24.74) in the older cohort. The volume of distribution at steady state was 58.58 (54.90, 62.27) mL/kg for the younger cohort and 52.13 (45.25, 59.01) mL/kg for the older cohort. The dose normalized area under the concentration-time curve was 30.04 (26.45, 33.63) IU*h/dL per IU/kg for the younger cohort and 41.87 (34.00, 49.75) IU*h/dL per IU/kg for the older cohort.

Example 16. Population Pharmacokinetic Analysis of Long-Acting Recombinant Factor VIII-Fc Fusion Protein (rFVIIIFc) in Adult, Adolescent, and Pediatric Patients with Severe Haemophilia A The population pharmacokinetic (popPK) data for the adult/adolescent (≥12 years) and pediatric studies discussed above were combined to develop a new rFVIIIFc popPK model. As before (see Examples 9 and 11; Tables 18, 24, and 25), a final model (Table 33) was developed from base and covariate models.

TABLE 33

Final Model Population Parameter Estimates and Bootstrap-derived Nonparametric 95% CI's

| Parameter | Population Estimate | % RSE | Nonparametric 95% CI[a] |
|---|---|---|---|
| Clearance, CL, [dL/h] | 1.56 | 2.01 | 1.49, 1.64 |
| Central Volume, V1, [dL] | 32.8 | 1.22 | 31.5, 33.6 |
| Intercompartmental Clearance, Q, [dL/h] | 0.157 | 77.1 | 0.0468, 1.18 |
| Peripheral Volume, V2, [dL] | 2.93 | 19.9 | 2.41, 5.43 |
| Allometric exponent on CL/Q | 0.704 | 4.47 | 0.640, 0.760 |
| Allometric exponent on V1/V2 | 0.945 | 2.17 | 0.908, 0.987 |
| Exponent on VWF~CL | −0.413 | 10.1 | −0.497, −0.330 |
| $\omega^2_{CL}$ (IIV; inter-individual variability) | 0.0585 | 12.4 | 0.0432, 0.0741 |
| $\omega^2_{V1}$ (IIV) | 0.0265 | 13.8 | 0.0198, 0.0337 |
| $\text{Covariance}_{CL:V1}$ (IIV) | 0.0185 | 23.5 | 0.0109, 0.0266 |
| ω2CL (IOV; inter-occasion variability) | 0.0470 | 13.9 | 0.0342, 0.0604 |
| $\omega^2_{V1}$ (IOV) | 0.00987 | 41.9 | 0.00323, 0.0197 |
| $\text{Covariance}_{CL:V1}$ (IOV) | 0.0110 | 40.2 | 0.00444, 0.0228 |
| Additive error, Phase 1/2a study, [IU/dL] | 0.402 | 20.3 | 0.172, 0.600 |
| Additive error, Phase 3 and Pediatric study, [IU/dL] | 0.217 | 14.6 | 0.161, 0.285 |
| Proportional error, Phase 1/2a and Phase 3 study [%] | 15.4 | 8.44 | 12.7, 17.7 |
| Proportional error, Pediatric study [%] | 21.2 | 6.70 | 18.1, 24.3 |

The model-predicted steady state (SS) peaks and troughs of the rFVIIIFc activity-time profiles for various rFVIIIFc dosing regimens are presented in Table 34 (for adult/adolescents (≥12 years)), Table 35 (6 to <12 year) and Table 36 (<6 year age cohorts). These results can be considered when determining the chronic dosing regimens for prophylaxis.

TABLE 34

Predicted steady state (SS) peaks and troughs of the rFVIIIFc activity-time profiles with 50 IU/kg dose administered every 3, 4, or 5 days for ≥12 years.

| Unit Dose Level | Percentile Of Subjects | Dosing Frequency: Every 3 Days Peak | Every 3 Days Trough | Every 4 Days Peak | Every 4 Days Trough | Every 5 Days Peak | Every 5 Days Trough | Every 7 Days Peak | Every 7 Days Trough |
|---|---|---|---|---|---|---|---|---|---|
| 25 IU/kg | 5% | 37.8 | <0.5[a] | 37.0 | <0.5[a] | 36.7 | <0.5[a] | — | — |
| | 25% | 46.4 | 1.07 | 45.0 | <0.5[a] | 44.1 | <0.5[a] | — | — |
| | 50% | 53.1 | 2.39 | 51.1 | 0.922 | 50.1 | <0.5[a] | — | — |
| | 75% | 60.2 | 4.71 | 58.2 | 2.10 | 56.7 | 0.932 | — | — |
| | 95% | 73.3 | 10.6 | 69.9 | 5.49 | 68.5 | 2.79 | — | — |
| 40 IU/kg | 5% | 60.5 | 0.522 | 59.2 | <0.5[a] | 58.7 | <0.5[a] | — | — |
| | 25% | 74.3 | 1.71 | 71.9 | 0.589 | 70.6 | <0.5[a] | — | — |
| | 50% | 85.0 | 3.83 | 81.7 | 1.48 | 80.2 | 0.613 | — | — |
| | 75% | 96.3 | 7.53 | 93.1 | 3.35 | 90.8 | 1.49 | — | — |
| | 95% | 117 | 16.9 | 112 | 8.78 | 110 | 4.47 | — | — |
| 50 IU/kg | 5% | 75.7 | 0.654 | 73.9 | <0.5[a] | 73.4 | <0.5[a] | — | — |
| | 25% | 92.9 | 2.14 | 89.9 | 0.737 | 88.3 | <0.5[a] | — | — |
| | 50% | 106 | 4.78 | 102 | 1.84 | 100 | 0.766 | — | — |
| | 75% | 120 | 9.41 | 116 | 4.19 | 113 | 1.86 | — | — |
| | 95% | 147 | 21.1 | 140 | 11.0 | 137 | 5.59 | — | — |
| 65 IU/kg | 5% | 98.3 | 0.850 | 96.1 | <0.5[a] | 95.4 | <0.5[a] | 94.2 | <0.5[a] |
| | 25% | 121 | 2.78 | 117 | 0.958 | 115 | <0.5[a] | 114 | <0.5[a] |
| | 50% | 138 | 6.22 | 133 | 2.40 | 130 | 0.995 | 130 | <0.5[a] |
| | 75% | 157 | 12.2 | 151 | 5.45 | 148 | 2.42 | 146 | 0.586 |
| | 95% | 191 | 27.5 | 182 | 14.3 | 178 | 7.27 | 177 | 2.63 |

[a]Below the level of quantitation of 0.5 IU/dL.

TABLE 35

Predicted steady state (SS) peaks and troughs of the rFVIIIFc activity-time profiles with various dose levels administered every 3, 4, or 5 days for 6 to <12 years.

| Unit Dose Level | Percentile Of Subjects | Dosing Frequency: Every 2 Days Peak | Every 2 Days Trough | Every 3 Days Peak | Every 3 Days Trough | Every 4 Days Peak | Every 4 Days Trough | Every 5 Days Peak | Every 5 Days Trough |
|---|---|---|---|---|---|---|---|---|---|
| 25 IU/kg | 5% | 37.7 | 0.868 | 35.3 | <0.5[a] | 35.2 | <0.5[a] | 34.2 | <0.5[a] |
| | 25% | 45.6 | 2.29 | 43.1 | 0.586 | 42.3 | <0.5[a] | 41.6 | <0.5[a] |
| | 50% | 52.1 | 3.97 | 49.3 | 1.25 | 48.4 | <0.5[a] | 47.5 | <0.5[a] |
| | 75% | 59.7 | 6.40 | 56.3 | 2.35 | 54.7 | 0.921 | 54.0 | <0.5[a] |
| | 95% | 72.5 | 12.9 | 67.7 | 5.07 | 66.1 | 2.43 | 65.7 | 1.15 |
| 40 IU/kg | 5% | 60.3 | 1.39 | 56.5 | <0.5[a] | 56.3 | <0.5[a] | 54.7 | <0.5[a] |
| | 25% | 73.0 | 3.67 | 69.0 | 0.937 | 67.6 | <0.5[a] | 66.5 | <0.5[a] |
| | 50% | 83.3 | 6.34 | 78.9 | 2.00 | 77.5 | 0.638 | 76.0 | <0.5[a] |
| | 75% | 95.5 | 10.2 | 90.1 | 3.76 | 87.6 | 1.47 | 86.4 | 0.585 |
| | 95% | 116 | 20.6 | 108 | 8.12 | 106 | 3.88 | 105 | 1.85 |
| 50 IU/kg | 5% | 75.4 | 1.74 | 70.6 | <0.5[a] | 70.3 | <0.5[a] | 68.4 | <0.5[a] |
| | 25% | 91.3 | 4.58 | 86.2 | 1.17 | 84.5 | <0.5[a] | 83.1 | <0.5[a] |
| | 50% | 104 | 7.93 | 98.6 | 2.49 | 96.8 | 0.797 | 95.0 | <0.5[a] |
| | 75% | 119 | 12.8 | 113 | 4.70 | 109 | 1.84 | 108 | 0.731 |
| | 95% | 145 | 25.7 | 135 | 10.1 | 132 | 4.86 | 131 | 2.31 |
| 65 IU/kg | 5% | 98.0 | 2.26 | 91.8 | <0.5[a] | 91.4 | <0.5[a] | 88.9 | <0.5[a] |
| | 25% | 119 | 5.96 | 112 | 1.52 | 110 | <0.5[a] | 108 | <0.5[a] |
| | 50% | 135 | 10.3 | 128 | 3.24 | 126 | 1.04 | 123 | <0.5[a] |
| | 75% | 155 | 16.6 | 146 | 6.10 | 142 | 2.39 | 140 | 0.950 |
| | 95% | 189 | 33.4 | 176 | 13.2 | 172 | 6.31 | 171 | 3.00 |
| 80 IU/kg | 5% | 121 | 2.78 | 113 | 0.599 | 113 | <0.5[a] | 109 | <0.5[a] |
| | 25% | 146 | 7.33 | 138 | 1.87 | 135 | 0.552 | 133 | <0.5[a] |
| | 50% | 167 | 12.7 | 158 | 3.99 | 155 | 1.28 | 152 | <0.5[a] |
| | 75% | 191 | 20.5 | 180 | 7.51 | 175 | 2.95 | 173 | 1.17 |
| | 95% | 232 | 41.1 | 217 | 16.2 | 212 | 7.77 | 210 | 3.69 |

[a]Below the level of quantitation of 0.5 IU/dL.

TABLE 36

Predicted steady state (SS) peaks and troughs of the rFVIIIFc activity-time profiles with various dose levels administered every 3, 4, or 5 days for <6 years.

| Unit Dose Level | Percentile Of Subjects | Dosing Frequency: Every 2 Days Peak | Every 2 Days Trough | Every 3 Days Peak | Every 3 Days Trough | Every 4 Days Peak | Every 4 Days Trough | Every 5 Day Peak | Every 5 Day Trough |
|---|---|---|---|---|---|---|---|---|---|
| 25 IU/kg | 5% | 35.6 | 0.512 | 33.7 | <0.5[a] | 33.8 | <0.5[a] | 32.9 | <0.5[a] |
| | 25% | 42.9 | 1.43 | 41.1 | <0.5[a] | 40.6 | <0.5[a] | 40.1 | <0.5[a] |
| | 50% | 48.8 | 2.54 | 47.0 | 0.700 | 46.5 | <0.5[a] | 45.8 | <0.5[a] |
| | 75% | 55.9 | 4.22 | 53.5 | 1.39 | 52.4 | <0.5[a] | 51.8 | <0.5[a] |
| | 95% | 67.3 | 8.75 | 64.2 | 3.13 | 63.3 | 1.42 | 63.2 | 0.586 |
| 40 IU/kg | 5% | 57.0 | 0.820 | 54.0 | <0.5[a] | 54.0 | <0.5[a] | 52.6 | <0.5[a] |
| | 25% | 68.7 | 2.28 | 65.8 | <0.5[a] | 65.0 | <0.5[a] | 64.2 | <0.5[a] |
| | 50% | 78.1 | 4.06 | 75.3 | 1.12 | 74.3 | <0.5[a] | 73.2 | <0.5[a] |
| | 75% | 89.5 | 6.75 | 85.5 | 2.22 | 83.8 | 0.738 | 82.8 | <0.5[a] |
| | 95% | 108 | 14.0 | 103 | 5.01 | 101 | 2.27 | 101 | 0.938 |
| 50 IU/kg | 5% | 71.2 | 1.03 | 67.4 | <0.5[a] | 67.5 | <0.5[a] | 65.8 | <0.5[a] |
| | 25% | 85.8 | 2.85 | 82.2 | 0.613 | 81.2 | <0.5[a] | 80.2 | <0.5[a] |
| | 50% | 97.7 | 5.07 | 94.1 | 1.40 | 92.9 | <0.5[a] | 91.5 | <0.5[a] |
| | 75% | 112 | 8.44 | 107 | 2.78 | 105 | 0.922 | 104 | <0.5[a] |
| | 95% | 135 | 17.5 | 128 | 6.26 | 127 | 2.84 | 126 | >1.17 |
| 65 IU/kg | 5% | 92.6 | 1.33 | 87.7 | <0.5[a] | 87.8 | <0.5[a] | 85.5 | <0.5[a] |
| | 25% | 112 | 3.71 | 107 | 0.797 | 106 | <0.5[a] | 104 | <0.5[a] |
| | 50% | 127 | 6.59 | 122 | 1.81 | 121 | 0.505 | 119 | <0.5[a] |
| | 75% | 145 | 11.0 | 139 | 3.61 | 136 | 1.20 | 135 | <0.5[a] |
| | 95% | 175 | 22.7 | 167 | 8.14 | 165 | 3.69 | 164 | 1.52 |
| 80 IU/kg | 5% | 114 | 1.64 | 108 | <0.5[a] | 108 | <0.5[a] | 105 | <0.5[a] |
| | 25% | 137 | 4.56 | 132 | 0.981 | 130 | <0.5[a] | 128 | <0.5[a] |
| | 50% | 156 | 8.12 | 151 | 2.32 | 149 | 0.621 | 146 | <0.5[a] |
| | 75% | 179 | 13.5 | 171 | 4.44 | 168 | 1.48 | 166 | 0.542 |
| | 95% | 215 | 28.0 | 206 | 10.0 | 203 | 4.54 | 202 | 1.88 |

[a]Below the level of quantitation of 0.5 IU/dL.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

TABLE 37

Polynucleotide Sequences: FIX-Fc

A. FIX-Fc Chain DNA Sequence (SEQ ID NO: 1, which encodes SEQ ID NO: 2)

pSYN-FIX-030 Nucleotide sequence (nt 1 to 7583):

FIX exon 1 (signal peptide, 1st amino acid propeptide); nt 690-777

FIX mini intron: nt 778-1076

FIX propeptide sequence: nt 1077-1126

Mature FIX sequence nt 1127-2371

Fc: nt 2372-3052

```
gcgcgcgttgacattgattattgactagttattaatagtaatcaattacggggtcattagttcatagcccatatatgg
agttccgcgttacataacttacggtaaatggcccgcctggctgaccgcccaacgacccccgcccattgacgtcaataa
tgacgtatgttcccatagtaacgccaatagggactttccattgacgtcaatgggtggagtatttacggtaaactgccc
acttggcagtacatcaagtgtatcatatgccaagtacgccccctattgacgtcaatgacggtaaatggcccgcctggc
attatgcccagtacatgaccttatgggactttcctacttggcagtacatctacgtattagtcatcgctattaccatgg
tgatgcggttttggcagtacatcaatgggcgtggatagcggtttgactcacggggatttccaagtctccaccccattg
acgtcaatgggagtttgttttggcaccaaaatcaacgggactttccaaaatgtcgtaacaactccgccccattgacgc
aaatgggcggtaggcgtgtacggtgggaggtctatataagcagagctctctggctaactagagaacccactgcttact
ggcttatcgaaattaatacgactcactatagggagacccaagcttcgcgacgtacggccgccaccatgcagcgcgtga
acatgatcatggcagaatcaccaggcctcatcaccatctgccttttaggatatctactcagtgctgaatgtacaggtt
tgtttcctttttaaaatacattgagtatgcttgccttttagatatagaaatatctgatgctgtcttcttcactaaat
tttgattacatgatttgacagcaatattgaagagtctaacagccagcacgcaggttggtaagtactgtgggaacatca
cagattttggctccatgccctaaagagaaattggctttcagattatttggattaaaaacaaagactttcttaagagat
gtaaaattttcatgatgttttcttttttgctaaaactaaagaattattcttttacatttcagtttctcttgatcatga
aaacgccaacaaaattctgaatcggccaaagaggtataattcaggtaaattggaagagtttgttcaagggaatctaga
gagagaatgtatggaagaaaagtgtagttttgaagaagcacgagaagtttttgaaaacactgaaagaacaactgaatt
ttggaagcagtatgttgatggagatcagtgtgagtccaatccatgtttaaatggcggcagttgcaaggatgacattaa
ttcctatgaatgttggtgtccctttggatttgaaggaaagaactgtgaattagatgtaacatgtaacattaagaatgg
cagatgcgagcagttttgtaaaaatagtgctgataacaaggtggtttgctcctgtactgagggatatcgacttgcaga
aaaccagaagtcctgtgaaccagcagtgccatttccatgtggaagagtttctgtttcacaaacttctaagctcacccg
tgctgagactgtttttcctgatgtggactatgtaaattctactgaagctgaaaccattttggataacatcactcaaag
cacccaatcatttaatgacttcactcgggttgttggtggagaagatgccaaaccaggtcaattcccttggcaggttgt
tttgaatggtaaagttgatgcattctgtggaggctctatcgttaatgaaaaatggattgtaactgctgcccactgtgt
tgaaactggtgttaaaattacagttgtcgcaggtgaacataatattgaggagacagaacatacagagcaaaagcgaaa
tgtgattcgaattattcctcaccacaactacaatgcagctattaataagtacaaccatgacattgcccttctggaact
ggacgaacccttagtgctaaacagctacgttacacctatttgcattgctgacaaggaatacacgaacatcttcctcaa
atttggatctggctatgtaagtggctggggaagagtcttccacaaagggagatcagctttagttcttcagtaccttag
agttccacttgttgaccgagccacatgtcttcgatctacaaagttcaccatctataacaacatgttctgtgctggctt
ccatgaaggaggtagagattcatgtcaaggagatagtggggaccccatgttactgaagtggaagggaccagtttctt
aactggaattattagctggggtgaagagtgtgcaatgaaaggcaaatatggaatatataccaaggtgtcccggtatgt
caactggattaaggaaaaaacaaagctcactgacaaaactcacacatgcccaccgtgcccagctccggaactcctggg
cggaccgtcagtcttcctcttccccccaaaacccaaggacaccctcatgatctcccggacccctgaggtcacatgcgt
ggtggtggacgtgagccacgaagaccctgaggtcaagttcaactggtacgtggacggcgtggaggtgcataatgccaa
gacaaagccgcgggaggagcagtacaacagcacgtaccgtgtggtcagcgtcctcaccgtcctgcaccaggactggct
gaatggcaaggagtacaagtgcaaggtctccaacaaagccctcccagcccccatcgagaaaaccatctccaaagccaa
agggcagccccgagaaccacaggtgtacaccctgcccccatcccgggatgagctgaccaagaaccaggtcagcctgac
ctgcctggtcaaaggcttctatcccagcgacatcgccgtggagtgggagagcaatgggcagccggagaacaactacaa
gaccacgcctcccgtgttggactccgacggctccttcttcctctacagcaagctcaccgtggacaagagcaggtggca
gcaggggaacgtcttctcatgctccgtgatgcatgaggctctgcacaaccactacacgcagaagagcctctccctgtc
tccgggtaaatgagaattcagacatgataagatacattgatgagtttggacaaaccacaactagaatgcagtgaaaaa
aatgctttatttgtgaaatttgtgatgctattgctttatttgtaaccattataagctgcaataaacaagttggggtgg
gcgaagaactccagcatgagatccccgcgctggaggatcatccagccggcgtcccggaaaacgattccgaagcccaac
ctttcatagaaggcggcggtggaatcgaaatctcgtagcacgtgtcagtcctgctcctcggccacgaagtgcacgcag
ttgccggccgggtcgcgcagggcgaactcccgcccccacggctgctcgccgatctcggtcatggccggcccggaggcg
tcccggaagttcgtggacacgacctccgaccactcggcgtacagctcgtccaggccgcgcacccacacccaggccagg
gtgctgtccggcaccacccggtcccggaccgcgctgacgaacagggccacgccgccccggaccacaccggcgaagtcg
tcctccacgaagtcccgggagaacccgagccggccggtccagaactcgaccgctccggcgacgccgcgcgcggtgagc
accggaacggcactggtcaacttggccatggtttagtccctcaccttgtcgCatcatactatgccgatatactatgcc
gatgattaattgtcaacacgtgctgatcagatccgaaaatggatatacaagctcccgggagctttttgcaaaagccta
ggccCccaaaaaagcccctcactacccctggaatagctcagaggcagaggcggcctcggcctctgcataaataaaaa
aaattagtcagccatggggcggagaatgggcggaactgggcggagttaggggcgggatgggcggagttaggggcggga
ctatggttgctgactaattgagatgcatgetttgeatacttctgcctgctggggagcctggggactttccacacctgg
ttgctgactaattgagatgcatgctttgcatacttctgcctgctggggagcctggggactttccacaccctcgtcgag
```

TABLE 37-continued

Polynucleotide Sequences: FIX-Fc ctagcttcgtgaggctccggtgcccgtcagtgggcagagcgcacatcgcccacagtccccgagaagttggggggaggg
gtcggcaattgaaccggtgcctagagaaggtggcgcggggtaaactgggaaagtgatgtcgtgtactggctccgcctt
tttcccgagggtgggggagaaccgtatataagtgcagtagtcgccgtgaacgttctttttcgcaacgggtttgccgcc
agaacacaggtaagtgccgtgtgtggttcccgcgggcctggcctctttacgggttatggcccttgcgtgccttgaatt
acttccacctggctccagtacgtgattcttgatcccgagctggagccaggggcgggccttgcgctttaggagcccctt
cgcctcgtgcttgagttgaggcctggcctgggcgctggggccgccgcgtgcgaatctggtggcaccttcgcgcctgtc
tcgctgctttcgataagtctctagccatttaaaatttttgatgacctgctgcgacgctttttttctggcaagatagtc
ttgtaaatgcgggccaggatctgcacactggtatttcggtttttggggccgcgggcggcgacggggcccgtgcgtccc
agcgcacatgttcggcgaggcggggcctgcgagcgcggccaccgagaatcggacgggggtagtctcaagctggccggc
ctgctctggtgcctggcctcgcgccgccgtgtatcgccccgccctgggcggcaaggctggcccggtcggcaccagttg
cgtgagcggaaagatggccgcttcccggccctgctccagggggctcaaaatggaggacgcggcgctcgggagagcggg
cgggtgagtcacccacacaaaggaaaggggcctttccgtcctcagccgtcgcttcatgtgactccacggagtaccggg
cgccgtccaggcacctcgattagttctggagcttttggagtacgtcgtctttaggttggggggaggggttttatgcga
tggagtttccccacactgagtgggtggagactgaagttaggccagcttggcacttgatgtaattctccttggaatttg
ccctttttgagtttggatcttggttcattctcaagcctcagacagtggttcaaagtttttttcttccatttcaggtgt
cgtgaacacgtggtcgcggccgcgccgccaccatggagacagacacactcctgctatgggtactgctgctctgggttc
caggttccactggtgacaaaactcacacatgcccaccgtgcccagcacccgaactcctgggaggaccgtcagtcttcc
tcttccccccaaaacccaaggacaccctcatgatctcccggacccctgaggtcacatgcgtggtggtggacgtgagcc
acgaagaccctgaggtcaagttcaactggtacgtggacggcgtggaggtgcataatgccaagacaaagccgcgggagg
agcagtacaacagcacgtaccgtgtggtcagcgtcctcaccgtcctgcaccaggactggctgaatggcaaggagtaca
agtgcaaggtctccaacaaagccctcccagcccccatcgagaaaaccatctccaaagccaaagggcagccccgagaac
cacaggtgtacaccctgcccccatcccgcgatgagctgaccaagaaccaggtcagcctgacctgcctggtcaaaggct
tctatcccagcgacatcgccgtggagtgggagagcaatgggcagccggagaacaactacaagaccacgcctcccgtgt
tggactccgacggctccttcttcctctacagcaagctcaccgtggacaagagcaggtggcagcaggggaacgtcttct
catgctccgtgatgcatgaggctctgcacaaccactacacgcagaagagcctctccctgtctccgggtaaatgactcg
agagatctggccggctgggcccgtttcgaaggtaagcctatccctaaccctctcctcggtctcgattctacgcgtacc
ggtcatcatcaccatcaccattgagtttaaacccgctgatcagcctcgactgtgccttctagttgccagccatctgtt
gtttgcccctcccccgtgccttccttgaccctggaaggtgccactcccactgtcctttcctaataaaatgaggaaatt
gcatcgcattgtctgagtaggtgtcattctattctggggggtggggtggggcaggacagcaagggggaggattgggaa
gacaatagcaggcatgctggggatgcggtgggctctatggcttctgaggcggaaagaaccagtggcggtaatacggtt
atccacagaatcaggggataacgcaggaaagaacatgtgagcaaaaggccagcaaaaggccaggaaccgtaaaaaggc
cgcgttgctggcgtttttccataggctccgcccccctgacgagcatcacaaaaatcgacgctcaagtcagaggtggcg
aaacccgacaggactataaagataccaggcgtttccccctagaagctccctcgtgcgctctcctgttccgaccctgcc
gcttaccggatacctgtccgcctttctcccttcgggaagcgtggcgctttctcatagctcacgctgtaggtatctcag
ttcggtgtaggtcgttcgctccaagctgggctgtgtgcacgaaccccccgttcagcccgaccgctgcgccttatccgg
taactatcgtcttgagtccaacccggtaagacacgacttatcgccactggcagcagccactggtaacaggattagcag
agcgaggtatgtaggcggtgctacagagttcttgaagtggtggcctaactacggctacactagaagaacagtatttgg
tatctgcgctctgctgaagccagttaccttcggaaaaagagttggtagctcttgatccggcaaacaaaccaccgctgg
tagcggtggtttttttgtttgcaagcagcagattacgcgcagaaaaaaaggatctcaagaagatcctttgatcttttc
tacggggtctgacgctcagtggaacgaaaactcacgttaagggattttggtcatgacattaacctataaaaataggcg
tatcacgaggccctttcgtctcgcgcgtttcggtgatgacggtgaaaacctccgacacatgcagctcccggagacggt
cacagcttgtctgtaagcggatgccgggagcagacaagcccgtcagggcgcgtcagcgggtgttggcgggtgtcgggg
ctggcttaactatgcggcatcagagcagattgtactgagagtgcaccatatatgcggtgtgaaataccgcacagatgc
gtaaggagaaaataccgcatcaggcgccattcgccattcaggctgcgcaactgttgggaagggcgatcggtgcgggcc
tcttcgctattacgcca B. Fc DNA sequence (mouse Igκ signal peptide underlined) (SEP ID NO: 3, which encodes SEQ ID NO: 4) This is the Fc cassette from pSYN-FIX-030. In addition, there is a separate Fc expression cassette that was transfected into the cell line in plasmid pSYN-Fc-015 that encodes the same amino acid sequence, but contains a few noncoding changes. The second copy of Fc encoding sequence enables a better monomer: dimer ratio.

Atggagacagacacactcctgctatgggtactgctgctctgggttccaggttccactggtgacaaaactcacacatgcc
caccgtgcccagcacctgaactcctgggaggaccgtcagtcttcctcttccccccaaaac-
ccaaggacaccctcatgat
ctcccggacccctgaggtcacatgcgtggtggtggacgtgagccacgaagaccctgaggtcaagttcaactggtacg
tggacggcgtggaggtgcataatgccaagacaaagccgcgggaggagcagtacaacagcacgtaccgtgtggtca
gcgtcctcaccgtcctgcaccaggactggctgaatggcaaggagtacaagtgcaaggtctccaacaaagccctccca
gcccccatcgagaaaaccatctccaaagccaaagggcagccccgagaaccacaggtgtacaccctgcccccatccc
gcgatgagctgaccaagaaccaggtcagcctgaccrgcctggtcaaaggcttctatcccagcgacatcgccgtggagt
gggagagcaatgggcagccggagaacaactacaagaccacgcctcccgtgttggactccgacggctccttcttcctct
acagcaagctcaccgtggacaagagcaggtggcagcaggggaacgtcttctcatgctccgtgatgcatgaggctctg
cacaaccactacacgcagaagagcctctccctgtctccgggtaaa

TABLE 38

FIX-Fc Monomer Hybrid: created by coexpressing FIX-Fc and Fc chains.

A. FIX-Fc chain (SEQ ID NO: 2):

(28 amino acid signal sequence underlined, 18 amino acid propeptide double underlined, Fc portion in italics.) The C-terminal lysine is not present in either subunit; this processing is often observed in recombinant proteins produced in mammalian cell culture, as well as with plasma derived proteins.

TABLE 38-continued

FIX-Fc Monomer Hybrid: created by coexpressing FIX-Fc and Fc chains.

FIXFC-SC SUBUNIT:

FIX Signal Peptide : -46 MQRVNMIMAE SPGLITICLL GYLLSAEC

FIX Propeptide : -18 TVFLDHENAN KILNRPKR

```
  1  YNSGKLEEFV QGNLERECME EKCSFEEARE VFENTERTTE FWKQYVDGDQ
 51  CESNPCLNGG SCKDDINSYE CWCPFGFEGK NCELDVTGNI KNGRCEQFCK
101  NSADNKVVCS CTEGYRLAEN QKSCEPAVPF PCGRVSVSQT SKLTRAETVF
151  PDVDYVNSTE AETILDNITQ STQSFNDFTR VVGGEDAKPG QFPWQVVLNG
201  KVDAFCGGSI VNEKWIVTAA HCVETGVKIT VVAGEKNIEE TEHTEQKRKV
251  IRIIPKHNYN AAINKYNHDI ALLELDEPLV LNSYVTPICI ADKEYTNIFL
301  KFGSGYVSGW GRVFHKGRSA LVLQYLRVPL VDRATCLRST KFTIYNNMFC
351  AGFHEGGRDS CQGDSGGPHV TEVEGTSFLT GIISWGEECA MKGKYGIYTK
401  VSRYVNWIKE KTKLTDKTHT CPPCPAPELL GGPSVFLFPP KPKDTLMISR
451  TPEVTCVVVD VSHEDPEVKF NWYVDGVEVH NAKTKPREEQ YNSTYRVVSV
501  LTVLHQDWLN GKEYKCKVSN KALPAPIEKT ISKAKGQPRE PQVYTLPPSR
551  DELTKNQVSL TCLVKGFYPS DIAVEWESNG QPENNYKTTP PVLDSDGSFF
601  LYSKLTVDKS RWQQGNVFSC SVMHEALHNH YTQKSLSLSP GK
```

B. Fc chain (SEQ ID NO: 4)

20 amino acid heterologous mouse Igκ liaht chain signal peptide (underlined):

-20 METDTLLLWV LLLWVPGSTG

Mature Fc sequence (corresponding to human IgG1 amino acids 221 to 447, EU numbering)
```
  1  DKTHTCPPCP APELLGGPSV FLFPPKPKDT LMISRTPEVT CVWDVSHED
 51  PEVKFNWYVD GVEVHNAKTK PREEQYNSTY RVVSVLTVLH QDWLNGKEYK
101  CKVSNKALPA PIEKTISKAK GQPREPQVYT LPPSRDELTK NQVSLTCLVK
151  GFYPSDIAVE WESNGQPENN YKTTPPVLDS DGSFFLYSKL TVDKSRWQQG
201  NVFSCSVMHE ALHNHYTQKS LSLSPGK
```

TABLE 39

FVIIIFc Polynucleotide Sequences

A. B-Domain Deleted FVIIIFc (i) B-Domain Deleted FVIIIFc Chain DNA Sequence (FVIII signal peptide underlined, Fc region in bold) (SEQ ID NO 5 which encodes SEQ ID NO: 6)

```
                                A TGCAAATAGA GCTCTCGACC TGCTTCTTTC
TGTGCCTTTT GCGATTCTGC TTTAGTGCCA CCAGAAGATA CTACCTGGGT GCAGTGGAAC
TGTCATGGGA CTATATGCAA AGTGATCTCG GTGAGCTGCC TGTGGACGCA AGATTTCCTC
CTAGAGTGCC AAAATCTTTT CCATTCAACA CCTCAGTCGT GTACAAAAAG ACTCTGTTTG
TAGAATTCAC GGATCACCTT TTCAACATCG CTAAGCCAAG GCCACCCTGG ATGGGTCTGC
TAGGTCCTAC CATCCAGGCT GAGGTTTATG ATACAGTGGT CATTACACTT AAGAACATGG
CTTCCCATCC TGTCAGTCTT CATGCTGTTG GTGTATCCTA CTGGAAAGCT TCTGAGGGAG
CTGAATATGA TGATCAGACC AGTCAAAGGG AGAAAGAAGA TGATAAAGTC TTCCCTGGTG
GAAGCCATAC ATATGTCTGG CAGGTCCTGA AAGAGAATGG TCCAATGGCC TCTGACCCAC
TGTGCCTTAC CTACTCATAT CTTTCTCATG TGGACCTGGT AAAAGACTTG AATTCAGGCC
TCATTGGAGC CCTACTAGTA TGTAGAGAAG GGAGTCTGGC CAAGGAAAAG ACACAGACCT
TGCACAAATT TATACTACTT TTTGCTGTAT TTGATGAAGG GAAAAGTTGG CACTCAGAAA
CAAAGAACTC CTTGATGCAG GATAGGGATG CTGCATCTGC TCGGGCCTGG CCTAAAATGC
ACACAGTCAA TGGTTATGTA AACAGGTCTC TGCCAGGTCT GATTGGATGC CACAGGAAAT
CAGTCTATTG GCATGTGATT GGAATGGGCA CCACTCCTGA AGTGCACTCA ATATTCCTCG
```

TABLE 39-continued

FVIIIFc Polynucleotide Sequences

AAGGTCACAC ATTTCTTGTG AGGAACCATC GCCAGGCGTC CTTGGAAATC TCGCCAATAA
CTTTCCTTAC TGCTCAAACA CTCTTGATGG ACCTTGGACA GTTTCTACTG TTTTGTCATA
TCTCTTCCCA CCAACATGAT GGCATGGAAG CTTATGTCAA AGTAGACAGC TGTCCAGAGG
AACCCCAACT ACGAATGAAA AATAATGAAG AAGCGGAAGA CTATGATGAT GATCTTACTG
ATTCTGAAAT GGATGTGGTC AGGTTTGATG ATGACAACTC TCCTTCCTTT ATCCAAATTC
GCTCAGTTGC CAAGAAGCAT CCTAAAACTT GGGTACATTA CATTGCTGCT GAAGAGGAGG
ACTGGGACTA TGCTCCCTTA GTCCTCGCCC CCGATGACAG AAGTTATAAA AGTCAATATT
TGAACAATGG CCCTCAGCGG ATTGGTAGGA AGTACAAAAA AGTCCGATTT ATGGCATACA
CAGATGAAAC CTTTAAGACT CGTGAAGCTA TTCAGCATGA ATCAGGAATC TTGGGACCTT
TACTTTATGG GGAAGTTGGA GACACACTGT TGATTATATT TAAGAATCAA GCAAGCAGAC
CATATAACAT CTACCCTCAC GGAATCACTG ATGTCCGTCC TTTGTATTCA AGGAGATTAC
CAAAAGGTGT AAAACATTTG AAGGATTTTC CAATTCTGCC AGGAGAAATA TTCAAATATA
AATGGACAGT GACTGTAGAA GATGGGCCAA CTAAATCAGA TCCTCGGTGC CTGACCCGCT
ATTACTCTAG TTTCGTTAAT ATGGAGAGAG ATCTAGCTTC AGGACTCATT GGCCCTCTCC
TCATCTGCTA CAAAGAATCT GTAGATCAAA GAGGAAACCA GATAATGTCA GACAAGAGGA
ATGTCATCCT GTTTTCTGTA TTTGATGAGA ACCGAAGCTG GTACCTCACA GAGAATATAC
AACGCTTTCT CCCCAATCCA GCTGGAGTGC AGCTTGAGGA TCCAGAGTTC CAAGCCTCCA
ACATCATGCA CAGCATCAAT GGCTATGTTT TTGATAGTTT GCAGTTGTCA GTTTGTTTGC
ATGAGGTGGC ATACTGGTAC ATTCTAAGCA TTGGAGCACA GACTGACTTC CTTTCTGTCT
TCTTCTCTGG ATATACCTTC AAACACAAAA TGGTCTATGA AGACACACTC ACCCTATTCC
CATTCTCAGG AGAAACTGTC TTCATGTCGA TGGAAAACCC AGGTCTATGG ATTCTGGGGT
GCCACAACTC AGACTTTCGG AACAGAGGCA TGACCGCCTT ACTGAAGGTT TCTAGTTGTG
ACAAGAACAC TGGTGATTAT TACGAGGACA GTTATGAAGA TATTTCAGCA TACTTGCTGA
GTAAAAACAA TGCCATTGAA CCAAGAAGCT TCTCTCAAAA CCCACCAGTC TTGAAACGCC
ATCAACGGGA AATAACTCGT ACTACTCTTC AGTCAGATCA AGAGGAAATT GACTATGATG
ATACCATATC AGTTGAAATG AAGAAGGAAG ATTTTGACAT TTATGATGAG GATGAAAATC
AGAGCCCCCG CAGCTTTCAA AAGAAAACAC GACACTATTT TATTGCTGCA GTGGAGAGGC
TCTGGGATTA TGGGATGAGT AGCTCCCCAC ATGTTCTAAG AAACAGGGCT CAGAGTGGCA
GTGTCCCTCA GTTCAAGAAA GTTGTTTTCC AGGAATTTAC TGATGGCTCC TTTACTCAGC
CCTTATACCG TGGAGAACTA AATGAACATT TGGGACTCCT GGGGCCATAT ATAAGAGCAG
AAGTTGAAGA TAATATCATG GTAACTTTCA GAAATCAGGC CTCTCGTCCC TATTCCTTCT
ATTCTAGCCT TATTTCTTAT GAGGAAGATC AGAGGCAAGG AGCAGAACCT AGAAAAAACT
TTGTCAAGCC TAATGAAACC AAAACTTACT TTTGGAAAGT GCAACATCAT ATGGCACCCA
CTAAAGATGA GTTTGACTGC AAAGCCTGGG CTTATTTCTC TGATGTTGAC CTGGAAAAAG
ATGTGCACTC AGGCCTGATT GGACCCCTTC TGGTCTGCCA CACTAACACA CTGAACCCTG
CTCATGGGAG ACAAGTGACA GTACAGGAAT TTGCTCTGTT TTTCACCATC TTTGATGAGA
CCAAAAGCTG GTACTTCACT GAAAATATGG AAAGAAACTG CAGGGCTCCC TGCAATATCC
AGATGGAAGA TCCCACTTTT AAAGAGAATT ATCGCTTCCA TGCAATCAAT GGCTACATAA
TGGATACACT ACCTGGCTTA GTAATGGCTC AGGATCAAAG GATTCGATGG TATCTGCTCA
GCATGGGCAG CAATGAAAAC ATCCATTCTA TTCATTTCAG TGGACATGTG TTCACTGTAC
GAAAAAAAGA GGAGTATAAA ATGGCACTGT ACAATCTCTA TCCAGGTGTT TTTGAGACAG
TGGAAATGTT ACCATCCAAA GCTGGAATTT GGCGGGTGGA ATGCCTTATT GGCGAGCATC
TACATGCTGG GATGAGCACA CTTTTTCTGG TGTACAGCAA TAAGTGTCAG ACTCCCCTGG
GAATGGCTTC TGGACACATT AGAGATTTTC AGATTACAGC TTCAGGACAA TATGGACAGT
GGGCCCCAAA GCTGGCCAGA CTTCATTATT CCGGATCAAT CAATGCCTGG AGAGGCAAGG
AGCCCTTTTC TTGGATCAAG GTGGATCTGT TGGCACCAAT GATTATTCAC GGCATCAAGA
CCCAGGGTGC CCGTCAGAAG TTCTCCAGCC TCTACATCTC TCAGTTTATC ATCATGTATA
GTCTTGATGG GAAGAAGTGG CAGACTTATC GAGGAAATTC CACTGGAACC TTAATGGTCT
TCTTTGGCAA TGTGGATTCA TCTGGGATAA AACACAATAT TTTTAACCCT CCAATTATTG
CTCGATACAT CCGTTTGCAC CCAACTCATT ATAGCATTCG CAGCACTCTT CGCATGGAGT
TGATGGGCTG TGATTTAAAT AGTTGCAGCA TGCCATTGGG AATGGAGAGT AAAGCAATAT
CAGATGCACA GATTACTGCT TCATCCTACT TTACCAATAT GTTTGCCACC TGGTCTCCTT
CAAAAGCTCG ACTTCACCTC CAAGGGAGGA GTAATGCCTG GAGACCTCAG GTGAATAATC
CAAAAGAGTG GCTGCAAGTG GACTTCCAGA AGACAATGAA AGTCACAGGA GTAACTACTC
AGGGAGTAAA ATCTCTGCTT ACCAGCATGT ATGTGAAGGA GTTCCTCATC TCCAGCAGTC
AAGATGGCCA TCAGTGGACT CTCTTTTTTC AGAATGGCAA AGTAAAGGTT TTTCAGGGAA
ATCAAGACTC CTTCACACCT GTGGTGAACT CTCTAGACCC ACCGTTACTG ACTCGCTACC
TTCGAATTCA CCCCCAGAGT TGGGTGCACC AGATTGCCCT GAGGATGGAG GTTCTGGGCT
GCGAGGCACA GGACCTCTAC GACAAAACTC ACACATGCCC ACCGTGCCCA GCTCCAGAAC
TCCTGGGCGG ACCGTCAGTC TTCCTCTTCC CCCCAAAACC CAAGGACACC CTCATGATCT
CCCGGACCCC TGAGGTCACA TGCGTGGTGG TGGACGTGAG CCACGAAGAC CCTGAGGTCA
AGTTCAACTG GTACGTGGAC GGCGTGGAGG TGCATAATGC CAAGACAAAG CCGCGGGAGG
AGCAGTACAA CAGCACGTAC CGTGTGGTCA GCGTCCTCAC CGTCCTGCAC CAGGACTGGC
TGAATGGCAA GGAGTACAAG TGCAAGGTCT CCAACAAAGC CCTCCCAGCC CCCATCGAGA
AAACCATCTC CAAAGCCAAA GGGCAGCCCC GAGAACCACA GGTGTACACC CTGCCCCCAT
CCCGGGATGA GCTGACCAAG AACCAGGTCA GCCTGACCTG CCTGGTCAAA GGCTTCTATC
CCAGCGACAT CGCCGTGGAG TGGGAGAGCA ATGGGCAGCC GGAGAACAAC TACAAGACCA
CGCCTCCCGT GTTGGACTCC GACGGCTCCT TCTTCCTCTA CAGCAAGCTC AeCGTGGACA
AGAGCAGGTG GCAGCAGGGG AACGTCTTCT CATGCTCCGT GATGCATGAG GCTCTGCACA
ACCACTACAC GCAGAAGAGC CTCTCCCTGT CTCCGGGTAA A

(ii) Fc DNA sequence (mouse Igκ signal peptide underlined)
(SEQ ID NO: 7, which encodes SEQ ID NO: 8)

ATGGA GACAGACACA
CTCCTGCTAT GGGTACTGCT GCTCTGGGTT CCAGGTTCCA CTGGTGACAA AACTCACACA
TGCCCACCGT GCCCAGCACC TGAACTCCTG GGAGGACCGT CAGTCTTCCT CTTCCCCCCA
AAACCCAAGG ACACCCTCAT GATCTCCCGG ACCCCTGAGG TCACATGCGT GGTGGTGGAC
GTGAGCCACG AAGACCCTGA GGTCAAGTTC AACTGGTACG TGGACGGCGT GGAGGTGCAT

TABLE 39-continued

FVIIIFc Polynucleotide Sequences

AATGCCAAGA CAAAGCCGCG GGAGGAGCAG TACAACAGCA CGTACCGTGT GGTCAGCGTC
CTCACCGTCC TGCACCAGGA CTGGCTGAAT GGCAAGGAGT ACAAGTGCAA GGTCTCCAAC
AAAGCCCTCC CAGCCCCCAT CGAGAAAACC ATCTCCAAAG CCAAAGGGCA GCCCCGAGAA
CCACAGGTGT ACACCCTGCC CCCATCCCGC GATGAGCTGA CCAAGAACCA GGTCAGCCTG
ACCTGCCTGG TCAAAGGCTT CTATCCCAGC GACATCGCCG TGGAGTGGGA GAGCAATGGG
CAGCCGGAGA ACAAGTACAA GACCACGCCT CCCGTGTTGG ACTCCGACCG CTCCTTCTTC
CTCTACAGCA AGCTCACCGT GGACAAGAGC AGGTGGCAGC AGGGGAACGT CTTCTCATGC
TCCGTGATGC ATGAGGCTCT GCACAACCAC TACACGCAGA AGAGCCTCTC CCTGTCTCCG
GGTAAA

B. Full Length FVIIIFc
(i) Full Length FVIIIFc DNA Sequence (FVIII signal peptide underlined, FC region in bold) (SEQ ID NO: 9, which encodes SEQ ID NO: 10)

ATG CAAATAGAGC TCTCCACCTC
CTTCTTTCTG TGCCTTTTGC GATTCTGCTT TAGTGCCACC AGAAGATACT ACCTGGGTGC
AGTGGAACTG TCATGGGACT ATATGCAAAG TGATCTCGGT GAGCTGCCTG TGGACGCAAG
ATTTCCTCCT AGAGTGCCAA AATCTTTTCC ATTCAACACC TCAGTCGTGT ACAAAAAGAC
TCTGTTTGTA GAATTCACGG ATCACCTTTT CAACATCGCT AAGCCAAGGC CACCCTGGAT
GGGTCTGCTA GGTCCTACCA TCCAGGCTGA GGTTTATGAT ACAGTGGTCA TTACACTTAA
GAACATGGCT TCCCATCCTG TCAGTCTTCA TGCTGTTGGT GTATCCTACT GGAAAGCTTC
TGAGGGAGCT GAATATGATG ATCAGACCAG TCAAAGGGAG AAAGAAGATG ATAAAGTCTT
CCCTGGTGGA AGCCATACAT ATGTCTGGCA GGTCCTGAAA GAGAATGGTC CAATGGCCTC
TGACCCACTG TGCCTTACCT ACTCATATCT TTCTCATGTG GACCTGGTAA AAGACTTGAA
TTCAGGCCTC ATTGGAGCCC TACTAGTATG TAGACAAGGG AGTCTGGCCA AGGAAAAGAC
ACAGACCTTG CACAAATTTA TACTACTTTT TGCTGTATTT GATGAAGGGA AAAGTTGGCA
CTCAGAAACA AAGAACTCCT TGATGCAGGA TAGGGATGCT GCATCTGCTC GGGCCTGGCC
TAAAATGCAC ACAGTCAATG GTTATGTAAA CAGGTCTCTG CCAGGTCTGA TTGGATGCCA
CAGGAAATCA GTCTATTGGC ATGTGATTGG AATGGGCACC ACTCCTGAAG TGCACTCAAT
ATTCCTCCAA GGTCAGACAT TTCTTGTGAG GAACCATCGC CAGCCGTCCT TGGAAATCTC
GCCAATAACT TTCCTTACTG CTCAAACACT CTTGATGGAC CTTGGACAGT TTCTACTGTT
TTGTCATATC TCTTCCCACC AACATGATGG CATGGAAGCT TATGTCAAAG TAGACAGCTG
TCCAGAGGAA CCCCAACTAC GAATGAAAAA TAATGAAGAA GCGGAAGACT ATGATGATGA
TCTTACTGAT TCTGAAATGG ATGTGGTCAG CTTTGATGAT GACAACTCTC CTTCCTTTAT
CCAAATTCGC TCAGTTGCCA AGAAGCATCC TAAAACTTGG GTACATTACA TTGCTGCTGA
AGAGGAGGAC TGGGACTATG CTCCCTTAGT CCTCGCCCCC GATGACAGAA GTTATAAAAG
TCAATATTTG AACAATGGCC CTCAGCGGAT TGGTAGGAAG TACAAAAAAG TCCGATTTAT
GGCATACACA GATGAAACCT TTAAGACTCG TGAAGCTATT CAGCATGAAT CAGGAATCTT
GGGACCTTTA CTTTATGGGG AAGTTGGAGA CACACTGTTG ATTATATTTA AGAATCAAGC
AAGCAGACCA TATAACATCT ACCCTCACGG AATCACTGAT GTCCGTCCTT TGTATTCAAG
GAGATTACCA AAAGGTGTAA AACATTTGAA GGATTTTCCA ATTCTGCCAG GAGAAATATT
CAAATATAAA TGGACAGTGA CTGGAGACAA TGGGCCAACT AAATCAGATC CTCGGTGCCT
GACCCGCTAT TACTCTAGTT TCGTTAATAT GGAGAGAGAT CTAGCTTCAG GACTCATTGG
CCCTCTCCTC ATCTGCTACA AAGAATCTGT AGATCAAAGA GGAAACCAGA TAATGTCAGA
CAAGAGGAAT GTCATCCTGT TTTCTGTATT TGATGAGAAC CGAAGCTGGT ACCTCACAGA
GAATATACAA CGCTTTCTCC CCAATCCAGC TGGAGTGCAG CTTGAGGATC CAGAGTTCCA
AGCCTCCAAC ATCATGCACA GCATCAATGG CTATGTTTTT GATAGTTTGC AGTTGTCAGT
TTGTTTGCAT GAGGTGGCAT ACTGGTACAT TCTAAGCATT GGAGCACAGA CTGACTTCCT
TTCTGTCTTC TTCTCTGGAT ATACCTTCAA ACACAAAATG GTCTATGAAG ACACACTCAC
CCTATTCCCA TTCTCAGGAG AAACTGTCTT CATGTCGATG GAAAACCCAG GTCTATGGAT
TCTGGGGTGC CACAACTCAG ACTTTCGGAA CAGAGGCATG ACCGCCTTAC TGAAGGTTTC
TAGTTGTGAC AAGAACACTG GTGATTATTA CGAGGACAGT TATGAAGATA TTTCAGCATA
CTTGCTGAGT AAAAACAATG CCATTGAACC AAGAAGCTTC TCCCAGAATT CAAGACACCC
TAGCACTAGG CAAAAGCAAT TTAATGCCAC CACAATTCAA GAAAATGACA TAGAGAAGAC
TGACCCTTGG TTTGCACACA GAACACCTAT GCCTAAAATA CAAAATGTCT CCTCTAGTGA
TTTGTTGATG CTCTTGCGAC AGAGTCCTAC TCCACATGGG CTATCCTTAT CTGATCTCCA
AGAAGCCAAA TATGAGACTT TTTCTGATGA TCCATCACCT GGAGCAATAG ACAGTAATAA
CAGCCTGTCT GAAATGACAC ACTTCAGGCC ACAGCTCCAT CACAGTGGGG ACATGGTATT
TACCCCTGAG TCAGGCCTCC AATTAAGATT AAATGAGAAA CTGGGGACAA CTGCAGCAAC
AGAGTTGAAG AAACTTGATT TCAAAGTTTC TAGTACATCA AATAATCTGA TTTCAACAAT
TCCATCAGAC AATTTGGCAG CAGGTACTGA TAATACAAGT TCCTTAGGAC CCCCAAGTAT
GCCAGTTCAT TATGATAGTC AATTAGATAC CACTCTATTT GGCAAAAAGT CATCTCCCCT
TACTGAGTCT GGTGGACCTC TGAGCTTGAG TGAAGAAAAT AATGATTCAA AGTTGTTAGA
ATCAGGTTTA ATGAATAGCC AAGAAAGTTC ATGGGGAAAA AATGTATCGT CAACAGAGAG
TGGTAGGTTA TTTAAAGGGA AAAGAGCTCA TGGACCTGCT TTGTTGACTA AAGATAATGC
CTTATTCAAA GTTAGCATCT CTTTGTTAAA GACAAACAAA ACTTCCAATA ATTCAGCAAC
TAATAGAAAG ACTCACATTG ATGGCCCATC ATTATTAATT GAGAATAGTC CATCAGTCTG
GCAAAATATA TTAGAAAGTG ACACTGAGTT TAAAAAAGTG ACACCTTTGA TTCATGACAG
AATGCTTATG GACAAAAATG CTACAGCTTT GAGGCTAAAT CATATGTCAA ATAAAACTAC
TTCATCAAAA AACATGGAAA TGGTCCAACA GAAAAAAGAG GGCCCCATTC CACCAGATGC
ACAAAATCCA GATATGTCGT TCTTTAAGAT GCTATTCTTG CCAGAATCAG CAAGGTGGAT
ACAAAGGACT CATGGAAAGA ACTCTCTGAA CTCTGGGCAA GGCCCCAGTC CAAAGCAATT
AGTATCCTTA GGACCAGAAA AATCTGTGGA AGGTCAGAAT TTCTTGTCTG AGAAAAACAA
AGTGGTAGTA GGAAAGGGTG AATTTACAAA GGACGTAGGA CTCAAAGAGA TGGTTTTTCC
AAGCAGCAGA AACCTATTTC TTACTAACTT GGATAATTTA CATGAAAATA ATACACACAA
TCAAGAAAAA AAAATTCAGG AAGAAATAGA AAAGAAGGAA ACATTAATCC AAGAGAATGT
AGTTTTGCCT CAGATACATA CAGTGACTGG CACTAAGAAT TTCATGAAGA ACCTTTTCTT
ACTGAGCACT AGGCAAAATG TAGAAGGTTC ATATGACGGG GCATATGCTC CAGTACTTCA

TABLE 39-continued

FVIIIFc Polynucleotide Sequences

AGATTTTAGG TCATTAAATG ATTCAACAAA TAGAACAAAG AAACACACAG CTCATTTCTC
AAAAAAAGGG GAGGAAGAAA ACTTGGAAGG CTTGGGAAAT CAAACCAAGC AAATTGTAGA
GAAATATGCA TGCACCACAA GGATATCTCC TAATACAAGC CAGCAGAATT TTGTCACGCA
ACGTAGTAAG AGAGCTTTGA AACAATTCAG ACTCCCACTA GAAGAAACAG AACTTGAAAA
AAGGATAATT GTGGATGACA CCTCAACCCA GTGGTCCAAA AACATGAAAC ATTTGACCCC
GAGCACCCTC ACACAGATAG ACTACAATGA GAAGGAGAAA GGGGCCATTA CTCAGTCTCC
CTTATCAGAT TGCCTTACGA GGAGTCATAG CATCCCTCAA GCAAATAGAT CTCCATTACC
CATTGCAAAG GTATCATCAT TTCCATCTAT TAGACCTATA TATCTGACCA GGGTCCTATT
CCAAGACAAC TCTTCTCATC TTCCAGCAGC ATCTTATAGA AAGAAAGATT CTGGGGTCCA
AGAAAGCAGT CATTTCTTAC AAGGAGCCAA AAAAAATAAC CTTTCTTTAG CCATTCTAAC
CTTGGAGATG ACTGGTGATC AAAGAGAGGT TGGCTCCCTG GGGACAAGTG CCACAAATTC
AGTCACATAC AAGAAAGTTG AGAACACTGT TCTCCCGAAA CCAGACTTGC CCAAAACATC
TGGCAAAGTT GAATTGCTTC CAAAAGTTCA CATTTATCAG AAGGACCTAT TCCCTACGGA
AACTAGCAAT GGGTCTCCTG GCCATCTGGA TCTCGTGGAA GGGAGCCTTC TTCAGGGAAC
AGAGGGAGCG ATTAAGTGGA ATGAAGCAAA CAGACCTGGA AAAGTTCCCT TTCTGAGAGT
AGCAACAGAA AGCTCTGCAA AGACTCCCTC CAAGCTATTG GATCCTCTTG CTTGGGATAA
CCACTATGGT ACTCAGATAC CAAAAGAAGA GTGGAAATCC CAAGAGAAGT CACCAGAAAA
AACAGCTTTT AAGAAAAAGG ATACCATTTT GTCCCTGAAC GCTTGTGAAA GCAATCATGC
AATAGCAGCA ATAAATGAGG GACAAAATAA GCCCGAAATA GAAGTCACCT GGGCAAAGCA
AGGTAGGACT GAAAGGCTGT GCTCTCAAAA CCCACCAGTC TTGAAACGCC ATCAACGGGA
AATAACTCGT ACTACTCTTC AGTCAGATCA AGAGGAAATT GACTATGATG ATACCATATC
AGTTGAAATG AAGAAGGAAG ATTTTGACAT TTATGATGAG GATGAAAATC AGAGCCCCCG
CAGCTTTCAA AAGAAAACAC GACTCTATTT TATTGCTGCA GTGGAGAGGC TCTGGGATTA
TGGGATGAGT AGCTCCCCAC ATGTTCTAAG AAACAGGGCT CAGAGTGGCA GTGTCCCTCA
GTTCAAGAAA GTTGTTTTCC AGGAATTTAC TGATGGCTCC TTTACTCAGC CCTTATACCG
TGGAGAACTA AATGAACATT TGGGACTCCT GGGGCCATAT ATAAGAGCAG AAGTTGAAGA
TAATATCATG GTAACTTTCA GAAATCAGGC CTCTCGTCCC TATTCCTTCT ATTCTAGCCT
TATTTCTTAT GAGGAAGATC AGAGGCAAGG AGCAGAACCT AGAAAAAACT TTGTCAAGCC
TAATGAAACC AAAACTTACT TTTGGAAAGT GCAACATCAT ATGGCACCCA CTAAAGATGA
GTTTGACTGC AAAGCCTGGG CTTATTTCTC TGATGTTGAC CTGGAAAAAG ATGTGCACTC
AGGCCTGATT GGACCCCTTC TGGTCTGCCA CACTAACACA CTGAACCCTG CTCATGGGAG
ACAAGTGACA GTACAGGAAT TTGCTCTGTT TTTCACCATC TTTGATGAGA CCAAAAGCTG
GTACTTCACT GAAAATATGG AAAGAAACTG CAGGGCTCCC TGCAATATCC TGATGGAAGA
TCCCACTTTT AAAGAGAATT ATCGCTTCCA TGCAATCAAT GGCTACATAA TGGATACACT
ACCTGGCTTA GTAATGGCTC AGGATCAAAG GATTCGATGG TATCTGCTCA GCATGGGCAG
CAATGAAAAC ATCCATTCTA TTCATTTCAG TGGACATGTG TTCACTGTAC GAAAAAAAGA
GGAGTATAAA ATGGCACTGT ACAATCTCTA TCCAGGTGTT TTTGAGACAG TGGAAATGTT
ACCATCCAAA GCTGGAATTT GGCGGGTGGA ATGCCTTATT GGCGAGCATC TACATGCTGG
GATGAGCACA CTTTTTCTGG TGTACAGCAA TAAGTGTCAG ACTCCCCTGG GAATGGCTTC
TGGACACATT AGAGATTTTC AGATTACAGC TTCAGGACAA TATGGACAGT GGGCCCCAAA
GCTGGCCAGA CTTCATTATT CCGGATCAAT CAATGCCTGG AGCACCAAGG AGCCCTTTTC
TTGGATCAAG GTGGATCTGT TGGCACCAAT GATTATTCAC GGCATCAAGA CCCAGGGTGC
CCGTCAGAAG TTCTCCAGCC TCTACATCTC TCAGTTTATC ATCATGTATA GTCTTGATGG
GAAGAAGTGG CAGACTTATC GAGGAAATTC CACTGGAACC TTAATGGTCT TCTTTGGCAA
TGTGGATTCA TCTGGGATAA AACACAATAT TTTTAACCCT CCAATTATTG CTCGATACAT
CCGTTTGCAC CCAACTCATT ATAGCATTCG CAGCACTCTT CGCATGGAGT TGATGGGCTG
TGATTTAAAT AGTTGCAGCA TGCCATTGGG AATGGAGAGT AAAGCAATAT CAGATGCACA
GATTACTGCT TCATCCTACT TTACCAATAT GTTTGCCACC TGGTCTCCTT CAAAAGCTCG
ACTTCACCTC CAAGGGAGGA GTAATGCCTG GAGACCTCAG GTGAATAATC CAAAAGAGTG
GCTGCAAGTG GACTTCCAGA AGACAATGAA AGTCACAGGA GTAACTACTC AGGGAGTAAA
ATCTCTGCTT ACCAGCATGT ATGTGAAGGA GTTCCTCATC TCCAGCAGTC AAGATGGCCA
TCAGTGGACT CTCTTTTTTC AGAATGGCAA AGTAAAGGTT TTTCAGGGAA ATCAAGACTC
CTTCACACCT GTGGTGAACT CTCTAGACCC AECOTTACTG ACTCGCTACC TTCGAACTCA
CCCCCAGAGT TGGGTGCACC AGATTGCCCT GAGGATGGAG GTTCTGGGCT GCGTGGCACA
GGACCTCTAC GACAAAACTC ACACATGCCC ACCGTGCCCA GCTCCAGAAC TCCTGGGCGG
ACCGTCAGTC TTCCTCTTCC CCCCAAAACC CAAGGACACC CTCATGATCT CCCGGACCCC
TGAGGTCACA TGCGTGGTGG TGGACGTGAG CCACGAAGAC CCTGAGGTCA AGTTCAACTG
GTACGTGGAC GGCGTGGAGG TGCATAATGC CAAGACAAAG CCGCGGGAGG AGCAGTACAA
CAGCACGTAC CGTGTGGTCA GCGTCCTCAC CGTCCTGCAC CAGGACTGGC TGAATGGCAA
GGAGTACAAG TGCAAGGTCT CCAACAAAGC CCTCCCAGCC CCCATCGAGA AAACCATCTC
CAAAGCCAAA GGGCAGCCCC GAGAACCACA GGTGTACACC CTGCCCCCAT CCCGGGATGA
GCTGACCAAG AACCAGGTCA GCCTGACCTG CCTGGTCAAA GGCTTCTATC CCAGCGACAT
CGCCGTGGAG TGGGAGAGCA ATGGGCAGCC GGAGAACAAC TACAAGACCA CGCCTCCCGT
GTTGGACTCC GACGGCTCCT TCTTCCTCTA CAGCAAGCTC AeCGTGGACA AGAGCAGGTG
GCAGCAGGGG AACGTCTTCT CATGCTCCGT GATGCATGAG GCTCTGCACA ACCACTACAC
GCAGAAGAGC CTCTCCCTGT CTCCGGGTAA A

(ii) Fc (same sequence as A (ii) (SEQ ID NO: 7))

TABLE 40

FVIII Polypeptide Sequences

A. B-Domain Deleted FVIII-Fc Monomer Hybrid (BDD FVIIIFc monomer dimer): created by coexpressing BDD FVIIIFc and Fc chains.

TABLE 40-continued

FVIII Polypeptide Sequences

Construct = HC-LC-Fc fusion. An Fc expression cassette is cotransfected with BDDFVIII-Fc to generate the BDD FVIIIFc monomer-. For the BDD FVIIIFc chain, the Fc sequence is shown in bold; HC sequence is shown in double underline; remaining B domain sequence is shown in italics. Signal peptides are underlined.

i) B domain deleted FVIII-Fc chain (19 amino acid signal sequence underlined) (SEQ ID NO: 6)

MQIELSTCFFLCLLRFCFS
ATRRYYLGAVELSWDYMQSDLGELPVDARFPPRVPKSFPFNTSVVYKKTLFVEFTDHLF
NIAKPRPPWMGLLGPTIQAEVYDTVVITLKNMASHPVSLHAVGVSYWKASEGAEYDDQ
TSQREKEDDKVFPGGSHTYVWQVLKENGPMASDPLCLTYSYLSHVDLVKDLNSGLIGA
LLVCREGSLAKEKTQTLHKFILLFAVFDEGKSWHSETKNSLMQDRDAASARAWPKMHT
VNGYVNRSLPGLIGCHRKSVYWHVIGMGTTPEVHSIFLEGHTFLVRNGRQASLEISPITFL
TAQTLLMDLGQFLLFCHISSHQHDGMEAYVKVDSCPEEPQLRMKNNEEAEDYDDDLTD
SEMDVVRFDDDNSPSFIQIRSVAKKHPKTWVHYIAAEEEDWDYAPLVLAPDDRSYKSQY
LNNGPQRIGRKYKKVRFMAYTDETFKTREAIQHESGILGPLLYGEVGDTLLIIFKNQASRP
YNIYPHGITDVRPLYSRRLPKGVKHLKDFPILPGEIFKYKWTVTVEDGPTKSDPRCLTRY
YSSFVNMERDLASGLIGPLLICYKESVDQRGNQIMSDKRNVILFSVFDENRSWYLTENIQ
RFLPNPAGVQLEDPEFQASNIMHSINGYVFDSLQLSVCLHEVAYWYILSIGAQTDFLSVFF
SGYTFKHKMVYEDTLTLFPFSGETVFMSMENPGLWILGCHNSDFRNRGMTALLKVSSC
DKNTGDYYEDSYEDISAYLLSKNNAIEPR*SFSQNPPVLKRHQR*EITRTTLQSDQEEIDYDD
TISVEMKKEDFDIYDEDENQSPRSFQKKTRHYFIAAVERLWDYGMSSSPFIVLRNRAQSG
SVPQFKKVVFQEFTDGSFTQPLYRGELNEHLGLLGPYIRAEVEDNIMVTFRNQASRPYSF
YSSLISYEEDQRQGAEPRKNFVKPNETKTYFWKVQHHMAPTKDEFDCKAWAYFSDVDL
EKDVHSGLIGPLLVCHTNTLNPAHGRQVTVQEFALFFTIFDETKSWYFTENMERNCRAP
CNIQMEDPTFKENYRFHAINGYIMDTLPGLVMAQDQRIRWYLLSMGSNENIHSIHFSGH
VFTVRKKEEYKMALYNLYPGVFETVEMLPSKAGIWRVECLIGEHLHAGMSTLFLVYSN
KGQTPLGMASGHIRDFQITASGQYGQWAPKLARLHYSGSINAWSTKEPFSWIKVDLLAP
MIIHGIKTQGARQKFSSLYISQFIIMYSLDGKKWQTYRGNSTGTLMVFFGNVDSSGIKHNI
FNPPIIARYIRLHPTHYSIRSTLRMELMGCDLNSCSMPLGMESKAISDAQITASSYFTNMF
ATWSPSKARIJILQGRSNAWRPQVNNPKEWLQVDFQKTMKVTGVTTQGVKSLLTSMY
VKEFLISSSQDGHQWTLFFQNGKVKVFQGNQDSFTPVVNSLDPPLLTRYLRIHPQSWVH
QIALRMEVLGCEAQDLYDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKG
FYPSDIAVEWESNGQPENNYKTTPPVLDSDGSFFLYSKLTVDKSRWQQGNVFSCSV
MHEALHNHYTQKSLSLSPGK

(ii) Fc chain (20 amino acid heterologous signal peptide from mouse Igκ chain underlined) (SEQ ID NO: 8)

METDTLLLWVLLLWVPGSTG
DKTHTCPPCPAPELLGGPSVFLFPPKPKDTLMISRTPEVTCVVVDVSHFDPEVKPNWYVD
GVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKITPPV
LDSDGSFFLYSKLTVDKSRWQQGNVFSCSVMHEALHNHY'IQKSLSLSPGK

B. Full length FVIIIFc monomer hybrid (Full length FVIIIFc monomer dimer): created by coexpressing FVIIIFc and Fc chains.
Construct = HC-B-LC-Fc fusion. An Fc expression cassette is cotransfected with full length FVIII-Fc to generate the full length FVIIIFc monomer. For the FVIIIFc chain, the Fc sequence is shown in bold; HC sequence is shown in double underline; B domain sequence is shown in italics. Signal peptides are underlined.

(i) Full length FVIIIFc chain (FVIII signal peptide underlined (SEQ ID NO: 10)

MQIELSTCFFLCLLRFCFS
ATRRYYLGAVELSWDYMQSDLGELPVDARFPPRVPKSFPFNTSVVYKKTLFVEFTDHLF
NIAKPRPPWMGLLGPTIQAEVYDTVVITLKNMASHPVSLHAVGVSYWKASEGAEYDDQ
TSQREKEDDKVFPGGSHTYVWQVLKENGPMASDPLCLTYSYLSHVDLVKDLNSGLIGA
LLVCREGSLAKEKTQTLHKFILLFAVFDEGKSWHSETKNSLMQDRDAASARAWPKMHT
VNGYVNRSLPGLIGCHRKSVYWHVIGMGTTPEVHSIFLEGHTFLVRNHRQASLEISPITFL
TAQTLLMDLGQFLLFCHISSHQHDGMEAYVKVDSCPEEPQLRMKNNEEAEDYDDDLTD
SEMDVVRFDDDNSPSFIQIRSVAKKHPKTWVHYIAAEEEDWDYAPLVLAPDDRSYKSQY
LNNGPQRIGRKYKKVRFMAYTDETFKTREAISQHESILGPLLYGEVGDTLLIIFKNQASRP
YNIYPHGITDVRPLYSRRLPKGVKHLKDFPILPGEIFKYKWTVTVEDGPTKSDPRCLTRY
YSSFVNMERDLASGLIGPLLICYKESVDQRGNQIMSDKRNVILFSVFDENRSWYLTENIQ
RFLPNPAGVQLEDPEFQASNIMHSINGYVFDSLQLSVCLHEVAYWYILSIGAQTDFLSVFF
SGYTFKHKMVYEDTLTLFPFSGETVFMSMENPGLWILGCHNSDFRNRGMTALLKVSSC
DKNTGDYYEDSYEDISAYLLSKNNAIEPR*SFSQNSRHPSTRQKQFNATTIPENDIEKTDPWF*
*AHRTPMPKIQNVSSSDLLMLLRQSPTPHGLSLSDLQEAKYETFSDDPSPGAIDSNNSLSEMTHF*
*RPQLHHSGDMVFTPESGLQLRLNEKLGTTAATELKKLDFKVSSTSNNLISTIPSDNLAAGTDNT*
*SSLGPPSMPVHYDSQLDTTLFGKKSSPLTESGGPLSLSEENNDSKLLESGLMNSQESSWGKNV*
*SSTESGRLFKGKRAHGPALLTKDNALFKVSISLLKTNKTSNNSAWRKTHIDGPSUJENSPSVW*
*QNILESDTEFKKVTPLIHDRMLMDKNATALRLNHMSNKTTSSKNMEMVQQKKEGPIPPDAQN*
*PDMSFFKMLFLPESARWIQRTHGKNSLNSGQGPSPKQLVSLGPEKSVEGQNFISEKNKVVVG*
*KGEFTKDMVGLKEMVFPSSRNLFLTNLDNLHENNTHNQEKKIQEEIEKKETLIQENVVLPQIHT*

TABLE 40-continued

FVIII Polypeptide Sequences

*VTGTKNFMKNLFLLSTRQNVEGSYDGAYAPVLQDFRSLNDSTNRTKKHTAHFSKKGEEENLE*
*GLGNQTKQIVEKYACTTRISPNTSQQNFVTQRSKRALKQFRLPLEETELEKRIIVDDTSTQWSK*
*NMKHLTPSTLTQIDWEKEKGAITQSPLSDCLTRSHSIPQANRSPLPIAKVSSFPSIRPIYLTRVLF*
*QDNSSHLPAASYRKKDSGVQESSHFLQGAKKNNLSLAILTLEMTGDQREVGSLGTSATNSVTY*
*KKVENTVLPKPDLPKTSGKVELLPKVHIYQKDLFPTETSNGSPGHLDLVEGSLLQGTEGAIKN*
*NEANRPGKVPFLRVATESSAKTPSKLLDPLAWDNHYGTQIPKEEWKSQEKSPEKTAFKKKDTI*
*LSLNACESNHAIAAINEGQNKPEIEVTWAKQGRTERLCQNPPVLKRHQRE*ITRTTLQSDQEEI
DYDDTISVEMKKEDFDIYDFDBKQSPRSFQKKTRHYFIAAVERLWDYGMSSSPHVLRNR
AQSGSVPQFKKVVFQFFTDGSFTQPLYRGELNEHLGLLGPYIRAEVEDNIMVTFRNQASR
PYSFYSSLISYEEDQRQGAEPRKNFVKPNETKTYFWKVQIIHMAPTKDFFDCKAWAYFS
DVDLEKDVIISGLIGPLLVCHTNTLNPAHGRQVTVQEFALHFTIFDETKSWYFTENMLRN
CRAPCNIQMEDPTFKENYRFHAINGYIMDTLPGLVMAQDQRIRVVYLLSMGSNENIHSIHF
SGHVFTVRKKEEYKMALYNLYPGVFETVEMLPSKAGIWRVECLIGEHLMAGMSTLFLV
YSNKCQTPLGMASGHIRDFQITASGQYGQWAPKLARLHYSGSINAWSTKEPFSWIKVDL
LAPMIIIIGIKTOGARQKFSSLYISQFIIMYSLDGKKWQTYRGNSTGTLMVFFGNVDSSG1K
HMIFNPPIIARYIRLHPTHYSIRSTLRMELMGCDLNSCSMPFGMESKAISDAQITASSYFTN
MFATWSPSKARLHLQGRSNAWKPOVNNPKFWLQVDFQKTMKVTGVTTQGVKSILLTS
MYVKEFLISSSQDGHQWTLFFQNGKVKVFQGNQDSFTPVVNSLDPPLLTRYLKHIPQSW
VHQIALRMEVLGCEAQDLYDKTHTCPPCPAPELLGGPSVFLFPPKPKDTLMISRTPEV
TCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQVSLTCLV
KGFYPSDIAVEWESNGQPENNYKTTPPVLDSDGSFFILYSKLTVDKSRWQQGNVFSC
SVMHEALHNHYTQKSLSLSPGK ii) Fc chain (20 amino acid heterologous signal peptide from mouse Igκ chain underlined) (SEQ ID NO: 8)
METDTLIXWVLLIAVVPGSTG
DKTHTCPPCPAPELLGOPSVFLFPPKPKDTLMISRTTEVTCVVVDVSHEDPEVKFNWYVD
GVEVHNAKTKPREEQYMSTYRVVSVLTVLHQDWLNOKEYKCKVSNKALPAPIEKTISK
AKGQPREPQVYTLPPSRDELTKNQVSLTCLVKGFYPSDIAVEWESNGQPENNYKTPPV
LDSDGSFFLYSKLTVDKSRWOQGNVFSCSVMHEALHNHYTQKSLSLSPGK

What is claimed is:

1. A method of treating hemophilia in a subject in need thereof comprising (i) calculating a therapeutic dose of a chimeric clotting factor and/or a dosing interval of the chimeric clotting factor for the subject using a web-based application that is accessible through a web server, wherein the application is programmed to implement a clotting factor population pharmacokinetic (popPK) model for said chimeric clotting factor and a Bayesian estimation program to calculate the therapeutic dose and/or dosing interval; and, (ii) administering the chimeric clotting factor at the calculated therapeutic dose and/or the dosing interval to the subject wherein (a) the chimeric clotting factor comprises a FVIII polypeptide and a neonatal Fc receptor binding partner (FcRn BP), and the clotting factor popK model for the chimeric clotting factor comprises the parameters in Table 18, 24 or 25; or (b) the chimeric clotting factor comprises a FIX polypeptide and an FcRn BP, and the clotting factor popK model for the chimeric clotting factor comprises the parameters in Table 10, 13 or 14.

2. The method of claim 1, further comprising entering clotting factor pharmacokinetic (PK) information of the subject, body weight and/or age of the subject, and/or desired treatment outcome.

3. The method of claim 2, further comprising updating the popPK model based on the subject's clotting factor PK information.

4. The method of claim 1, wherein the application continuously updates the popPK model based on newly inputted clotting factor PK information of the subject.

5. The method of claim 1, further comprising, before the calculating, inputting a body weight of the subject, the subject's age, or both.

6. The method of claim 1, further comprising inputting a rise of plasma clotting factor activity level desired following the administrating.

7. The method of claim 1, further comprising, before the calculating, measuring a clotting factor activity level in plasma at various time points after an initial dose of the chimeric clotting factor, wherein the subject's clotting factor PK information is, optionally contemporaneously, calculated based on the chimeric clotting factor activity level.

8. The method of claim 7, further comprising, before the measuring, administering an initial dose of the chimeric clotting factor.

9. The method of claim 8, wherein the initial dose is a fixed interval dose.

10. The method of claim 1, wherein the clotting factor popPK model is updated, optionally contemporaneously, and is, optionally immediately, available through the web server.

11. The method of claim 1, wherein the clotting factor popPK model is updated, optionally immediately, after the subject's clotting factor PK information is added to the application and wherein an updated clotting factor popPK model is available for a next use.

12. The method of claim 1, wherein the chimeric clotting factor comprises a FVIII polypeptide and an FcRn BP, and the clotting factor popK model for the chimeric clotting factor comprises the parameters in Table 18, 24 or 25.

13. The method of claim 1, wherein the chimeric clotting factor comprises FIX polypeptide and an FcRn BP, and the clotting factor popK model for the chimeric clotting factor comprises the parameters in Table 10, 13 or 14.

14. The method of claim 1, wherein the FcRn BP an Fc domain or albumin.

15. The method of claim 1, wherein the FIX polypeptide or the FVIII polypeptide is a human FIX polypeptide or a human FVIII polypeptide, respectively.

16. The method of claim 1, wherein the FIX polypeptide or the FVIII polypeptide is a mutant FIX polypeptide or a mutant FVIII polypeptide, respectively.

17. The method of claim 1, wherein the FVIII polypeptide has a full or partial deletion of the B domain.

18. The method of claim 1, wherein the dosing regimen is a prophylaxis regimen.

19. The method of claim 1, wherein the dosing regimen is an on-demand regimen.

20. The method of claim 14, wherein the Fc domain is a human Fc domain.

21. The method of claim 2, wherein the subject's clotting factor PK information comprises subject's endogenous level of clotting factor, pre-PK dose through, clotting factor PK dose, post clotting factor PK dose, or a combination thereof.

22. The method of claim 2, wherein the desired treatment outcome data is the desired rise in plasma clotting factor activity level following the administration.

23. The method of claim 1, wherein the calculations further provide estimated PK data for the subject comprising clotting factor half-like, time to 1%, time to 3%, time to 5%, percentage of recovery, Cmax, or a combination thereof.

* * * * *